(12) United States Patent
White et al.

(10) Patent No.: US 9,296,759 B2
(45) Date of Patent: Mar. 29, 2016

(54) AMINO-OXAZINE AND AMINO-DIHYDROTHIAZINE COMPOUNDS AS BETA-SECRETASE MODULATORS AND METHODS OF USE

(71) Applicant: AMGEN INC., Thousand Oaks, CA (US)

(72) Inventors: Ryan White, Somerville, MA (US); Yuan Cheng, Newbury Park, CA (US); Ana Elena Minatti, Santa Monica, CA (US); Bryant Yang, Agoura Hills, CA (US); Xiao Mei Zheng, Natick, MA (US); Patricia Lopez, Woodland Hills, CA (US); Jason B. Human, Boston, MA (US); Oleg Epstein, Belmont, MA (US); Ted Judd, Granada Hills, CA (US); Kelvin Sham, Thousand Oaks, CA (US); Qiufen Xue, Newbury Park, CA (US)

(73) Assignee: Amgen Inc., Thousand Oaks, CA (US)

( * ) Notice: Subject to any disclaimer, the term of this patent is extended or adjusted under 35 U.S.C. 154(b) by 0 days.

(21) Appl. No.: 14/346,252

(22) PCT Filed: Sep. 21, 2012

(86) PCT No.: PCT/US2012/056658
§ 371 (c)(1),
(2) Date: Mar. 20, 2014

(87) PCT Pub. No.: WO2013/044092
PCT Pub. Date: Mar. 28, 2013

(65) Prior Publication Data
US 2014/0296226 A1     Oct. 2, 2014

Related U.S. Application Data

(60) Provisional application No. 61/537,461, filed on Sep. 21, 2011.

(51) Int. Cl.
| | | |
|---|---|---|
| C07D 498/20 | (2006.01) |
| C07D 513/20 | (2006.01) |
| A61K 31/537 | (2006.01) |
| A61K 31/547 | (2006.01) |
| C07D 513/10 | (2006.01) |
| C07D 498/10 | (2006.01) |

(52) U.S. Cl.
CPC ............ *C07D 513/10* (2013.01); *C07D 498/10* (2013.01); *C07D 498/20* (2013.01); *C07D 513/20* (2013.01)

(58) Field of Classification Search
CPC .......................... C07D 498/20; C07D 513/20
See application file for complete search history.

(56) References Cited

U.S. PATENT DOCUMENTS

| | | |
|---|---|---|
| 2,683,718 A | 7/1954 | Clinton et al. |
| 3,185,696 A | 5/1965 | Tien et al. |
| 5,441,870 A | 8/1995 | Seubert et al. |
| 5,712,130 A | 1/1998 | Hajko et al. |
| 5,942,400 A | 8/1999 | Anderson |
| 6,835,565 B1 | 12/2004 | Gurney et al. |
| 6,864,290 B2 | 3/2005 | Schostarez et al. |
| 6,962,934 B2 | 11/2005 | Warpehoski et al. |

(Continued)

FOREIGN PATENT DOCUMENTS

| | | |
|---|---|---|
| EP | 01942105 A1 | 7/2008 |
| EP | 2305672 | 4/2011 |

(Continued)

OTHER PUBLICATIONS

International Search Report for parent PCT Application No. PCT/US2012/056658, mailed on Oct. 12, 2012.

(Continued)

*Primary Examiner* — Brian McDowell
(74) *Attorney, Agent, or Firm* — G. Prabhakar Reddy; Bernard P. Friedrichsen; Markus Bergauer

(57) ABSTRACT

The present invention comprises a new class of compounds useful for the modulation of Beta-secretase enzyme activity and for the treatment of Beta-secretase mediated diseases, including Alzheimer's disease (AD) and related conditions. In one embodiment, the compounds have a general Formula I wherein $A^1$, $A^2$, $A^3$, $A^4$, $A^5$, $A^6$, L, $R^2$, $R^7$, X, Y and Z of Formula I are defined herein. The invention also includes use of these compounds in pharmaceutical compositions for treatment, prophylactic or therapeutic, of disorders and conditions related to the activity of beta-secretase protein. Such disorders include, for example, Alzheimer's Disease, cognitive deficits, cognitive impairment, schizophrenia and other central nervous system conditions related to and/or caused by the formation and/or deposition of plaque on the brain. The invention also comprises further embodiments of Formula I, intermediates and processes useful for the preparation of compounds of Formula I.

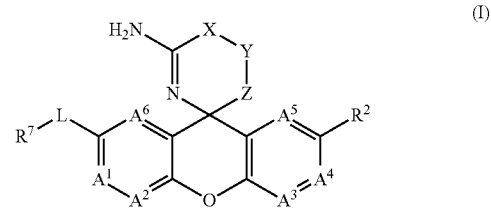

11 Claims, No Drawings

(56) References Cited

U.S. PATENT DOCUMENTS

| | | |
|---|---|---|
| 6,982,264 B2 | 1/2006 | John et al. |
| 6,992,103 B2 | 1/2006 | Faller et al. |
| 7,034,182 B2 | 4/2006 | Fang et al. |
| 7,067,542 B2 | 6/2006 | Schostarez et al. |
| 7,074,799 B2 | 7/2006 | Bakthavatchalam et al. |
| 7,109,217 B2 | 9/2006 | Coburn et al. |
| 7,115,652 B2 | 10/2006 | Yang et al. |
| 7,132,568 B2 | 11/2006 | Yang et al. |
| 7,176,242 B2 | 2/2007 | John et al. |
| 7,223,774 B2 | 5/2007 | Aquino et al. |
| 7,244,725 B2 | 7/2007 | John et al. |
| 7,244,755 B2 | 7/2007 | Fisher et al. |
| 7,253,198 B2 | 8/2007 | Demont et al. |
| 7,291,620 B2 | 11/2007 | Coburn et al. |
| 7,312,360 B2 | 12/2007 | TenBrink et al. |
| 7,348,448 B2 | 3/2008 | Nantermet et al. |
| 7,371,853 B2 | 5/2008 | Coburn et al. |
| 7,582,650 B2 | 9/2009 | DeCorte et al. |
| 7,592,348 B2 | 9/2009 | Zhu et al. |
| 8,426,447 B2 | 4/2013 | White et al. |
| 8,497,264 B2 | 7/2013 | Chen et al. |
| 8,883,782 B2 | 11/2014 | Cheng et al. |
| 8,921,363 B2 | 12/2014 | Minatti et al. |
| 8,957,083 B2 | 2/2015 | Minatti et al. |
| 8,962,859 B2 | 2/2015 | Epstein et al. |
| 9,012,446 B2 | 4/2015 | Chen et al. |
| 2003/0109559 A1 | 6/2003 | Gailunas et al. |
| 2005/0038019 A1 | 2/2005 | Beck |
| 2005/0054690 A1 | 3/2005 | Aquino et al. |
| 2005/0282825 A1 | 12/2005 | Malamas et al. |
| 2006/0111370 A1 | 5/2006 | Zhu et al. |
| 2006/0211740 A1 | 9/2006 | Demont et al. |
| 2006/0241133 A1 | 10/2006 | Shearman et al. |
| 2006/0287297 A1 | 12/2006 | DeCorte et al. |
| 2007/0004786 A1 | 1/2007 | Malamas et al. |
| 2007/0027199 A1 | 2/2007 | Malamas et al. |
| 2007/0072925 A1 | 3/2007 | Malamas et al. |
| 2007/0203116 A1 | 8/2007 | Quagliato et al. |
| 2007/0287692 A1 | 12/2007 | Wu et al. |
| 2008/0200445 A1 | 8/2008 | Zhu et al. |
| 2009/0082560 A1 | 3/2009 | Kobayashi et al. |
| 2009/0209529 A1 | 8/2009 | Andreini et al. |
| 2009/0209755 A1 | 8/2009 | Suzuki et al. |
| 2009/0306047 A1 | 12/2009 | Zhu et al. |
| 2010/0075957 A1 | 3/2010 | Tamura et al. |
| 2010/0087429 A1 | 4/2010 | White et al. |
| 2010/0160290 A1 | 6/2010 | Kobayashi et al. |
| 2014/0031340 A1 | 1/2014 | Dineen et al. |
| 2015/0307521 A1 | 10/2015 | White et al. |

FOREIGN PATENT DOCUMENTS

| | | |
|---|---|---|
| WO | 96/14844 A1 | 5/1996 |
| WO | 2000/017369 | 3/2000 |
| WO | 01/70671 A2 | 9/2001 |
| WO | 03/002518 A1 | 1/2003 |
| WO | 03/030886 A2 | 4/2003 |
| WO | 04/000821 A1 | 12/2003 |
| WO | 2004/099376 A2 | 11/2004 |
| WO | 2005/058311 A1 | 6/2005 |
| WO | 2005/097767 A1 | 10/2005 |
| WO | 2006/041404 A1 | 4/2006 |
| WO | 2006/076284 A2 | 7/2006 |
| WO | 2006/083760 A1 | 8/2006 |
| WO | 2006/138230 A2 | 12/2006 |
| WO | 2006/138265 A2 | 12/2006 |
| WO | 2007/005404 A1 | 1/2007 |
| WO | 2007/011810 A1 | 1/2007 |
| WO | 2007/011833 A2 | 1/2007 |
| WO | 2007/038271 A1 | 4/2007 |
| WO | 2007/049532 A1 | 5/2007 |
| WO | 2007/058602 A2 | 5/2007 |
| WO | 2007/100536 A1 | 9/2007 |
| WO | 2007/114771 A1 | 10/2007 |
| WO | 2007/120096 A1 | 10/2007 |
| WO | 2007/145571 A1 | 12/2007 |
| WO | 2007/149033 A1 | 12/2007 |
| WO | 2008/054698 A2 | 5/2008 |
| WO | 2008/076045 A1 | 6/2008 |
| WO | 2008/076046 A1 | 6/2008 |
| WO | 2008/092785 A1 | 8/2008 |
| WO | 2008/103351 A2 | 8/2008 |
| WO | 2008/108378 A2 | 9/2008 |
| WO | 2008/118379 A2 | 10/2008 |
| WO | 2008/133273 | 11/2008 |
| WO | 2008/133274 A1 | 11/2008 |
| WO | 2008/150217 A1 | 12/2008 |
| WO | 2009/091016 A1 | 7/2009 |
| WO | 2009/131974 A1 | 10/2009 |
| WO | 2009/131975 A1 | 10/2009 |
| WO | 2009/134617 A1 | 11/2009 |
| WO | 2010/010014 A1 | 1/2010 |
| WO | 2010/013794 A1 | 2/2010 |
| WO | 2010/021680 A2 | 2/2010 |
| WO | 2010/030954 A1 | 3/2010 |
| WO | 2010/105179 A2 | 9/2010 |
| WO | 2010/128058 A1 | 11/2010 |
| WO | 2011/020806 A1 | 2/2011 |
| WO | 2011/115928 A1 | 9/2011 |
| WO | 2011/115938 A1 | 9/2011 |
| WO | 2011/123674 A1 | 10/2011 |
| WO | 2011/130741 A1 | 10/2011 |
| WO | 2012/019056 A1 | 2/2012 |
| WO | 2012/040641 A2 | 3/2012 |
| WO | 2012/071279 A1 | 5/2012 |
| WO | 2012/109165 A1 | 8/2012 |
| WO | 2012/112462 A1 | 8/2012 |
| WO | 2014/078314 A1 | 5/2014 |

OTHER PUBLICATIONS

International Preliminary Report on Patentability and Written Opinion for parent PCT Application No. PCT/US2012/056658, issued on Mar. 25, 2014.

Henley, D. B. et al, "Development of Semagacestat (LY450139), a Functional γ-Secretase Inhibitor. For the Treatment of Alzheimer's Disease", *Expert Opin. Pharmacother.* vol. 10(10) pp. 1657-1664 (2009).

Joachim et al., "The Seminal Role of β-Amyloid in the Pathogenesis of Alzheimer Disease," *Alz. Dis. Assoc. Dis.*, 6(1), pp. 7-34 (1992).

Selkoe, D.J. "The Molecular Pathology of Alzheimer's Disease," *Neuron*, 6, pp. 487-498 (1991).

Seubert, P. et al., "Isolation and Quantification of Soluble Alzheimer's β-Peptide from Biological Fluids," *Nature*, 359 pp. 325-327 (1992).

Citron, M. "β-Secretase Inhibition for the Treatment of Alzheimer's Disease—Promise and Challenge," *Trends in Pharmacological Sciences*, 25(2) pp. 92-97 (2004).

Town, T. et al., "Blocking TGF-β-Smad2/3 Innate Immune Signaling Mitigates Alzheimer-Like Pathology," *Nature Medicine* 14(6) pp. 681-687 (2008).

Sinha, S. et al., "Purification and Cloning of Amyloid Precursor Protein β-Secretase From Human Brain," *Nature*, 402 pp. 537-540 (1999).

Sabbagh, M. et al., "β-Amyloid and Treatment Opportunities for Alzheimer's Disease," *Alz. Dis. Rev.* 3 pp. 1-19 (1997).

Cole, S.L. e al., "The Alzheimer's Disease β-Secretase Enzyme, BACE1," *Molecular Neurodegeneration* 2:22, pp. 1-25 (2007).

Luo, Y. et al., "Mice Deficient in BACE1, the Alzheimer's β-Secretase, have Normal Phenotype and Abolished β-Amyoid Generation," *Nature Neuroscience*, 4(3) pp. 231-232 (2001).

Malamas, M. J. et al., "Novel Pyrrolyl 2-Aminopyridines as Potent and Selective Human β-Secretase (BACE1) Inhibitors," *Bioorganic & Medicinal Chemistry Letters* 20 pp. 2068-2073 (2010).

Malamas, M. J. et al., "Aminoimidazoles as Potent and Selective Human β-Secretase (BACE1) Inhibitors," *J. Med. Chem.* 2009 (Page Numbers not Present in Attached Article).

Aisen, P .S. "Alzheimer's Disease Therapeutic Research: The Path Forward," *Alzheimer's Research & Therapy* 1(1) pp. 1-6 (2009).

(56) References Cited

OTHER PUBLICATIONS

Lukiw, W. J. "Emerging Amyloid Beta (Aβ) Peptide Modulators for the Treatment of Alzheimer's Disease (AD)," *Expert Opin. Emerging Drugs* 13(2) pp. 255-271 (2008).
Barrow, J. C. et al., "Discover and X-ray Crystallographic Analysis of a Spiropiperidine Iminohydantoin Inhibitor of #-Secretase," *J. Med. Chem.* 51(20), 6259-6262 (2008).
Rauk, A, "The Chemistry of Alzheimer's Disease," *Chem. Soc. Rev.*, 38, pp. 2698-2715 (2009).
Sabbagh, M. N. "Drug Development for Alzheimer's Disease: Where Are We Now and Where Are We Headed?" *Clinical Dev.* 7(3) pp. 167-185 (2009).
Vassar, R. et al., "The β-Secretase Enzyme BACE in Health and Alzheimer's Disease: Regulation, Cell Biology, Function, and Therapeutic Potential," *J. Neurosci.* 29(41) pp. 12787-12794 (2009).
Zhou, P. et al. "An Efficient Synthesis of 2-Amino-4-(4-fluoro-3-(2-fluoropyridine-3-yl)phenyl)-4-(4-methoxy-3-methylphenyl)-1-methyl-1H-imidazol-5(4H)-one, a Potent BACE1 Inhibitor," *ARKIVOC* vi 84-88 (2010).
Nowak, P. et al., "Discovery and Initial Optimization of 5,5'-Disubstituted Aminohydantoins as Potent β-Secretase (BACE1) Inhibitors," *Bioorganic Medicinal Chemistry Letters* Accepted Manuscript (2009).
Malamas, M. S. et al., "Di-substituted Pyridinyl Aminohydantoins as Potent and Highly Selective Human β-Secretase (BACE1) Inhibitors," *Bioorganic Medicinal Chemistry Letters* Accepted Manuscript (2009).
Zhou, P. et al., "Pyridinyl Aminohydantoins as Small Molecule BACE1 Inhibitors," *Bioorganic Medicinal Chemistry Letters* 20, pp. 2326-2329 (2010).
Malamas, M. S. et al., "Design and Synthesis of 5,5'-Disubstituted Aminohydantoins as Potent and Selective Human β-Secretase (BACE1) Inhibitors," *J. Med. Chem.*2009 (Page Numbers not Present in Attached Article).
Saxena, U. "Alzheimer's Disease Amyloid Hypothesis at Crossroads: Where Do We Go from Here?" *Expert Opin. Ther. Targets* 14(12) pp. 1273-1277 (2010).
Sabbagh, M. N. et al., "β-Amyloid and Treatment Opportunities for Alzheimer's Disease," *Alzheimer's Disease Review* 3 pp. 1-19 (1997).
Hamada, Y. "Recent progress in the drug discovery of non-peptidic BACE1 inhibitors," Expert Opin. Drug Discov. 4(4):391-416 (2009).
Harris, J. A. et al., "Transsynaptic Progression of Amyloid-β-Induced Neuronal Dysfunction within the Entorhinal-Hippocampal Network," Neuron 68:428-441 (2010).
International Preliminary Report on Patentability and Written Opinion for International Patent Application No. PCT/US2013/069697, issued May 19, 2015, pp. 1-7.
International Preliminary Report on Patentability and Written Opinion for International Patent Application No. PCT/US2011/028401, issued Sep. 18, 2012, pp. 1-6.
International Preliminary Report on Patentability and Written Opinion for International Patent Application No. PCT/US2011/061473, issued May 28, 2013, pp. 1-5.
International Preliminary Report on Patentability and Written Opinion for International Patent Application No. PCT/US2012/024029, issued Aug. 13, 2013, pp. 1-7.
International Preliminary Report on Patentability and Written Opinion for International Patent Application No. PCT/US2011/028417, issued Sep. 18, 2012, pp. 1-5.
International Preliminary Report on Patentability and Written Opinion for International Patent Application No. PCT/US2009/056748, issued Mar. 15, 2011, pp. 1-7.
International Search Report for International Patent Application No. PCT/US2013/069697, mailed Dec. 20, 2013, pp. 1-4.
International Search Report for International Patent Application No. PCT/US2011/028401, mailed Jun. 15, 2011, pp. 1-4.
International Search Report for International Patent Application No. PCT/US2011/061473, mailed Mar. 27, 2012, pp. 1-4.
International Search Report for International Patent Application No. PCT/US2012/024029, mailed May 4, 2012, pp. 1-3.
International Search Report for International Patent Application No. PCT/US2011/028417, mailed Oct. 5, 2011, pp. 1-4.
International Search Report for International Patent Application No. PCT/US2009/056748, mailed Nov. 11, 2009, pp. 1-3.
May, P. C. et al., "Robust Central Reduction of Amyloid-β in Humans with an Orally Available, Non-Peptidic β-Secretase Inhibitor," J. Neurosci. 31(46):16507-16516 (2011).
Office Action mailed Apr. 23, 2015 for U.S. Appl. No. 13/982,222, filed Oct. 18, 2013, pp. 1-10.
Office Action mailed Dec. 27, 2013 for U.S. Appl. No. 13/047,734, filed Mar. 14, 2011, pp. 1-14.
Office Action mailed Dec. 30, 2013 for U.S. Appl. No. 13/929,483, filed Jun. 27, 2013, pp. 1-6.
Office Action mailed Jun. 8, 2011 for U.S. Appl. No. 12/558,426, filed Sep. 11, 2009, pp. 1-11.
Office Action mailed May 28, 2014 for U.S. Appl. No. 13/988,745, filed Sep. 5, 2013, pp. 1-5.
Office Action mailed Nov. 28, 2012 for U.S. Appl. No. 13/047,693, filed Mar. 14, 2011, pp. 1-5.
Office Action mailed Sep. 15, 2015 for U.S. Appl. No. 13/982,222, filed Oct. 18, 2013, pp. 1-8.
Office Action mailed Sep. 6, 2012 for U.S. Appl. No. 12/558,426, filed Sep. 11, 2009, pp. 1-8.
Patani, G. A. And Lavoie, E. J., "Bioisosterism: A Rational Approach in Drug Design," Chem. Rev. 96:3147-3176 (1996).
Siemers, E. R. et al., "Effects of a γ-secretase inhibitor in a randomized study of patients with Alzheimer's disease," Neurology 66:602-604 (2006).
Siemers, E. R. et al., "Safety, Tolerability, and Effects on Plasma and Cerebrospinal Fluid Amyloid-β After Inhibition of γ-Secretase," Clinical Neuropharmacology 30(6):317-325 (2007).
West, A. R., Solid State Chemistry and Its Applications, Wiley, New York, 1988, pp. 358, 365.

AMINO-OXAZINE AND AMINO-DIHYDROTHIAZINE COMPOUNDS AS BETA-SECRETASE MODULATORS AND METHODS OF USE

RELATED APPLICATIONS

This application is a US national stage application under 35 U.S.C. §371 of International Application No. PCT/US2012/56658, having an international filing date of Sep. 21, 2012, which claims the benefit of, and priority to, U.S. Provisional Application No. 61/537,461, filed on Sep. 21, 2011, which specification is hereby incorporated herein by reference in its entirety.

FIELD OF THE INVENTION

The invention relates generally to pharmaceutically active compounds, pharmaceutical compositions and uses of both the compounds and the compositions to treat Beta-Secretase mediated diseases and conditions, including, without limitation, Alzheimer's disease and other amyloid plaque related disorders.

BACKGROUND OF THE INVENTION

Alzheimer's disease (AD) affects greater than 12 million aging people worldwide. AD accounts for the majority of dementia clinically diagnosed after the age of 60. AD is generally characterized by the progressive decline of memory, reasoning, judgement and orientation. As the disease progresses, motor, sensory, and vocal abilities are affected until there is global impairment of multiple cognitive functions. The loss of cognitive function occurs gradually, typically leading to a diminished cognition of self, family and friends. Patients with severe cognitive impairment and/or diagnosed as end-stage AD are generally bedridden, incontinent, and dependent on custodial care. The AD patient eventually dies in about nine to ten years, on average, after initial diagnosis. Due to the incapacitating, generally humiliating and ultimately fatal effects of AD, there is a need to effectively treat AD upon diagnosis.

AD is characterized by two major physiological changes in the brain. The first change, beta amyloid plaque formation, supports the "amyloid cascade hypothesis" which believes that AD is caused by the formation of characteristic beta amyloid peptide (A-beta), or A-beta fragments thereof, deposits in the brain (commonly referred to as beta amyloid "plaques" or "plaque deposits") and in cerebral blood vessels (beta amyloid angiopathy). A wealth of evidence suggests that beta-amyloid and accompanying amyloid plaque formation is central to the pathophysiology of AD and is likely to play an early role in this intractable neurodegenerative disorder. The second change in AD is the formation of intraneuronal tangles, consisting of an aggregate form of the protein tau. Besides being found in patients with AD, intraneuronal tangles are also found in other dementia-inducing disorders. Joachim et al., *Alz. Dis. Assoc. Dis.*, 6:7-34 (1992).

Several lines of evidence indicate that progressive cerebral deposition of A-beta plays a seminal role in the pathogenesis of AD and can precede cognitive symptoms by years or even decades. Selkoe, *Neuron*, 6:487 (1991). Release of A-beta from neuronal cells grown in culture and the presence of A-beta in cerebrospinal fluid (CSF) of both normal individuals and AD patients has been demonstrated. Seubert et al., *Nature*, 359:325-327 (1992). Autopsies of AD patients have revealed large numbers of lesions comprising these 2 factors in areas of the human brain believed to be important for memory and cognition.

Smaller numbers of these lesions in a more restricted anatomical distribution are found in the brains of most aged humans who do not have clinical AD. Amyloid containing plaques and vascular amyloid angiopathy were also found in the brains of individuals with Down's Syndrome, Hereditary Cerebral Hemorrhage with Amyloidosis of the Dutch-type (HCHWA-D), and other neurodegenerative disorders.

It has been hypothesized that A-beta formation is a causative precursor or factor in the development of AD. More specifically, deposition of A-beta in areas of the brain responsible for cognitive factors is believed to be a major factor in the development of AD. Beta amyloid plaques are primarily composed of amyloid beta peptide (A-beta peptide). A-beta peptide is derived from the proteolytic cleavage of a large transmembrane amyloid precursor protein (APP), and is a peptide ranging in about 39-42 amino acid residues. A-beta 42 (42 amino acids long) is thought to be the major component of these plaque deposits in the brains of Alzheimer's Disease patients. Citron, *Trends in Pharmacological Sciences*, 25(2):92-97 (2004).

Similar plaques appear in some variants of Lewy body dementia and in inclusion body myositis, a muscle disease. Aβ also forms aggregates coating cerebral blood vessels in cerebral amyloid angiopathy. These plaques are composed of a tangle of regularly ordered fibrillar aggregates called amyloid fibers, a protein fold shared by other peptides such as prions associated with protein misfolding diseases. Research on laboratory rats suggest that the two-molecule, soluble form of the peptide is a causative agent in the development of Alzheimer's and that the two-molecule form is the smallest synaptotoxic species of soluble amyloid beta oligomer. Shankar, G. M., *Nature Medicine* (Jun. 22, 2008) online doi 10:1038 nm 1782.

Several aspartyl proteases are thought to be involved in the processing or cleavage of APP, resulting in the formation of A-beta peptide. Beta secretase (BACE, also commonly referred to as memapsin) is thought to first cleave APP to generate two fragments: (1) a first N-terminus fragment (beta APP) and (2) a second C-99 fragment, which is subsequently cleaved by gamma secretase to generate the A-beta peptide. APP has also found to be cleaved by alpha-secretase to produce alpha-sAPP, a secreted form of APP that does not result in beta-amyloid plaque formation. This alternate pathway precludes the formation of A-beta peptide. A description of the proteolytic processing fragments of APP is found, for example, in U.S. Pat. Nos. 5,441,870, 5,712,130 and 5,942,400.

BACE is an aspartyl protease enzyme comprising 501 amino acids and responsible for processing APP at the beta-secretase specific cleavage site. BACE is present in two forms, BACE 1 and BACE 2, designated as such depending upon the specific cleavage site of APP. Beta secretase is described in Sinha et al., *Nature*, 402:537-554 (1999) (p510) and PCT application WO 2000/17369. It has been proposed that A-beta peptide accumulates as a result of APP processing by BACE. Moreover, in vivo processing of APP at the beta secretase cleavage site is thought to be a rate-limiting step in A-beta production. Sabbagh, M. et al., *Alz. Dis. Rev.* 3:1-19 (1997). Thus, inhibition of the BACE enzyme activity is desirable for the treatment of AD.

Studies have shown that the inhibition of BACE may be linked to the treatment of AD. The BACE enzyme is essential for the generation of beta-amyloid or A-beta. BACE knockout mice do not produce beta-amyloid and are free from Alzheimer's associated pathologies including neuronal loss and certain memory deficits. Cole, S. L., Vasser, R., *Molecular Degeneration* 2:22, 2007. When crossed with transgenic mice that over express APP, the progeny of BACE deficient mice show reduced amounts of A-beta in brain extracts as compares with control animals (Luo et al., *Nature Neuroscience*, 4:231-232 (2001)). The fact that BACE initiates the formation of beta-amyloid, and the observation that BACE levels are elevated in this disease provide direct and compelling reasons to develop therapies directed at BACE inhibition thus reducing beta-amyloid and its associated toxicities. To this end, inhibition of beta secretase activity and a corresponding reduction of A-beta in the brain should provide a therapeutic method for treating AD and other beta amyloid or plaque related disorders.

Several approaches have been taken to potentially treat AD and plaque-related disorders. One approach has been to attempt to reduce the formation of plaque on the brain, by inhibiting or reducing the activity of BACE. For example, each of the following PCT publications: WO 09/091016, WO 08/108378, WO 09/134617, WO 05/097767, WO 08/092785, WO 06/138265, WO 08/103351, WO 06/138230, WO 08/200445, WO 06/111370, WO 07/287692, WO 05/058311, EP 01/942105, WO 08/133273, WO 08/133274, WO 07/049532, US20070027199, WO 07/038271, US20070072925, US20070203116, WO 08/118379, WO 06/076284, US20070004786, WO 06/083760, WO 07/011810, WO 07/011833, WO11/009943 and WO 08/054698, describe inhibitors of BACE, useful for treating AD and other beta-secretase mediated disorders.

The lysosomal aspartic protease Cathepsin D (CatD) is ubiquitously expressed in eukaryotic organisms. CatD activity is essential to accomplish the acid-dependent extensive or partial proteolysis of protein substrates within endosomal and lysosomal compartments therein delivered via endocytosis, phagocytosis or autophagocytosis. CatD may also act at physiological pH on small-size substrates in the cytosol and in the extracellular milieu. Mouse and fruit fly CatD knock-out models have highlighted the multi-pathophysiological roles of CatD in tissue homeostasis and organ development.

Inhibition of protein Cathepsin D has been implicated in undesirable side effects. For instance, the inhibition of Cathepsin D is believed to be linked to adverse retinal development and retinal atrophy. Particularly, in mice it was found that cathepsin D is essential for the metabolic maintenance of retinal photoreceptor cells and that its deficiency induces apoptosis of the cells, while the loss of INL neurons is mediated by NO from microglial cells. However, in the very same mice, it was also found that no atrophic change was detected in the retina of mice deficient in cathepsin B or L. *Mol. Cell. Neurosci*, 2003, Feb. 22(2):146-161. Further, Animal models of cathepsin D (CatD) deficiency are characterized by a progressive and relentless neurodegenerative phenotype similar to that observed in Neuronal Ceroid Lipofuscinoses (NCL), a group of pediatric neurodegenerative diseases known collectively as Batten Disease. It has been shown that the targeted deletion of the pro-apoptotic molecule Bax prevents apoptotic markers but not neuron death and neurodegeneration induced by CatD deficiency, which suggests that alterations in the macroautophagy-lysosomal degradation pathway can mediate neuron death in NCL/Batten Disease in the absence of apoptosis. *Autophagy*, 2007, September-October; 3(5):474-476. Finally, an adverse effect of the inhibition of Cat D is evident from the data presented in *PLoS One*, 2011; 6(7):e21908, published Jul. 1, 2011. The authors of the PLoS One paper found that knock-down of cathepsin D affects the retinal pigment epithelium, impairs swim-bladder ontogenesis and causes premature death in zebrafish. The main phenotypic alterations produced by CatD knock-down in zebrafish were: 1. abnormal development of the eye and of retinal pigment epithelium; 2. absence of the swim-bladder; 3. skin hyper-pigmentation; 4. reduced growth and premature death. Rescue experiments confirmed the involvement of CatD in the developmental processes leading to these phenotypic alterations.

Moreover, such toxicity findings thought to be related to the inhibition of CatD has played a role in the termination of a human Bace-mediated Alzheimer's Disease clinical trial. Eli Lilly terminated a phase I clinical trial of LY 2811376 after rat toxicology studies showed that a higher compound dose given for three months ravaged the pigment epithelium of the rat's eye. The retinal layer had inclusions and extensive damage. Lilly ended the Ph I dosing and brought people in for eye assessments, which did not show any abnormalities (Alzheimer's Research Forum News, Mar. 31, 2011 reporting on Martin Citron's presentation at the ADPD Conference 3-2011 in Barcelona, Spain)

Hence, it is desirable to provide compounds which modulate the activity of BACE while not suffering from the undesirable retinal side effects possibly due to intervention in the CatD pathway or due to the reduction and/or direct inhibition of the cathepsin D protein.

BRIEF DESCRIPTION OF THE INVENTION

The present invention provides a new class of compounds useful for the modulation of beta secretase activity, while minimizing, reducing or eliminating any potential for adverse retinal side effects due to CatD. To that end, the compounds of the invention are useful for the regulation or reduction of the formation of A-beta peptide and, consequently, the regulation and/or reduction of beta amyloid plaque formation on the brain. Accordingly, the compounds are useful for the treatment of Alzheimer's disease and other beta secretase and/or plaque mediated disorders. For example, the compounds are useful for the prophylaxis and/or treatment, acute and/or chronic, of AD and other diseases or conditions involving the deposition or accumulation of beta amyloid peptide, and formation of plaque, on the brain. In addition, the compounds of the invention are practically or completely devoid of activity for CatD, thereby reducing or eliminating the potential for adverse retinal side effects.

The compounds provided by the invention, including stereoisomers, tautomers, solvates, pharmaceutically acceptable salts, derivatives or prodrugs thereof, are generally defined by Formula I

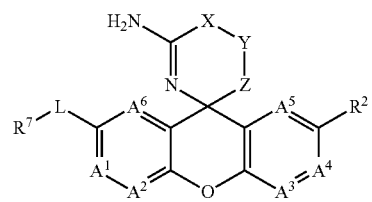

wherein $A^1$, $A^2$, $A^3$, $A^4$, $A^5$, $A^6$, L, $R^2$, $R^7$, X, Y and Z of Formula I are described below. The invention also provides procedures for making compounds of sub-Formulas thereof, as well as intermediates useful in such procedures.

The invention further provides pharmaceutical compositions, which comprise one or more compounds of the invention, methods for the treatment of beta secretase mediated diseases, such as AD, using the compounds and compositions of the invention. For example, and in one embodiment, the invention provides a pharmaceutical composition comprising an effective dosage amount of a compound of Formula I in association with at least one pharmaceutically acceptable excipient.

The foregoing merely summarizes certain aspects of the invention and is not intended, nor should it be construed, as limiting the invention in any way. All patents and other publications recited herein are hereby incorporated by reference in their entirety.

DETAILED DESCRIPTION OF THE INVENTION

In one embodiment of the invention, the compounds, including stereoisomers, tautomers, solvates, pharmaceutically acceptable salts thereof, are generally defined by the compound of Formula I:

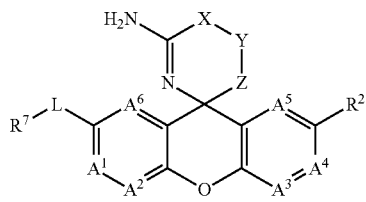

I or a stereoisomer, tautomer, hydrate, solvate or pharmaceutically acceptable salt thereof, wherein $A^1$ is $CR^6$ or N;
$A^2$ is $CR^5$ or N;
$A^3$ is $CR^4$ or N;
$A^4$ is $CR^3$ or N;
$A^5$ is $CR^1$ or N;
$A^6$ is $CR^8$ or N, provided that no more than one of $A^1$, $A^2$, $A^3$, $A^4$, $A^5$ and $A^6$ is N;

L is —C(=O)NH—, —C(=O)N(CH$_3$)—, —NH—, —N(CH$_3$)— or —O—;

each of $R^1$, $R^4$, $R^5$ and $R^8$, independently, is H, F, Cl, Br, CF$_3$, OCF$_3$, C$_{1-6}$-alkyl, CN, OH, —OC$_{1-6}$-alkyl, —S(O)$_o$C$_{1-6}$-alkyl, —NHC$_{1-6}$-alkyl or —C(O)C$_{1-6}$-alkyl, wherein the C$_{1-6}$-alkyl and C$_{1-6}$-alkyl portion of —OC$_{1-6}$-alkyl, —S(O)$_o$C$_{1-6}$-alkyl, —NHC$_{1-6}$-alkyl and —C(O)C$_{1-6}$-alkyl are optionally substituted with 1-3 substituents of F, oxo or OH;

each of $R^2$ and $R^7$, independently, is F, Cl, Br, I, haloalkyl, haloalkoxyl, C$_{1-6}$-alkyl, C$_{2-6}$alkenyl, C$_{2-6}$alkynyl, CN, —OC$_{1-6}$alkyl, —SC$_{1-6}$alkyl, —NHC$_{1-6}$alkyl, —N(C$_{1-3}$alkyl)$_2$, —NH-phenyl, —NH-benzyl, —Si(CH$_3$)$_3$ or a ring selected from the group consisting of phenyl, pyridyl, pyrimidyl, pyrazinyl, pyridazinyl, triazinyl, thienyl, pyrazolyl, imidazolyl, oxazolyl, isoxazolyl, thiazolyl, isothiazolyl, diazolyl, triazolyl, tetrazolyl, pyranyl, dihydropyranyl, tetrahydropyranyl, furanyl, dihydrofuranyl, tetrahydrofuranyl, pyrrolyl, dihydropyrrolyl, pyrrolidinyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopropyl, cyclobutyl, cyclopentyl and cyclohexyl, wherein the C$_{1-6}$-alkyl, C$_{2-4}$alkenyl, C$_{2-4}$alkynyl, —OC$_{1-6}$alkyl, —SC$_{1-6}$alkyl, —NHC$_{1-6}$alkyl, —N(C$_{1-3}$alkyl)$_2$, —NH-phenyl, —NH-benzyl and ring are optionally substituted, independently, with 1-3 substituents of $R^9$;

each of $R^3$ and $R^6$, independently, is H, halo, haloalkyl, haloalkoxyl, C$_{1-6}$-alkyl, CN, OH, OC$_{1-6}$-alkyl, S(O)$_o$C$_{1-6}$-alkyl, NHC$_{1-6}$-alkyl or C(O)C$_{1-6}$-alkyl;

each $R^9$, independently, is halo, haloalkyl, haloalkoxyl, CN, OH, NO$_2$, NH$_2$, acetyl, —C(O)NHCH$_3$, oxo, C$_{1-6}$alkyl, C$_{2-6}$alkenyl, C$_{2-6}$alkynyl, C$_{3-6}$cycloalkyl, C$_{1-6}$alkylamino-, C$_{1-6}$dialkylamino-, C$_{1-6}$alkoxyl, C$_{1-6}$thioalkoxyl, morpholinyl, pyrazolyl, isoxazolyl, dihydropyranyl, pyrrolidinyl, piperazinyl, oxetanyl or dioxolyl, wherein each of the C$_{1-6}$alkyl, C$_{2-6}$alkenyl, C$_{2-6}$alkynyl, C$_{3-6}$cycloalkyl, C$_{1-6}$alkylamino-, C$_{1-6}$dialkylamino-, C$_{1-6}$alkoxyl, C$_{1-6}$thioalkoxyl, morpholinyl, pyrazolyl, isoxazolyl, dihydropyranyl, pyrrolidinyl, oxetanyl or dioxolyl, is optionally substituted independently with 1-5 substituents of F, Cl, CN, NO$_2$, NH$_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, C$_{1-3}$alkylamino-, C$_{1-3}$-dialkylamino, C$_{1-3}$thioalkoxyl, C$_{1-4}$alkenyl, C$_{1-4}$alkynyl or oxetanyl;

X is —CR$^{10}$R$^{10}$—, —O— or —S—, wherein each R$^{10}$, independently, is H, halo, haloalkyl, C$_{1-6}$alkyl, C$_{2-6}$alkenyl, C$_{2-6}$alkynyl, C$_{3-6}$cycloalkyl or a ring selected from the group consisting of morpholinyl, piperidinyl, piperizinyl, tetrahydrofuranyl, furanyl, thienyl, phenyl, pyrdinyl, pyrimidinyl, pyridazinyl, pyrazinyl, pyranyl, dihydropyranyl, tetrahydropyranyl, pyrrolyl, dihydropyrrolyl, tetrahydropyrrolyl and oxetanyl;

Y is —O—, —S— or CH$_2$—, provided that (1) when X is —O— or —S—, then Y is —CH$_2$—, or (2) when X is —CR$^{10}$R$^{10}$—, then Y is —O— or —S—; and Z is CH$_2$, CHF, CF$_2$, CH(CH$_3$), C(CH$_3$)$_2$ or CH(CF$_3$).

In another embodiment of the present invention, the compounds, and solvates, tautomers, stereoisomers and pharmaceutically acceptable salts thereof, are defined by Formula II

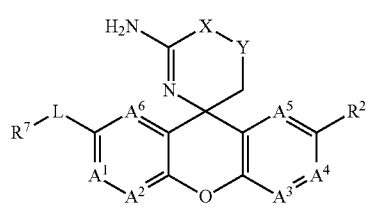

II wherein $A^1$ is $CR^6$ or N;
$A^2$ is $CR^5$ or N;
$A^3$ is $CR^4$ or N;
$A^4$ is $CR^3$ or N;
$A^5$ is $CR^1$ or N;
$A^6$ is $CR^8$ or N, provided that no more than one of $A^1$, $A^2$, $A^3$, $A^4$, $A^5$ and $A^6$ is N;

L is —C(=O)NH—, —C(=O)N(CH$_3$)—, —NH—, —N(CH$_3$)— or —O—;

each of $R^1$, $R^4$, $R^5$ and $R^8$, independently, is H, F, Cl, Br, CF$_3$, OCF$_3$, C$_{1-6}$-alkyl, CN, OH, —OC$_{1-6}$-alkyl, —S(O)$_o$C$_{1-6}$-alkyl, —NHC$_{1-6}$-alkyl or —C(O)C$_{1-6}$-alkyl, wherein the C$_{1-6}$-alkyl and C$_{1-6}$-alkyl portion of —OC$_{1-6}$-alkyl, —S(O)$_o$C$_{1-6}$-alkyl, —NHC$_{1-6}$alkyl and —C(O)C$_{1-6}$-alkyl are optionally substituted with 1-3 substituents of F, oxo or OH;

$R^2$ is Cl, Br, C$_{1-6}$-alkyl, C$_{2-4}$alkenyl, C$_{2-4}$alkynyl, CN, —OC$_{1-6}$alkyl, —SC$_{1-6}$alkyl, —NHC$_{1-6}$alkyl, —N(C$_{1-3}$alkyl)$_2$, —NH-phenyl, —NH-benzyl, phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, pyrrolidinyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopentyl, cyclohexyl or —Si(CH$_3$)$_3$, wherein the C$_{1-6}$-alkyl, C$_{2-4}$alkenyl, C$_{2-4}$alkynyl, —OC$_{1-6}$ alkyl, —SC$_{1-6}$alkyl, —NHC$_{1-6}$alkyl, —N(C$_{1-3}$alkyl)$_2$, —NH-phenyl, —NH-benzyl, phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, pyrrolidinyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopentyl and cyclohexyl are optionally substituted, independently, with 1-3 substituents of R$^9$;

each of R$^3$ and R$^6$, independently, is H, halo, haloalkyl, haloalkoxyl, C$_{1-6}$-alkyl, CN, OH, OC$_{1-6}$-alkyl, S(O)$_o$C$_{1-6}$-alkyl, NHC$_{1-6}$-alkyl or C(O)C$_{1-6}$-alkyl;

R$^7$ is C$_{1-6}$-alkyl, C$_{2-4}$alkenyl, C$_{2-4}$alkynyl, CN, —OC$_{1-6}$ alkyl, —SC$_{1-6}$alkyl, —NHC$_{1-6}$alkyl, —N(C$_{1-3}$alkyl)$_2$, —NH-phenyl, —NH-benzyl, phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, pyrrolidinyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopentyl or cyclohexyl, wherein the C$_{1-6}$-alkyl, C$_{2-4}$alkenyl, C$_{2-4}$alkynyl, —OC$_{1-6}$alkyl, —SC$_{1-6}$alkyl, —NHC$_{1-6}$alkyl, —N(C$_{1-3}$alkyl)$_2$, —NH-phenyl, —NH-benzyl, phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, pyrrolidinyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopentyl and cyclohexyl are optionally substituted, independently, with 1-3 substituents of R$^9$;

each R$^9$, independently, is halo, haloalkyl, CN, OH, NO$_2$, NH$_2$, acetyl, —C(O)NHCH$_3$, oxo, C$_{1-6}$alkyl, C$_{2-6}$alkenyl, C$_{2-6}$alkynyl, C$_{3-6}$cycloalkyl, C$_{1-6}$alkylamino-, C$_{1-6}$dialkylamino-, C$_{1-6}$alkoxyl, C$_{1-6}$thioalkoxyl, morpholinyl, pyrazolyl, isoxazolyl, dihydropyranyl, pyrrolidinyl, piperazinyl, oxetanyl or dioxolyl, wherein each of the C$_{1-6}$alkyl, C$_{2-6}$alkenyl, C$_{2-6}$alkynyl, C$_{3-6}$cycloalkyl, C$_{1-6}$alkylamino-, C$_{1-6}$dialkylamino-, C$_{1-6}$alkoxyl, C$_{1-6}$thioalkoxyl, morpholinyl, pyrazolyl, isoxazolyl, dihydropyranyl, pyrrolidinyl, oxetanyl or dioxolyl, is optionally substituted independently with 1-5 substituents of F, Cl, CN, NO$_2$, NH$_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, C$_{1-3}$alkylamino-, C$_{1-3}$dialkylamino, C$_{1-3}$thioalkoxyl, C$_{1-4}$alkenyl, C$_{1-4}$alkynyl or oxetanyl;

X is —CH$_2$—, —O— or —S—; and

Y is —O—, —S— or —CH$_2$—, provided that (1) when X is either —O— or —S—, then Y is —CH$_2$— or (2) when X is —CH$_2$—, then Y is —O— or —S—.

In another embodiment of the present invention, the compounds, and solvates, tautomers, stereoisomers and pharmaceutically acceptable salts thereof, are defined by Formula III

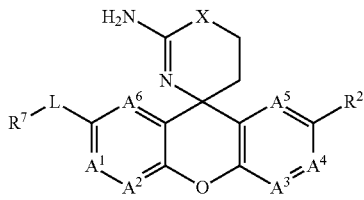

wherein
A$^1$ is CR$^6$ or N;
A$^2$ is CR$^5$ or N;
A$^3$ is CR$^4$ or N;
A$^4$ is CR$^3$ or N;
A$^5$ is CR$^1$ or N;
A$^6$ is CR$^8$ or N, provided that no more than one of A$^1$, A$^2$, A$^3$, A$^4$, A$^5$ and A$^6$ is N;

L is —C(=O)NH—, —C(=O)N(CH$_3$)—, —NH—, —N(CH$_3$)— or —O—;

each of R$^1$, R$^4$, R$^5$ and R$^8$, independently, is H, F, Cl, Br, CF$_3$, OCF$_3$, C$_{1-6}$-alkyl, CN, OH, —OC$_{1-6}$-alkyl, —S(O)$_o$C$_{1-6}$-alkyl, —NHC$_{1-6}$-alkyl or —C(O)C$_{1-6}$-alkyl, wherein the C$_{1-6}$-alkyl and C$_{1-6}$-alkyl portion of —OC$_{1-6}$-alkyl, —S(O)$_o$C$_{1-6}$-alkyl, —NHC$_{1-6}$-alkyl and —C(O)C$_{1-6}$-alkyl are optionally substituted with 1-3 substituents of F, oxo or OH;

R$^2$ is Cl, Br, C$_{1-6}$-alkyl, C$_{2-4}$alkenyl, C$_{2-4}$alkynyl, CN, —OC$_{1-6}$alkyl, —SC$_{1-6}$alkyl, —NHC$_{1-6}$alkyl, —N(C$_{1-3}$alkyl)$_2$, —NH-phenyl, —NH-benzyl, phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, pyrrolidinyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopentyl, cyclohexyl or —Si(CH$_3$)$_3$, wherein the C$_{1-6}$-alkyl, C$_2$ alkenyl, C$_{2-4}$alkynyl, —OC$_{1-6}$ alkyl, —SC$_{1-6}$alkyl, —NHC$_{1-6}$alkyl, —N(C$_{1-3}$alkyl)$_2$, —NH-phenyl, —NH-benzyl, phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, pyrrolidinyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopentyl and cyclohexyl are optionally substituted, independently, with 1-3 substituents of R$^9$;

each of R$^3$ and R$^6$, independently, is H, halo, haloalkyl, haloalkoxyl, C$_{1-6}$-alkyl, CN, OH, OC$_{1-6}$-alkyl, S(O)$_o$C$_{1-6}$-alkyl, NHC$_{1-6}$-alkyl or C(O)C$_{1-6}$-alkyl;

R$^7$ is C$_{1-6}$-alkyl, C$_{2-4}$alkenyl, C$_{2-4}$alkynyl, CN, —OC$_{1-6}$ alkyl, —SC$_{1-6}$alkyl, —NHC$_{1-6}$alkyl, —N(C$_{1-3}$alkyl)$_2$, —NH-phenyl, —NH-benzyl, phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, pyrrolidinyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopentyl or cyclohexyl, wherein the C$_{1-6}$-alkyl, C$_{2-4}$alkenyl, C$_{2-4}$alkynyl, —OC$_{1-6}$alkyl, —SC$_{1-6}$alkyl, —NHC$_{1-6}$alkyl, —N(C$_{1-3}$alkyl)$_2$, —NH-phenyl, —NH-benzyl, phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, pyrrolidinyl, piperidinyl, piperazinyl, morpholinyl, azetidinyl, 8-oxo-3-aza-bicyclo[3.2.1]oct-3-yl, aza-bicyclo[2.2.1]

hept-5-yl, 2-oxo-7-aza-[3,5]-spironon-7-yl, cyclopentyl and cyclohexyl are optionally substituted, independently, with 1-3 substituents of $R^9$;

each $R^9$, independently, is halo, haloalkyl, CN, OH, $NO_2$, $NH_2$, acetyl, —C(O)$NHCH_3$, oxo, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolidinyl, piperazinyl, oxetanyl or dioxolyl, wherein each of the $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolidinyl, oxetanyl or dioxolyl, is optionally substituted independently with 1-5 substituents of F, Cl, CN, $NO_2$, $NH_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, $C_{1-3}$alkylamino-, $C_{1-3}$dialkylamino, $C_{1-3}$thioalkoxyl, $C_{1-4}$alkenyl, $C_{1-4}$alkynyl or oxetanyl; and X is —O— or —S—.

In another embodiment of the present invention, the compounds, and solvates, tautomers, stereoisomers and pharmaceutically acceptable salts thereof, are defined by Formula I-A

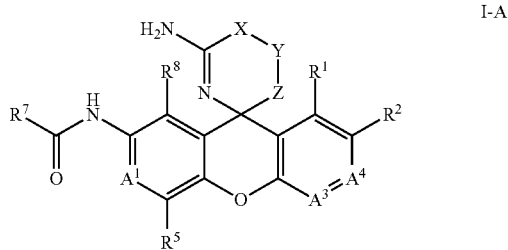

wherein each of $A^1$, $A^3$, $A^4$, $R^1$, $R^2$, $R^5$, $R^7$, $R^8$, X, Y and Z is as defined above with respect to Formula I or as independently defined below.

In another embodiment of the present invention, the compounds, and solvates, tautomers, stereoisomers and pharmaceutically acceptable salts thereof, are defined by Formula I-A wherein $A^1$ is $CR^6$;

$A^3$ is $CR^4$ or N;

$A^4$ is $CR^3$ or N, provided that no more than one of $A^3$ and $A^4$ is N;

each of $R^1$, $R^3$, $R^4$, $R^5$, $R^6$ and $R^8$, independently, is H, F, Cl, $CF_3$, $OCF_3$, methyl, ethyl, CN, OH, $OCH_3$, $SCH_3$, $NHCH_3$ or C(O)$CH_3$;

one of $R^2$ and $R^7$, independently, is F, Cl, Br, I, haloalkyl, haloalkoxyl, $C_{1-6}$-alkyl, $C_{2-6}$alkenyl, $C_{2-6}$alkynyl, CN, —O$C_{1-6}$alkyl, —S$C_{1-6}$alkyl, —NH$C_{1-6}$alkyl, —N($C_{1-3}$alkyl)$_2$, —NH-phenyl, —NH-benzyl, —Si($CH_3$)$_3$ or a ring selected from the group consisting of phenyl, pyridyl, pyrimidyl, pyrazinyl, pyridazinyl, triazinyl, thienyl, pyrazolyl, imidazolyl, oxazolyl, isoxazolyl, thiazolyl, isothiazolyl, diazolyl, triazolyl, tetrazolyl, pyranyl, dihydropyranyl, tetrahydropyranyl, furanyl, dihydrofuranyl, tetrahydrofuranyl, pyrrolyl, dihydropyrrolyl, pyrrolidinyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopropyl, cyclobutyl, cyclopentyl and cyclohexyl, wherein the $C_{1-6}$-alkyl, $C_{2-4}$alkenyl, $C_{2-4}$alkynyl, —O$C_{1-6}$alkyl, —S$C_{1-6}$alkyl, —NH$C_{1-6}$alkyl, —N($C_{1-3}$alkyl)$_2$, —NH-phenyl, —NH-benzyl and ring are optionally substituted, independently, with 1-3 substituents of $R^9$;

the other of $R^2$ and $R^7$, independently, is $C_{1-6}$-alkyl, $C_2$alkenyl, $C_{2-4}$alkynyl, CN, —O$C_{1-6}$alkyl, —S$C_{1-6}$alkyl, —NH$C_{1-6}$alkyl, —N($C_{1-3}$alkyl)$_2$, —NH-phenyl or —NH-benzyl, phenyl, pyridyl, pyrimidyl or thienyl, wherein the $C_{1-6}$-alkyl, $C_{2-4}$alkenyl, $C_{2-4}$alkynyl, CN, —O$C_{1-6}$alkyl, —S$C_{1-6}$alkyl, —NH$C_{1-6}$alkyl, —N($C_{1-3}$alkyl)$_2$, —NH-phenyl, —NH-benzyl, phenyl, pyridyl, pyrimidinyl and thienyl are optionally substituted, independently, with 1-3 substituents of $R^9$;

each $R^9$, independently, is halo, haloalkyl, CN, OH, $NO_2$, $NH_2$, acetyl, —C(O)$NHCH_3$, oxo, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolidinyl, piperazinyl, oxetanyl or dioxolyl, wherein each of the $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolidinyl, oxetanyl or dioxolyl, is optionally substituted independently with 1-5 substituents of F, Cl, CN, $NO_2$, $NH_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, $C_{1-3}$alkylamino-, $C_{1-3}$dialkylamino, $C_{1-3}$thioalkoxyl, $C_{1-4}$alkenyl, $C_{1-4}$alkynyl or oxetanyl;

X is —$CH_2$—, —O— or —S—;

Y is —O—, —S— or —$CH_2$—, provided that (1) when X is —O— or —S—, then Y is —$CH_2$—, or (2) when X is —$CH_2$, then Y is —O— or —S—; and Z is $CH_2$, $CF_2$ or CH($CH_3$).

In another embodiment, the present invention provides a compound, or a solvate, tautomer, stereoisomer or pharmaceutically acceptable salt thereof, which is defined by Formula I-A, wherein $A^1$ is $CR^6$;

$A^3$ is CH, CF, $OCH_3$ or N;

$A^4$ is CH, CF or N, provided that no more than one of $A^3$ and $A^4$ is N; and each of $R^1$, $R^5$, $R^6$ and $R^8$, independently, is H, F, $CF_3$, methyl or CN.

$R^2$ is F, Cl, Br, I, $C_{1-6}$-alkyl, $C_{2-6}$alkenyl, $C_{2-6}$alkynyl, CN, —O$C_{1-6}$alkyl, —S$C_{1-6}$alkyl, 3-methyl-3-oxetanyl-ethynyl, 3-methyl-3-oxetanyl-methoxyl, 3,3-dimethyl-butyn-1-yl, 3-methyl-3-butyn-1-yl, 2,2-dimethyl-3-cyano-propoxyl, 2-fluoro-2-methyl-propoxyl, or a ring selected from the group consisting of phenyl, 2-pyridyl, 3-pyridyl, 4-pyridyl, dihydro-2H-pyran-4-yl, dihydro-2H-pyran-3-yl, tetrahydropyran-4-yl, dihydrofuranyl, tetrahydrofuranyl, pyrrolidin-1-yl, piperidin-1-yl, morpholinyl, 8-oxo-3-aza-bicyclo[3.2.1]oct-3-yl, aza-bicyclo[2.2.1]hept-5-yl and 2-oxo-7-aza-[3,5]-spironon-7-yl, wherein the $C_{1-6}$-alkyl, $C_{2-4}$alkenyl, $C_{2-4}$alkynyl, —O$C_{1-6}$alkyl, —S$C_{1-6}$alkyl, 3-methyl-3-oxetanyl-ethynyl, 3-methyl-3-oxetanyl-methoxyl, 3,3-dimethyl-butyn-1-yl, 3-methyl-3-butyn-1-yl, 2,2-dimethyl-3-cyano-propoxyl, 2-fluoro-2-methyl-propoxyl and ring are optionally substituted, independently, with 1-3 substituents of $R^9$;

$R^7$ is a ring selected from the group consisting of phenyl, pyridyl, pyrimidyl, pyrazinyl, pyridazinyl, thiazolyl or thienyl, said ring optionally substituted, independently, with 1-3 substituents of $R^9$;

each $R^9$, independently, is halo, haloalkyl, CN, OH, $NO_2$, $NH_2$, acetyl, —C(O)$NHCH_3$, oxo, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolidinyl, piperazinyl, oxetanyl or dioxolyl, wherein each of the $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolidinyl, oxetanyl or dioxolyl, is optionally substituted independently with 1-5 substituents of F, Cl, CN, $NO_2$, $NH_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, $C_{1-3}$alkylamino-, $C_{1-3}$dialkylamino, $C_{1-3}$thioalkoxyl, $C_{1-4}$alkenyl, $C_{1-4}$alkynyl or oxetanyl;

X is $-CH_2-$, $-O-$ or $-S-$;

Y is $-O-$, $-S-$ or $-CH_2-$, provided that (1) when X is $-O-$ or $-S-$, then Y is $-CH_2-$, or (2) when X is $-CH_2$, then Y is $-O-$ or $-S-$; and Z is $CH_2$ or $CH(CH_3)$.

In another embodiment, the present invention provides a compound, or a solvate, tautomer, stereoisomer or pharmaceutically acceptable salt thereof, which is defined by Formula I-B,

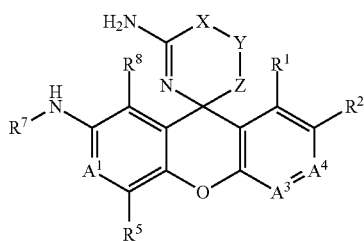

I-B wherein $A^1$ is $CR^6$;

$A^3$ is $CR^4$ or N;

$A^4$ is $CR^3$ or N, provided that no more than one of $A^3$ and $A^4$ is N;

each of $R^1$, $R^3$, $R^4$, $R^5$, $R^6$ and $R^8$, independently, is H, F, Cl, $CF_3$, $OCF_3$, methyl, ethyl, CN, OH, $OCH_3$, $SCH_3$, $NHCH_3$ or $C(O)CH_3$;

one of $R^2$ and $R^7$, independently, is F, Cl, Br, I, haloalkyl, haloalkoxyl, $C_{1-6}$-alkyl, $C_{2-6}$alkenyl, $C_{2-6}$alkynyl, CN, $-OC_{1-6}$alkyl, $-SC_{1-6}$alkyl, $-NHC_{1-6}$alkyl, $-N(C_{1-3}$alkyl$)_2$, $-NH$-phenyl, $-NH$-benzyl, $-Si(CH_3)_3$ or a ring selected from the group consisting of phenyl, pyridyl, pyrimidyl, pyrazinyl, pyridazinyl, triazinyl, thienyl, pyrazolyl, imidazolyl, oxazolyl, isoxazolyl, thiazolyl, isothiazolyl, diazolyl, triazolyl, tetrazolyl, pyranyl, dihydropyranyl, tetrahydropyranyl, furanyl, dihydrofuranyl, tetrahydrofuranyl, pyrrolyl, dihydropyrrolyl, pyrrolidinyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopropyl, cyclobutyl, cyclopentyl and cyclohexyl, wherein the $C_{1-6}$-alkyl, $C_{2-4}$alkenyl, $C_{2-4}$alkynyl, $-OC_{1-6}$alkyl, $-SC_{1-6}$alkyl, $-NHC_{1-6}$alkyl, $-N(C_{1-3}$alkyl$)_2$, $-NH$-phenyl, $-NH$-benzyl and ring are optionally substituted, independently, with 1-3 substituents of $R^9$;

the other of $R^2$ and $R^7$, independently, is $C_{1-6}$-alkyl, $C_{2-4}$alkenyl, $C_{2-4}$alkynyl, CN, $-OC_{1-6}$alkyl, $-SC_{1-6}$alkyl, $-NHC_{1-6}$alkyl, $-N(C_{1-3}$alkyl$)_2$, $-NH$-phenyl or $-NH$-benzyl, phenyl, pyridyl, pyrimidyl or thienyl, wherein the $C_{1-6}$-alkyl, $C_{2-4}$alkenyl, $C_{2-4}$alkynyl, CN, $-OC_{1-6}$alkyl, $-SC_{1-6}$alkyl, $-NHC_{1-6}$alkyl, $-N(C_{1-3}$alkyl$)_2$, $-NH$-phenyl, $-NH$-benzyl, phenyl, pyridyl, pyrimidinyl and thienyl are optionally substituted, independently, with 1-3 substituents of $R^9$;

each $R^9$, independently, is halo, haloalkyl, CN, OH, $NO_2$, $NH_2$, acetyl, $-C(O)NHCH_3$, oxo, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolidinyl, piperazinyl, oxetanyl or dioxolyl, wherein each of the $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolidinyl, oxetanyl or dioxolyl, is optionally substituted independently with 1-5 substituents of F, Cl, CN, $NO_2$, $NH_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, $C_{1-3}$alkylamino-, $C_{1-3}$dialkylamino, $C_{1-3}$thioalkoxyl, $C_{1-4}$alkenyl, $C_{1-4}$alkynyl or oxetanyl;

X is $-CH_2-$, $-O-$ or $-S-$;

Y is $-O-$, $-S-$ or $-CH_2-$, provided that (1) when X is $-O-$ or $-S-$, then Y is $-CH_2-$, or (2) when X is $-CH_2$, then Y is $-O-$ or $-S-$; and Z is $CH_2$, $CF_2$ or $CH(CH_3)$.

In another embodiment, the present invention provides a compound, or a solvate, tautomer, stereoisomer or pharmaceutically acceptable salt thereof, which is defined by Formula I-B, wherein $A^1$ is $CR^6$;

$A^3$ is CH, CF, $OCH_3$ or N;

$A^4$ is CH, CF or N, provided that no more than one of $A^3$ and $A^4$ is N; and each of $R^1$, $R^5$, $R^6$ and $R^8$, independently, is H, F, $CF_3$, methyl or CN.

$R^2$ is F, Cl, Br, I, $C_{1-6}$-alkyl, $C_{2-6}$alkenyl, $C_{2-6}$alkynyl, CN, $-OC_{1-6}$alkyl, $-SC_{1-6}$alkyl, 3-methyl-3-oxetanyl-ethynyl, 3-methyl-3-oxetanyl-methoxyl, 3,3-dimethyl-butyn-1-yl, 3-methyl-3-butyn-1-yl, 2,2-dimethyl-3-cyano-propoxyl, 2-fluoro-2-methyl-propoxyl, or a ring selected from the group consisting of phenyl, 2-pyridyl, 3-pyridyl, 4-pyridyl, dihydro-2H-pyran-4-yl, dihydro-2H-pyran-3-yl, tetrahydropyran-4-yl, dihydrofuranyl, tetrahydrofuranyl, pyrrolidin-1-yl, piperidin-1-yl, morpholinyl, 8-oxo-3-aza-bicyclo[3.2.1]oct-3-yl, aza-bicyclo[2.2.1]hept-5-yl and 2-oxo-7-aza-[3,5]-spironon-7-yl, wherein the $C_{1-6}$-alkyl, $C_{2-4}$alkenyl, $C_{2-4}$alkynyl, $-OC_{1-6}$alkyl, $-SC_{1-6}$alkyl, 3-methyl-3-oxetanyl-ethynyl, 3-methyl-3-oxetanyl-methoxyl, 3,3-dimethyl-butyn-1-yl, 3-methyl-3-Butyn-1-yl, 2,2-dimethyl-3-cyano-propoxyl, 2-fluoro-2-methyl-propoxyl and ring are optionally substituted, independently, with 1-3 substituents of $R^9$;

$R^7$ is a ring selected from the group consisting of phenyl, pyridyl, pyrimidyl, pyrazinyl, pyridazinyl, thiazolyl or thienyl, said ring optionally substituted, independently, with 1-3 substituents of $R^9$;

each $R^9$, independently, is halo, haloalkyl, CN, OH, $NO_2$, $NH_2$, acetyl, $-C(O)NHCH_3$, oxo, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolidinyl, piperazinyl, oxetanyl or dioxolyl, wherein each of the $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolidinyl, oxetanyl or dioxolyl, is optionally substituted independently with 1-5 substituents of F, Cl, CN, $NO_2$, $NH_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, $C_{1-3}$alkylamino-, $C_{1-3}$dialkylamino, $C_{1-3}$thioalkoxyl, $C_{1-4}$alkenyl, $C_{1-4}$alkynyl or oxetanyl;

X is —$CH_2$—, —O— or —S—;

Y is —O—, —S— or —$CH_2$—, provided that (1) when X is —O— or —S—, then Y is —$CH_2$—, or (2) when X is —$CH_2$—, then Y is —O— or —S—; and Z is $CH_2$ or $CH(CH_3)$.

In another embodiment, the present invention provides a compound, or a solvate, tautomer, stereoisomer or pharmaceutically acceptable salt thereof, which is defined by Formula I-C,

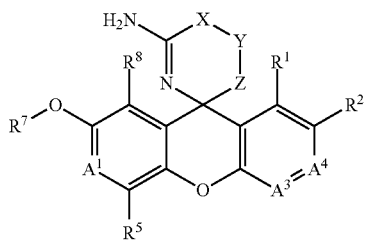

I-C wherein $A^1$ is $CR^6$;

$A^3$ is $CR^4$ or N;

$A^4$ is $CR^3$ or N, provided that no more than one of $A^3$ and $A^4$ is N;

each of $R^1$, $R^3$, $R^4$, $R^5$, $R^6$ and $R^8$, independently, is H, F, Cl, $CF_3$, $OCF_3$, methyl, ethyl, CN, OH, $OCH_3$, $SCH_3$, $NHCH_3$ or $C(O)CH_3$;

one of $R^2$ and $R^7$, independently, is F, Cl, Br, I, haloalkyl, haloalkoxyl, $C_{1-6}$-alkyl, $C_{2-6}$alkenyl, $C_{2-6}$alkynyl, CN, —$OC_{1-6}$alkyl, —$SC_{1-6}$alkyl, —$NHC_{1-6}$alkyl, —$N(C_{1-3}$alkyl$)_2$, —NH-phenyl, —NH-benzyl, —$Si(CH_3)_3$ or a ring selected from the group consisting of phenyl, pyridyl, pyrimidyl, pyrazinyl, pyridazinyl, triazinyl, thienyl, pyrazolyl, imidazolyl, oxazolyl, isoxazolyl, thiazolyl, isothiazolyl, diazolyl, triazolyl, tetrazolyl, pyranyl, dihydropyranyl, tetrahydropyranyl, furanyl, dihydrofuranyl, tetrahydrofuranyl, pyrrolyl, dihydropyrrolyl, pyrrolidinyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopropyl, cyclobutyl, cyclopentyl and cyclohexyl, wherein the $C_{1-6}$-alkyl, $C_{2-4}$alkenyl, $C_{2-4}$alkynyl, —$OC_{1-6}$alkyl, —$SC_{1-6}$alkyl, —$NHC_{1-6}$alkyl, —$N(C_{1-3}$alkyl$)_2$, —NH-phenyl, —NH-benzyl and ring are optionally substituted, independently, with 1-3 substituents of $R^9$;

the other of $R^2$ and $R^7$, independently, is $C_{1-6}$-alkyl, $C_2$alkenyl, $C_{2-4}$alkynyl, CN, —$OC_{1-6}$alkyl, —$SC_{1-6}$alkyl, —$NHC_{1-6}$alkyl, —$N(C_{1-3}$alkyl$)_2$, —NH-phenyl or —NH-benzyl, phenyl, pyridyl, pyrimidyl or thienyl, wherein the $C_{1-6}$-alkyl, $C_{2-4}$alkenyl, $C_{2-4}$alkynyl, CN, —$OC_{1-6}$alkyl, —$SC_{1-6}$alkyl, —$NHC_{1-6}$alkyl, —$N(C_{1-3}$alkyl$)_2$, —NH-phenyl, —NH-benzyl, phenyl, pyridyl, pyrimidinyl and thienyl are optionally substituted, independently, with 1-3 substituents of $R^9$;

each $R^9$, independently, is halo, haloalkyl, CN, OH, $NO_2$, $NH_2$, acetyl, —$C(O)NHCH_3$, oxo, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolidinyl, piperazinyl, oxetanyl or dioxolyl, wherein each of the $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolidinyl, oxetanyl or dioxolyl, is optionally substituted independently with 1-5 substituents of F, Cl, CN, $NO_2$, $NH_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, $C_{1-3}$alkylamino-, $C_{1-3}$dialkylamino, $C_{1-3}$thioalkoxyl, $C_{1-4}$alkenyl, $C_{1-4}$alkynyl or oxetanyl;

X is —$CH_2$—, —O— or —S—;

Y is —O—, —S— or —$CH_2$—, provided that (1) when X is —O— or —S—, then Y is —$CH_2$—, or (2) when X is —$CH_2$—, then Y is —O— or —S—; and Z is $CH_2$, $CF_2$ or $CH(CH_3)$.

In another embodiment, the present invention provides a compound, or a solvate, tautomer, stereoisomer or pharmaceutically acceptable salt thereof, which is defined by Formula I-C wherein $A^1$ is $CR^6$;

$A^3$ is CH, CF or N;

$A^4$ is CH, CF or N, provided that no more than one of $A^3$ and $A^4$ is N; and each of $R^1$, $R^5$, $R^6$ and $R^8$, independently, is H, F, $CF_3$, methyl or CN.

$R^2$ is F, Cl, Br, I, $C_{1-6}$-alkyl, $C_{2-6}$alkenyl, $C_{2-6}$alkynyl, CN, —$OC_{1-6}$alkyl, —$SC_{1-6}$alkyl, 3-methyl-3-oxetanyl-ethynyl, 3-methyl-3-oxetanyl-methoxyl, 3,3-dimethyl-butyn-1-yl, 3-methyl-3-butyn-1-yl, 2,2-dimethyl-3-cyano-propoxyl, 2-fluoro-2-methyl-propoxyl, or a ring selected from the group consisting of phenyl, 2-pyridyl, 3-pyridyl, 4-pyridyl, dihydro-2H-pyran-4-yl, dihydro-2H-pyran-3-yl, tetrahydropyran-4-yl, dihydrofuranyl, tetrahydrofuranyl, pyrrolidin-1-yl, piperidin-1-yl, morpholinyl, 8-oxo-3-aza-bicyclo[3.2.1]oct-3-yl, aza-bicyclo[2.2.1]hept-5-yl and 2-oxo-7-aza-[3,5]-spironon-7-yl, wherein the $C_{1-6}$-alkyl, $C_{2-4}$alkenyl, $C_{2-4}$alkynyl, —$OC_{1-6}$alkyl, —$SC_{1-6}$alkyl, 3-methyl-3-oxetanyl-ethynyl, 3-methyl-3-oxetanyl-methoxyl, 3,3-dimethyl-butyn-1-yl, 3-methyl-3-butyn-1-yl, 2,2-dimethyl-3-cyano-propoxyl, 2-fluoro-2-methyl-propoxyl and ring are optionally substituted, independently, with 1-3 substituents of $R^9$;

$R^7$ is a ring selected from the group consisting of phenyl, pyridyl, pyrimidyl, pyrazinyl, pyridazinyl, thiazolyl or thienyl, said ring optionally substituted, independently, with 1-3 substituents of $R^9$;

each $R^9$, independently, is halo, haloalkyl, CN, OH, $NO_2$, $NH_2$, acetyl, —$C(O)NHCH_3$, oxo, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolidinyl, piperazinyl, oxetanyl or dioxolyl, wherein each of the $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolidinyl, oxetanyl or dioxolyl, is optionally substituted independently with 1-5 substituents of F, Cl, CN, $NO_2$, $NH_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, $C_{1-3}$alkylamino-, $C_{1-3}$dialkylamino, $C_{1-3}$thioalkoxyl, $C_{1-4}$alkenyl, $C_{1-4}$alkynyl or oxetanyl;

X is —$CH_2$—, —O— or —S—;

Y is —O—, —S— or —$CH_2$—, provided that (1) when X is —O— or —S—, then Y is —$CH_2$—, or (2) when X is —$CH_2$—, then Y is —O— or —S—; and Z is $CH_2$ or $CH(CH_3)$.

In another embodiment, the present invention provides a compound, or a solvate, tautomer, stereoisomer or pharmaceutically acceptable salt thereof, which is defined by either of Formulas I-A, I-B or I-C wherein
  $A^1$ is CH;
  $A^3$ is CH, CF or N;
  $A^4$ is CH, CF or N, provided that no more than one of $A^3$ and $A^4$ is N; and
  each of $R^1$, $R^5$, $R^6$ and $R^8$, independently, is H, F, $CF_3$, methyl or CN;
  $R^2$ is F, Cl, Br, I, $C_{1-6}$-alkyl, $C_{2-6}$alkenyl, $C_{2-6}$alkynyl, CN, —$OC_{1-6}$alkyl, —$SC_{1-6}$alkyl, 3-methyl-3-oxetanyl-ethynyl, 3-methyl-3-oxetanyl-methoxyl, 3,3-dimethyl-butyn-1-yl, 3-methyl-3-butyn-1-yl, 2,2-dimethyl-3-cyano-propoxyl, 2-fluoro-2-methyl-propoxyl, or a ring selected from the group consisting of phenyl, 2-pyridyl, 3-pyridyl, 4-pyridyl, dihydro-2H-pyran-4-yl, dihydro-2H-pyran-3-yl, tetrahydropyran-4-yl, dihydrofuranyl, tetrahydrofuranyl, pyrrolidin-1-yl, piperidin-1-yl, morpholinyl, 8-oxo-3-aza-bicyclo[3.2.1]oct-3-yl, aza-bicyclo[2.2.1]hept-5-yl and 2-oxo-7-aza-[3,5]-spirononon-7-yl, wherein the $C_{1-6}$-alkyl, $C_{2-4}$alkenyl, $C_{2-4}$alkynyl, —$OC_{1-6}$alkyl, —$SC_{1-6}$alkyl, 3-methyl-3-oxetanyl-ethynyl, 3-methyl-3-oxetanyl-methoxyl, 3,3-dimethyl-butyn-1-yl, 3-methyl-3-butyn-1-yl, 2,2-dimethyl-3-cyano-propoxyl, 2-fluoro-2-methyl-propoxyl and ring are optionally substituted, independently, with 1-3 substituents of $R^9$;
  $R^7$ is a ring selected from the group consisting of phenyl, pyridyl, pyrimidyl, pyrazinyl, pyridazinyl, thiazolyl or thienyl, said ring optionally substituted, independently, with 1-3 substituents of $R^9$;
  each $R^9$, independently, is halo, haloalkyl, CN, OH, $NO_2$, $NH_2$, acetyl, —C(O)$NHCH_3$, oxo, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolidinyl, piperazinyl, oxetanyl or dioxolyl, wherein each of the $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolidinyl, oxetanyl or dioxolyl, is optionally substituted independently with 1-5 substituents of F, Cl, CN, $NO_2$, $NH_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, $C_{1-3}$alkylamino-, $C_{1-3}$dialkylamino, $C_{1-3}$thioalkoxyl, or oxetanyl;
  X is —O— or —S—;
  Y is —$CH_2$; and
  Z is $CH_2$.
  In another embodiment of the present invention, the compounds, and solvates, tautomers, stereoisomers and pharmaceutically acceptable salts thereof, are defined by Formula II-A

II-A wherein each of $A^1$, $A^3$, $A^4$, $R^1$, $R^2$, $R^5$, $R^7$, $R^8$, X and Y is as defined above with respect to Formula II or as independently defined below.
  In another embodiment of the present invention, the compounds, and solvates, tautomers, stereoisomers and pharmaceutically acceptable salts thereof, are defined by Formula II-A wherein
  $A^1$ is $CR^6$;
  $A^3$ is $CR^4$ or N;
  $A^4$ is $CR^3$ or N, provided that no more than one of $A^3$ and $A^4$ is N;
  each of $R^1$, $R^3$, $R^4$, $R^5$, $R^6$ and $R^8$, independently, is H, F, Cl, $CF_3$, $OCF_3$, methyl, ethyl, CN, OH, $OCH_3$, $SCH_3$, $NHCH_3$ or C(O)$CH_3$;
  one of $R^2$ and $R^7$, independently, is F, Cl, Br, I, haloalkyl, haloalkoxyl, $C_{1-6}$-alkyl, $C_{2-6}$alkenyl, $C_{2-6}$alkynyl, CN, —$OC_{1-6}$alkyl, —$SC_{1-6}$alkyl, —$NHC_{1-6}$alkyl, —$N(C_{1-3}$alkyl$)_2$, —NH-phenyl, —NH-benzyl, —$Si(CH_3)_3$ or a ring selected from the group consisting of phenyl, pyridyl, pyrimidyl, pyrazinyl, pyridazinyl, triazinyl, thienyl, pyrazolyl, imidazolyl, oxazolyl, isoxazolyl, thiazolyl, isothiazolyl, diazolyl, triazolyl, tetrazolyl, pyranyl, dihydropyranyl, tetrahydropyranyl, furanyl, dihydrofuranyl, tetrahydrofuranyl, pyrrolyl, dihydropyrrolyl, pyrrolidinyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spirononon-7-yl, cyclopropyl, cyclobutyl, cyclopentyl and cyclohexyl, wherein the $C_{1-6}$-alkyl, $C_{2-4}$alkenyl, $C_{2-4}$alkynyl, —$OC_{1-6}$alkyl, —$SC_{1-6}$alkyl, —$NHC_{1-6}$alkyl, —$N(C_{1-3}$alkyl$)_2$, —NH-phenyl, —NH-benzyl and ring are optionally substituted, independently, with 1-3 substituents of $R^9$;
  the other of $R^2$ and $R^7$, independently, is $C_{1-6}$-alkyl, $C_{2-4}$alkenyl, $C_{2-4}$alkynyl, CN, —$OC_{1-6}$alkyl, —$SC_{1-6}$alkyl, —$NHC_{1-6}$alkyl, —$N(C_{1-3}$alkyl$)_2$, —NH-phenyl or —NH-benzyl, phenyl, pyridyl, pyrimidyl or thienyl, wherein the $C_{1-6}$-alkyl, $C_{2-4}$alkenyl, $C_{2-4}$alkynyl, CN, —$OC_{1-6}$alkyl, —$SC_{1-6}$alkyl, —$NHC_{1-6}$alkyl, —$N(C_{1-3}$alkyl$)_2$, —NH-phenyl, —NH-benzyl, phenyl, pyridyl, pyrimidinyl and thienyl are optionally substituted, independently, with 1-3 substituents of $R^9$;
  each $R^9$, independently, is halo, haloalkyl, CN, OH, $NO_2$, $NH_2$, acetyl, —C(O)$NHCH_3$, oxo, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolidinyl, piperazinyl, oxetanyl or dioxolyl, wherein each of the $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolidinyl, oxetanyl or dioxolyl, is optionally substituted independently with 1-5 substituents of F, Cl, CN, $NO_2$, $NH_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, $C_{1-3}$alkylamino-, $C_{1-3}$dialkylamino, $C_{1-3}$thioalkoxyl, $C_{1-4}$alkenyl, $C_{1-4}$alkynyl or oxetanyl;
  X is —$CH_2$—, —O— or —S—; and
  Y is —O—, —S— or —$CH_2$—, provided that (1) when X is —O— or —S—, then Y is —$CH_2$—, or (2) when X is —$CH_2$—, then Y is —O— or —S—.
  In another embodiment, the present invention provides a compound, or a solvate, tautomer, stereoisomer or pharmaceutically acceptable salt thereof, which is defined by Formula II-A, wherein
  $A^1$ is $CR^6$;
  $A^3$ is CH, CF, $OCH_3$ or N;

A⁴ is CH, CF or N, provided that no more than one of A³ and A⁴ is N; and each of $R^1$, $R^5$, $R^6$ and $R^8$, independently, is H, F, $CF_3$, methyl or CN.

$R^2$ is F, Cl, Br, I, $C_{1-6}$-alkyl, $C_{2-6}$alkenyl, $C_{2-6}$alkynyl, CN, —$OC_{1-6}$alkyl, —$SC_{1-6}$alkyl, 3-methyl-3-oxetanyl-ethynyl, 3-methyl-3-oxetanyl-methoxyl, 3,3-dimethyl-butyn-1-yl, 3-methyl-3-butyn-1-yl, 2,2-dimethyl-3-cyano-propoxyl, 2-fluoro-2-methyl-propoxyl, or a ring selected from the group consisting of phenyl, 2-pyridyl, 3-pyridyl, 4-pyridyl, dihydro-2H-pyran-4-yl, dihydro-2H-pyran-3-yl, tetrahydropyran-4-yl, dihydrofuranyl, tetrahydrofuranyl, pyrrolidin-1-yl, piperidin-1-yl, morpholinyl, 8-oxo-3-aza-bicyclo[3.2.1]oct-3-yl, aza-bicyclo[2.2.1]hept-5-yl and 2-oxo-7-aza-[3,5]-spironon-7-yl, wherein the $C_{1-6}$-alkyl, $C_{2-4}$alkenyl, $C_{2-4}$alkynyl, —$OC_{1-6}$alkyl, —$SC_{1-6}$alkyl, 3-methyl-3-oxetanyl-ethynyl, 3-methyl-3-oxetanyl-methoxyl, 3,3-dimethyl-butyn-1-yl, 3-methyl-3-butyn-1-yl, 2,2-dimethyl-3-cyano-propoxyl, 2-fluoro-2-methyl-propoxyl and ring are optionally substituted, independently, with 1-3 substituents of $R^9$;

$R^7$ is a ring selected from the group consisting of phenyl, pyridyl, pyrimidyl, pyrazinyl, pyridazinyl, thiazolyl or thienyl, said ring optionally substituted, independently, with 1-3 substituents of $R^9$;

each $R^9$, independently, is halo, haloalkyl, CN, OH, $NO_2$, $NH_2$, acetyl, —$C(O)NHCH_3$, oxo, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolidinyl, piperazinyl, oxetanyl or dioxolyl, wherein each of the $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolidinyl, oxetanyl or dioxolyl, is optionally substituted independently with 1-5 substituents of F, Cl, CN, $NO_2$, $NH_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, $C_{1-3}$alkylamino-, $C_{1-3}$dialkylamino, $C_{1-3}$thioalkoxyl, $C_{1-4}$alkenyl, $C_{1-4}$alkynyl or oxetanyl;

X is $CH_2$—, O— or S—; and

Y is —O—, —S— or $CH_2$—, provided that (1) when X is —O— or —S—, then Y is $CH_2$—, or (2) when X is $CH_2$, then Y is —O— or —S—.

In another embodiment, the present invention provides a compound, or a solvate, tautomer, stereoisomer or pharmaceutically acceptable salt thereof, which is defined by Formula II-B,

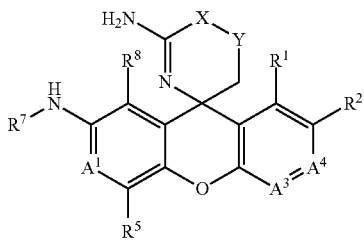

II-B wherein $A^1$ is $CR^6$;

$A^3$ is $CR^4$ or N;

$A^4$ is $CR^3$ or N, provided that no more than one of $A^3$ and $A^4$ is N;

each of $R^1$, $R^3$, $R^4$, $R^5$, $R^6$ and $R^8$, independently, is H, F, Cl, $CF_3$, $OCF_3$, methyl, ethyl, CN, OH, $OCH_3$, $SCH_3$, $NHCH_3$ or $C(O)CH_3$;

one of $R^2$ and $R^7$, independently, is F, Cl, Br, I, haloalkyl, haloalkoxyl, $C_{1-6}$-alkyl, $C_{2-6}$alkenyl, $C_{2-6}$alkynyl, CN, —$OC_{1-6}$alkyl, —$SC_{1-6}$alkyl, —$NHC_{1-6}$alkyl, —$N(C_{1-3}$alkyl$)_2$, —NH-phenyl, —NH-benzyl, —$Si(CH_3)_3$ or a ring selected from the group consisting of phenyl, pyridyl, pyrimidyl, pyrazinyl, pyridazinyl, triazinyl, thienyl, pyrazolyl, imidazolyl, oxazolyl, isoxazolyl, thiazolyl, isothiazolyl, diazolyl, triazolyl, tetrazolyl, pyranyl, dihydropyranyl, tetrahydropyranyl, furanyl, dihydrofuranyl, tetrahydrofuranyl, pyrrolyl, dihydropyrrolyl, pyrrolidinyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopropyl, cyclobutyl, cyclopentyl and cyclohexyl, wherein the $C_{1-6}$-alkyl, $C_{2-4}$alkynyl, $C_{2-4}$alkynyl, —$OC_{1-6}$alkyl, —$SC_{1-6}$alkyl, —$NHC_{1-6}$alkyl, —$N(C_{1-3}$alkyl$)_2$, —NH-phenyl, —NH-benzyl and ring are optionally substituted, independently, with 1-3 substituents of $R^9$;

the other of $R^2$ and $R^7$, independently, is $C_{1-6}$-alkyl, $C_2$alkenyl, $C_{2-4}$alkynyl, CN, —$OC_{1-6}$alkyl, —$SC_{1-6}$alkyl, —$NHC_{1-6}$alkyl, —$N(C_{1-3}$alkyl$)_2$, —NH-phenyl or —NH-benzyl, phenyl, pyridyl, pyrimidyl or thienyl, wherein the $C_{1-6}$-alkyl, $C_{2-4}$alkenyl, $C_{2-4}$alkynyl, CN, —$OC_{1-6}$alkyl, —$SC_{1-6}$alkyl, —$NHC_{1-6}$alkyl, —$N(C_{1-3}$alkyl$)_2$, —NH-phenyl, —NH-benzyl, phenyl, pyridyl, pyrimidinyl and thienyl are optionally substituted, independently, with 1-3 substituents of $R^9$;

each $R^9$, independently, is halo, haloalkyl, CN, OH, $NO_2$, $NH_2$, acetyl, —$C(O)NHCH_3$, oxo, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolidinyl, piperazinyl, oxetanyl or dioxolyl, wherein each of the $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolidinyl, oxetanyl or dioxolyl, is optionally substituted independently with 1-5 substituents of F, Cl, CN, $NO_2$, $NH_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, $C_{1-3}$alkylamino-, $C_{1-3}$dialkylamino, $C_{1-3}$thioalkoxyl, $C_{1-4}$alkenyl, $C_{1-4}$alkynyl or oxetanyl;

X is —$CH_2$—, —O— or —S—; and

Y is —O—, —S— or —$CH_2$—, provided that (1) when X is —O— or —S—, then Y is —$CH_2$—, or (2) when X is —$CH_2$, then Y is —O— or —S—.

In another embodiment, the present invention provides a compound, or a solvate, tautomer, stereoisomer or pharmaceutically acceptable salt thereof, which is defined by Formula II-B, wherein $A^1$ is $CR^6$;

$A^3$ is CH, CF or N;

$A^4$ is CH, CF or N, provided that no more than one of $A^3$ and $A^4$ is N; and each of $R^1$, $R^5$, $R^6$ and $R^8$, independently, is H, F, $CF_3$, methyl or CN.

$R^2$ is F, Cl, Br, I, $C_{1-6}$-alkyl, $C_{2-6}$alkenyl, $C_{2-6}$alkynyl, CN, —$OC_{1-6}$alkyl, —$SC_{1-6}$alkyl, 3-methyl-3-oxetanyl-ethynyl, 3-methyl-3-oxetanyl-methoxyl, 3,3-dimethyl-butyn-1-yl, 3-methyl-3-butyn-1-yl, 2,2-dimethyl-3-cyano-propoxyl, 2-fluoro-2-methyl-propoxyl, or a ring selected from the group consisting of phenyl, 2-pyridyl, 3-pyridyl, 4-pyridyl, dihydro-2H-pyran-4-yl, dihydro-2H-pyran-3-yl, tetrahydropyran-4-yl, dihydrofuranyl, tetrahydrofuranyl, pyrrolidin-1- yl, piperidin-1-yl, morpholinyl, 8-oxo-3-aza-bicyclo[3.2.1]oct-3-yl, aza-bicyclo[2.2.1]hept-5-yl and 2-oxo-7-aza-[3,5]-spironon-7-yl, wherein the $C_{1-6}$-alkyl, $C_{2-4}$alkenyl, $C_{2-4}$alkynyl, —$OC_{1-6}$alkyl, —$SC_{1-6}$alkyl, 3-methyl-3-oxetanyl-ethynyl, 3-methyl-3-oxetanyl-methoxyl, 3,3-dimethyl-butyn-1-yl, 3-methyl-3-Butyn-1-yl, 2,2-dimethyl-3-cyano-propoxyl, 2-fluoro-2-methyl-propoxyl and ring are optionally substituted, independently, with 1-3 substituents of $R^9$;

$R^7$ is a ring selected from the group consisting of phenyl, pyridyl, pyrimidyl, pyrazinyl, pyridazinyl, thiazolyl or thienyl, said ring optionally substituted, independently, with 1-3 substituents of $R^9$;

each $R^9$, independently, is halo, haloalkyl, CN, OH, $NO_2$, $NH_2$, acetyl, —$C(O)NHCH_3$, oxo, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolidinyl, piperazinyl, oxetanyl or dioxolyl, wherein each of the $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolidinyl, oxetanyl or dioxolyl, is optionally substituted independently with 1-5 substituents of F, Cl, CN, $NO_2$, $NH_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, $C_{1-3}$alkylamino-, $C_{1-3}$dialkylamino, $C_{1-3}$thioalkoxyl, $C_{1-4}$alkenyl, $C_{1-4}$alkynyl or oxetanyl;

X is —$CH_2$—, —O— or —S—; and

Y is —O—, —S— or —$CH_2$—, provided that (1) when X is —O— or —S—, then Y is —$CH_2$—, or (2) when X is —$CH_2$, then Y is —O— or —S—.

In another embodiment, the present invention provides a compound, or a solvate, tautomer, stereoisomer or pharmaceutically acceptable salt thereof, which is defined by Formula II-C,

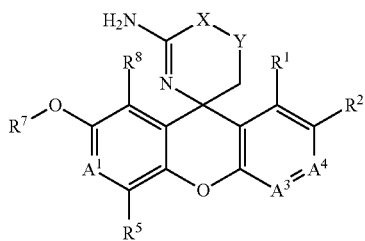

II-C wherein $A^1$ is $CR^6$;

$A^3$ is $CR^4$ or N;

$A^4$ is $CR^3$ or N, provided that no more than one of $A^3$ and $A^4$ is N;

each of $R^1$, $R^3$, $R^4$, $R^5$, $R^6$ and $R^8$, independently, is H, F, Cl, $CF_3$, $OCF_3$, methyl, ethyl, CN, OH, $OCH_3$, $SCH_3$, $NHCH_3$ or $C(O)CH_3$;

one of $R^2$ and $R^7$, independently, is F, Cl, Br, I, haloalkyl, haloalkoxyl, $C_{1-6}$-alkyl, $C_{2-6}$alkenyl, $C_{2-6}$alkynyl, CN, —$OC_{1-6}$alkyl, —$SC_{1-6}$alkyl, —$NHC_{1-6}$alkyl, —$N(C_{1-3}$alkyl$)_2$, —NH-phenyl, —NH-benzyl, —$Si(CH_3)_3$ or a ring selected from the group consisting of phenyl, pyridyl, pyrimidyl, pyrazinyl, pyridazinyl, triazinyl, thienyl, pyrazolyl, imidazolyl, oxazolyl, isoxazolyl, thiazolyl, isothiazolyl, diazolyl, triazolyl, tetrazolyl, pyranyl, dihydropyranyl, tetrahydropyranyl, furanyl, dihydrofuranyl, tetrahydrofuranyl, pyrrolyl, dihydropyrrolyl, pyrrolidinyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopropyl, cyclobutyl, cyclopentyl and cyclohexyl, wherein the $C_{1-6}$-alkyl, $C_{2-4}$alkenyl, $C_{2-4}$alkynyl, —$OC_{1-6}$alkyl, —$SC_{1-6}$alkyl, —$NHC_{1-6}$alkyl, —$N(C_{1-3}$alkyl$)_2$, —NH-phenyl, —NH-benzyl and ring are optionally substituted, independently, with 1-3 substituents of $R^9$;

the other of $R^2$ and $R^7$, independently, is $C_{1-6}$-alkyl, $C_{2-4}$alkenyl, $C_{2-4}$alkynyl, CN, —$OC_{1-6}$alkyl, —$SC_{1-6}$alkyl, —$NHC_{1-6}$alkyl, —$N(C_{1-3}$alkyl$)_2$, —NH-phenyl or —NH-benzyl, phenyl, pyridyl, pyrimidyl or thienyl, wherein the $C_{1-6}$-alkyl, $C_{2-4}$alkenyl, $C_{2-4}$alkynyl, CN, —$OC_{1-6}$alkyl, —$SC_{1-6}$alkyl, —$NHC_{1-6}$alkyl, —$N(C_{1-3}$alkyl$)_2$, —NH-phenyl, —NH-benzyl, phenyl, pyridyl, pyrimidinyl and thienyl are optionally substituted, independently, with 1-3 substituents of $R^9$;

each $R^9$, independently, is halo, haloalkyl, CN, OH, $NO_2$, $NH_2$, acetyl, —$C(O)NHCH_3$, oxo, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolidinyl, piperazinyl, oxetanyl or dioxolyl, wherein each of the $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolidinyl, oxetanyl or dioxolyl, is optionally substituted independently with 1-5 substituents of F, Cl, CN, $NO_2$, $NH_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, $C_{1-3}$alkylamino-, $C_{1-3}$dialkylamino, $C_{1-3}$thioalkoxyl, $C_{1-4}$alkenyl, $C_{1-4}$alkynyl or oxetanyl;

X is —$CH_2$—, —O— or —S—; and

Y is —O—, —S— or —$CH_2$—, provided that (1) when X is —O— or —S—, then Y is —$CH_2$—, or (2) when X is —$CH_2$, then Y is —O— or —S—.

In another embodiment, the present invention provides a compound, or a solvate, tautomer, stereoisomer or pharmaceutically acceptable salt thereof, which is defined by Formula II-C wherein $A^1$ is $CR^6$;

$A^3$ is CH, CF or N;

$A^4$ is CH, CF or N, provided that no more than one of $A^3$ and $A^4$ is N; and each of $R^1$, $R^5$, $R^6$ and $R^8$, independently, is H, F, $CF_3$, methyl or CN.

$R^2$ is F, Cl, Br, I, $C_{1-6}$-alkyl, $C_{2-6}$alkenyl, $C_{2-6}$alkynyl, CN, —$OC_{1-6}$alkyl, —$SC_{1-6}$alkyl, 3-methyl-3-oxetanyl-ethynyl, 3-methyl-3-oxetanyl-methoxyl, 3,3-dimethyl-butyn-1-yl, 3-methyl-3-butyn-1-yl, 2,2-dimethyl-3-cyano-propoxyl, 2-fluoro-2-methyl-propoxyl, or a ring selected from the group consisting of phenyl, 2-pyridyl, 3-pyridyl, 4-pyridyl, dihydro-2H-pyran-4-yl, dihydro-2H-pyran-3-yl, tetrahydropyran-4-yl, dihydrofuranyl, tetrahydrofuranyl, pyrrolidin-1-yl, piperidin-1-yl, morpholinyl, 8-oxo-3-aza-bicyclo[3.2.1]oct-3-yl, aza-bicyclo[2.2.1]hept-5-yl and 2-oxo-7-aza-[3,5]-spironon-7-yl, wherein the $C_{1-6}$-alkyl, $C_{2-4}$alkenyl, $C_{2-4}$alkynyl, —$OC_{1-6}$alkyl, —$SC_{1-6}$alkyl, 3-methyl-3-oxetanyl-ethynyl, 3-methyl-3-oxetanyl-methoxyl, 3,3-dimethyl-butyn-1-yl, 3-methyl-3-Butyn-1-yl, 2,2-dimethyl-3-cyano-propoxyl, 2-fluoro-2-methyl-propoxyl and ring are optionally substituted, independently, with 1-3 substituents of $R^9$;

R$^7$ is a ring selected from the group consisting of phenyl, pyridyl, pyrimidyl, pyrazinyl, pyridazinyl, thiazolyl or thienyl, said ring optionally substituted, independently, with 1-3 substituents of R$^9$;

each R$^9$, independently, is halo, haloalkyl, CN, OH, NO$_2$, NH$_2$, acetyl, —C(O)NHCH$_3$, oxo, C$_{1-6}$alkyl, C$_{2-6}$alkenyl, C$_{2-6}$alkynyl, C$_{3-6}$cycloalkyl, C$_{1-6}$alkylamino-, C$_{1-6}$dialkylamino-, C$_{1-6}$alkoxyl, C$_{1-6}$thioalkoxyl, morpholinyl, pyrazolyl, isoxazolyl, dihydropyranyl, pyrrolidinyl, piperazinyl, oxetanyl or dioxolyl, wherein each of the C$_{1-6}$alkyl, C$_{2-6}$alkenyl, C$_{2-6}$alkynyl, C$_{3-6}$cycloalkyl, C$_{1-6}$alkylamino-, C$_{1-6}$dialkylamino-, C$_{1-6}$alkoxyl, C$_{1-6}$thioalkoxyl, morpholinyl, pyrazolyl, isoxazolyl, dihydropyranyl, pyrrolidinyl, oxetanyl or dioxolyl, is optionally substituted independently with 1-5 substituents of F, Cl, CN, NO$_2$, NH$_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, C$_{1-3}$alkylamino-, C$_{1-3}$dialkylamino, C$_{1-3}$thioalkoxyl, C$_{1-4}$alkenyl, C$_{1-4}$alkynyl or oxetanyl;

X is CH$_2$—, O— or S—; and

Y is —O—, —S— or CH$_2$—, provided that (1) when X is —O— or —S—, then Y is CH$_2$—, or (2) when X is CH$_2$, then Y is —O— or —S—.

In another embodiment, the present invention provides compounds defined by Formula III

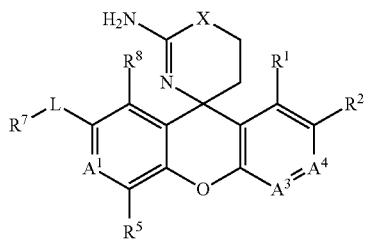

III or a stereoisomer, tautomer, hydrate, solvate or pharmaceutically acceptable salt thereof, wherein A$^1$ is CR$^6$ or N;

A$^3$ is CR$^4$ or N;

A$^4$ is CR$^3$ or N; provided that no more than one of A$^1$, A$^3$ and A$^4$ is N;

L is —C(=O)NH—, —C(=O)N(CH$_3$)—, —NH—, —N(CH$_3$)— or —O—;

each of R$^1$, R$^4$, R$^5$ and R$^8$, independently, is H, F, Cl, Br, CF$_3$, OCF$_3$, C$_{1-6}$-alkyl, CN, OH, —OC$_{1-6}$-alkyl, —S(O)$_o$C$_{1-6}$-alkyl, —NHC$_{1-6}$-alkyl or —C(O)C$_{1-6}$-alkyl, wherein the C$_{1-6}$-alkyl and C$_{1-6}$-alkyl portion of —OC$_{1-6}$-alkyl, —S(O)$_o$C$_{1-6}$-alkyl, —NHC$_{1-6}$-alkyl and —C(O)C$_{1-6}$-alkyl are optionally substituted with 1-3 substituents of F, oxo or OH;

each of R$^2$ and R$^7$, independently, is F, Cl, Br, I, haloalkyl, haloalkoxyl, C$_{1-6}$-alkyl, C$_{2-6}$alkenyl, C$_{2-6}$alkynyl, CN, —OC$_{1-6}$alkyl, —SC$_{1-6}$alkyl, —NHC$_{1-6}$alkyl, —N(C$_{1-3}$alkyl)$_2$, —NH-phenyl, —NH-benzyl, —Si(CH$_3$)$_3$ or a ring selected from the group consisting of phenyl, pyridyl, pyrimidyl, pyrazinyl, pyridazinyl, triazinyl, thienyl, pyrazolyl, imidazolyl, oxazolyl, isoxazolyl, thiazolyl, isothiazolyl, diazolyl, triazolyl, tetrazolyl, pyranyl, dihydropyranyl, tetrahydropyranyl, furanyl, dihydrofuranyl, tetrahydrofuranyl, pyrrolyl, dihydropyrrolyl, pyrrolidinyl, piperidinyl, piperazinyl, morpholinyl, azetidinyl, 8-oxo-3-aza-bicyclo [3.2.1]oct-3-yl, aza-bicyclo[2.2.1]hept-5-yl, 2-oxo-7-aza-[3,5]-spironon-7-yl, cyclopropyl, cyclobutyl, cyclopentyl and cyclohexyl, wherein the C$_{1-6}$-alkyl, C$_{2-4}$alkenyl, C$_{2-4}$alkynyl, —OC$_{1-6}$alkyl, —SC$_{1-6}$alkyl, —NHC$_{1-6}$alkyl, —N(C$_{1-3}$alkyl)$_2$, —NH-phenyl, —NH-benzyl and ring are optionally substituted, independently, with 1-3 substituents of R$^9$;

each of R$^3$ and R$^6$, independently, is H, halo, haloalkyl, haloalkoxyl, C$_{1-6}$-alkyl, CN, OH, OC$_{1-6}$-alkyl, S(O)$_o$C$_{1-6}$-alkyl, NHC$_{1-6}$-alkyl or C(O)C$_{1-6}$-alkyl;

each R$^9$, independently, is halo, haloalkyl, haloalkoxyl, CN, OH, NO$_2$, NH$_2$, acetyl, —C(O)NHCH$_3$, oxo, C$_{1-6}$alkyl, C$_{2-6}$alkenyl, C$_{2-6}$alkynyl, C$_{3-6}$cycloalkyl, C$_{1-6}$alkylamino-, C$_{1-6}$dialkylamino-, C$_{1-6}$alkoxyl, C$_{1-6}$thioalkoxyl, morpholinyl, pyrazolyl, isoxazolyl, dihydropyranyl, pyrrolidinyl, piperazinyl, oxetanyl or dioxolyl, wherein each of the C$_{1-6}$alkyl, C$_{2-6}$alkenyl, C$_{2-6}$alkynyl, C$_{3-6}$cycloalkyl, C$_{1-6}$alkylamino-, C$_{1-6}$dialkylamino-, C$_{1-6}$alkoxyl, C$_{1-6}$thioalkoxyl, morpholinyl, pyrazolyl, isoxazolyl, dihydropyranyl, pyrrolidinyl, oxetanyl or dioxolyl, is optionally substituted independently with 1-5 substituents of F, Cl, CN, NO$_2$, NH$_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, C$_{1-3}$alkylamino-, C$_{1-3}$dialkylamino, C$_{1-3}$thioalkoxyl, C$_{1-4}$alkenyl, C$_{1-4}$alkynyl or oxetanyl; and X is —O— or —S—.

In another embodiment, the present invention provides compounds defined by Formula III or a stereoisomer, tautomer, hydrate, solvate or pharmaceutically acceptable salt thereof, wherein A$^1$ is CH or CF;

A$^3$ is CH, CF, OCH$_3$ or N;

A$^4$ is CH, CF or N; provided that no more than one of A$^3$ and A$^4$ is N;

L is —C(=O)NH—, —C(=O)N(CH$_3$)—, —NH— or —N(CH$_3$)—;

each of R$^2$ and R$^7$, independently, is F, Cl, Br, I, haloalkyl, haloalkoxyl, C$_{1-6}$-alkyl, C$_{2-6}$alkenyl, C$_{2-6}$alkynyl, CN, —OC$_{1-6}$alkyl, —SC$_{1-6}$alkyl, —NHC$_{1-6}$alkyl, —N(C$_{1-3}$alkyl)$_2$, —NH-phenyl, —NH-benzyl, —Si(CH$_3$)$_3$ or a ring selected from the group consisting of phenyl, pyridyl, pyrimidyl, pyrazinyl, pyridazinyl, triazinyl, thienyl, pyrazolyl, imidazolyl, oxazolyl, isoxazolyl, thiazolyl, isothiazolyl, diazolyl, triazolyl, tetrazolyl, pyranyl, dihydropyranyl, tetrahydropyranyl, furanyl, dihydrofuranyl, tetrahydrofuranyl, pyrrolyl, dihydropyrrolyl, pyrrolidinyl, piperidinyl, piperazinyl, morpholinyl, azetidinyl, 8-oxo-3-aza-bicyclo [3.2.1]oct-3-yl, aza-bicyclo[2.2.1]hept-5-yl, 2-oxo-7-aza-[3,5]-spironon-7-yl, cyclopropyl, cyclobutyl, cyclopentyl and cyclohexyl, wherein the C$_{1-6}$-alkyl, C$_{2-4}$alkenyl, C$_{2-4}$alkynyl, —OC$_{1-6}$alkyl, —SC$_{1-6}$alkyl, —NHC$_{1-6}$alkyl, —N(C$_{1-3}$alkyl)$_2$, —NH-phenyl, —NH-benzyl and ring are optionally substituted, independently, with 1-3 substituents of R$^9$;

each of R$^1$, R$^5$ and R$^8$, independently, is H, F, Cl, Br, CF$_3$, OCF$_3$, C$_{1-3}$-alkyl, CN, OH, —OC$_{1-3}$-alkyl, —S(O)$_o$C$_{1-3}$-alkyl, —NHC$_{1-3}$-alkyl or —C(O)C$_{1-3}$-alkyl, wherein the C$_{1-3}$-alkyl and C$_{1-3}$-alkyl portion of —OC$_{1-3}$-alkyl, —S(O)$_o$C$_{1-3}$-alkyl, —NHC$_{1-3}$-alkyl and —C(O)C$_{1-3}$-alkyl are optionally substituted with 1-3 substituents of F, oxo or OH;

each R$^9$, independently, is halo, haloalkyl, CN, OH, NO$_2$, NH$_2$, acetyl, —C(O)NHCH$_3$, oxo, C$_{1-6}$alkyl, C$_{2-6}$alkenyl, C$_{2-6}$alkynyl, C$_{3-6}$cycloalkyl, C$_{1-6}$alkylamino-, C$_{1-6}$dialkylamino-, C$_{1-6}$alkoxyl, C$_{1-6}$thioalkoxyl, morpholinyl, pyrazolyl, isoxazolyl, dihydropyranyl, pyrrolidinyl, piperazinyl, oxetanyl or dioxolyl, wherein each of the C$_{1-6}$alkyl, C$_{2-6}$alkenyl, C$_{2-6}$alkynyl, C$_{3-6}$cycloalkyl, C$_{1-6}$alkylamino-, C$_{1-6}$dialkylamino-, C$_{1-6}$alkoxyl, C$_{1-6}$thioalkoxyl, morpholinyl, pyrazolyl, isoxazolyl, dihydropyranyl, pyrrolidinyl, oxetanyl or dioxolyl, is optionally substituted independently with 1-5 substituents of F, Cl, CN, $NO_2$, $NH_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, $C_{1-3}$alkylamino-, $C_{1-3}$dialkylamino, $C_{1-3}$thioalkoxyl, $C_{1-4}$alkenyl, $C_{1-4}$alkynyl or oxetanyl; and X is —O— or —S—.

In another embodiment of the present invention provides compounds, and solvates, tautomers, stereoisomers and pharmaceutically acceptable salts thereof, defined by Formula III, wherein $A^1$ is CH or CF;
$A^3$ is CH or CF;
$A^4$ is N;
L is —C(═O)NH— or —NH—;
$R^2$ is F, Cl, Br, I, haloalkyl, haloalkoxyl, $C_{1-6}$-alkyl, $C_{2-6}$alkenyl, $C_{2-6}$alkynyl, $C_{3-6}$cycloalkyl, CN, —$OC_{1-6}$alkyl, —$SC_{1-6}$alkyl, —$NHC_{1-6}$alkyl, —$N(C_{1-3}$alkyl$)_2$, —NH-phenyl, —NH-benzyl or a ring selected from the group consisting of dihydropyranyl, tetrahydropyranyl, pyrrolidinyl, piperidinyl, morpholinyl and 8-oxo-3-aza-bicyclo[3.2.1]oct-3-yl, wherein the $C_{3-6}$-alkyl, $C_{2-4}$alkynyl, —$OC_{1-6}$alkyl, —$SC_{1-6}$alkyl and ring are optionally substituted, independently, with 1-3 substituents of $R^9$;
each of $R^1$, $R^5$ and $R^8$, independently, is H, F, Cl, Br, $CF_3$, $OCF_3$, $C_{1-3}$-alkyl, CN, OH, —$OC_{1-3}$-alkyl, —$S(O)_oC_{1-3}$-alkyl, —$NHC_{1-3}$-alkyl or —$C(O)C_{1-3}$-alkyl, wherein the $C_{1-3}$-alkyl and $C_{1-3}$-alkyl portion of —$OC_{1-3}$-alkyl, —$S(O)_oC_{1-3}$-alkyl, —$NHC_{1-3}$-alkyl and —$C(O)C_{1-3}$-alkyl are optionally substituted with 1-3 substituents of F, oxo or OH;
$R^7$ is phenyl, pyridyl, pyrimidyl, pyrazinyl, pyridazinyl, thiazolyl or thienyl, each of which is optionally substituted, independently, with 1-3 substituents of $R^9$;
each $R^9$, independently, is F, Cl, Br, $CF_3$, $OCF_3$, CN, OH, $NH_2$, acetyl, —$C(O)NHCH_3$, oxo, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl or oxetanyl; and X is —O— or —S—.

In another embodiment of the present invention provides compounds, and solvates, tautomers, stereoisomers and pharmaceutically acceptable salts thereof, defined by Formula III, wherein $A^1$ is CH or CF;
$A^3$ is N;
$A^4$ is CH or CF;
$R^2$ is F, Cl, Br, I, haloalkyl, haloalkoxyl, $C_{1-6}$-alkyl, $C_{2-6}$alkenyl, $C_{2-6}$alkynyl, $C_{3-6}$cycloalkyl, CN, —$OC_{1-6}$alkyl, —$SC_{1-6}$alkyl, —$NHC_{1-6}$alkyl, —$N(C_{1-3}$alkyl$)_2$, —NH-phenyl, —NH-benzyl or a ring selected from the group consisting of dihydropyranyl, tetrahydropyranyl, pyrrolidinyl, piperidinyl, morpholinyl and 8-oxo-3-aza-bicyclo[3.2.1]oct-3-yl, wherein the $C_{3-6}$-alkyl, $C_{2-4}$alkynyl, —$OC_{1-6}$alkyl, —$SC_{1-6}$alkyl and ring are optionally substituted, independently, with 1-3 substituents of $R^9$;
each of $R^1$, $R^5$ and $R^8$, independently, is H, F, Cl, $CF_3$, $OCF_3$, $CH_3$, CN, OH, —$OCH_3$, —$S(O)_oCH_3$, —$NHCH_3$ or —$C(O)CH_3$;
$R^7$ is phenyl, pyridyl, pyrimidyl, pyrazinyl, pyridazinyl, thiazolyl or thienyl, each of which is optionally substituted, independently, with 1-3 substituents of $R^9$;
each $R^9$, independently, is F, Cl, Br, $CF_3$, $OCF_3$, CN, OH, $NH_2$, acetyl, —$C(O)NHCH_3$, oxo, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl or oxetanyl; and X is —O—.

In another embodiment of the present invention provides compounds, and solvates, tautomers, stereoisomers and pharmaceutically acceptable salts thereof, defined by Formula III, wherein $A^1$ is CH or CF;
$A^3$ is N;
$A^4$ is CH or CF;
$R^2$ is F, Cl, Br, I, haloalkyl, haloalkoxyl, $C_{1-6}$-alkyl, $C_{2-6}$alkenyl, $C_{2-6}$alkynyl, $C_{3-6}$cycloalkyl, CN, —$OC_{1-6}$alkyl, —$SC_{1-6}$alkyl, —$NHC_{1-6}$alkyl, —$N(C_{1-3}$alkyl$)_2$, —NH-phenyl, —NH-benzyl or a ring selected from the group consisting of dihydropyranyl, tetrahydropyranyl, pyrrolidinyl, piperidinyl, morpholinyl and 8-oxo-3-aza-bicyclo[3.2.1]oct-3-yl, wherein the $C_{3-6}$-alkyl, $C_{2-4}$alkynyl, —$OC_{1-6}$alkyl, —$SC_{1-6}$alkyl and ring are optionally substituted, independently, with 1-3 substituents of $R^9$;
each of $R^1$, $R^5$ and $R^8$, independently, is H, F, $CF_3$, $CH_3$ or CN;
$R^7$ is phenyl, pyridyl, pyrimidyl, pyrazinyl, pyridazinyl, thiazolyl or thienyl, each of which is optionally substituted, independently, with 1-3 substituents of $R^9$;
each $R^9$, independently, is F, Cl, Br, $CF_3$, $OCF_3$, CN, OH, $NH_2$, acetyl, —$C(O)NHCH_3$, oxo, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl or oxetanyl; and X is —O—.

In another embodiment of the present invention, the compounds, and solvates, tautomers, stereoisomers and pharmaceutically acceptable salts thereof, are defined by Formula III-A

III-A wherein each of $A^1$, $A^3$, $A^4$, $R^1$, $R^2$, $R^5$, $R^7$, $R^8$, X, Y and Z is as defined above with respect to Formula III or as independently defined below.

In another embodiment of the present invention provides compounds, and solvates, tautomers, stereoisomers and pharmaceutically acceptable salts thereof, defined by Formula III-A, wherein $A^1$ is CH or CF;
$A^3$ is CH, CF, $OCH_3$ or N;
$A^4$ is CH, CF or N, provided that no more than one of $A^3$ and $A^4$ is N;
$R^2$ is F, Cl, Br, I, haloalkyl, haloalkoxyl, $C_{1-6}$-alkyl, $C_{2-6}$alkenyl, $C_{2-6}$alkynyl, $C_{3-6}$cycloalkyl, CN, —$OC_{1-6}$alkyl, —$SC_{1-6}$alkyl, —$NHC_{1-6}$alkyl, —$N(C_{1-3}$alkyl$)_2$, —NH-phenyl, —NH-benzyl or a ring selected from the group consisting of dihydropyranyl, tetrahydropyranyl, pyrrolidinyl, piperidinyl, pyridyl, pyrimidyl, morpholinyl and 8-oxo-3-aza-bicyclo[3.2.1]oct-3-yl, wherein the $C_{3-6}$-alkyl, $C_{2-4}$alkynyl, —$OC_{1-6}$alkyl, —$SC_{1-6}$alkyl and ring are optionally substituted, independently, with 1-3 substituents of $R^9$;
each of $R^1$, $R^5$ and $R^8$, independently, is H, F, $CF_3$, $OCF_3$, $CH_3$, CN, OH, —$OCH_3$, —$S(O)_oCH_3$, —$NHCH_3$ or —$C(O)CH_3$;

$R^7$ is phenyl, pyridyl, pyrimidyl, pyrazinyl, pyridazinyl, thiazolyl or thienyl, each of which is optionally substituted, independently, with 1-3 substituents of $R^9$;

each $R^9$, independently, is F, Cl, Br, $CF_3$, $OCF_3$, CN, OH, $NH_2$, acetyl, —C(O)$NHCH_3$, oxo, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl or oxetanyl; and X is —O— or —S—.

In another embodiment of the present invention provides compounds, and solvates, tautomers, stereoisomers and pharmaceutically acceptable salts thereof, defined by Formula III-A, wherein $A^1$ is CH or CF;

$A^3$ is CH, CF, $OCH_3$ or N;

$A^4$ is CH, CF or N, provided that no more than one of $A^3$ and $A^4$ is N;

$R^2$ is F, Cl, Br, I, haloalkyl, haloalkoxyl, $C_{1-6}$-alkyl, $C_{2-6}$alkenyl, $C_{2-6}$alkynyl, $C_{3-6}$cycloalkyl, CN, —O$C_{1-6}$alkyl, —S$C_{1-6}$alkyl, —NH$C_{1-6}$alkyl, —N($C_{1-3}$alkyl)$_2$, —NH-phenyl, —NH-benzyl or a ring selected from the group consisting of dihydropyranyl, tetrahydropyranyl, pyrrolidinyl, piperidinyl, pyridyl, pyrimidyl, morpholinyl and 8-oxo-3-aza-bicyclo[3.2.1]oct-3-yl, wherein the $C_{3-6}$-alkyl, $C_{2-4}$alkynyl, —O$C_{1-6}$alkyl, —S$C_{1-6}$alkyl and ring are optionally substituted, independently, with 1-3 substituents of $R^9$;

each of $R^1$, $R^5$ and $R^8$, independently, is H, F, $CF_3$, $CH_3$ or CN;

$R^7$ is phenyl, pyridyl, pyrimidyl, pyrazinyl, pyridazinyl, thiazolyl or thienyl, each of which is optionally substituted, independently, with 1-3 substituents of $R^9$;

each $R^9$, independently, is F, Cl, Br, $CF_3$, $OCF_3$, CN, OH, $NH_2$, acetyl, —C(O)$NHCH_3$, oxo, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl or oxetanyl; and X is —O— or —S—.

In another embodiment of the present invention provides compounds, and solvates, tautomers, stereoisomers and pharmaceutically acceptable salts thereof, defined by Formula III, wherein $A^1$ is CH or CF;

$A^3$ is CH, $OCH_3$ or CF;

$A^4$ is N;

L is —C(=O)NH— or —NH—;

$R^2$ is F, Cl, Br, I, haloalkyl, haloalkoxyl, $C_{1-6}$-alkyl, $C_{2-6}$alkenyl, $C_{2-6}$alkynyl, $C_{3-6}$cycloalkyl, CN, —O$C_{1-6}$alkyl, —S$C_{1-6}$alkyl, —NH$C_{1-6}$alkyl, —N($C_{1-3}$alkyl)$_2$, —NH-phenyl, —NH-benzyl or a ring selected from the group consisting of dihydropyranyl, tetrahydropyranyl, pyrrolidinyl, piperidinyl, morpholinyl and 8-oxo-3-aza-bicyclo[3.2.1]oct-3-yl, wherein the $C_{3-6}$-alkyl, $C_{2-4}$alkynyl, —O$C_{1-6}$alkyl, —S$C_{1-6}$alkyl and ring are optionally substituted, independently, with 1-3 substituents of $R^9$;

$R^7$ is phenyl, pyridyl, pyrimidyl, pyrazinyl or pyridazinyl, each of which is optionally substituted, independently, with 1-3 substituents of $R^9$;

each $R^9$, independently, is F, Cl, Br, $CF_3$, $OCF_3$, CN, OH, $NH_2$, acetyl, —C(O)$NHCH_3$, oxo, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl or oxetanyl; and Y is —O—.

In another embodiment of the present invention provides compounds, and solvates, tautomers, stereoisomers and pharmaceutically acceptable salts thereof, defined by Formula III, wherein $A^1$ is CH or CF;

$A^3$ is N;

$A^4$ is CH or CF;

$R^2$ is F, Cl, Br, I, haloalkyl, haloalkoxyl, $C_{1-6}$-alkyl, $C_{2-6}$alkenyl, $C_{2-6}$alkynyl, $C_{3-6}$cycloalkyl, CN, —O$C_{1-6}$alkyl, —S$C_{1-6}$alkyl, —NH$C_{1-6}$alkyl, —N($C_{1-3}$alkyl)$_2$, —NH-phenyl, —NH-benzyl or a ring selected from the group consisting of dihydropyranyl, tetrahydropyranyl, pyrrolidinyl, piperidinyl, morpholinyl and 8-oxo-3-aza-bicyclo[3.2.1]oct-3-yl, wherein the $C_{3-6}$-alkyl, $C_{2-4}$alkynyl, —O$C_{1-6}$alkyl, —S$C_{1-6}$alkyl and ring are optionally substituted, independently, with 1-3 substituents of $R^9$;

$R^7$ is phenyl, pyridyl, pyrimidyl, pyrazinyl or pyridazinyl, each of which is optionally substituted, independently, with 1-3 substituents of $R^9$;

each $R^9$, independently, is F, Cl, Br, $CF_3$, $OCF_3$, CN, OH, $NH_2$, acetyl, —C(O)$NHCH_3$, oxo, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl or oxetanyl; and Y is —O—.

In another embodiment, the invention provides compounds, including stereoisomers, tautomers, solvates, pharmaceutically acceptable salts thereof, which are generally defined by Formula III-A

III-A wherein each of $R^1$, $R^5$ and $R^8$, independently, is H;

$A^1$ is CH or CF;

$A^3$ is CH, CF, $OCH_3$ or N;

$A^4$ is CH, CF or N, provided that no more than one of $A^3$ and $A^4$ is N;

$R^2$ is F, Cl, Br, I, haloalkyl, haloalkoxyl, $C_{1-6}$-alkyl, $C_{2-6}$alkenyl, $C_{2-6}$alkynyl, CN, —O$C_{1-6}$alkyl, —S$C_{1-6}$alkyl, —NH$C_{1-6}$alkyl, —N($C_{1-3}$alkyl)$_2$, —Si($CH_3$)$_3$ or a ring selected from the group consisting of phenyl, pyridyl, pyrimidyl, pyrazinyl, pyridazinyl, triazinyl, thienyl, pyrazolyl, imidazolyl, oxazolyl, isoxazolyl, thiazolyl, isothiazolyl, diazolyl, triazolyl, tetrazolyl, pyranyl, dihydropyranyl, tetrahydropyranyl, furanyl, dihydrofuranyl, tetrahydrofuranyl, pyrrolyl, dihydropyrrolyl, pyrrolidinyl, piperidinyl, piperazinyl, morpholinyl, azetidinyl, cyclopropyl, cyclobutyl, cyclopentyl and cyclohexyl, wherein the $C_{1-6}$-alkyl, $C_{2-4}$alkenyl, $C_{2-4}$alkynyl, —O$C_{1-6}$alkyl, —S$C_{1-6}$alkyl, —NH$C_{1-6}$alkyl, —N($C_{1-3}$alkyl)$_2$ and ring are optionally substituted, independently, with 1-3 substituents of $R^9$;

$R^7$ is $C_{2-4}$alkynyl, —O$C_{1-6}$alkyl, phenyl, pyridyl, pyrimidyl, pyrazinyl, pyridazinyl, thiazolyl or thienyl, wherein the $C_{2-4}$alkynyl, —O$C_{1-6}$alkyl, pyridyl, pyrimidyl, pyrazinyl, pyridazinyl, thiazolyl and thienyl are optionally substituted, independently, with 1-3 substituents of $R^9$;

each $R^9$, independently, is halo, haloalkyl, CN, OH, $NO_2$, $NH_2$, acetyl, —C(O)$NHCH_3$, oxo, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolidinyl, piperazinyl, oxetanyl or dioxolyl, wherein each of the $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolidinyl, oxetanyl or dioxolyl, is optionally substituted independently with 1-5 substituents of F, Cl, CN, NO$_2$, NH$_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, C$_{1-3}$alkylamino-, C$_{1-3}$dialkylamino, C$_{1-3}$thioalkoxyl, C$_{1-4}$alkenyl, C$_{1-4}$alkynyl or oxetanyl; and X is —O— or —S—.

In another embodiment of the invention, the compounds, including stereoisomers, tautomers, solvates, pharmaceutically acceptable salts, are generally defined by Formula III-A, wherein A$^1$ is CH;

A$^3$ is CH, CF, OCH$_3$ or N;

A$^4$ is CH, CF or N, provided that no more than one of A$^3$ and A$^4$ is N;

R$^2$ is F, Cl, Br, —OC$_{1-6}$alkyl, cyclopropyl, dihydropyranyl or tetrahydropyranyl, wherein the —OC$_{1-6}$alkyl, cyclopropyl, dihydropyranyl or tetrahydropyranyl are optionally substituted independently with 1-5 substituents of R$^9$;

each of R$^1$, R$^5$ and R$^8$, independently, is H or F;

R$^7$ is pyridinyl, pyrimidinyl, pyridazinyl, pyrazinyl or thiazolyl, each of which is optionally substituted independently with 1-3 substituents of R$^9$;

each R$^9$, independently, is F, Cl, Br, CF$_3$, OCF$_3$, CN, OH, NH$_2$, acetyl, —C(O)NHCH$_3$, oxo, C$_{1-6}$alkyl, C$_{2-6}$alkenyl, C$_{2-6}$alkynyl, C$_{3-6}$cycloalkyl, C$_{1-6}$alkylamino-, C$_{1-6}$dialkylamino-, C$_{1-6}$alkoxyl, C$_{1-6}$thioalkoxyl or oxetanyl; and X is —O— or —S—.

In another embodiment of the invention, the compounds, including stereoisomers, and pharmaceutically acceptable salts, are generally defined by Formula III-A, wherein A$^1$ is CH;

A$^3$ is CH, CF, OCH$_3$ or N;

A$^4$ is CH, CF or N, provided that no more than one of A$^3$ and A$^4$ is N;

each of R$^1$, R$^5$ and R$^8$, independently, is H;

R$^2$ is F, Cl, Br, —OC$_{1-6}$alkyl, cyclopropyl, dihydropyranyl or tetrahydropyranyl, wherein the —OC$_{1-6}$alkyl, cyclopropyl, dihydropyranyl or tetrahydropyranyl are optionally substituted independently with 1-5 substituents of R$^9$;

R$^7$ is pyridinyl, pyrimidinyl, pyridazinyl, pyrazinyl or thiazolyl, each of which is optionally substituted independently with 1-3 substituents of R$^9$;

each R$^9$ is, independently, F, Cl, Br, C$_{1-6}$alkyl, C$_{1-6}$alkenyl, C$_{1-6}$alkynyl, —OC$_{1-6}$alkyl, CN, CF3, —OCF$_3$ or spiro-oxetanyl;

X is —O— or —S—.

In another embodiment, the invention provides compounds, including stereoisomers, tautomers, solvates, pharmaceutically acceptable salts thereof, which are generally defined by Formula III-A-a III-A-a wherein A$^1$ is CH or CF;

A$^3$ is CH, CF, OCH$_3$ or N;

A$^4$ is CH, CF or N, provided that no more than one of A$^3$ and A$^4$ is N;

each of R$^1$, R$^5$ and R$^8$, independently, is H or F;

R$^2$ is F, Cl, Br, I, haloalkyl, haloalkoxyl, C$_{1-6}$-alkyl, C$_{2-6}$alkenyl, C$_{2-6}$alkynyl, CN, —OC$_{1-6}$alkyl, —SC$_{1-6}$alkyl, —NHC$_{1-6}$alkyl, —N(C$_{1-3}$alkyl)$_2$, —Si(CH$_3$)$_3$ or a ring selected from the group consisting of phenyl, pyridyl, pyrimidyl, pyrazinyl, pyridazinyl, triazinyl, thienyl, pyrazolyl, imidazolyl, oxazolyl, isoxazolyl, thiazolyl, isothiazolyl, diazolyl, triazolyl, tetrazolyl, pyranyl, dihydropyranyl, tetrahydropyranyl, furanyl, dihydrofuranyl, tetrahydrofuranyl, pyrrolyl, dihydropyrrolyl, pyrrolidinyl, piperidinyl, piperazinyl, morpholinyl, azetidinyl, cyclopropyl, cyclobutyl, cyclopentyl and cyclohexyl, wherein the C$_{1-6}$-alkyl, C$_{2-4}$alkenyl, C$_{2-4}$alkynyl, —OC$_{1-6}$alkyl, —SC$_{1-6}$alkyl, —NHC$_{1-6}$alkyl, —N(C$_{1-3}$alkyl)$_2$ and ring are optionally substituted, independently, with 1-3 substituents of R$^9$;

R$^7$ is C$_{2-4}$alkynyl, —OC$_{1-6}$alkyl, phenyl, pyridyl, pyrimidyl, pyrazinyl, pyridazinyl, thiazolyl or thienyl, wherein the C$_{2-4}$alkynyl, —OC$_{1-6}$alkyl, pyridyl, pyrimidyl, pyrazinyl, pyridazinyl, thiazolyl and thienyl are optionally substituted, independently, with 1-3 substituents of R$^9$;

each R$^9$, independently, is halo, haloalkyl, CN, OH, NO$_2$, NH$_2$, acetyl, —C(O)NHCH$_3$, oxo, C$_{1-6}$alkyl, C$_{2-6}$alkenyl, C$_{2-6}$alkynyl, C$_{3-6}$cycloalkyl, C$_{1-6}$alkylamino-, C$_{1-6}$dialkylamino-, C$_{1-6}$alkoxyl, C$_{1-6}$thioalkoxyl, morpholinyl, pyrazolyl, isoxazolyl, dihydropyranyl, pyrrolidinyl, piperazinyl, oxetanyl or dioxolyl, wherein each of the C$_{1-6}$alkyl, C$_{2-6}$alkenyl, C$_{2-6}$alkynyl, C$_{3-6}$cycloalkyl, C$_{1-6}$alkylamino-, C$_{1-6}$dialkylamino-, C$_{1-6}$alkoxyl, C$_{1-6}$thioalkoxyl, morpholinyl, pyrazolyl, isoxazolyl, dihydropyranyl, pyrrolidinyl, oxetanyl or dioxolyl, is optionally substituted independently with 1-5 substituents of F, Cl, CN, NO$_2$, NH$_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, C$_{1-3}$alkylamino-, C$_{1-3}$dialkylamino, C$_{1-3}$thioalkoxyl, C$_{1-4}$alkenyl, C$_{1-4}$alkynyl or oxetanyl; and X is —O— or —S—.

In another embodiment, the invention provides compounds, including stereoisomers, tautomers, solvates, pharmaceutically acceptable salts thereof, which are generally defined by Formula III-A-1

III-A-1 wherein

A$^1$ is CH or CF;

each of R$^1$, R$^5$ and R$^8$, independently, is H;

R$^2$ is F, Cl, Br, I, haloalkyl, haloalkoxyl, C$_{1-6}$-alkyl, C$_{2-6}$alkenyl, C$_{2-6}$alkynyl, CN, —OC$_{1-6}$alkyl, —SC$_{1-6}$alkyl, —NHC$_{1-6}$alkyl, —N(C$_{1-3}$alkyl)$_2$, —Si(CH$_3$)$_3$ or a ring selected from the group consisting of phenyl, pyridyl, pyrimidyl, pyrazinyl, pyridazinyl, triazinyl, thienyl, pyrazolyl, imidazolyl, oxazolyl, isoxazolyl, thiazolyl, isothiazolyl, diazolyl, triazolyl, tetrazolyl, pyranyl, dihydropyranyl, tetrahydropyranyl, furanyl, dihydrofuranyl, tetrahydrofuranyl, pyrrolyl, dihydropyrrolyl, pyrrolidinyl, piperidinyl, piperazinyl, morpholinyl, azetidinyl, cyclopropyl, cyclobutyl, cyclopentyl and cyclohexyl, wherein the $C_{1-6}$-alkyl, $C_{2-4}$alkenyl, $C_{2-4}$alkynyl, —$OC_{1-6}$alkyl, —$SC_{1-6}$alkyl, —$NHC_{1-6}$alkyl, —$N(C_{1-3}$ alkyl$)_2$ and ring are optionally substituted, independently, with 1-3 substituents of $R^9$;

$R^4$ is H, $OCH_3$ or F;

$R^7$ is $C_{2-4}$alkynyl, —$OC_{1-6}$alkyl, phenyl, pyridyl, pyrimidyl, pyrazinyl, pyridazinyl or thiazolyl, wherein the $C_{2-4}$alkynyl, —$OC_{1-6}$alkyl, pyridyl, pyrimidyl, pyrazinyl, pyridazinyl and thiazolyl are optionally substituted, independently, with 1-3 substituents of $R^9$;

each $R^9$, independently, is halo, haloalkyl, CN, OH, $NO_2$, $NH_2$, acetyl, —$C(O)NHCH_3$, oxo, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolidinyl, piperazinyl, oxetanyl or dioxolyl, wherein each of the $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolidinyl, oxetanyl or dioxolyl, is optionally substituted independently with 1-5 substituents of F, Cl, CN, $NO_2$, $NH_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, $C_{1-3}$alkylamino-, $C_{1-3}$dialkylamino, $C_{1-3}$thioalkoxyl, $C_{1-4}$alkenyl, $C_{1-4}$alkynyl or oxetanyl; and X is —O— or —S—.

In another embodiment, the invention provides compounds, including stereoisomers, tautomers, solvates, pharmaceutically acceptable salts thereof, which are generally defined by Formula III-A-2

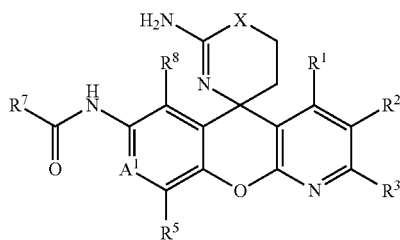

III-A-2 wherein $A^1$ is CH or CF;

each of $R^1$, $R^5$ and $R^8$, independently, is H;

$R^2$ is F, Cl, Br, I, haloalkyl, haloalkoxyl, $C_{1-6}$-alkyl, $C_{2-6}$alkenyl, $C_{2-6}$alkynyl, CN, —$OC_{1-6}$alkyl, —$SC_{1-6}$alkyl, —$NHC_{1-6}$alkyl, —$N(C_{1-3}$alkyl$)_2$, —$Si(CH_3)_3$ or a ring selected from the group consisting of phenyl, pyridyl, pyrimidyl, pyrazinyl, pyridazinyl, triazinyl, thienyl, pyrazolyl, imidazolyl, oxazolyl, isoxazolyl, thiazolyl, isothiazolyl, diazolyl, triazolyl, tetrazolyl, pyranyl, dihydropyranyl, tetrahydropyranyl, furanyl, dihydrofuranyl, tetrahydrofuranyl, pyrrolyl, dihydropyrrolyl, pyrrolidinyl, piperidinyl, piperazinyl, morpholinyl, azetidinyl, cyclopropyl, cyclobutyl, cyclopentyl and cyclohexyl, wherein the $C_{1-6}$-alkyl, $C_{2-4}$alkenyl, $C_{2-4}$alkynyl, —$OC_{1-6}$alkyl, —$SC_{1-6}$alkyl, —$NHC_{1-6}$alkyl, —$N(C_{1-3}$ alkyl$)_2$ and ring are optionally substituted, independently, with 1-3 substituents of $R^9$;

$R^3$ is H or F;

$R^7$ is $C_{2-4}$alkynyl, —$OC_{1-6}$alkyl, phenyl, pyridinyl, pyrimidinyl, pyridazinyl, pyrazinyl or thiazolyl, wherein the $C_{2-4}$alkynyl, —$OC_{1-6}$alkyl, phenyl, pyridinyl, pyrimidinyl, pyridazinyl, pyrazinyl and thiazolyl are optionally substituted, independently, with 1-3 substituents of $R^9$;

each $R^9$, independently, is halo, haloalkyl, CN, OH, $NO_2$, $NH_2$, acetyl, —$C(O)NHCH_3$, oxo, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolidinyl, piperazinyl, oxetanyl or dioxolyl, wherein each of the $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolidinyl, oxetanyl or dioxolyl, is optionally substituted independently with 1-5 substituents of F, Cl, CN, $NO_2$, $NH_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, $C_{1-3}$alkylamino-, $C_{1-3}$dialkylamino, $C_{1-3}$thioalkoxyl, $C_{1-4}$alkenyl, $C_{1-4}$alkynyl or oxetanyl; and X is —O— or —S—.

In another embodiment, the present invention provides compounds defined by Formula IV

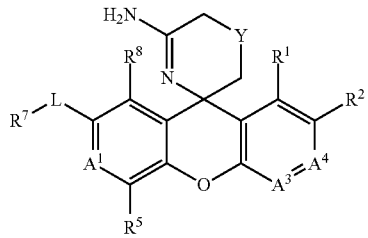

IV or a stereoisomer, tautomer, hydrate, solvate or pharmaceutically acceptable salt thereof, wherein $A^1$ is $CR^6$ or N;

$A^3$ is $CR^4$ or N;

$A^4$ is $CR^3$ or N; provided that no more than one of $A^1$, $A^3$ and $A^4$ is N;

L is —C(=O)NH—, —C(=O)N($CH_3$)—, —NH—, —N($CH_3$)— or —O—;

each of $R^1$, $R^4$, $R^5$ and $R^8$, independently, is H, F, Cl, Br, $CF_3$, $OCF_3$, $C_{1-6}$-alkyl, CN, OH, —$OC_{1-6}$-alkyl, —$S(O)_o C_{1-6}$-alkyl, —$NHC_{1-6}$-alkyl or —$C(O)C_{1-6}$-alkyl, wherein the $C_{1-6}$-alkyl and $C_{1-6}$-alkyl portion of —$OC_{1-6}$-alkyl, —$S(O)_o C_{1-6}$-alkyl, —$NHC_{1-6}$-alkyl and —$C(O)C_{1-6}$-alkyl are optionally substituted with 1-3 substituents of F, oxo or OH;

each of $R^2$ and $R^7$, independently, is F, Cl, Br, I, haloalkyl, haloalkoxyl, $C_{1-6}$-alkyl, $C_{2-6}$alkenyl, $C_{2-6}$alkynyl, CN, —$OC_{1-6}$alkyl, —$SC_{1-6}$alkyl, —$NHC_{1-6}$alkyl, —$N(C_{1-3}$alkyl$)_2$, —NH-phenyl, —NH-benzyl, —$Si(CH_3)_3$ or a ring selected from the group consisting of phenyl, pyridyl, pyrimidyl, pyrazinyl, pyridazinyl, triazinyl, thienyl, pyrazolyl, imidazolyl, oxazolyl, isoxazolyl, thiazolyl, isothiazolyl, diazolyl, triazolyl, tetrazolyl, pyranyl, dihydropyranyl, tetrahydropyranyl, furanyl, dihydrofuranyl, tetrahydrofuranyl, pyrrolyl, dihydropyrrolyl, pyrrolidinyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopropyl, cyclobutyl, cyclopentyl and cyclohexyl, wherein the $C_{1-6}$-alkyl, $C_{2-4}$alkenyl, $C_{2-4}$alkynyl, —$OC_{1-6}$alkyl, —$SC_{1-6}$alkyl, —$NHC_{1-6}$alkyl, —$N(C_{1-3}$ alkyl$)_2$, —NH-phenyl, —NH-benzyl and ring are optionally substituted, independently, with 1-3 substituents of $R^9$;

each of $R^3$ and $R^6$, independently, is H, halo, haloalkyl, haloalkoxyl, $C_{1-6}$-alkyl, CN, OH, $OC_{1-6}$-alkyl, $S(O)_oC_{1-6}$-alkyl, $NHC_{1-6}$-alkyl or $C(O)C_{1-6}$-alkyl;

each $R^9$, independently, is halo, haloalkyl, haloalkoxyl, CN, OH, $NO_2$, $NH_2$, acetyl, —$C(O)NHCH_3$, oxo, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolidinyl, piperazinyl, oxetanyl or dioxolyl, wherein each of the $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolidinyl, oxetanyl or dioxolyl, is optionally substituted independently with 1-5 substituents of F, Cl, CN, $NO_2$, $NH_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, $C_{1-3}$alkylamino-, $C_{1-3}$dialkylamino, $C_{1-3}$thioalkoxyl, $C_{1-4}$alkenyl, $C_{1-4}$alkynyl or oxetanyl; and Y is —O— or —S—.

In another embodiment, the present invention provides compounds defined by Formula IV or a stereoisomer, tautomer, hydrate, solvate or pharmaceutically acceptable salt thereof, wherein $A^1$ is CH or CF;

$A^3$ is CH, CF or N;

$A^4$ is CH, CF or N; provided that no more than one of $A^3$ and $A^4$ is N;

L is —C(=O)NH—, —C(=O)N($CH_3$)—, —NH— or —N($CH_3$)—;

each of $R^2$ and $R^7$, independently, is F, Cl, Br, I, haloalkyl, haloalkoxyl, $C_{1-6}$-alkyl, $C_{2-6}$alkenyl, $C_{2-6}$alkynyl, CN, —$OC_{1-6}$alkyl, —$SC_{1-6}$alkyl, —$NHC_{1-6}$alkyl, —$N(C_{1-3}$alkyl$)_2$, —NH-phenyl, —NH-benzyl, —$Si(CH_3)_3$ or a ring selected from the group consisting of phenyl, pyridyl, pyrimidyl, pyrazinyl, pyridazinyl, triazinyl, thienyl, pyrazolyl, imidazolyl, oxazolyl, isoxazolyl, thiazolyl, isothiazolyl, diazolyl, triazolyl, tetrazolyl, pyranyl, dihydropyranyl, tetrahydropyranyl, furanyl, dihydrofuranyl, tetrahydrofuranyl, pyrrolyl, dihydropyrrolyl, pyrrolidinyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopropyl, cyclobutyl, cyclopentyl and cyclohexyl, wherein the $C_{1-6}$-alkyl, $C_{2-4}$alkenyl, $C_{2-4}$alkynyl, —$OC_{1-6}$alkyl, —$SC_{1-6}$alkyl, —$NHC_{1-6}$alkyl, —$N(C_{1-3}$alkyl$)_2$, —NH-phenyl, —NH-benzyl and ring are optionally substituted, independently, with 1-3 substituents of $R^9$;

each $R^9$, independently, is halo, haloalkyl, CN, OH, $NO_2$, $NH_2$, acetyl, —$C(O)NHCH_3$, oxo, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolidinyl, piperazinyl, oxetanyl or dioxolyl, wherein each of the $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolidinyl, oxetanyl or dioxolyl, is optionally substituted independently with 1-5 substituents of F, Cl, CN, $NO_2$, $NH_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, $C_{1-3}$alkylamino-, $C_{1-3}$dialkylamino, $C_{1-3}$thioalkoxyl, $C_{1-4}$alkenyl, $C_{1-4}$alkynyl or oxetanyl; and Y is —O— or —S—.

In another embodiment of the invention, the compounds, including stereoisomers, tautomers, solvates, pharmaceutically acceptable salts, are generally defined by Formula IV-A

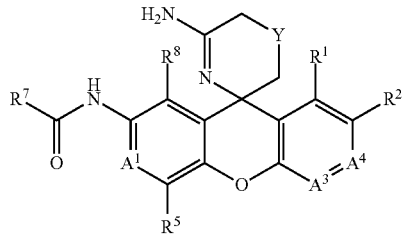

IV-A wherein each of $R^1$, $R^5$ and $R^8$, independently, is H;

$A^1$ is CH or CF;

$A^3$ is CH, CF or N;

$A^4$ is CH, CF or N, provided that no more than one of $A^3$ and $A^4$ is N;

$R^2$ is F, Cl, Br, I, haloalkyl, haloalkoxyl, $C_{1-6}$-alkyl, $C_{2-6}$alkenyl, $C_{2-6}$alkynyl, CN, —$OC_{1-6}$alkyl, —$SC_{1-6}$alkyl, —$NHC_{1-6}$alkyl, —$N(C_{1-3}$alkyl$)_2$, —$Si(CH_3)_3$ or a ring selected from the group consisting of phenyl, pyridyl, pyrimidyl, pyrazinyl, pyridazinyl, triazinyl, thienyl, pyrazolyl, imidazolyl, oxazolyl, isoxazolyl, thiazolyl, isothiazolyl, diazolyl, triazolyl, tetrazolyl, pyranyl, dihydropyranyl, tetrahydropyranyl, furanyl, dihydrofuranyl, tetrahydrofuranyl, pyrrolyl, dihydropyrrolyl, pyrrolidinyl, piperidinyl, piperazinyl, morpholinyl, azetidinyl, cyclopropyl, cyclobutyl, cyclopentyl and cyclohexyl, wherein the $C_{1-6}$-alkyl, $C_{2-4}$alkenyl, $C_{2-4}$alkynyl, —$OC_{1-6}$alkyl, —$SC_{1-6}$alkyl, —$NHC_{1-6}$alkyl, —$N(C_{1-3}$alkyl$)_2$ and ring are optionally substituted, independently, with 1-3 substituents of $R^9$;

$R^7$ is $C_{2-4}$alkynyl, —$OC_{1-6}$alkyl, phenyl, pyridyl, pyrimidyl, pyrazinyl, pyridazinyl or thiazolyl, wherein the $C_{2-4}$alkynyl, —$OC_{1-6}$alkyl, pyridyl, pyrimidyl, pyrazinyl, pyridazinyl and thiazolyl are optionally substituted, independently, with 1-3 substituents of $R^9$;

each $R^9$, independently, is halo, haloalkyl, CN, OH, $NO_2$, $NH_2$, acetyl, —$C(O)NHCH_3$, oxo, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolidinyl, piperazinyl, oxetanyl or dioxolyl, wherein each of the $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolidinyl, oxetanyl or dioxolyl, is optionally substituted independently with 1-5 substituents of F, Cl, CN, $NO_2$, $NH_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, $C_{1-3}$alkylamino-, $C_{1-3}$dialkylamino, $C_{1-3}$thioalkoxyl, $C_{1-4}$alkenyl, $C_{1-4}$alkynyl or oxetanyl; and Y is —O— or —S—.

In another embodiment of the invention, the compounds, including stereoisomers, tautomers, solvates, pharmaceutically acceptable salts, are generally defined by Formula IV-A, wherein each of $R^1$, $R^5$ and $R^8$, independently, is H;

$A^1$ is CH;

$A^3$ is CH, CF or N;

$A^4$ is CH, CF or N, provided that no more than one of $A^3$ and $A^4$ is N;

$R^2$ is F, Cl, Br, —$OC_{1-6}$alkyl, cyclopropyl, dihydropyranyl or tetrahydropyranyl, wherein the —$OC_{1-6}$alkyl, cyclopropyl, dihydropyranyl or tetrahydropyranyl are optionally substituted independently with 1-5 substituents of $R^9$;

$R^7$ is pyridyl, pyrimidyl, pyrazinyl, pyridazinyl or thiazolyl, each of which is optionally substituted independently with 1-3 substituents of $R^9$;

each $R^9$, independently, is F, Cl, Br, $CF_3$, $OCF_3$, CN, OH, $NH_2$, acetyl, —C(O)$NHCH_3$, oxo, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl or oxetanyl; and Y is —O— or —S—.

In another embodiment of the invention, the compounds, including stereoisomers, and pharmaceutically acceptable salts, are generally defined by Formula IV-A, wherein each of $R^1$, $R^5$ and $R^8$, independently, is H;

$A^1$ is CH;

$A^3$ is CH, CF or N;

$A^4$ is CH, CF or N, provided that no more than one of $A^3$ and $A^4$ is N;

$R^2$ is F, Cl, Br, —$OC_{1-6}$alkyl, pyridyl, cyclopropyl, dihydropyranyl or tetrahydropyranyl, wherein the —$OC_{1-6}$alkyl, pyridyl, cyclopropyl, dihydropyranyl or tetrahydropyranyl are optionally substituted independently with 1-5 substituents of $R^9$;

$R^7$ is pyridyl, pyrimidyl, pyrazinyl, pyridazinyl and thiazolyl, each of which is optionally substituted independently with 1-3 substituents of $R^9$;

each $R^9$ is, independently, F, Cl, Br, $C_{1-6}$alkyl, $C_{1-6}$alkenyl, $C_{1-6}$alkynyl, —$OC_{1-6}$alkyl, CN, CF3, —$OCF_3$ or spiro-oxetanyl;

Y is —O— or —S—.

In another embodiment of the invention, the compounds of the invention include compounds wherein X is O or S when Y and Z are each —$CH_2$—, in conjunction with any of the above or below embodiments.

In another embodiment of the invention, the compounds of the invention include compounds wherein Y is O or S when X and Z are each —$CH_2$—, in conjunction with any of the above or below embodiments.

In another embodiment of the invention, the compounds of the invention include compounds wherein X is O, and Y and Z are each $CH_2$, in conjunction with any of the above or below embodiments.

In another embodiment of the invention, the compounds of the invention include compounds wherein X is S, and Y and Z are each $CH_2$, in conjunction with any of the above or below embodiments.

In another embodiment of the invention, the compounds of the invention include compounds wherein X and Z are each $CH_2$— and Y is O, in conjunction with any of the above or below embodiments.

In another embodiment of the invention, the compounds of the invention include compounds wherein X and Z are each —$CH_2$— and Y is S, in conjunction with any of the above or below embodiments.

In another embodiment of the invention, the compounds of the invention include compounds wherein Z is $CH_2$, CHF, $CF_2$, CH($CH_3$), C($CH_3$)$_2$ or CH($CF_3$), in conjunction with any of the above or below embodiments.

In another embodiment of the invention, the compounds of the invention include compounds wherein Z is $CH_2$, $CF_2$ or C(H$CH_3$), in conjunction with any of the above or below embodiments.

In another embodiment of the invention, the compounds of the invention include compounds wherein Z is $CH_2$ or C($CH_3$), in conjunction with any of the above or below embodiments.

In another embodiment of the invention, the compounds of the invention include compounds wherein Z is $CH_2$, in conjunction with any of the above or below embodiments.

The present invention contemplates that the various different embodiments below of each individual variable $A^1$, $A^2$, $A^3$, $A^4$, $A^5$, $A^6$, $R^2$, $R^7$, X, Y and Z, as described below, may be applied "in conjunction with any of the other {above and below} embodiments" to create various embodiments of general Formulas I, II, III and IV, and each sub-formula thereof, described hereinabove, which are not literally described herein.

In another embodiment, the invention includes compounds wherein $A^1$ is CH, CF or N, in conjunction with any of the above or below embodiments.

In another embodiment, the invention includes compounds wherein $A^1$ is CH, in conjunction with any of the above or below embodiments.

In another embodiment, the invention includes compounds wherein $A^1$ is CF, in conjunction with any of the above or below embodiments.

In another embodiment, the invention includes compounds wherein $A^1$ is N, in conjunction with any of the above or below embodiments.

In another embodiment, the invention includes compounds wherein $A^2$ is CH, CF or N, in conjunction with any of the above or below embodiments.

In another embodiment, the invention includes compounds wherein $A^2$ is CH, in conjunction with any of the above or below embodiments.

In another embodiment, the invention includes compounds wherein $A^2$ is CF, in conjunction with any of the above or below embodiments.

In another embodiment, the invention includes compounds wherein $A^2$ is N, in conjunction with any of the above or below embodiments.

In another embodiment, the invention includes compounds wherein $A^3$ is CH, CF or N, in conjunction with any of the above or below embodiments.

In another embodiment, the invention includes compounds wherein $A^3$ is CH, in conjunction with any of the above or below embodiments.

In another embodiment, the invention includes compounds wherein $A^3$ is CF, in conjunction with any of the above or below embodiments.

In another embodiment, the invention includes compounds wherein $A^3$ is N, in conjunction with any of the above or below embodiments.

In another embodiment, the invention includes compounds wherein $A^4$ is CH, CF or N, in conjunction with any of the above or below embodiments.

In another embodiment, the invention includes compounds wherein $A^4$ is CH, in conjunction with any of the above or below embodiments.

In another embodiment, the invention includes compounds wherein $A^4$ is CF, in conjunction with any of the above or below embodiments.

In another embodiment, the invention includes compounds wherein $A^4$ is N, in conjunction with any of the above or below embodiments.

In another embodiment, the invention includes compounds wherein $A^5$ is CH, $CR^1$ wherein $R^1$ is F, Br or

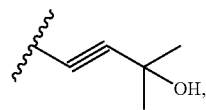 [SMILES: *C#CC(C)(C)O]

or $A^5$ is N, in conjunction with any of the above or below embodiments.

In another embodiment, the invention includes compounds wherein $A^5$ is CH, in conjunction with any of the above or below embodiments.

In another embodiment, the invention includes compounds wherein $A^5$ is N, in conjunction with any of the above or below embodiments.

In another embodiment, the invention includes compounds wherein $A^6$ is CH, CF or N, in conjunction with any of the above or below embodiments.

In another embodiment, the invention includes compounds wherein $A^6$ is CH, in conjunction with any of the above or below embodiments.

In another embodiment, the invention includes compounds wherein $A^6$ is CF, in conjunction with any of the above or below embodiments.

In another embodiment, the invention includes compounds wherein $A^6$ is N, in conjunction with any of the above or below embodiments.

In another embodiment, the invention includes compounds wherein $R^2$ is Cl, Br, $C_{1-6}$-alkyl, $C_{3-6}$-cycloalkyl, $C_{2-6}$alkenyl, $C_{2-6}$alkynyl, CN, —$OC_{1-6}$alkyl, —$SC_{1-6}$alkyl, —$NHC_{1-6}$alkyl, —$N(C_{1-3}$alkyl$)_2$, —NH-phenyl, —NH-benzyl, phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, pyrrolidinyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza[3,5]-spironon-7-yl or —$Si(CH_3)_3$, wherein the $C_{1-6}$-alkyl, $C_{3-6}$-cycloalkyl, $C_{2-6}$alkenyl, $C_{2-6}$alkynyl, —$NHC_{1-6}$alkyl, —$N(C_{1-3}$alkyl$)_2$, —NH-phenyl, —NH-benzyl, phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, pyrrolidinyl, piperidinyl, piperazinyl, morpholinyl, azetidinyl, 8-oxo-3-aza-bicyclo[3.2.1]oct-3-yl, aza-bicyclo[2.2.1]hept-5-yl and 2-oxo-7-aza-[3,5]-spironon-7-yl are optionally substituted, independently, with 1-3 substituents of $R^9$, in conjunction with any of the above or below embodiments.

In another embodiment, the invention includes compounds wherein $R^2$ is F, Cl, Br, I, haloalkyl, haloalkoxyl, $C_{1-6}$alkyl, $C_{2-6}$alkenyl, $C_{2-6}$alkynyl, CN, —$OC_{1-6}$alkyl, —$SC_{1-6}$alkyl, —$NHC_{1-6}$alkyl, —$N(C_{1-3}$alkyl$)_2$, —NH-phenyl, —NH-benzyl, —$Si(CH_3)_3$ or a ring selected from the group consisting of phenyl, pyridyl, pyrimidyl, pyrazinyl, pyridazinyl, triazinyl, thienyl, pyrazolyl, imidazolyl, oxazolyl, isoxazolyl, thiazolyl, isothiazolyl, diazolyl, triazolyl, tetrazolyl, pyranyl, dihydropyranyl, tetrahydropyranyl, furanyl, dihydrofuranyl, tetrahydrofuranyl, pyrrolyl, dihydropyrrolyl, pyrrolidinyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopropyl, cyclobutyl, cyclopentyl and cyclohexyl, wherein the $C_{1-6}$-alkyl, $C_{2-4}$alkenyl, $C_{2-4}$alkynyl, —$OC_{1-6}$alkyl, —$SC_{1-6}$alkyl, —$NHC_{1-6}$alkyl, —$N(C_{1-3}$alkyl$)_2$, —NH-phenyl, —NH-benzyl and ring are optionally substituted, independently, with 1-3 substituents of $R^9$, in conjunction with any of the above or below embodiments.

In another embodiment, the invention includes compounds wherein $R^2$ is $C_{3-6}$alkyl, $C_{2-6}$alkynyl, —$OC_{1-6}$alkyl, —$SC_{1-6}$alkyl, phenyl, pyridyl, pyrimidyl, pyrazinyl, pyridazinyl, dihydropyranyl, tetrahydropyranyl, pyrrolidinyl, piperidinyl, morpholinyl, cyclopropyl or 8-oxo-3-aza-bicyclo[3.2.1]oct-3-yl, wherein the $C_{3-6}$-alkyl, $C_{2-6}$alkynyl, —$OC_{1-6}$alkyl, —$SC_{1-6}$alkyl, phenyl, pyridyl, pyrimidyl, pyrazinyl, pyridazinyl, dihydropyranyl, tetrahydropyranyl, pyrrolidinyl, piperidinyl, morpholinyl, cyclopropyl and 8-oxo-3-aza-bicyclo[3.2.1]oct-3-yl are optionally substituted, independently, with 1-3 substituents of $R^9$, in conjunction with any of the above or below embodiments.

In another embodiment, the invention includes compounds wherein $R^2$ is $C_{2-6}$alkynyl, —$OC_{1-6}$alkyl, pyridyl, pyrimidyl, dihydropyranyl, tetrahydropyranyl, cyclopropyl, pyrrolidinyl or piperidinyl, wherein the $C_{2-6}$alkynyl, —$OC_{1-6}$alkyl, pyridyl, pyrimidyl, dihydropyranyl, tetrahydropyranyl, cyclopropyl, pyrrolidinyl and piperidinyl are optionally substituted, independently, with 1-3 substituents of $R^9$, in conjunction with any of the above or below embodiments.

In another embodiment, the invention includes compounds wherein $R^2$ is F, Cl, Br, I, $C_{1-6}$-alkyl, $C_{2-6}$alkenyl, $C_{2-6}$alkynyl, CN, —$OC_{1-6}$alkyl, —$SC_{1-6}$alkyl, 3-methyl-3-oxetanyl-ethynyl, 3-methyl-3-oxetanyl-methoxyl, 3,3-dimethyl-butyn-1-yl, 3-methyl-3-butyn-1-yl, 2,2-dimethyl-3-cyano-propoxyl, 2-fluoro-2-methyl-propoxyl, or a ring selected from the group consisting of phenyl, 2-pyridyl, 3-pyridyl, 4-pyridyl, dihydro-2H-pyran-4-yl, dihydro-2H-pyran-3-yl, tetrahydropyran-4-yl, dihydrofuranyl, tetrahydrofuranyl, pyrrolidin-1-yl, piperidin-1-yl, morpholinyl, cyclopropyl, 8-oxo-3-aza-bicyclo[3.2.1]oct-3-yl, aza-bicyclo[2.2.1]hept-5-yl and 2-oxo-7-aza-[3,5]-spironon-7-yl, wherein the $C_{1-6}$-alkyl, $C_{2-4}$alkenyl, $C_{2-4}$alkynyl, —$OC_{1-6}$alkyl, —$SC_{1-6}$alkyl, 3-methyl-3-oxetanyl-ethynyl, 3-methyl-3-oxetanyl-methoxyl, 3,3-dimethyl-butyn-1-yl, 3-methyl-3-butyn-1-yl, 2,2-dimethyl-3-cyano-propoxyl, 2-fluoro-2-methyl-propoxyl and ring are optionally substituted, independently, with 1-3 substituents of $R^9$, in conjunction with any of the above or below embodiments.

In another embodiment, the invention includes compounds wherein $R^2$ is 2-fluoro-4-pyridyl, 2-methyl-4-pyridyl, 5-fluoro-3-pyridyl, 4-pyridyl, 2-fluoro-2-methylpropoxyl, 3 fluoro pyrrolidin 1-yl, 4,4-difluoro-1-piperidinyl, 3-methyl-3-oxetanyl-ethyn-1-yl, 3,3-dimethyl-butyn-1-yl, 4-methylphenyl, 4-fluorophenyl, 5,6-dihydro-2H-pyran-3-yl, 3,6-dihydro-2H-pyran-4-yl, 3,4-difluorophenyl, 2,2-dimethylpropoxyl, 2,2-dimethyl-2-cyano-propoxyl, 3,3-difluoro-1-pyrrolidinyl, 4-morpholinyl or cyclopropyl, in conjunction with any of the above or below embodiments.

In another embodiment, the invention includes compounds wherein $R^2$ is F, Cl, Br, I, haloalkyl, haloalkoxyl, $C_{1-6}$alkyl, $C_{2-6}$alkenyl, $C_{2-6}$alkynyl, CN, —$OC_{1-6}$alkyl, —$SC_{1-6}$alkyl, —$NHC_{1-6}$alkyl, —$N(C_{1-3}$alkyl$)_2$, —$Si(CH_3)_3$ or a ring selected from the group consisting of phenyl, pyridyl, pyrimidyl, pyrazinyl, pyridazinyl, triazinyl, thienyl, pyrazolyl, imidazolyl, oxazolyl, isoxazolyl, thiazolyl, isothiazolyl, diazolyl, triazolyl, tetrazolyl, pyranyl, dihydropyranyl, tetrahydropyranyl, furanyl, dihydrofuranyl, tetrahydrofuranyl, pyrrolyl, dihydropyrrolyl, pyrrolidinyl, piperidinyl, piperazinyl, morpholinyl, azetidinyl, cyclopropyl, cyclobutyl, cyclopentyl and cyclohexyl, wherein the $C_{1-6}$ alkyl, $C_{2-4}$alkenyl, $C_{2-4}$alkynyl, —$OC_{1-6}$alkyl, —$SC_{1-6}$alkyl, —$NHC_{1-6}$alkyl, —$N(C_{1-3}$alkyl$)_2$ and ring are optionally substituted, independently, with 1-3 substituents of $R^9$, in conjunction with any of the above or below embodiments.

In another embodiment, the invention includes compounds wherein $R^2$ is F, Cl, Br, —$OC_{1-6}$alkyl, cyclopropyl, dihydropyranyl or tetrahydropyranyl, wherein the —$OC_{1-6}$alkyl, cyclopropyl, dihydropyranyl or tetrahydropyranyl are optionally substituted independently with 1-5 substituents of $R^9$, in conjunction with any of the above or below embodiments.

In another embodiment, the invention includes compounds wherein $R^2$ is a ring selected from the group consisting of pyridine, pyrrolidine, piperidine, phenyl, dihydropyran and morpholine or $R^2$ is —O—$C_{1-6}$alkyl, $C_{1-6}$alkynyl, wherein the ring, —O—$C_{1-6}$alkyl and $C_{1-6}$alkynyl are optionally substituted independently with 1-5 substituents of $R^9$, in conjunction with any of the above or below embodiments.

In another embodiment, the invention includes compounds wherein $R^3$ is H or F, in conjunction with any of the above or below embodiments.

In another embodiment, the invention includes compounds wherein $R^3$ is F, in conjunction with any of the above or below embodiments.

In another embodiment, the invention includes compounds wherein $R^4$ is H or F, in conjunction with any of the above or below embodiments.

In another embodiment, the invention includes compounds wherein $R^4$ is F, in conjunction with any of the above or below embodiments.

In another embodiment, the invention includes compounds wherein $R^7$ is F, Cl, Br, I, haloalkyl, haloalkoxyl, $C_{1-6}$-alkyl, $C_{2-6}$alkenyl, $C_{2-6}$alkynyl, CN, —$OC_{1-6}$alkyl, —$SC_{1-6}$alkyl, —$NHC_{1-6}$alkyl, —$N(C_{1-3}$alkyl$)_2$, —NH-phenyl, —NH-benzyl, —Si(CH$_3$)$_3$ or a ring selected from the group consisting of phenyl, pyridyl, pyrimidyl, pyrazinyl, pyridazinyl, triazinyl, thienyl, pyrazolyl, imidazolyl, oxazolyl, isoxazolyl, thiazolyl, isothiazolyl, diazolyl, triazolyl, tetrazolyl, pyranyl, dihydropyranyl, tetrahydropyranyl, furanyl, dihydrofuranyl, tetrahydrofuranyl, pyrrolyl, dihydropyrrolyl, pyrrolidinyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopropyl, cyclobutyl, cyclopentyl and cyclohexyl, wherein the $C_{1-6}$-alkyl, $C_{2-4}$alkenyl, $C_{2-4}$alkynyl, —$OC_{1-6}$alkyl, —$SC_{1-6}$alkyl, —$NHC_{1-6}$alkyl, —$N(C_{1-3}$alkyl$)_2$, —NH-phenyl, —NH-benzyl and ring are optionally substituted, independently, with 1-3 substituents of $R^9$, in conjunction with any of the above or below embodiments.

In another embodiment, the invention includes compounds wherein $R^7$ is $C_{2-4}$alkynyl, —$OC_{1-6}$alkyl, phenyl, pyridyl, pyrimidyl, pyrazinyl, pyridazinyl or thiazolyl, wherein the $C_{2-4}$alkynyl, —$OC_{1-6}$alkyl, pyridyl, pyrimidyl, pyrazinyl, pyridazinyl and thiazolyl are optionally substituted, independently, with 1-3 substituents of $R^9$, in conjunction with any of the above or below embodiments.

In another embodiment, the invention includes compounds wherein $R^7$ is $C_{2-4}$alkynyl, —$OC_{1-6}$alkyl, phenyl, 3-pyridyl, 5-pyrimidyl, 2-pyrazinyl, thiazolyl or 2-pyridazinyl, wherein the $C_{2-4}$alkynyl, —$OC_{1-6}$alkyl, 3-pyridyl, 5-pyrimidyl, 2-pyrazinyl, thiazolyl and 2-pyridazinyl are optionally substituted, independently, with 1-3 substituents of $R^9$, in conjunction with any of the above or below embodiments.

In another embodiment, the invention includes compounds wherein $R^7$ is a ring selected from the group consisting of phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, pyrrolidinyl, piperidinyl, piperazinyl and morpholinyl, said ring optionally substituted, independently, with 1-3 substituents of R, in conjunction with any of the above or below embodiments.

In another embodiment, the invention includes compounds wherein $R^7$ is a ring selected from phenyl, 3-pyridyl, 5-pyrimidyl, 1,3-thiazolyl or 2-pyrazinyl, said ring optionally substituted, independently, with 1-5 substituents of $R^9$, in conjunction with any of the above or below embodiments.

In another embodiment, the invention includes compounds wherein $R^7$ is phenyl, 3-pyridyl, 5-pyrimidyl, 1,3-thiazolyl or 2-pyridazinyl, each of which is optionally substituted with 1-5 substituents of F, Cl, Br, I, CN, CF$_3$, C$_2$F$_5$, haloalkoxyl, $C_{1-6}$-alkyl, CN, OH, $OC_{1-6}$-alkyl, $SC_{1-6}$-alkyl, oxetanyl or $C_{2-3}$alkynyl, in conjunction with any of the above or below embodiments.

In another embodiment, the invention includes compounds wherein $R^7$ is 3-pyridyl, 2-fluoro-3-pyridyl, 2,5-difluorophenyl, 3,3-dimethyl-1-butynyl, 3-cyanophenyl, 5-fluoro-3-pyridyl, 3,4-difluorophenyl or 1,3-thiazolyl, in conjunction with any of the above or below embodiments.

In another embodiment, the invention includes compounds wherein $R^7$ is 2-fluoro-3-pyridyl, 3-pyridyl, 5-fluoro-3-pyridyl, 2,5-difluorophenyl or 3-fluorophenyl, in conjunction with any of the above or below embodiments.

In another embodiment, the invention includes compounds wherein $R^7$ is a ring selected from the group consisting of pyridine and phenyl, wherein the ring is optionally substituted independently with 1-3 substituents of $R^9$, in conjunction with any of the above or below embodiments.

In another embodiment, the invention includes compounds wherein $R^7$ is phenyl, pyridyl, pyrimidyl, pyrazinyl or pyridazinyl, each of which is optionally substituted, independently, with 1-3 substituents of $R^9$, in conjunction with any of the above or below embodiments.

In another embodiment, the invention includes compounds wherein $R^7$ is $C_{2-4}$alkynyl, —$OC_{1-6}$alkyl, phenyl, pyridyl, pyrimidyl, pyrazinyl or pyridazinyl, wherein the $C_{2-4}$alkynyl, —$OC_{1-6}$alkyl, pyridyl, pyrimidyl, pyrazinyl and pyridazinyl are optionally substituted, independently, with 1-3 substituents of $R^9$, in conjunction with any of the above or below embodiments.

In another embodiment, the invention includes compounds wherein L is —C(=O)NH—, —C(=O)N(CH$_3$)—, —NH—, —N(CH$_3$)— or —O—, in conjunction with any of the above or below embodiments.

In another embodiment, the invention includes compounds wherein L is —C(=O)NH—, —C(=O)N(CH$_3$)—, —NH— or —N(CH$_3$)—, in conjunction with any of the above or below embodiments.

In another embodiment, the invention includes compounds wherein L is —C(=O)NH—, —NH— or —O—, in conjunction with any of the above or below embodiments.

In another embodiment, the invention includes compounds wherein L is —C(=O)NH—, in conjunction with any of the above or below embodiments.

In another embodiment, the invention includes compounds wherein L is —C(=O)NH— or —NH—, in conjunction with any of the above or below embodiments.

In another embodiment, the invention includes compounds wherein L is —NH—, in conjunction with any of the above or below embodiments.

In another embodiment, the invention includes compounds wherein L is —O—, in conjunction with any of the above or below embodiments.

In another embodiment, the invention includes compounds of Formulas I, II, III and IV, or a sub-Formulas thereof, wherein L is —C(=O)NH— or —NH—;

$R^2$ is halo, haloalkyl, haloalkoxyl, $C_{1-6}$-alkyl, $C_{2-6}$alkenyl, $C_{2-6}$alkynyl, CN, —$OC_{1-6}$alkyl, —$SC_{1-6}$alkyl, phenyl, pyridyl, pyrimidyl, pyrazinyl, pyridazinyl, dihydropyranyl, tetrahydropyranyl, pyrrolidinyl, piperidinyl, morpholinyl, cyclopropyl or 8-oxo-3-aza-bicyclo[3.2.1]oct-3-yl, wherein the $C_{1-6}$-alkyl, $C_{2-6}$alkenyl, $C_{2-6}$alkynyl —$OC_{1-6}$alkyl, —$SC_{1-6}$alkyl, phenyl, pyridyl, pyrimidyl, pyrazinyl, pyridazinyl, dihydropyranyl, tetrahydropyranyl, pyrrolidinyl, piperidinyl, morpholinyl, cyclopropyl and 8-oxo-3-aza-bicyclo[3.2.1]oct-3-yl, are optionally substituted, independently, with 1-3 substituents of $R^9$;

each of $R^1$, $R^4$, $R^5$ and $R^8$, independently, is H, F, methyl, CN or OH;

each of $R^3$ and $R^6$, independently, is H, F, Cl, $CF_3$, methyl, CN, OH, $OCH_3$, $SCH_3$ or $NHCH_3$;

$R^7$ is a ring selected from the group consisting of phenyl, pyridyl, pyrimidyl, pyridazinyl, pyrazinyl, triazinyl, thiazolyl and thienyl, said ring optionally substituted, independently, with 1-3 substituents of $R^9$;

each $R^9$, independently, is halo, haloalkyl, CN, OH, $NO_2$, $NH_2$, acetyl, —C(O)$NHCH_3$, oxo, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolidinyl, piperazinyl, oxetanyl or dioxolyl, wherein each of the $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolidinyl, oxetanyl, spiro-oxetanyl or dioxolyl, is optionally substituted independently with 1-5 substituents of F, Cl, CN, $NO_2$, $NH_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, $C_{1-3}$alkylamino-, $C_{1-3}$dialkylamino, $C_{1-3}$thioalkoxyl, or oxetanyl;

X is —$CH_2$—, —O— or —S—;

Y is —O—, —S— or —$CH_2$—, provided that (1) when X is —O— or —S—, then Y is —$CH_2$—, or (2) when X is —$CH_2$—, then Y is —O— or —S—; and Z is $CH_2$ (Z is present only in formula I)

In another embodiment, the invention includes compounds wherein each $R^8$, independently, is F, Cl, $CF_3$, $OCF_3$, methyl, CN, OH, $OCH_3$, $SCH_3$, $NHCH_3$, oxetanyl or $C_{2-3}$alkynyl, in conjunction with any of the above or below embodiments.

In another embodiment, the invention includes compounds wherein each $R^9$, independently, is halo, haloalkyl, CN, OH, $NO_2$, $NH_2$, acetyl, —C(O)$NHCH_3$, oxo, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolidinyl, piperazinyl, oxetanyl or dioxolyl, wherein each of the $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolidinyl, oxetanyl or dioxolyl, is optionally substituted independently with 1-5 substituents of F, Cl, CN, $NO_2$, $NH_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, $C_{1-3}$alkylamino-, $C_{1-3}$dialkylamino, $C_{1-3}$thioalkoxyl, $C_{1-4}$alkenyl, $C_{1-4}$alkynyl or oxetanyl, in conjunction with any of the above or below embodiments.

In another embodiment, the invention includes compounds wherein each $R^9$, independently, is F, Cl, Br, $CF_3$, $OCF_3$, CN, OH, $NH_2$, acetyl, —C(O)$NHCH_3$, oxo, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl or oxetanyl, in conjunction with any of the above or below embodiments.

In another embodiment, the invention includes compounds wherein each $R^9$ is, independently, F, Cl, Br, $C_{1-6}$alkyl, $C_{1-6}$alkenyl, $C_{1-6}$alkynyl, —$OC_{1-6}$alkyl, CN, CF3, —$OCF_3$ or spiro-oxetanyl, in conjunction with any of the above or below embodiments.

In another embodiment, the invention includes compounds wherein each $R^9$, independently, is F, $CF_3$, CN, $CH_3$, —$OCH_3$, —$SCH_3$, —$NHCH_3$, spiro-oxetanyl or $C_{2-3}$alkynyl, in conjunction with any of the above or below embodiments.

In another embodiment, the invention includes compounds wherein each $R^9$ is, independently, F, Cl, Br, $C_{1-6}$alkyl, $C_{1-6}$alkenyl, $C_{1-6}$alkynyl, —$OC_{1-6}$alkyl, CN, CF3, —$OCF_3$ or spiro-oxetanyl, in conjunction with any of the above or below embodiments.

In another embodiment, the invention provides the compounds, individually and collectively, of Formulas I, II, III and IV, and sub-Formulas thereof, or a pharmaceutically acceptable salt thereof, selected from the individual compounds described and listed in Table I.

In another embodiment SP1, the invention provides the compound of Formulas I, II and III, or a stereoisomer or pharmaceutically acceptable salt thereof, selected from N-((5S)-2'-amino-3-bromo-5',6'-dihydrospiro[chromeno[2,3-b]pyridine-5,4'-[1,3]oxazin]-7-yl)-5-chloro-2-pyridinecarboxamide;

N-((5S)-2'-amino-3-bromo-5',6'-dihydrospiro[chromeno[2,3-b]pyridine-5,4'-[1,3]oxazin]-7-yl)-5-hydroxy-2-pyrazinecarboxamide;

N-((5S)-2'-amino-3-bromo-5',6'-dihydrospiro[chromeno[2,3-b]pyridine-5,4'-[1,3]oxazin]-7-yl)-5-methoxy-2-pyrazinecarboxamide;

N-((5S)-2'-amino-3-chloro-1-fluoro-5',6'-dihydrospiro[chromeno[2,3-c]pyridine-5,4'-[1,3]oxazin]-7-yl)-5-chloro-2-pyridinecarboxamide;

N-((5S)-2'-amino-3-chloro-1-fluoro-5',6'-dihydrospiro[chromeno[2,3-c]pyridine-5,4'-[1,3]oxazin]-7-yl)-5-cyano-2-pyridinecarboxamide;

N-((5S)-2'-amino-3-chloro-1-fluoro-5',6'-dihydrospiro[chromeno[2,3-c]pyridine-5,4'-[1,3]oxazin]-7-yl)-5-methoxy-2-pyrazinecarboxamide;

N-((5S)-2'-amino-3-chloro-1-fluoro-5',6'-dihydrospiro[chromeno[2,3-c]pyridine-5,4'-[1,3]oxazin]-7-yl)-5-(2-butyn-1-yloxy)-2-pyrazinecarboxamide;

N-((5S)-2'-amino-3-chloro-1-fluoro-5',6'-dihydrospiro[chromeno[2,3-c]pyridine-5,4'-[1,3]oxazin]-7-yl)-5-chloro-2-pyrazinecarboxamide;

N-((4S)-2-amino-5'-fluoro-7'-methoxy-5,6-dihydrospiro[1,3-thiazine-4,9'-xanthen]-2'-yl)-5-chloro-2-pyridinecarboxamide;

N-((4S)-2-amino-5'-fluoro-7'-methoxy-5,6-dihydrospiro[1,3-thiazine-4,9'-xanthen]-2'-yl)-5-methoxy-2-pyrazinecarboxamide;

N-((5S)-2'-amino-3-(3,6-dihydro-2H-pyran-4-yl)-5',6'-dihydrospiro[chromeno[2,3-b]pyridine-5,4'-[1,3]oxazin]-7-yl)-5-chloro-2-pyridinecarboxamide;

N-((4S)-2-amino-5'-fluoro-7'-methoxy-5,6-dihydrospiro[1,3-oxazine-4,9'-xanthen]-2'-yl)-5-chloro-2-pyridinecarboxamide;

N-((5S)-2'-amino-5',6'-dihydrospiro[chromeno[2,3-b]pyridine-5,4'-[1,3]oxazin]-7-yl)-5-chloro-2-pyridinecarboxamide;

N-((5S)-2'-amino-3-bromo-5',6'-dihydrospiro[chromeno[2,3-b]pyridine-5,4'-[1,3]oxazin]-7-yl)-4-chloro-2-fluorobenzamide;

N-((5S)-2'-amino-3-(5,6-dihydro-2H-pyran-3-yl)-1-fluoro-5',6'-dihydrospiro[chromeno[2,3-c]pyridine-5,4'-[1,3]oxazin]-7-yl)-5-chloro-2-pyridinecarboxamide;

N-((5S)-2'-amino-3-(5,6-dihydro-2H-pyran-3-yl)-1-fluoro-5',6'-dihydrospiro[chromeno[2,3-c]pyridine-5,4'-[1,3]oxazin]-7-yl)-5-methoxy-2-pyrazinecarboxamide;

N-((5S)-2'-amino-3-(5,6-dihydro-2H-pyran-3-yl)-1-fluoro-5',6'-dihydrospiro[chromeno[2,3-c]pyridine-5,4'-[1,3]oxazin]-7-yl)-5-cyano-2-pyridinecarboxamide;

N-((5S)-2'-amino-3-cyclopropyl-1-methoxy-5',6'-dihydrospiro[chromeno[2,3-c]pyridine-5,4'-[1,3]oxazin]-7-yl)-5-chloro-2-pyridinecarboxamide;

N-((5S)-2'-amino-3-cyclopropyl-1-fluoro-5',6'-dihydrospiro[chromeno[2,3-c]pyridine-5,4'-[1,3]oxazin]-7-yl)-5-chloro-2-pyridinecarboxamide;

N-((5S)-2'-amino-3-cyclopropyl-1-fluoro-5',6'-dihydrospiro[chromeno[2,3-c]pyridine-5,4'-[1,3]oxazin]-7-yl)-5-methoxy-2-pyrazinecarboxamide;

N-((5S)-2'-amino-3-(5,6-dihydro-2H-pyran-3-yl)-5',6'-dihydrospiro[chromeno[2,3-b]pyridine-5,4'-[1,3]oxazin]-7-yl)-5-chloro-2-pyridinecarboxamide;

N-((5R)-2'-amino-3-chloro-1-fluoro-5',6'-dihydrospiro[chromeno[2,3-c]pyridine-5,4'-[1,3]thiazin]-7-yl)-5-methoxy-2-pyrazinecarboxamide; and N-((5S)-2'-amino-3-chloro-1-fluoro-5',6'-dihydrospiro[chromeno[2,3-c]pyridine-5,4'-[1,3]thiazin]-7-yl)-5-methoxy-2-pyrazinecarboxamide.

In another embodiment, the invention provides the compound of Formulas I, II and III, or a stereoisomer or pharmaceutically acceptable salt thereof, selected from (5S)-3-chloro-1-fluoro-N~7~-(3-methyl-2-pyridinyl)-5',6'-dihydrospiro[chromeno[2,3-c]pyridine-5,4'-[1,3]oxazine]-2',7-diamine;

(4S)—N~2~'-(3-ethoxy-2-pyridinyl)-5'-fluoro-7'-methoxy-5,6-dihydrospiro[1,3-thiazine-4,9'-xanthene]-2,2'-diamine;

(4S)—N~2~'-(3-(benzyloxy)-2-pyridinyl)-5'-fluoro-7'-methoxy-5,6-dihydrospiro[1,3-oxazine-4,9'-xanthene]-2,2'-diamine; and (4S)—N~2~'-(3-ethoxy-2-pyridinyl)-5'-fluoro-7'-methoxy-5,6-dihydrospiro[1,3-oxazine-4,9'-xanthene]-2,2'-diamine.

In another embodiment SP2, the invention provides the compounds individually and collectively, of Formulas I, II, III and IV, and sub-Formulas thereof, or a pharmaceutically acceptable salt thereof, selected from the individual compounds described and listed in Table II.

In another embodiment SP3, the invention provides the compound of Formulas I, II and III, or a pharmaceutically acceptable salt thereof, selected from N-((5S)-2'-amino-3-(5,6-dihydro-2H-pyran-3-yl)-5',6'-dihydrospiro[chromeno[2,3-c]pyridine-5,4'-[1,3]oxazin]-7-yl)-5-methoxy-2-pyrazinecarboxamide;

N-((5S)-2'-amino-3-(5,6-dihydro-2H-pyran-3-yl)-5',6'-dihydrospiro[chromeno[2,3-c]pyridine-5,4'-[1,3]oxazin]-7-yl)-5-chloro-2-pyridinecarboxamide;

N-((5S)-2'-amino-3-(3,6-dihydro-2H-pyran-4-yl)-1-fluoro-5',6'-dihydrospiro[chromeno[2,3-c]pyridine-5,4'-[1,3]oxazin]-7-yl)-5-chloro-2-pyridinecarboxamide;

N-((5S)-2'-amino-3-(3,6-dihydro-2H-pyran-4-yl)-1-fluoro-5',6'-dihydrospiro[chromeno[2,3-c]pyridine-5,4'-[1,3]oxazin]-7-yl)-5-cyano-2-pyridinecarboxamide;

N-((5S)-2'-amino-3-(3,6-dihydro-2H-pyran-4-yl)-1-fluoro-5',6'-dihydrospiro[chromeno[2,3-c]pyridine-5,4'-[1,3]oxazin]-7-yl)-5-methoxy-2-pyrazinecarboxamide;

N-((5S)-2'-amino-3-(5,6-dihydro-2H-pyran-3-yl)-1-fluoro-5',6'-dihydrospiro[chromeno[2,3-c]pyridine-5,4'-[1,3]thiazin]-7-yl)-5-methoxy-2-pyrazinecarboxamide;

N-((5S)-2'-amino-3-(3,6-dihydro-2H-pyran-4-yl)-1-fluoro-5',6'-dihydrospiro[chromeno[2,3-c]pyridine-5,4'-[1,3]thiazin]-7-yl)-5-methoxy-2-pyrazinecarboxamide;

N-((5S)-2'-amino-3-(5,6-dihydro-2H-pyran-3-yl)-1-fluoro-5',6'-dihydrospiro[chromeno[2,3-c]pyridine-5,4'-[1,3]thiazin]-7-yl)-5-chloro-2-pyridinecarboxamide;

N-((5S)-2'-amino-1-fluoro-3-(5-fluoro-3-pyridinyl)-5',6'-dihydrospiro[chromeno[2,3-c]pyridine-5,4'-[1,3]oxazin]-7-yl)-5-cyano-2-pyridinecarboxamide;

N-((5S)-2'-amino-1-fluoro-3-(5-fluoro-3-pyridinyl)-5',6'-dihydrospiro[chromeno[2,3-c]pyridine-5,4'-[1,3]oxazin]-7-yl)-5-methoxy-2-pyrazinecarboxamide;

N-((5S)-2'-amino-1-fluoro-3-(5-fluoro-3-pyridinyl)-5',6'-dihydrospiro[chromeno[2,3-c]pyridine-5,4'-[1,3]oxazin]-7-yl)-5-chloro-2-pyridinecarboxamide;

N-((5S)-2'-amino-3-(3,6-dihydro-2H-pyran-4-yl)-1-fluoro-5',6'-dihydrospiro[chromeno[2,3-c]pyridine-5,4'-[1,3]oxazin]-7-yl)-5-fluoro-2-pyridinecarboxamide;

N-((5S)-2'-amino-3-cyclopropyl-5',6'-dihydrospiro[chromeno[2,3-b]pyridine-5,4'-[1,3]oxazin]-7-yl)-5-chloro-2-pyridinecarboxamide;

N-((4S)-2-amino-5'-fluoro-7'-methoxy-5,6-dihydrospiro[1,3-oxazine-4,9'-xanthen]-2'-yl)-5-cyano-2-pyridinecarboxamide;

N-((4S)-2-amino-5'-fluoro-7'-methoxy-5,6-dihydrospiro[1,3-oxazine-4,9'-xanthen]-2'-yl)-5-methoxy-2-pyrazinecarboxamide;

N-((4S)-2-amino-5'-fluoro-7'-methoxy-5,6-dihydrospiro[1,3-oxazine-4,9'-xanthen]-2'-yl)-4-chloro-2-fluorobenzamide;

N-((4S)-2-amino-5'-fluoro-7'-methoxy-5,6-dihydrospiro[1,3-oxazine-4,9'-xanthen]-2'-yl)-2-fluoro-4-methoxybenzamide;

N-((5S)-2'-amino-3-(3,6-dihydro-2H-pyran-4-yl)-1-fluoro-5',6'-dihydrospiro[chromeno[2,3-c]pyridine-5,4'-[1,3]oxazin]-7-yl)-5-methoxy-2-pyridinecarboxamide;

N-((5S)-2'-amino-3-chloro-5',6'-dihydrospiro[chromeno[2,3-c]pyridine-5,4'-[1,3]oxazin]-7-yl)-5-chloro-2-pyridinecarboxamide;

N-((5S)-2'-amino-3-cyclopropyl-5',6'-dihydrospiro[chromeno[2,3-c]pyridine-5,4'-[1,3]oxazin]-7-yl)-5-methoxy-2-pyrazinecarboxamide;

N-((5S)-2'-amino-3-cyclopropyl-5',6'-dihydrospiro[chromeno[2,3-c]pyridine-5,4'-[1,3]oxazin]-7-yl)-5-chloro-2-pyridinecarboxamide;

N-((5S)-2'-amino-3-(3,3-dimethyl-1-butyn-1-yl)-5',6'-dihydrospiro[chromeno[2,3-c]pyridine-5,4'-[1,3]oxazin]-7-yl)-5-chloro-2-pyridinecarboxamide;

N-((5S)-2'-amino-3-(5,6-dihydro-2H-pyran-3-yl)-1-fluoro-5',6'-dihydrospiro[chromeno[2,3-c]pyridine-5,4'-[1,3]oxazin]-7-yl)-5-fluoro-2-pyridinecarboxamide;

N-((5S)-2'-amino-3-(5,6-dihydro-2H-pyran-3-yl)-1-fluoro-5',6'-dihydrospiro[chromeno[2,3-c]pyridine-5,4'-[1,3]oxazin]-7-yl)-5-methoxy-2-pyridinecarboxamide;

N-((5S)-2'-amino-3-(5,6-dihydro-2H-pyran-3-yl)-1-fluoro-5',6'-dihydrospiro[chromeno[2,3-c]pyridine-5,4'-[1,3]oxazin]-7-yl)-2-methyl-1,3-thiazole-4-carboxamide;

N-((5S)-2'-amino-3-(3,3-dimethyl-1-butyn-1-yl)-5',6'-dihydrospiro[chromeno[2,3-c]pyridine-5,4'-[1,3]oxazin]-7-yl)-5-methoxy-2-pyrazinecarboxamide;

N-((5S)-2'-amino-1-fluoro-3-(5-fluoro-3-pyridinyl)-5',6'-dihydrospiro[chromeno[2,3-c]pyridine-5,4'-[1,3]oxazin]-7-yl)-5-methoxy-2-pyridinecarboxamide;

N-((5S)-2'-amino-1-fluoro-3-(5-fluoro-3-pyridinyl)-5',6'-dihydrospiro[chromeno[2,3-c]pyridine-5,4'-[1,3]oxazin]-7-yl)-2-methyl-1,3-thiazole-4-carboxamide;

N-((5S)-2'-amino-1-fluoro-3-(5-fluoro-3-pyridinyl)-5',6'-dihydrospiro[chromeno[2,3-c]pyridine-5,4'-[1,3]oxazin]-7-yl)-5-fluoro-2-pyridinecarboxamide;

N-((5S)-2'-amino-3-(2-fluoro-4-pyridinyl)-5',6'-dihydrospiro[chromeno[2,3-b]pyridine-5,4'-[1,3]oxazin]-7-yl)-5-chloro-2-pyridinecarboxamide;

N-((5S)-2'-amino-1-fluoro-3-(2-fluoro-4-pyridinyl)-5',6'-dihydrospiro[chromeno[2,3-c]pyridine-5,4'-[1,3]oxazin]-7-yl)-5-chloro-2-pyridinecarboxamide;

N-((5S)-2'-amino-1-fluoro-3-(2-fluoro-4-pyridinyl)-5',6'-dihydrospiro[chromeno[2,3-c]pyridine-5,4'-[1,3]oxazin]-7-yl)-5-methoxy-2-pyrazinecarboxamide;
N-((5S)-2'-amino-3-(2-fluoro-4-pyridinyl)-5',6'-dihydrospiro[chromeno[2,3-c]pyridine-5,4'-[1,3]oxazin]-7-yl)-5-methoxy-2-pyrazinecarboxamide;
N-((5S)-2'-amino-3-(2-fluoro-4-pyridinyl)-5',6'-dihydrospiro[chromeno[2,3-c]pyridine-5,4'-[1,3]oxazin]-7-yl)-5-chloro-2-pyridinecarboxamide;
N-((4S)-2-amino-5'-fluoro-7'-(2-fluoro-4-pyridinyl)-5,6-dihydrospiro[1,3-oxazine-4,9'-xanthen]-2'-yl)-5-methoxy-2-pyrazinecarboxamide;
N-((5S)-2'-amino-3-(3,6-dihydro-2H-pyran-4-yl)-1-methoxy-5',6'-dihydrospiro[chromeno[2,3-c]pyridine-5,4'-[1,3]oxazin]-7-yl)-5-chloro-2-pyridinecarboxamide;
N-((5S)-2'-amino-3-(3,6-dihydro-2H-pyran-4-yl)-1-methoxy-5',6'-dihydrospiro[chromeno[2,3-c]pyridine-5,4'-[1,3]oxazin]-7-yl)-5-fluoro-2-pyridinecarboxamide;
N-((5S)-2'-amino-1-fluoro-3-(2-fluoro-4-pyridinyl)-5',6'-dihydrospiro[chromeno[2,3-c]pyridine-5,4'-[1,3]oxazin]-7-yl)-5-fluoro-2-pyridinecarboxamide;
N-((5S)-2'-amino-1-fluoro-3-(2-fluoro-4-pyridinyl)-5',6'-dihydrospiro[chromeno[2,3-c]pyridine-5,4'-[1,3]oxazin]-7-yl)-5-methoxy-2-pyridinecarboxamide;
N-((5S)-2'-amino-1-fluoro-3-(2-fluoro-4-pyridinyl)-5',6'-dihydrospiro[chromeno[2,3-c]pyridine-5,4'-[1,3]oxazin]-7-yl)-2-methyl-1,3-thiazole-4-carboxamide;
N-((5S)-2'-amino-1-fluoro-3-(2-fluoro-4-pyridinyl)-5',6'-dihydrospiro[chromeno[2,3-c]pyridine-5,4'-[1,3]oxazin]-7-yl)-5-cyano-2-pyridinecarboxamide;
N-((5S)-2'-amino-3-(3,6-dihydro-2H-pyran-4-yl)-1-fluoro-5',6'-dihydrospiro[chromeno[2,3-c]pyridine-5,4'-[1,3]thiazin]-7-yl)-5-methoxy-2-pyridinecarboxamide;
N-((4S)-2-amino-5'-fluoro-7'-(tetrahydro-2H-pyran-4-yl)-5,6-dihydrospiro[1,3-oxazine-4,9'-xanthen]-2'-yl)-5-methoxy-2-pyrazinecarboxamide;
N-((4S)-2-amino-5'-fluoro-7'-(2-fluoro-4-pyridinyl)-5,6-dihydrospiro[1,3-oxazine-4,9'-xanthen]-2'-yl)-5-fluoro-2-pyridinecarboxamide;
N-((5S)-2'-amino-3-(3,6-dihydro-2H-pyran-4-yl)-5',6'-dihydrospiro[chromeno[2,3-c]pyridine-5,4'-[1,3]thiazin]-7-yl)-5-methoxy-2-pyrazinecarboxamide;
N-((5S)-2'-amino-3-(5,6-dihydro-2H-pyran-3-yl)-5',6'-dihydrospiro[chromeno[2,3-c]pyridine-5,4'-[1,3]thiazin]-7-yl)-5-methoxy-2-pyrazinecarboxamide;
N-((4S)-2-amino-5'-fluoro-7'-hydroxy-5,6-dihydrospiro[1,3-thiazine-4,9'-xanthen]-2'-yl)-5-methoxy-2-pyridinecarboxamide;
N-((4S)-2-amino-7'-(5,6-dihydro-2H-pyran-3-yl)-5'-fluoro-5,6-dihydrospiro[1,3-oxazine-4,9'-xanthen]-2'-yl)-5-methoxy-2-pyrazinecarboxamide;
N-((4S)-2-amino-5'-fluoro-7'-(4-morpholinyl)-5,6-dihydrospiro[1,3-thiazine-4,9'-xanthen]-2'-yl)-5-methoxy-2-pyridinecarboxamide;
N-((4S)-2-amino-5'-fluoro-7'-(2-fluoro-4-pyridinyl)-5,6-dihydrospiro[1,3-oxazine-4,9'-xanthen]-2'-yl)-5-cyano-2-pyridinecarboxamide;
N-((4S)-2-amino-5'-fluoro-7'-hydroxy-5,6-dihydrospiro[1,3-thiazine-4,9'-xanthen]-2'-yl)-5-methoxy-2-pyrazinecarboxamide;
N-((4S)-2-amino-5'-fluoro-7'-(4-morpholinyl)-5,6-dihydrospiro[1,3-thiazine-4,9'-xanthen]-2'-yl)-5-methoxy-2-pyrazinecarboxamide;
N-((4S)-2-amino-7'-(3,6-dihydro-2H-pyran-4-yl)-5'-fluoro-5,6-dihydrospiro[1,3-thiazine-4,9'-xanthen]-2'-yl)-5-methoxy-2-pyrazinecarboxamide;
N-((5S)-2'-amino-3-(5,6-dihydro-2H-pyran-3-yl)-1-fluoro-5',6'-dihydrospiro[chromeno[2,3-c]pyridine-5,4'-[1,3]thiazin]-7-yl)-5-methoxy-2-pyridinecarboxamide;
N-((5S)-2'-amino-1-fluoro-3-(5-fluoro-3-pyridinyl)-5',6'-dihydrospiro[chromeno[2,3-c]pyridine-5,4'-[1,3]thiazin]-7-yl)-5-methoxy-2-pyrazinecarboxamide;
N-((5S)-2'-amino-1-fluoro-3-(5-fluoro-3-pyridinyl)-5',6'-dihydrospiro[chromeno[2,3-c]pyridine-5,4'-[1,3]thiazin]-7-yl)-5-methoxy-2-pyridinecarboxamide;
N-((5S)-2'-amino-1-fluoro-3-(2-fluoro-4-pyridinyl)-5',6'-dihydrospiro[chromeno[2,3-c]pyridine-5,4'-[1,3]thiazin]-7-yl)-5-methoxy-2-pyrazinecarboxamide;
N-((5S)-2'-amino-1-fluoro-3-(2-fluoro-4-pyridinyl)-5',6'-dihydrospiro[chromeno[2,3-c]pyridine-5,4'-[1,3]thiazin]-7-yl)-5-methoxy-2-pyridinecarboxamide;
N-((5S)-2'-amino-3-(3,6-dihydro-2H-pyran-4-yl)-1-fluoro-5',6'-dihydrospiro[chromeno[2,3-c]pyridine-5,4'-[1,3]thiazin]-7-yl)-5-fluoro-2-pyridinecarboxamide;
N-((5S)-2'-amino-3-(3,6-dihydro-2H-pyran-4-yl)-1-fluoro-5',6'-dihydrospiro[chromeno[2,3-c]pyridine-5,4'-[1,3]thiazin]-7-yl)-5-chloro-2-pyridinecarboxamide;
N-((5S)-2'-amino-1-fluoro-3-(2-fluoro-4-pyridinyl)-5',6'-dihydrospiro[chromeno[2,3-c]pyridine-5,4'-[1,3]thiazin]-7-yl)-5-fluoro-2-pyridinecarboxamide;
N-((5S)-2'-amino-3-(3,6-dihydro-2H-pyran-4-yl)-1-fluoro-5',6'-dihydrospiro[chromeno[2,3-c]pyridine-5,4'-[1,3]thiazin]-7-yl)-5-chloro-3-fluoro-2-pyridinecarboxamide;
N-((5S)-2'-amino-3-(3,6-dihydro-2H-pyran-4-yl)-1-fluoro-5',6'-dihydrospiro[chromeno[2,3-c]pyridine-5,4'-[1,3]thiazin]-7-yl)-5-bromo-3-methyl-2-pyridinecarboxamide;
N-((5S)-2'-amino-3-(3,6-dihydro-2H-pyran-4-yl)-1-fluoro-5',6'-dihydrospiro[chromeno[2,3-c]pyridine-5,4'-[1,3]thiazin]-7-yl)-5-methoxy-3-methyl-2-pyridinecarboxamide; and
N-((5S)-2'-amino-3-(3,6-dihydro-2H-pyran-4-yl)-1-fluoro-5',6'-dihydrospiro[chromeno[2,3-c]pyridine-5,4'-[1,3]thiazin]-7-yl)-5-chloro-3-methyl-2-pyridinecarboxamide.

All of the possible embodiments described herein for various of the R groups of the compounds of Formula I may be applied, as appropriate, to compounds of Formulas II, III and IV and any sub-formulas thereof. For instance, the embodiment described for $R^2$ in Formula I may also be included for $R^2$ in Formulas II, III, IV and sub-formulas thereof and vice versa.

In another embodiment, the invention provides each of the exemplified compounds, and stereoisomers, tautomers, solvates, pharmaceutically acceptable salts, derivatives or prodrugs thereof, and related intermediates, described herein.

In another embodiment, the invention provides the exemplified compounds described herein, and pharmaceutically acceptable salt forms of each thereof.

DEFINITIONS

The following definitions should assist in understanding the invention described herein.

The term "comprising" is meant to be open ended, i.e., all encompassing and non-limiting. It may be used herein synonymously with "including" or "having." Comprising is intended to include each and every indicated or recited component or element(s) while not excluding any other components or elements.

The term "$C_{\alpha-\beta}$alkyl", when used either alone or within other terms such as "haloalkyl" and "alkylamino", embraces linear or branched radicals having $\alpha$ to $\beta$ number of carbon atoms (such as $C_1$-$C_{10}$; $C_1$-$C_6$; or $C_1$-$C_4$). Unless otherwise specified, one or more carbon atoms of the "alkyl" radical may be substituted, such as with a cycloalkyl moiety. Examples of "alkyl" radicals include methyl, cyclopropylmethyl, cyclobutylmethyl, cyclopentylmethyl, ethyl, cyclopropylethyl, cyclobutylethyl, cyclopentylethyl, n-propyl, isopropyl, n-butyl, cyclopropylbutyl, isobutyl, sec-butyl, tert-butyl, pentyl, isoamyl, hexyl and the like.

The term "$C_{\alpha-\beta}$alkenyl", when used alone or in combination, embraces linear or branched radicals having at least one carbon-carbon double bond in a moiety having a number of carbon atoms in the range from $\alpha$ and $\beta$. Included within alkenyl radicals are "lower alkenyl" radicals having two to about six carbon atoms and, for example, those radicals having two to about four carbon atoms. Examples of alkenyl radicals include, without limitation, ethenyl, propenyl, allyl, propenyl, butenyl and 4-methylbutenyl. The terms "alkenyl" and "lower alkenyl", embrace radicals having "cis" and "trans" orientations, or alternatively, "E" and "Z" orientations, as appreciated by those of ordinary skill in the art.

The term "$C_{\alpha-\beta}$alkynyl", when used alone or in combination, denotes linear or branched radicals having at least one carbon-carbon triple bond in a moiety having a number of carbon atoms in the range from $\alpha$ and $\beta$. Examples of alkynyl radicals include "lower alkynyl" radicals having two to about six carbon atoms and, for example, lower alkynyl radicals having two to about four carbon atoms. Examples of such radicals include, without limitation, ethynyl, propynyl (propargyl), butynyl, and the like.

The term "$C_{\alpha-\beta}$-alkyl", "$C_{\alpha-\beta}$-alkenyl" and "$C_{\alpha-\beta}$-alkynyl", when used with other terms such as "wherein 1, 2 or 3 carbon atoms of said $C_{\alpha-\beta}$-alkyl, $C_{\alpha-\beta}$-alkenyl or $C_{2\alpha-\beta}$-alkynyl is optionally replaced with a heteroatom selected from O, S, S(O), S(O)$_2$ and N" embraces linear or branched radicals wherein one or more of the carbon atoms may be replaced with a heteroatom. Examples of such "alkyl" radicals include —O-methyl, —O-ethyl, —CH$_2$—O—CH$_3$, —CH$_2$CH$_2$—O—CH$_3$, —NH—CH$_2$, —CH$_2$CH$_2$—N(CH$_3$)—CH$_3$, —S—(CH$_2$)$_3$CH$_2$, —CH$_2$CH$_2$—S—CH$_3$ and the like. Accordingly, such radicals also include radicals encompassed by —R$^7$ where R$^7$ may be defined as a $C_{\alpha-\beta}$-alkyl. Examples of such "alkenyl" radicals include —NH—CH$_2$CH=CH$_2$, —S—CH$_2$CH$_2$CH=CHCH$_3$ and the like. Similar examples exist for such "alkynyl" radicals, as appreciated by those skilled in the art.

The term "$C_{\alpha-\beta}$alkoxyl" when used alone or in combination, embraces linear or branched oxygen-containing alkyl radicals each having $\alpha$ to $\beta$ number of carbon atoms (such as $C_1$-$C_{10}$). The terms "alkoxy" and "alkoxyl", when used alone or in combination, embraces linear or branched oxygen-containing radicals each having alkyl and substituted alkyl portions of one or more carbon atoms. Examples of such radicals include methoxy (—OCH$_3$), ethoxy, propoxy, butoxy and tert-butoxy. Alkoxy radicals may be further substituted with one or more halo atoms, such as fluoro, chloro or bromo, to provide "haloalkoxyl" radicals or with other substitution. Examples of such radicals include fluoromethoxy, chloromethoxy, trifluoromethoxy (—OCF$_3$), trifluoroethoxy, fluoroethoxy, fluoropropoxy and cyclopropylmethoxy.

The term "aryl", when used alone or in combination, means a carbocyclic aromatic moiety containing one, two or even three rings wherein such rings may be attached together in a fused manner. Every ring of an "aryl" multi-ring system need not be aromatic, and the ring(s) fused to the aromatic ring may be partially or fully unsaturated and include one or more heteroatoms selected from nitrogen, oxygen and sulfur. Thus, the term "aryl" embraces aromatic radicals such as phenyl, naphthyl, indenyl, tetrahydronaphthyl, dihydrobenzafuranyl, anthracenyl, indanyl, benzodioxazinyl, and the like. The "aryl" group may be substituted, such as with 1 to 5 substituents including lower alkyl, hydroxyl, halo, haloalkyl, nitro, cyano, alkoxy and lower alkylamino, and the like. Phenyl substituted with —O—CH$_2$—O— or —O—CH$_2$—CH$_2$—O— forms an aryl benzodioxolyl substituent.

The term "carbocyclic", also referred to herein as "cycloalkyl" or, when used alone or in combination, means a partially or fully saturated ring moiety containing one ("monocyclic"), two ("bicyclic") or even three ("tricyclic") rings wherein such rings may be attached together in a fused manner and formed from carbon atoms. The term "$C_{\alpha-\beta}$cycloalkyl" means cycloalkyl radicals each having $\alpha$ to $\beta$ number of carbon atoms. Examples of saturated carbocyclic radicals include saturated 3 to 6-membered monocyclic groups such as cyclopropane, cyclobutane, cyclopentane and cyclohexane. Carbocyclic may be substituted as described herein.

The term "cycloalkenyl", when used alone or in combination, means a partially or fully saturated cycloalkyl containing one, two or even three rings in a structure having at least one carbon-carbon double bond in the structure. Examples of cycloalkenyl groups include $C_3$-$C_6$ rings, such as compounds including, without limitation, cyclopropene, cyclobutene, cyclopentene and cyclohexene. The term also includes carbocyclic groups having two or more carbon-carbon double bonds such as "cycloalkyldienyl" compounds. Examples of cycloalkyldienyl groups include, without limitation, cyclopentadiene and cycloheptadiene.

The term "halo", when used alone or in combination, means halogens such as fluorine (F), chlorine (Cl), bromine (Br) or iodine (I) atoms.

The term "haloalkyl", when used alone or in combination, embraces $C_{1-6}$alkyl radicals wherein any one or more of the alkyl carbon atoms is substituted with halo as defined above. For example, this term includes monohaloalkyl, dihaloalkyl and polyhaloalkyl radicals such as a perhaloalkyl. A monohaloalkyl radical, for example, may have either an iodo, bromo, chloro or fluoro atom within the radical. Dihalo and polyhaloalkyl radicals may have two or more of the same halo atoms or a combination of different halo radicals. Examples of haloalkyl radicals include fluoromethyl, difluoromethyl, trifluoromethyl (—CF$_3$), chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Perfluoroalkyl", as used herein, refers to alkyl radicals having all hydrogen atoms replaced with fluoro atoms. Examples include trifluoromethyl and pentafluoroethyl.

The term "haloalkoxyl", when used alone or in combination, embraces $C_{1-6}$alkoxyl radicals wherein any one or more of the alkoxyl carbon atoms is substituted with halo as defined above. For example, this term includes monohaloalkoxyl, dihaloalkoxyl and polyhaloalkoxyl radicals such as a perhaloalkoxyl. Examples of haloalkoxyl radicals include fluoromethoxyl, difluoromethoxyl, trifluoromethoxyl (—OCF$_3$), chloromethoxyl, dichloromethoxyl, trichloromethoxyl, pentafluoroethoxyl, heptafluoropropoxyl, difluorochloromethoxyl, dichlorofluoromethoxyl, difluoroethoxyl, difluoropropoxyl, dichloroethoxyl and dichloropropoxyl.

The term "heteroaryl", as used herein, either alone or in combination, means a fully unsaturated (aromatic) ring moiety formed from carbon atoms and having one or more heteroatoms selected from nitrogen, oxygen and sulfur. The ring moiety or ring system may contain one ("monocyclic"), two ("bicyclic") or even three ("tricyclic") rings wherein such rings are attached together in a fused manner. Every ring of a "heteroaryl" ring system need not be aromatic, and the ring(s) fused thereto (to the heteroaromatic ring) may be partially or fully saturated and optionally include one or more heteroatoms selected from nitrogen, oxygen and sulfur. The term "heteroaryl" does not include rings having ring members of —O—O—, —O—S— or —S—S—.

Examples of unsaturated heteroaryl radicals, include unsaturated 5- to 6-membered heteromonocyclyl groups containing 1 to 4 nitrogen atoms, including for example, pyrrolyl, imidazolyl, pyrazolyl, 2-pyridyl, 3-pyridyl, 4-pyridyl, pyrimidyl, pyrazinyl, pyridazinyl, triazolyl [e.g., 4H-1,2,4-triazolyl, 1H-1,2,3-triazolyl, 2H-1,2,3-triazolyl] and tetrazole; unsaturated 7- to 10-membered heterobicyclyl groups containing 1 to 4 nitrogen atoms, including for example, quinolinyl, isoquinolinyl, quinazolinyl, isoquinazolinyl, azaquinazolinyl, and the like; unsaturated 5- to 6-membered heteromonocyclic group containing an oxygen atom, for example, pyranyl, 2-furyl, 3-furyl, benzofuryl, etc.; unsaturated 5 to 6-membered heteromonocyclic group containing a sulfur atom, for example, 2-thienyl, 3-thienyl, benzothienyl, etc.; unsaturated 5- to 6-membered heteromonocyclic group containing 1 to 2 oxygen atoms and 1 to 3 nitrogen atoms, for example, oxazolyl, isoxazolyl, oxadiazolyl [e.g., 1,2,4-oxadiazolyl, 1,3,4-oxadiazolyl, 1,2,5-oxadiazolyl]; unsaturated 5 to 6-membered heteromonocyclic group containing 1 to 2 sulfur atoms and 1 to 3 nitrogen atoms, for example, thiazolyl, isothiazolyl, thiadiazolyl [e.g., 1,2,4-thiadiazolyl, 1,3,4-thiadiazolyl, 1,2,5-thiadiazolyl].

The term "heterocyclic", when used alone or in combination, means a partially or fully saturated ring moiety containing one, two or even three rings wherein such rings may be attached together in a fused manner, formed from carbon atoms and including one or more heteroatoms selected from N, O or S. Examples of saturated heterocyclic radicals include saturated 3 to 6-membered heteromonocyclic groups containing 1 to 4 nitrogen atoms [e.g. pyrrolidinyl, imidazolidinyl, piperidinyl, pyrrolinyl, piperazinyl]; saturated 3 to 6-membered heteromonocyclic group containing 1 to 2 oxygen atoms and 1 to 3 nitrogen atoms [e.g. morpholinyl]; saturated 3 to 6-membered heteromonocyclic group containing 1 to 2 sulfur atoms and 1 to 3 nitrogen atoms [e.g., thiazolidinyl]. Examples of partially saturated heterocyclyl radicals include dihydrothienyl, dihydropyranyl, dihydrofuryl and dihydrothiazolyl.

The term "heterocycle" also embraces radicals where heterocyclic radicals are fused/condensed with aryl radicals: unsaturated condensed heterocyclic group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl [e.g., tetrazolo[1,5-b]pyridazinyl]; unsaturated condensed heterocyclic group containing 1 to 2 oxygen atoms and 1 to 3 nitrogen atoms [e.g. benzoxazolyl, benzoxadiazolyl]; unsaturated condensed heterocyclic group containing 1 to 2 sulfur atoms and 1 to 3 nitrogen atoms [e.g., benzothiazolyl, benzothiadiazolyl]; and saturated, partially unsaturated and unsaturated condensed heterocyclic group containing 1 to 2 oxygen or sulfur atoms [e.g. benzofuryl, benzothienyl, 2,3-dihydro-benzo[1,4]dioxinyl and dihydrobenzofuryl]. Examples of heterocyclic radicals include five to ten membered fused or unfused radicals.

Examples of partially saturated and fully saturated heterocyclyls include, without limitation, pyrrolidinyl, imidazolidinyl, piperidinyl, pyrrolinyl, pyrazolidinyl, piperazinyl, morpholinyl, tetrahydropyranyl, thiazolidinyl, dihydrothienyl, 2,3-dihydro-benzo[1,4]dioxanyl, indolinyl, isoindolinyl, dihydrobenzothienyl, dihydrobenzofuryl, isochromanyl, chromanyl, 1,2-dihydroquinolyl, 1,2,3,4-tetrahydro-isoquinolyl, 1,2,3,4-tetrahydro-quinolyl, 2,3,4,4a,9,9a-hexahydro-1H-3-aza-fluorenyl, 5,6,7-trihydro-1,2,4-triazolo[3,4-a] isoquinolyl, 3,4-dihydro-2H-benzo[1,4]oxazinyl, benzo[1,4] dioxanyl, 2,3-dihydro-1H-1λ'-benzo[d]isothiazol-6-yl, dihydropyranyl, dihydrofuryl and dihydrothiazolyl, and the like.

The term "alkylamino" includes "N-alkylamino" where amino radicals are independently substituted with one alkyl radical. Preferred alkylamino radicals are "lower alkylamino" radicals having one to six carbon atoms. Even more preferred are lower alkylamino radicals having one to three carbon atoms. Examples of such lower alkylamino radicals include N-methylamino, and N-ethylamino, N-propylamino, N-isopropylamino and the like.

The term "dialkylamino" includes "N,N-dialkylamino" where amino radicals are independently substituted with two alkyl radicals. Preferred alkylamino radicals are "lower alkylamino" radicals having one to six carbon atoms. Even more preferred are lower alkylamino radicals having one to three carbon atoms. Examples of such lower alkylamino radicals include N,N-dimethylamino, N,N-diethylamino, and the like.

The term "carbonyl", whether used alone or with other terms, such as "aminocarbonyl", denotes —(C=O)—. "Carbonyl" is also used herein synonymously with the term "oxo".

The term "aminocarbonyl" denotes an amide group of the formula —C(=O)NH$_2$.

The term "alkylthio" or "thioalkoxy" embraces radicals containing a linear or branched alkyl radical, of one to ten carbon atoms, attached to a divalent sulfur atom. An example of "alkylthio" or "thioalkoxy" is methylthio, (CH$_3$S—).

The term "compounds of the invention" are intended to encompass compounds of Formula I, which in turn encompasses compounds of Formula II, III and IV, as well as compounds of any sub-formulas thereof, such as Formulas I-A, I-B, I-C, II-A, II-B and the like.

The term "pharmaceutically-acceptable" when used with reference to a compound of Formulas I-IV, and sub-formulas thereof, is intended to refer to a form of the compound that is safe for administration. For example, a salt form, a solvate, a hydrate, a prodrug or derivative form of a compound of Formulas I-IV, which has been approved for mammalian use, via oral ingestion or other routes of administration, by a governing body or regulatory agency, such as the Food and Drug Administration (FDA) of the United States, is pharmaceutically acceptable.

Included in the compounds of Formulas I-IV, Formulas I-IV, and sub-formulas thereof, are the pharmaceutically acceptable salt forms of the free-base compounds. The term "pharmaceutically-acceptable salts" embraces salts commonly used to form alkali metal salts and to form addition salts of free acids or free bases. As appreciated by those of ordinary skill in the art, salts may be formed from ionic associations, charge-charge interactions, covalent bonding, complexation, coordination, etc. The nature of the salt is not critical, provided that it is pharmaceutically acceptable.

Suitable pharmaceutically acceptable acid addition salts of compounds of Formulas I-IV, and sub-formulas thereof, may be prepared from an inorganic acid or from an organic acid. Examples of such inorganic acids are hydrochloric, hydrobromic, hydroiodic, hydrofluoric, nitric, carbonic, sulfuric and phosphoric acid. Appropriate organic acids may be selected from aliphatic, cycloaliphatic, aromatic, arylaliphatic, heterocyclic, carboxylic and sulfonic classes of organic acids, examples of which include, without limitation, formic, acetic, adipic, butyric, propionic, succinic, glycolic, gluconic, lactic, malic, tartaric, citric, ascorbic, glucuronic, maleic, fumaric, pyruvic, aspartic, glutamic, benzoic, anthranilic, mesylic, 4-hydroxybenzoic, phenylacetic, mandelic, embonic (pamoic), methanesulfonic, ethanesulfonic, ethanedisulfonic, benzenesulfonic, pantothenic, 2-hydroxyethanesulfonic, toluenesulfonic, sulfanilic, cyclohexylaminosulfonic, camphoric, camphorsulfonic, digluconic, cyclopentanepropionic, dodecylsulfonic, glucoheptanoic, glycerophosphonic, heptanoic, hexanoic, 2-hydroxy-ethanesulfonic, nicotinic, 2-naphthalenesulfonic, oxalic, palmoic, pectinic, persulfuric, 2-phenylpropionic, picric, pivalic propionic, succinic, thiocyanic, undecanoic, stearic, algenic, β-hydroxybutyric, salicylic, galactaric and galacturonic acid. Suitable pharmaceutically-acceptable base addition salts of compounds of Formulas I-IV include metallic salts, such as salts made from aluminum, calcium, lithium, magnesium, potassium, sodium and zinc, or salts made from organic bases including, without limitation, primary, secondary and tertiary amines, substituted amines including cyclic amines, such as caffeine, arginine, diethylamine, N-ethyl piperidine, histidine, glucamine, isopropylamine, lysine, morpholine, N-ethyl morpholine, piperazine, piperidine, triethylamine, disopropylethylamine and trimethylamine. All of these salts may be prepared by conventional means from the corresponding compound of the invention by reacting, for example, the appropriate acid or base with the compound of Formulas I-IV.

Also, the basic nitrogen-containing groups can be quaternized with such agents as lower alkyl halides, such as methyl, ethyl, propyl, and butyl chloride, bromides and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Additional examples of such salts can be found in Berge et al., J. Pharm. Sci., 66:1 (1977). Conventional methods may be used to form the salts. For example, a phosphate salt of a compound of the invention may be made by combining the desired compound free base in a desired solvent, or combination of solvents, with phosphoric acid in a desired stoichiometric amount, at a desired temperature, typically under heat (depending upon the boiling point of the solvent). The salt can be precipitated upon cooling (slow or fast) and may crystallize (i.e., if crystalline in nature), as appreciated by those of ordinary skill in the art. Multiple counter-ions may form the salts of the compounds of the invention. Thus, hemi-, mono-, di, tri- and poly-salt forms of the compounds of the present invention are also contemplated herein. For example, the salt may be a mono-ionic salt, di-ionic salt or tri-ionic salt, such as mono- or di-hydrochloride salt, bis-methansulfonate salt or a monofumarate salt. Similarly, hemi-, mono-, di, tri- and poly-hydrated forms of the compounds, salts and derivatives thereof, are also contemplated herein.

The term "derivative" is intended to encompass any salt of a compound of this invention, any ester of a compound of this invention, or any other compound, which upon administration to a patient is capable of providing (directly or indirectly) a compound of this invention, or a metabolite or residue thereof, characterized by the ability to the ability to modulate an enzyme.

The term "pharmaceutically-acceptable derivative" as used herein, denotes a derivative which is pharmaceutically acceptable.

The term "prodrug", as used herein, denotes a compound which upon administration to a subject or patient is capable of providing (directly or indirectly) a compound of this invention. Examples of prodrugs would include esterified or hydroxylated compounds where the ester or hydroxyl groups would cleave in vivo, such as in the gut, to produce a compound according to Formula I-IV. A "pharmaceutically-acceptable prodrug" as used herein, denotes a prodrug which is pharmaceutically acceptable. Pharmaceutically acceptable modifications to the compounds of Formula I-IV are readily appreciated by those of ordinary skill in the art.

The compound(s) of Formulas I-IV, and sub-formulas thereof, may be used to treat a subject by administering the compound(s) as a pharmaceutical composition. To this end, the compound(s) can be combined with one or more excipients, including without limitation, carriers, diluents or adjuvants to form a suitable composition, which is described in more detail herein.

The term "excipient", as used herein, denotes any pharmaceutically acceptable additive, carrier, adjuvant, or other suitable ingredient, other than the active pharmaceutical ingredient (API), which is typically included for formulation and/or administration purposes. "Diluent" and "adjuvant" are defined hereinafter.

The terms "treat", "treating," "treatment," and "therapy" as used herein refer to therapy, including without limitation, curative therapy, prophylactic therapy, and preventative therapy. Prophylactic treatment generally constitutes either preventing the onset of disorders altogether or delaying the onset of a pre-clinically evident stage of disorders in individuals.

The phrase "effective dosage amount" is intended to quantify the amount of each agent, which will achieve the goal of improvement in disorder severity and the frequency of incidence over treatment of each agent by itself, while avoiding adverse side effects typically associated with alternative therapies. Accordingly, this term is not limited to a single dose, but may comprise multiple dosages required to bring about a therapeutic or prophylactic response in the subject. For example, "effective dosage amount" is not limited to a single capsule or tablet, but may include more than one capsule or tablet, which is the dose prescribed by a qualified physician or medical care giver to the subject.

The term "leaving group" (also denoted as "LG") generally refers to groups that are displaceable by a nucleophile. Such leaving groups are known in the art. Examples of leaving groups include, but are not limited to, halides (e.g., I, Br, F, Cl), sulfonates (e.g., mesylate, tosylate), sulfides (e.g., $SCH_3$), N-hydroxsuccinimide, N-hydroxybenzotriazole, and the like. Nucleophiles are species that are capable of attacking a molecule at the point of attachment of the leaving group causing displacement of the leaving group. Nucleophiles are known in the art. Examples of nucleophilic groups include, but are not limited to, amines, thiols, alcohols, Grignard reagents, anionic species (e.g., alkoxides, amides, carbanions) and the like.

General Synthetic Procedures

The present invention further comprises procedures for the preparation of compounds of Formulas I-IV, and sub-formulas thereof. The compounds of Formulas I-IV can be synthesized according to the procedures described in the following Schemes 1 and 2, wherein the substituents are as defined for Formulas I-IV above, except where further noted. The synthetic methods described below are merely exemplary, and the compounds of the invention may also be synthesized by alternate routes utilizing alternative synthetic strategies, as appreciated by persons of ordinary skill in the art.

The following list of abbreviations used throughout the specification represent the following and should assist in understanding the invention:

ACN, MeCN—acetonitrile
Aq., aq.—aqueous
Ar—argon (gas)
BOP—benzotriazol-1-yl-oxy Hexafluorophosphate
BuLi—Butyllithium
$Cs_2CO_3$—cesium carbonate
$CHCl_3$—chloroform
$CH_2Cl_2$, DCM—dichloromethane, methylene chloride
Cu(1)I—copper(1) iodide
DCC—dicyclohexylcarbodiimide
DCE—dichloroethane
DIBAL—diisobutylaluminumhydride
DIC—1,3-diisopropylcarbodiimide
DIEA, DIPEA—diisopropylethylamine
DIPA—diisopropylamine
DME—dimethoxyethane
DMF—dimethylformamide
DMAP—4-dimethylaminopyridine
DMS—dimethylsulfide
DMSO—dimethylsulfoxide
EDC, EDCI—1-(3-dimethylaminopropyl)-3-ethylcarbodiimide
$Et_2O$—diethyl ether
EtOAc—ethyl acetate
FBS—fetal bovine serum
G, gm—gram
h, hr—hour
$H_2$—hydrogen
$H_2O$—water
HATU—O-(7-azabenzotriazol-1-yl)-N,N,N',N'-tetramethyluroniumhexafluorophosphate
HBr—hydrobromic acid
HCl—hydrochloric acid
HOBt—1-hydroxybenzotriazole hydrate
HOAc—acetic acid
HPLC—high pressure liquid chromatography
IPA, IpOH—isopropyl alcohol
$K_2CO_3$—potassium carbonate
KI—potassium iodide
LG—leaving group
LDA—Lithium diisopropylamide
LiOH—lithium hydroxide
$MgSO_4$—magnesium sulfate
MS—mass spectrum
MeOH—methanol
$N_2$—nitrogen
$NaCNBH_3$—sodium cyanoborohydride
$Na_2CO_3$—sodium carbonate
$NaHCO_3$—sodium bicarbonate
NaH—sodium hydride
NaI—sodium iodide
$NaBH_4$—sodium borohydride
NaOH—sodium hydroxide
$Na_2SO_4$—sodium sulfate
$NH_4Cl$—ammonium chloride
$NH_4OH$—ammonium hydroxide
$P(t-bu)_3$—tri(tert-butyl)phosphine
PBS—phosphate buffered saline
Pd/C—palladium on carbon
$Pd(PPh_3)_4$—palladium(0)triphenylphosphine tetrakis
$Pd(dppf)Cl_2$—palladium(1,1-bisdiphenylphosphinoferrocene) II chloride
$Pd(PhCN)_2Cl_2$—palladium di-cyanophenyl dichloride
$Pd(OAc)_2$—palladium acetate
$Pd_2(dba)_3$—tris(dibenzylideneacetone)dipalladium
PyBop—benzotriazol-1-yl-oxy-tripyrrolidino-phosphonium hexafluorophosphate
RT, rt—room temperature
RBF, rbf—round bottom flask
TLC, tlc—thin layer chromatography
TBAF—Tetrabutylammonium fluoride
TBTU—O-benzotriazol-1-yl-N,N,N',N'-tetramethyluronium tetrafluoroborate
TEA, $Et_3N$—triethylamine
TFA—trifluoroacetic acid
THF—tetrahydrofuran
UV—ultraviolet light Scheme 1

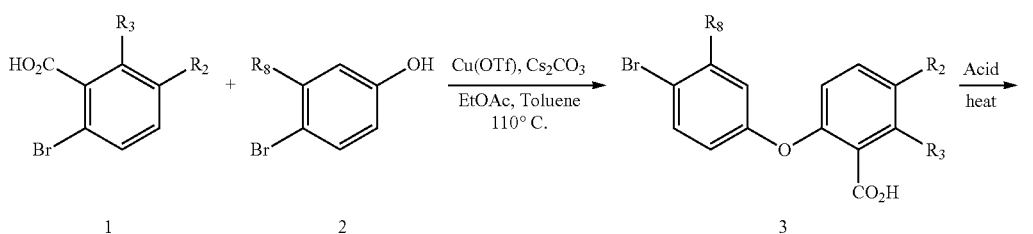

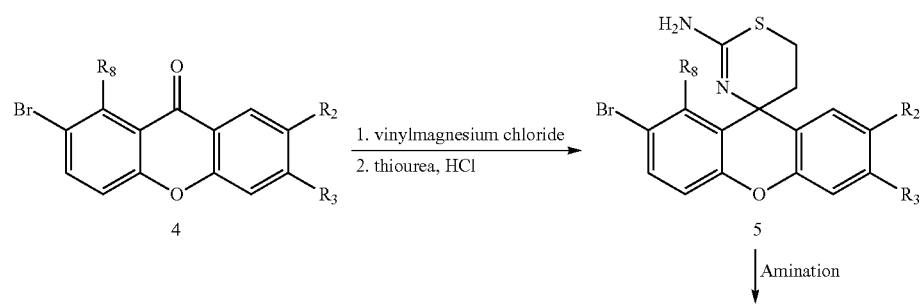

Amination

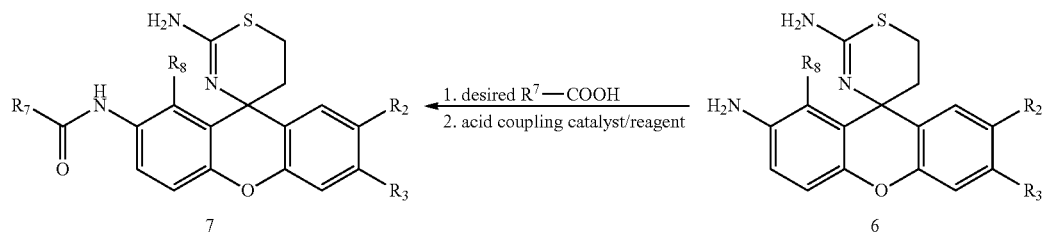

Scheme 1 describes an exemplary method for preparing compounds 7 of Formulas I-IV, wherein X is S, Y is $CH_2$, (Z is $CH_2$ where applicable) $A^1$ is $CR^6$ and $R^1$, $R^4$, $R^5$, $R^6$ and $R^8$ are each H, respectively, and L is —C(O)NH—. As shown, a bromo-benzoic acid 1 can be coupled to a bromo-phenol 2 using a copper reagent in conjunction with a suitable base, such cesium carbonate, under suitable conditions. The coupled ether 3 can then be treated with an acid, such as sulfuric acid, to effect ring closure to the corresponding bromo-xanthene 4. The ketone of xanthene 4 can be converted to the corresponding spiro amino-thiazine 5 as shown under suitable conditions, such as using vinyl magnesium chloride and thiourea in the presence of an acid, such as HCl. Bromo-intermediate 5 (where $R^2$ is a desired group, such as methoxy) can be converted to amino compounds 6 via halogen-amine exchange via a reactive intermediate, such as an azide, at the site of the bromide. See examples 32, 34, 36 and 37 described herein for exemplary conditions to insert the primary amine at the position of the bromide in compound 6. Compound 6 may then be converted into desired final compounds 7 via creation of an amide linkage by reaction with a desired acid in the presence of conventional known coupling reagents, such as for example, carbodiimides, acid chloride, or even propylphosphonic anhydride (PPPA).

Desired compounds 7 of Formulas I-III, and sub-formulas thereof wherein L is an amine linker to desired $R^7$ groups may be made as generally described in Scheme 3. As shown, desired $R^7$ amines may be coupled directed to the bromide intermediate 14 using XPhos in the presence of a suitable palladium catalyst under suitable conditions to afford desired products 15. For example, see the methods described in Examples 31 and 33.

Similarly, compound 14 can be transformed into the corresponding amine 16 using conditions like those described in scheme 1 hereinabove. Compound 16 may then be reacted with a desired acid in the presence of conventional amide coupling conditions to afford desired compound 17.

Scheme 3

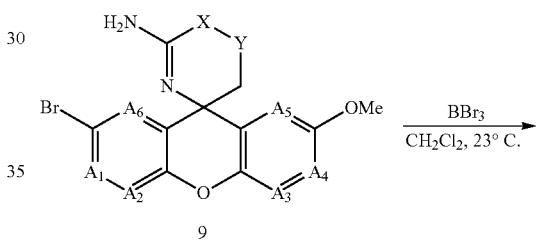

Scheme 2

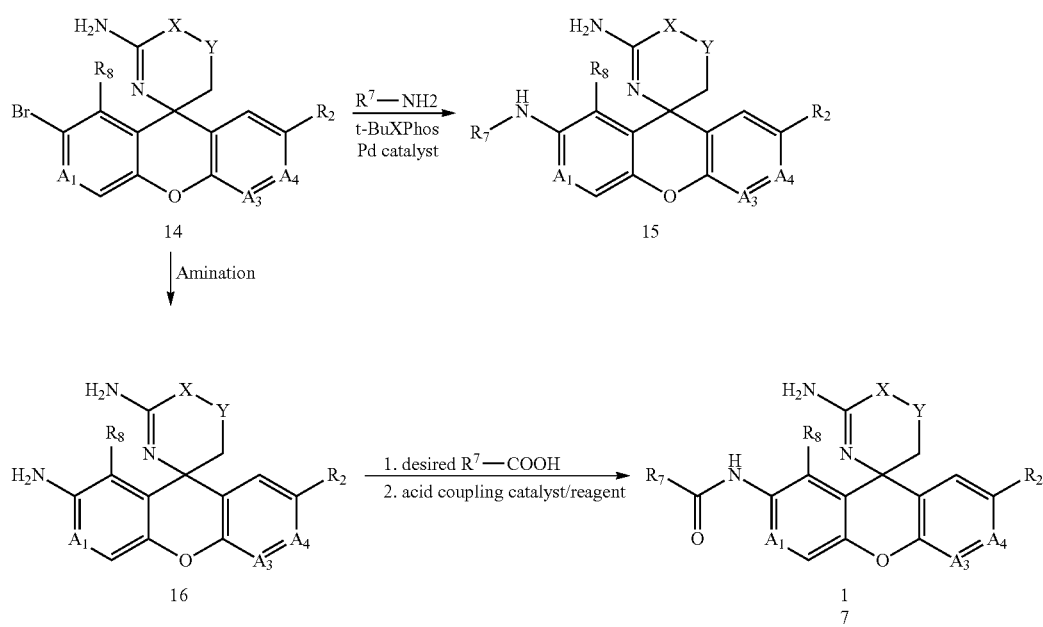

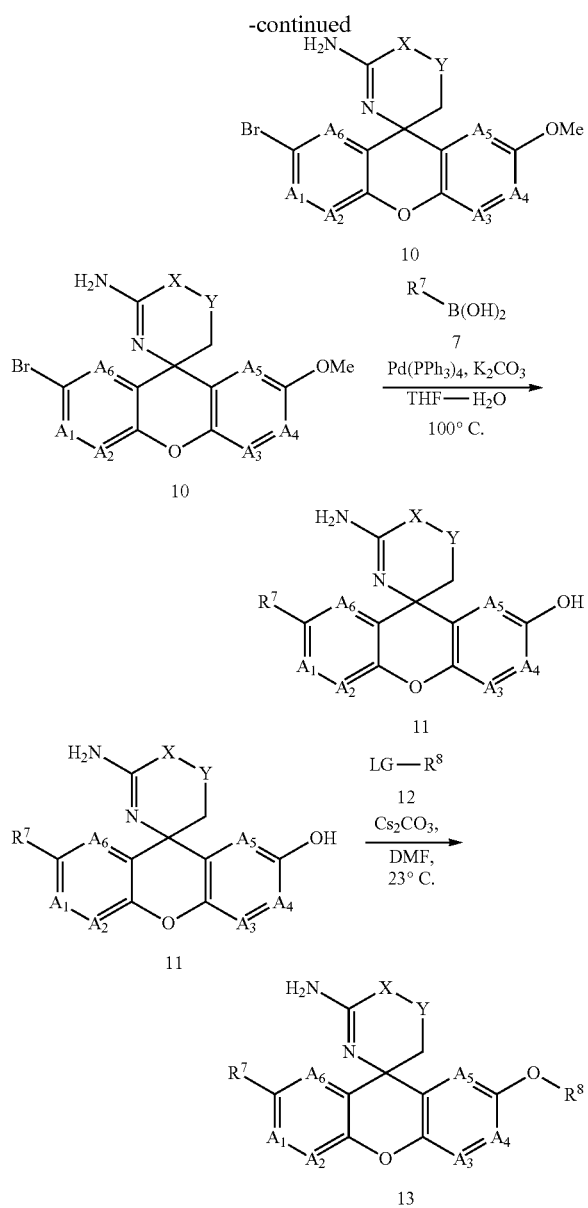

Desired compounds 13 of Formula I, and sub-formulas of II, III and IV, wherein the $R^2$ group is —$OR^8$ may be made as generally described in Scheme 3. As shown, bromo-methoxy intermediate 9 can be O-d-methylate using known reagents, such as borontribromide to afford the alcohol product 10. The bromide of alcohol 10 can be coupled as described above in scheme 1 to provide the desired $R^7$ group intermediate 11. The alcohol of intermediate 11 can be functionalized as desired, such as by alkylation as shown, by reaction with an alkyl halide in the presence of a suitable base, such as cesium carbonate as shown, in suitable solvents to afford the finally desired product 13.

"LG" in this instance is a "leaving group" which may be a halide such as an iodide, bromide, chloride or fluoride. LG may also be a non-halide moiety such as an alkylsulfonate or other known groups which generally form an electrophilic species ($E^+$). Coupling reactions generally occur more readily in one or a combination of solvents and a base. Suitable solvents include, without limitation, generally non-nucleophilic, anhydrous solvents such as toluene, $CH_2Cl_2$, THF, DMF, N,N-dimethylacetamide and the like. The solvent may range in polarity, as appreciated by those skilled in the art. Suitable bases include, for example, tertiary amine bases such as DIEA, TEA, carbonate bases such as $Na_2CO_3$, $K_2CO_3$, $Cs_2CO_3$, hydrides such as NaH, KH and the like, alkoxides such as $NaOCH_3$, and the like. The base itself may also serve as a solvent. These coupling reactions are generally fast and conversion occurs typically in ambient conditions. However, depending upon the particular substrate, such reactions may require heat, as appreciated by those skilled in the art.

Alternatively, the desired aromatic $R^2$ groups may be installed via a Suzuki or Suzuki-like coupling reaction, as discussed further herein, via an $R^2$-bronic acid with a corresponding core bromide intermediate.

The boronic ester intermediates may be prepared by methods described in the following references: (1) PCT Int. Patent Appl. No. WO 2005073189, titled "Preparation of fused heteroaryl derivatives as p38 kinase inhibitors" or (2) PCT Int. Patent Appl. No. WO 2006094187, titled "Preparation of phthalazine, aza- and diaza-phthalazine compounds as protein kinase, especially p38 kinase, inhibitors for treating inflammation and related conditions". Also, desired boronic acids may be purchased commercially in catalogs, or specially made by the vendor or by persons skilled in the art.

The Suzuki method is a reaction using a borane reagent, such as a boronic acid 7 or ester such as a dioxaborolane (not shown), and a suitable leaving group containing reagent, such as the Br-xanthene (Br is a suitable halogen leaving group "LG"). As appreciated to one of ordinary skill in the art, Suzuki reactions also utilize a palladium catalyst. Suitable palladium catalysts include, without limitation, $Pd(PPh_3)_4$, $Pd(OAc)_2$ or $Pd(dppf)Cl_2$. Where LG is a halide, the halide may be an iodide, a bromide or even a chloride. Chloropyridyl rings (where $A^1$=N) undergo Suzuki reactions in the presence of Pd catalysts. Other LGs are also suitable. For example, Suzuki couplings are known to occur with a sulfonate, such as trifluoromethanesulfonate, as the leaving group. The Suzuki reaction conditions may vary. For example, Suzuki reactions are generally run in the presence of a suitable base such as a carbonate base, bicarbonate or an acetate base, in a suitable solvent such as toluene, acetonitrile, DMF or an aqueous-organic solvent combination or a biphasic system of solvents. Further, the reaction may require heat depending upon the particular bromide and/or boronic acid or ester, as appreciated by those skilled in the art. In addition, where the bromide is an aromatic moiety, such as phenyl, the reaction may be complete in a short period of time with heat.

Other coupling methods are known. For example metal catalyzed coupling chemistry, such Stille, Kumada, Negishi coupling methods, and the like, may be employed to the xanthene cores 5 to prepare desired cyclic products 6. In addition, for compounds wherein X is S, the free amino group may need to be protected for effective coupling reactions to install either $R^2$ or $R^7$ groups, and later deprotected to afford the final desired compounds 6, as appreciated by persons of ordinary skill in the art.

EXAMPLES

The Examples, described herein below, represent various exemplary starting materials, intermediates and compounds of Formulas I-IV, which should assist in a better understanding and appreciation of the scope of the present invention and of the various methods which may be used to synthesize compounds of Formulas I-IV. Starting materials and intermediates used in the Examples herein may also be prepared using the procedures described in co-pending U.S. patent application Ser. No. 13/047,693, filed Mar. 14, 2011, which specification and disclosure is hereby incorporated herein by reference in its entirety. It should be appreciated that the general methods above and specific examples below are illustrative only, for the purpose of assistance and of understanding the present invention, and should not be construed as limiting the scope of the present invention in any manner.

Chromatography:

Unless otherwise indicated, crude product-containing residues were purified by passing the crude material or concentrate through an ISCO brand silica gel column (pre-packed or individually packed with $SiO_2$) and eluting the product off the column with a solvent gradient as indicated. For example a description of (330 g $SiO_2$, 0-40% EtOAc/Hexane) means the product was obtained by elution from the column packed with 330 gms of silica, with a suitable solvent gradient, such as 0% to 40% EtOAc in hexanes.

Preparative HPLC Method:

Unless otherwise indicated, the compounds described herein were purified via reverse phase HPLC using one of the following instruments: Shimadzu, varian, Gilson; utilizing one of the following two HPLC columns: (a) a Phenomenex Luna or (b) a Gemini column (5 micron or 10 micron, C18, 150×50 mm)

A typical run through the instrument included: eluting at 45 ml/min with a linear gradient of 10% (v/v) to 100% MeCN (0.1% v/v TFA) in water (0.1% TFA) over 10 minutes; conditions can be varied to achieve optimal separations.

Proton NMR Spectra:

Unless otherwise indicated, all $^1H$ NMR spectra were run on a Bruker series 300 MHz instrument or a Bruker series 400 MHz instrument. Where so characterized, all observed protons are reported as parts-per-million (ppm) downfield from tetramethylsilane (TMS) or other internal reference in the appropriate solvent indicated.

Mass Spectra (MS)

Unless otherwise indicated, all mass spectral data for starting materials, intermediates and/or exemplary compounds are reported as mass/charge (m/z), having an $(M+H^+)$ molecular ion. The molecular ion reported was obtained by electrospray detection method (commonly referred to as an ESI MS) utilizing a PE SCIEX API 150EX MS instrument or an Agilent 1100 series LC/MSD system. Compounds having an isotopic atom, such as bromine and the like, are generally reported according to the detected isotopic pattern, as appreciated by those skilled in the art.

The compounds disclosed and described herein have been named using either (1) the naming convention provided with Chem-Draw Ultra 8.0 software, available in Chem Office or higher version, or (2) by the ISIS database software (Advanced Chemistry Design Labs or ACD software).

Example 1

Procedure A

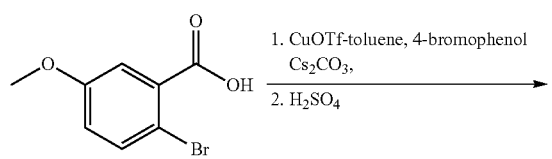

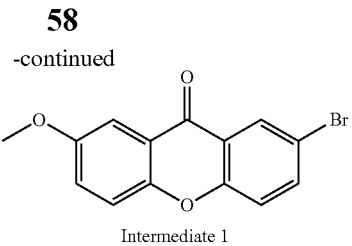

Intermediate 1

Synthesis of Intermediate 1

Step 1:

A RBF equipped with a reflux condenser was charged with 2-bromo-5-methoxy benzoic acid (430 g, 1.8614 mol), 4-bromo phenol (322 g, 1.8614 mol), potassium carbonate (514.5 g, 3.7 228 mol) and CuOTf-toluene complex (24.08 g, 0.04653 mol). EtOAc (9.0 ml 0.09679 mol, 0.052) and toluene (1.3 L) were carefully added portion wise. After stirring at RT for 10 min, the mixture was heated to 50° C. for 30 min and then to 110° C. for 20 hrs. The reaction mixture was cooled to RT and diluted with water and acidified with 2N HCl. The reaction mixture was extracted with EtOAc (3.0×2 L) and filtered through celite. The combined extracts were dried over $NaSO_4$ and concentrated to provide 590 g of a brown solid that was carried on without further purification.

Step 2:

Sulfuric acid (1.6 L) was added to 2-(4-bromophenoxy)-5-methoxybenzoic acid (530 g, 1.6401 mol) at RT. The resulting dark mixture was heated to 60° C. for 1 hour. The brown solution was cooled to RT and poured onto ice while stirring. The resulting tan precipitate was collected by filtration, washed sequentially with water (2 L), 1N NaOH (2.0 L) and ethanol (800 mL). The derived solid was suspended in 2 L of acetone and stirred vigorously for 1 hour. The mixture was filtered and dried under a vacuum to afford 1.3 kg of 2-bromo-7-methoxy-9H-xanthen-9-one as a white solid.

Example 2

Procedure B

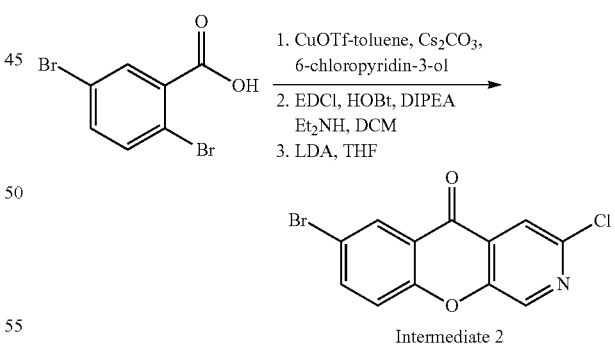

Intermediate 2

Synthesis of Intermediate 2

Step 1:

A mixture of 2,5-dibromobenzoic acid (1244 g, 4.44 mol), 5-hydroxy-2-chloropyridine (663.3 g, 5.12 mol) and cesium carbonate (2893.3 g, 8.88 mol) was stirred for 20 minutes under a nitrogen atmosphere. To this slurry were added copper (I) trifluoromethanesulfonate toluene complex (59.7 g, 0.115 mol), toluene (9 L) and EtOAc (39 mL). The resulting suspension was heated to 105° C. and stirred for 2 h before being cooled to RT. The toluene was decanted, and water (8 L)

and EtOAc (8 L) were added. The resulting mixture was stirred until the solid was completely dissolved. The EtOAc layer was separated and the pH of the aqueous layer was adjusted to pH 2~3 with 6N HCl. The aqueous layer was extracted with EtOAc (3×5 L). The combined organic layers were dried over $Na_2SO_4$, filtered and concentrated to give 1.28 Kg of 5-bromo-2-(6-chloropyridin-3-yloxy)benzoic acid as brown solid. This material was used in next step without further purification.

Step 2:

A mixture of compound 5-bromo-2-(6-chloropyridin-3-yloxy)benzoic acid (1.28 Kg, 4.44 mol), DEA (461 mL, 4.44 mol), HOBT (600 g, 4.44 mol), DIPEA (1.547 L, 8.88 mol) in anhydrous DCM (8 L) was cooled to 0° C. and EDCI (851.2 g, 4.44 mol, 1 eq) was added. The mixture was stirred at 0° C. for 30 minutes and then at RT overnight. The reaction mixture was washed with an aqueous, saturated solution of $NaHCO_3$, brine and water. The organic phase was separated, dried over $MgSO_4$ and concentrated under reduced pressure. The resulting crude mixture was purified by silica gel chromatography (5 to 20% ethyl acetate in hexane) to afford 950 g of 5-bromo-2-(6-chloropyridin-3-yloxy)-N,N-diethylbenzamide as a yellow oil.

Step 3:

5-Bromo-2-(6-chloropyridin-3-yloxy)-N,N-diethylbenzamide (457.5 g, 1.23 mol, 1 eq) was dissolved in anhydrous THF (3 L) and cooled to 78° C. To this solution was added a solution of LDA (2M in heptane/THF/ethyl benzene, 2.25 L, 4.5 mol, 3.65 eq) maintaining the temperature below 70° C. After the addition was complete, the solution was stirred for additional 30 min at 78° C. The acetone-dry ice bath was removed and the reaction was quenched with a saturated aqueous solution of $NH_4Cl$ (1 L), maintaining the temperature below 10° C. Another batch of 5-bromo-2-(6-chloropyridin-3-yloxy)-N,N-diethylbenzamide (457.5 g) was processed using the same protocol. The crude reaction mixtures from both reactions were combined and the layers were separated. The aqueous layer was extracted with ethyl acetate (3×5 L). The combined organic layers were dried and passed through a pad of silica gel. The filtrate was evaporated, and the residue was triturated with DCM to give 70 g of 7-bromo-3-chloro-5H-chromeno[2,3-c]pyridin-5-one. The mother liquor was evaporated and the solid thus obtained was purified by recrystallization using DCM/hexanes to give 180 g of 7-bromo-3-chloro-5H-chromeno[2,3-c]pyridin-5-one.

Example 3

Procedure C

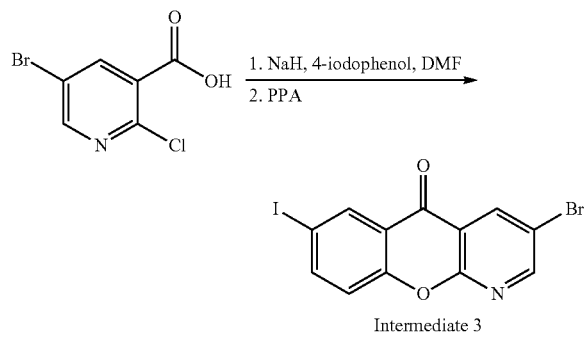

Intermediate 3

Synthesis of Intermediate 3

Step 1:

A 3-neck 12 L flask equipped with an overhead stirrer, thermometer, condenser and nitrogen inlet was charged with NaH (186.1 g, 4.653 mol) and DMF (1500 mL). The slurry was cooled to 0° C. and a solution of 4-iodophenol (488.6 g, 2.221 mol) in DMF (1500 mL) and added. The temperature of the reaction mixture was maintained below 25-30° C. during this addition. After complete addition, the cooling bath was promptly removed and the mixture continued to stir at RT for 1 h. 5-Bromo-2-chloronicotinic acid (500 g, 2.115 mol) was then added to the slurry portion wise. The reaction mixture was heated to 115° C. overnight. The dark brown reaction mixture was cooled to 20° C. and diluted with water (2 L). The reaction mixture was acidified using HOAc (845 ml). The black homogenous solution (pH=5) was allowed to stir for 1 h at RT and poured slowly onto ice-water (20 L). The slurry was filtered at RT, washed with water (2×2 L) and dried in air to give 765 g of 5-Bromo-2-(4-iodophenoxy)-nicotinic acid as light orange solid.

Step 2:

A 5 L 3-neck flask equipped with an overhead stirrer, a thermometer and nitrogen inlet was charged with PPA (4 Kg, 1942 mL) (115% $H_3PO_4$) and heated to 115-120° C. 5-Bromo-2-(4-iodophenoxy)nicotinic acid (400 g, 952 mmol) was charged portion wise to the hot PPA. The viscous mixture was then allowed to stir overnight (16-18 h) at 115-120° C. The dark viscous mixture was cooled to 60-65° C. and poured slowly onto a mixture of ice (3000 g) and water (2000 mL) under mechanical stirring. The light brown slurry was allowed to stir overnight and filtered at RT. The wet cake was washed with water (2×1000 mL) followed by IPA (1500 mL) and hexane (2×1000 mL). The solid was dried to obtain 326.4 g of 3-Bromo-7-iodo-5H-chromeno[2,3-b]pyridine-5-one as a grey solid.

Example 4

Procedure D

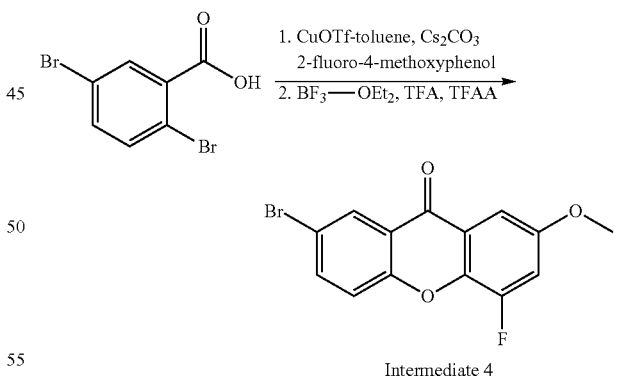

Intermediate 4

Synthesis of Intermediate 4

Step 1:

A dry 100 L glass jacketed reactor equipped with an addition funnel, reflux condenser, solids addition system and temperature probe was charged with 2,5-dibromobenzoic acid (2685 g, 9.6 mol) and copper (I) triflate toluene complex (2:1, 50.0 g, 0.2 mol). Toluene (30 L) and EtOAc (20 mL) were then charged, followed by 2-methoxy-4-fluorophenol (1500 g, 10.6 mol). Cesium carbonate (6258 g, 19.2 mol) was added in portions while stirring vigorously. The mixture was heated to 90° C. for 4 hours. The mixture was cooled to 35° C. and water (15 L) was added. After 15 minutes of stirring the phases were separated and the aqueous phase was washed with toluene (7.5 L). With stirring, EtOAc (15.0 L) was added to the aqueous phase, followed by 6 M HCl (5.6 L) keeping the internal temperature below 30° C. The layers were separated and the organics were dried over magnesium sulfate. Filtration through a pad of celite and concentration provided a solid that was reslurried in 915 mL of EtAOc and 9.2 L of heptanes. Stirring was continued for 1 hour before the solids were filtered and washed with heptanes. Drying provided 2560 g of 5-bromo-2-(2-fluoro-4-methoxyphenoxy)benzoic acid as a cream colored solid.

Step 2:

A dry 100 L glass jacketed reactor equipped with an addition funnel, reflux condenser and temperature probe was charged with 5-bromo-2-(2-fluoro-4-methoxyphenoxy)benzoic acid (2340 g, 6.9 mol). TFA (11.7 L) was carefully added followed by TFAA (1144 mL). Boron trifluoride diethyl etherate (85 mL, 0.68 mol) was then carefully added. Stirring was continued to 4 hours at which point the reaction was transferred to another 100 L glass reactor containing 35.1 L of water cooled to 0° C. The resulting slurry was allowed to warm to RT and stir for 1 hour. The solids were filtered and washed with water (4.7 L) and 3 N NaOH (2×3.5 L) and water (7 L). The solids were transferred into a 22 L reactor and acetone (4.7 L) was added. The solids were slurried for 1.5 hour and the filtered, washing well with acetone (4.7 L). An additional slurry with acetone (6.4 L @ 45° C.) provided 1310 g of 7-bromo-4-fluoro-2-methoxy-9H-xanthen-9-one as an off white solid.

Example 5

Procedure E

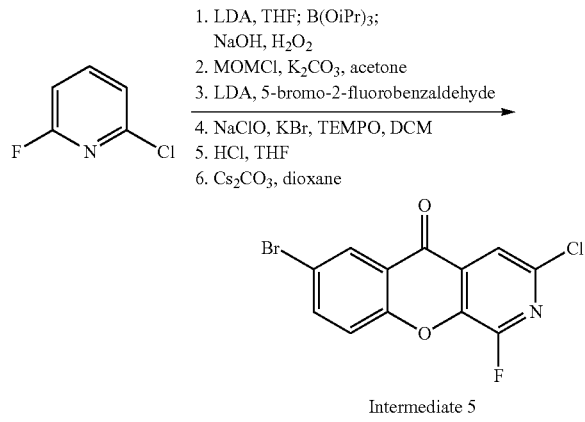

Intermediate 5

Synthesis of Intermediate 5

Step 1:

A solution of i-Pr$_2$NH (828 mL, 5.85 mol) in anhydrous THF (1.3 L) was cooled to −10° C. n-BuLi (1.6 M in hexanes, 3660 mL, 5.85 mol) was added and the solution was stirred for 10 min at 0° C. The reaction mixture was cooled to −78° C. and a solution of 2-chloro-6-fluoropyridine (700 g, 5.32 mol) in anhydrous THF (1.3 L) was slowly added keeping the internal temperature below −60° C. After the addition was complete, the reaction mixture was stirred for an additional hour and then a solution of triisopropyl borate (1221 mL, 5.32 mol) in anhydrous THF (620 mL) was added drop wise keeping the internal temperature below −60° C. After the addition, the reaction mixture was warmed to RT and stirred over night. Water (3 L) was added and the mixture was stirred vigorously. The reaction mixture was concentrated under reduced pressure. The residue was treated with a cold aqueous solution of NaOH (10 M, 1610 mL, 16.0 mol) and 50% H$_2$O$_2$ (392 mL, 6.92 mol) and stirred over night (Note: the internal temperature increased slowly from 5 to 60° C.). The reaction mixture was quenched with ice and 4N HCl until pH of the mixture was ~5. EtOAc (5 L) was added and stirred well. After phase separation, the aqueous layer was extracted with EtOAc (1.5 L×2). The combined organic layers were washed with brine, dried over anhydrous Na$_2$SO$_4$, and concentrated under reduced pressure to provide 6-chloro-2-fluoropyridin-3-ol as an off white solid.

Step 2:

A solution of 6-chloro-2-fluoropyridin-3-ol (1.4 Kg, 9.49 mol) was dissolved in acetone (13 L), and treated with K$_2$CO$_3$ (1574 g, 11.39 mol, 1.2 eq) and MOMCl (840 g, 10.44 mol, 1.1 eq). The mixture was heated at 60° C. for 2 hrs. After cooling to RT, the reaction mixture was filtered to remove inorganic salts. The filtrate was concentrated under reduced pressure. The residue was purified by flash column chromatography (0-10% EtOAc/hexanes), affording 6-chloro-2-fluoro-3-(methoxymethoxy)pyridine (1496 g) as a colorless oil in 80% yield over two steps.

Step 3:

A solution of i-Pr$_2$NH (1100 mL, 7.72 mol) in anhydrous THF (3.5 L) was cooled to −10° C. n-BuLi (2.5 M in hexanes, 3087 mL, 7.72 mol) was added drop wise and the solution was stirred for 10 min at 0° C. The reaction mixture was cooled to −78° C. and a solution of 6-chloro-2-fluoro-3-(methoxymethoxy)pyridine (1344 g, 7.02 mol) in anhydrous THF (2 L) was added slowly, keeping the internal temperature below −60° C. The resulting solution was stirred at 75° C. for 1 hr. A solution of 5-bromo-2-fluorobenzaldehyde (1430 g, 7.02 mol) in THF (1.7 L) was added dropwise. After the addition was complete, the reaction mixture was stirred at 75° C. for 30 min. The reaction mixture was warmed to RT and quenched with saturated aqueous NH$_4$Cl solution (3 L). EtOAc (5 L) was added and the mixture was stirred vigorously. After phase separation, the aqueous layer was extracted with EtOAc (3 L×2). The combined organics were washed with brine and dried over anhydrous Na$_2$SO$_4$. The solvent was removed under reduced pressure and the residue was purified by column chromatography (0-10% EtOAc/hexanes) to provide 2128 g of (5-bromo-2-fluorophenyl)(6-chloro-2-fluoro-3-(methoxymethoxy)pyridin-4-yl)methanol as a light yellow solid.

Step 4:

A solution of KBr (65.1 g, 0.55 mol) in water (5.9 L) was added to a solution of (5-bromo-2-fluorophenyl)(6-chloro-2-fluoro-3-(methoxymethoxy)pyridin-4-yl)methanol (2157 g, 5.47 mol) in DCM (5.9 L). The resulting biphasic mixture was cooled to 5° C. TEMPO (8.6 g, 0.055 mol) was added and the reaction mixture was stirred for 5 min. A solution of NaHCO$_3$ (106 g, 1.26 mol, 0.23 eq) in bleach (6170 mL, 6.01 mol, 1.1 eq) was added slowly keeping the internal temperature below 10° C. After the addition was completed, the organic phase was separated. The aqueous layer was extracted with DCM (4 L×2). The combined organic layers were washed with 5% aqueous solution of sodium metabisulfite (6 L×1), brine (3 L×1) and dried over anhydrous Na$_2$SO$_4$. The solution was concentrated under reduced pressure to give 2200 g of (5-bromo-2-fluorophenyl)(6-chloro-2-fluoro-3-(methoxymethoxy)pyridin-4-yl)methanone as a yellow solid.

Step 5:

To a solution of (5-bromo-2-fluorophenyl)(6-chloro-2-fluoro-3-(methoxymethoxy)pyridin-4-yl)methanone (1200 g, 3.06 mol) in THF (4.8 L) was added 6 N aqueous HCl solution (1600 mL, 9.17 mol) and the reaction mixture was heated to 60° C. for 5 hours. The reaction mixture was cooled to RT, and then water (3 L) and EtOAc (3 L) were added. After the phases were separated, the aqueous layer was extracted with EtOAc (3 L×2). The combined organic layers was washed with brine (2 L×1) and dried over Na$_2$SO$_4$. The solution was concentrated under reduced pressure. The residue was dissolved in hot MTBE (700 mL). The solution was triturated with hexanes until a solid began to precipitate. The slurry was cooled to RT overnight. The solid was filtered, washed with hexanes (500 mL×2), and dried to give 821 g of (5-bromo-2-fluorophenyl)(6-chloro-2-fluoro-3-hydroxypyridin-4-yl)methanone as a yellow solid.

Step 6:

A solution of (5-bromo-2-fluorophenyl)(6-chloro-2-fluoro-3-hydroxypyridin-4-yl)methanone (730 g, 2.10 mol) in dioxane (6 L) was treated with Cs$_2$CO$_3$ (1024 g, 3.14 mol). The reaction mixture was heated to 100° C. for 5 hours and then cooled to RT. Water (9 L) was added and the mixture was stirred vigorously. The resulting solids were filtered, washed with water (1 L×2), hexanes (1 L×1), and EtOAc (700 mL) to provide 602 g of 7-bromo-3-chloro-1-fluoro-5H-chromeno[2,3-c]pyridin-5-one as a light yellow solid.

Example 6

Procedure F

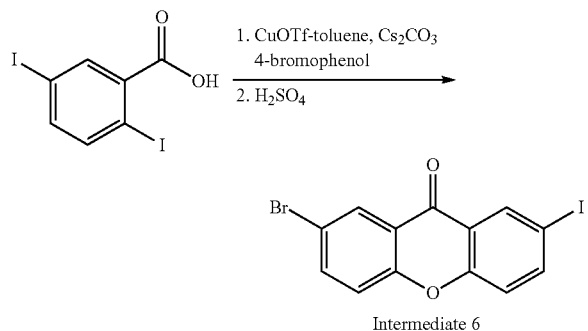

Intermediate 6

Synthesis of Intermediate 6

Step 1:

A RBF equipped with a reflux condenser was charged with 4-bromophenol (15.5 g, 89.4 mmol), 2,5-diiodobenzoic acid (25.700 g, 68.7 mmol), EtOAc (0.337 ml, 3.44 mmol), and toluene (100 mL). Cs$_2$CO$_3$ (44.8 g, 137 mmol) was carefully added portionwise. After stirring at RT for 1 min, the mixture was heated to 50° C. for 40 min and then heated to 100° C. for 20 hrs. The reaction mixture was allowed to cool to RT. The mixture was filtered through Celite and the solids were washed with EtOAc. The filtrate was diluted with water (200 mL), acidified with 2N HCl (300 mL), and extracted with EtOAc (4×500 mL). The organic extract was washed with brine and dried over sodium sulfate. The organic fraction was concentrated under reduced pressure to afford crude 2-(4-bromophenoxy)-5-iodobenzoic acid (31.1 g) as a tan oil that solidified upon standing.

Step 2:

H$_2$SO$_4$ (73.3 ml, 1375 mmol) was added to 2-(4-bromophenoxy)-5-iodobenzoic acid (28.800 g, 68.7 mmol) at rt. The resulting dark mixture was heated to 60° C. for 45 minutes. The brown solution was poured slowly onto ice-water (1 L) with stirring. The resulting tan precipitant was collected by filtration, washed with water a 1 N solution of NaOH, again with water, and dried under reduced pressure to afford 2-bromo-7-iodo-9H-xanthen-9-one (23.4 g) as a tan solid that was used without further purification.

Example 7

Procedure G

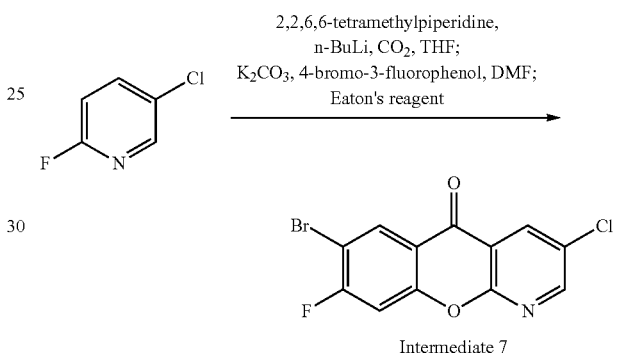

Intermediate 7

Synthesis of Intermediate 7

A solution of n-butyllithium (2.7N in heptanes; 165 mL, 445 mmol) in THF (300 mL) was cooled to −78° C. and treated with 2,2,6,6-tetramethylpiperidine (77 mL, 456 mmol). The reaction mixture was allowed to stir for 30 minutes. A solution of 5-chloro-2-fluoropyridine (50.0 g, 380 mmol) in THF (200 mL) was added drop wise over 30 minutes. After stirring for an additional 30 minutes, the reaction mixture was quenched by bubbling CO$_2$ through the reaction mixture for 10 minutes. The reaction mixture was allowed to warm to RT, and CO$_2$ was bubbled through for an additional 30 minutes. The reaction mixture was then concentrated under reduced pressure and dissolved in DMF (400 mL). 4-Bromo-3-fluorophenol (72.6 g, 380 mmol) was added, followed by potassium carbonate (68.3 g, 494 mmol). The reaction mixture was heated to 120° C. overnight. The reaction mixture was diluted with EtOAc and washed with 4N HCl. The organic layer was separated, washed with water and dried over MgSO$_4$. The solvent was removed under reduced pressure. The crude residue was dissolved in Eaton's Reagent (700 mL, 54.0 g, 380 mmol) and the reaction mixture was heated to 120° C. overnight. The reaction mixture was poured onto a mixture of ice and MeOH. The resulting solid was filtered off and washed with water. The solid was suspended in a mixture of MeOH (100 mL) and cyclopropyl methyl ether (200 mL) and filtered off. The grey solid was washed with hexanes and dried yielding 7-bromo-3-chloro-8-fluoro-5H-chromeno[2,3-b]pyridin-5-one (53.76 g, 164 mmol, 43.0% yield) as a ~4:1 mixture of isomers.

Example 8

Procedure H

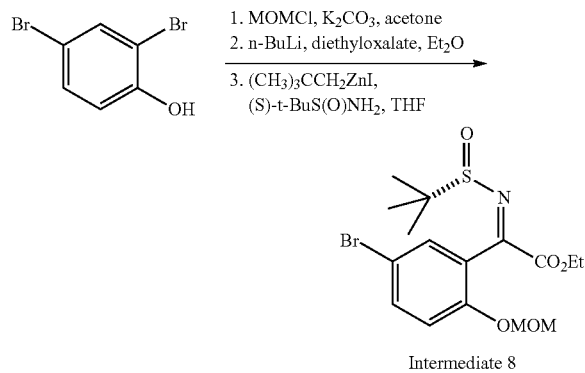

Intermediate 8

Synthesis of Intermediate 8
Step 1:
A flask was charged with 2,4-dibromophenol (50.4 g, 200 mmol), potassium carbonate (69.1 g, 500 mmol) and acetone (500 mL). The suspension was stirred at RT for 30 minutes and then treated dropwise with chloromethyl ethyl ether (19 mL, 213 mmol). After 3 h at RT the mixture was filtered and the filtrate was partitioned between EtOAc and water. The organic phase was separated, washed with water, aqueous saturated $NaHCO_3$ and brine. The organic phase was dried over $MgSO_4$ and the solvent was removed under reduced pressure to afford 54.2 g 2,4-dibromo-1-(methoxymethoxy) benzene, which was used in the next step without further purification.

Step 2:
A solution of 2,4-dibromo-1-(methoxymethoxy)benzene (40.5 g, 137 mmol) in $Et_2O$ (140 mL) was cooled to −78° C. and treated with n-BuLi (2.5M in hexanes; 60.2 mL, 151 mmol) under nitrogen atmosphere. After 30 minutes a solution of diethyl oxalate (27.9 mL, 205 mmol) in $Et_2O$ (20 mL) was added dropwise. The reaction mixture was stirred for 45 minutes at that temperature then quenched cold with saturated ammonium chloride solution. The mixture was partitioned between $Et_2O$ and water. The organic phase was separated, washed with water, brine, then dried over $MgSO_4$. The solvent was removed under reduced pressure to afford 49 g of ethyl 2-(5-bromo-2-(methoxymethoxy)phenyl)-2-oxoacetate, which was used in the next step without further purification.

Step 3:
A flask was charged with (S)-2-methylpropane-2-sulfinamide (0.764 g, 6.31 mmol) and neopentylzinc(II) iodide (0.5 M in THF, 10.0 mL, 5.00 mmol) was added under nitrogen atmosphere. The mixture was stirred at RT for 15 minutes and ethyl 2-(5-bromo-2-(methoxymethoxy)phenyl)-2-oxoacetate (1.00 g, 3.15 mmol) was added in one portion. The reaction mixture was quenched with saturated aqueous ammonium chloride after 8 h. The reaction was partitioned between EtOAc and water. The organic phase was separated, washed with $NH_4Cl$, water and brine. The organic phase was dried over $MgSO_4$ and the solvent was removed under reduced pressure. The crude material was purified by silica gel chromatography (10-30% EtOAc/hexane) to provide 0.675 g (S)-ethyl 2-(5-bromo-2-(methoxymethoxy)phenyl)-2-(tert-butylsulfinylimino)acetate.

Example 9

Procedure I

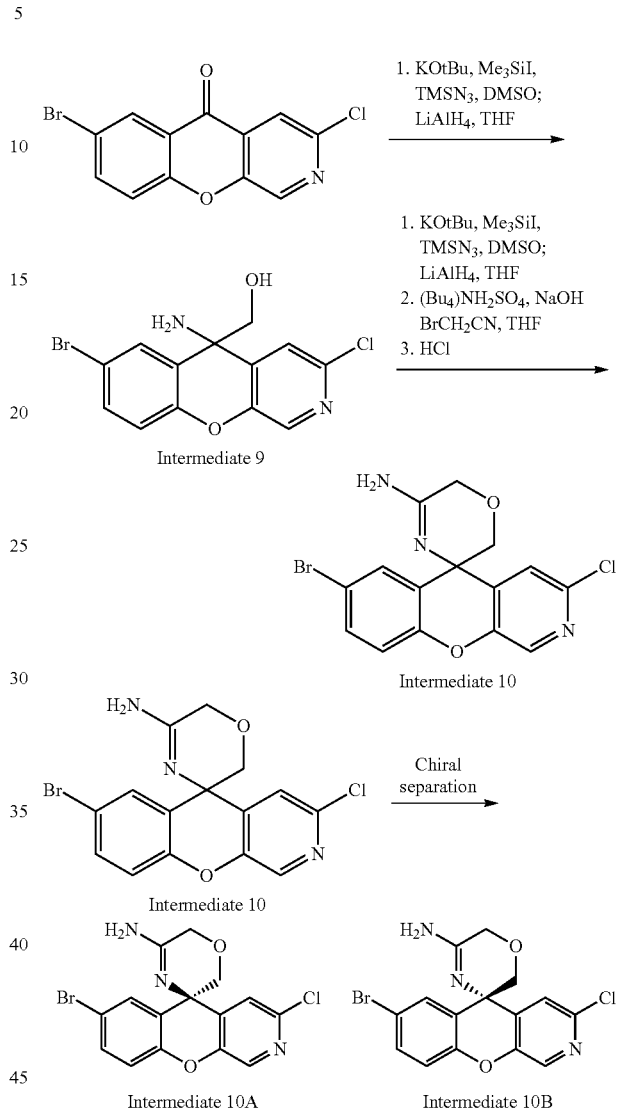

Synthesis of Intermediates 9, 10, 10A and 10B
Step 1:
A 500-mL RBF was charged with 7-bromo-3-chloro-5H-chromeno[2,3-c]pyridin-5-one (12.3789 g, 39.9 mmol), trimethylsulfonium iodide (8.95 g, 43.9 mmol), and DMSO (199 mL). The resulting slurry was stirred vigorously for 5 minutes leading to a tan slurry before potassium 2-methylpropan-2-olate (4.92 g, 43.9 mmol) was added in one portion. The resulting reddish orange solution was maintained at rt for 2 hours at which time azidotrimethylsilane (10.49 mL, 80 mmol) was added in one portion. The heterogeneous mixture became homogeneous after 2-3 hours. The solution was maintained at RT overnight before being diluted with EtOAc and transferred to a separatory funnel containing saturated $NaHCO_3$ (500 mL). The layers were separated and the aqueous layer was extracted with EtOAc (3×250 mL). The combined organic layers were sequentially washed with water and brine and dried over sodium sulfate. The solution was concentrated in vacuo to provide an orange oil that was evaporated from DCM (3×250 mL) to provide 5-azido-7-bromo-3-chloro-5-((trimethylsilyloxy)methyl)-5H-chromeno[2,3-c]pyridine which was carried on without further purification. A solution of the derived foam in THF (250 mL) was cooled to 0° C. and LAH (2M in THF) (39.9 mL, 80 mmol) was. The reaction was maintained at 0° C. for 2 hours then allowed to warm to RT for 30 minutes. The reaction was diluted with 150 mL of THF and quenched by the addition of sodium sulfate decahydrate (38.5 g, 120 mmol). After the addition was complete the slurry was stirred at RT for 1.5 hours before being filtered through a pad of celite. The filter pad was washed with THF. The filtrate was concentrated under vacuum to give a brown foam. The foam was concentrated from DCM twice and left under vacuum overnight. The solid was taken up in DCM (75 mL) and heated to boiling for 1 minute. The mixture was cooled to RT, and then placed in the fridge for 1 hour. The solid was filtered, washed with DCM (50 mL) and dried to provide (5-amino-7-bromo-3-chloro-5H-chromeno[2,3-c]pyridin-5-yl)methanol (8.94 g) as a light orange solid.

Step 2:

A 4-neck 3000-mL RBF with a mechanical stirrer was charged with (5-amino-7-bromo-3-chloro-5H-chromeno[2,3-c]pyridin-5-yl)methanol (29.43 g, 86 mmol), tetrabutylammonium hydrogen sulfate (5.85 g, 17.23 mmol), THF (431 mL), and bromoacetonitrile (30.0 mL, 431 mmol) to give a clear, brown solution. The resulting solution was stirred vigorously for 5 min, then a 2N aq. solution of NaOH (431 mL, 862 mmol) was added in one portion. The mixture was stirred overnight and concentrated under vacuum. The remaining material was partitioned between EtOAc (500 mL) and water (500 mL). The layers were separated and the aqueous layer was extracted with EtOAc (2×250 mL). The combined organic layers were washed with brine and dried over magnesium sulfate. The solvent was removed under reduced pressure. The residue was taken up in DCM and filtered through a short pad of silica gel. The filtrate was concentrated and purified by silica gel chromatography (0.5% MeOH/DCM) to provide 2-((5-amino-7-bromo-3-chloro-5H-chromeno[2,3-c]pyridin-5-yl)methoxy)acetonitrile.

Step 3:

A flask was charged with 2-((5-amino-7-bromo-3-chloro-5H-chromeno[2,3-c]pyridin-5-yl)methoxy)acetonitrile (21 g, 55.2 mmol), dioxane (460 mL) and HCl (4M in dioxane) (55.2 mL, 221 mmol) under nitrogen atmosphere. The reaction mixture was heated to 100° C. overnight. The mixture was cooled to RT and filtered. The filter cake was washed sequentially with dioxane and ether. The collected material was dried to give 15.72 g of a cream-colored solid, which was dissolved in DCM (100 mL) and saturated aqueous sodium bicarbonate (750 mL). The mixture was extracted with DCM (2×250 mL) and EtOAc (2×250 mL). The combined organic extracts were dried over sodium sulfate and concentrated to give 7-bromo-3-chloro-2',6'-dihydrospiro[chromeno[2,3-c]pyridine-5,3'-[1,4]oxazin]-5'-amine (Intermediate 1, 14.63 g) as an off-white solid.

Step 4:

7-Bromo-3-chloro-2',6'-dihydrospiro[chromeno[2,3-c]pyridine-5,3'-[1,4]oxazin]-5'-amine was chromatographed using supercritical CO$_2$ (additives 25% MeOH with 0.2% DEA) on a Chiralpak AD-H column (50×150 mm, 5 μm) eluting at a flow rate 300 ml/min (100 bar pressure, 40° C. column temperature). The first peak (retention time=1.6 min) provided (R)-7-bromo-3-chloro-2',6'-dihydrospiro[chromeno[2,3-c]pyridine-5,3'-[1,4]oxazin]-5'-amine (example 9B; intermediate 10A; >99% ee), and the second peak (retention time=2.4 min) provided (S)-7-bromo-3-chloro-2', 6'-dihydrospiro[chromeno[2,3-c]pyridine-5,3'-[1,4]oxazin]-5'-amine (example 9A; intermediate 10B; >99% ee).

Example 10

Procedure J

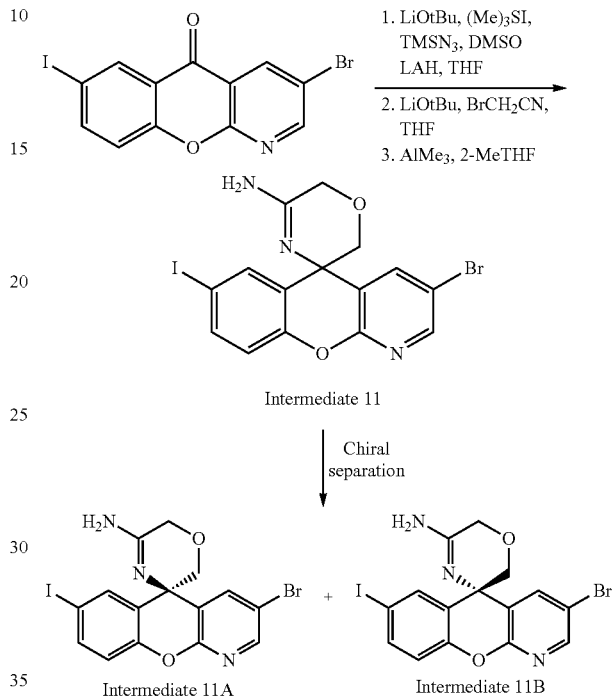

Intermediate 11

Intermediate 11A     Intermediate 11B

Synthesis of Intermediates 11, 11A and 11B

Step 1:

To a suspension of 3-bromo-7-iodo-5H-chromeno[2,3-b]pyridin-5-one (20.00 g, 49.8 mmol) and trimethylsulfonium iodide (11.17 g, 54.7 mmol) in 250 mL DMSO under nitrogen atmosphere was added lithium tert-butoxide [1N in heptane (54.7 mL, 54.7 mmol)] drop wise over 40 minutes. After stirring for an additional 30 minutes, trimethylsilylazide (13.21 mL, 100 mmol) was added. After stirring for an additional hour, the reaction mixture was concentrated under reduced pressure. The remaining solution was diluted with water. The resulting solid was filtered off and washed with water. The solid was dissolved in 2-MeTHF, dried over MgSO$_4$ and concentrated. The crude residue was dissolved in 200 mL THF, cooled to 0° C. and treated with LAH (1.888 g, 49.8 mmol). After stirring for 30 minutes, the cooling bath was removed, and the reaction mixture was allowed to stir for an additional 30 minutes. The reaction mixture was then cooled to 0° C. and quenched with sodium sulfate decahydrate (32.1 g, 100 mmol). The reaction mixture was vigorously stirred for one hour, filtered through a plug of celite and concentrated. Purification of the crude residue by column chromatography [0-80% (95:5 EtOAc/MeOH)/DCM] gave (5-amino-3-bromo-7-iodo-5H-chromeno[2,3-b]pyridin-5-yl)methanol (8.80 g, 20.32 mmol, 40.8% yield).

Step 2:

A solution of (5-amino-3-bromo-7-iodo-5H-chromeno[2,3-b]pyridin-5-yl)methanol (10.00 g, 23.09 mmol) and bromoacetonitrile (12.06 mL, 173 mmol) in 25 mL THF was heated to 40° C. Lithium tert-butoxide [1N in THF (173 mL, 173 mmol)] was added drop wise via addition funnel over 5 hours. After completed addition, the reaction mixture was concentrated. The residue was purified by column chromatography [0-80% (95:5 EtOAc/MeOH)/heptane] to yield 2-((5-amino-3-bromo-7-iodo-5H-chromeno[2,3-b]pyridin-5-yl)methoxy)acetonitrile (5.58 g, 11.82 mmol, 51.2% yield).

Step 3:

A solution of 2-((5-amino-3-bromo-7-iodo-5H-chromeno[2,3-b]pyridin-5-yl)methoxy)acetonitrile (5.58 g, 11.82 mmol) in 100 mL 2-MeTHF under nitrogen atmosphere was treated with trimethylaluminum [2N in heptane (7.98 mL, 15.96 mmol)]. After stirring for 10 minutes at RT, the reaction mixture was heated to 80° C. for 90 minutes. The reaction mixture was cooled to RT and quenched with MeOH. The reaction mixture was treated with saturated Rochelle's salt solution and vigorously stirred for an additional hour. The organic layer was separated, washed with brine, dried over MgSO$_4$ and concentrated under reduced pressure. Purification of the crude residue by column chromatography [0-80% (90:10:1 DCM/MeOH/NH4OH)/DCM] gave 3-bromo-7-iodo-2',6'-dihydrospiro[chromeno[2,3-b]pyridine-5,3'-[1,4]oxazin]-5'-amine (Intermediate 2, 2.97 g).

Step 4:

Intermediates (R)-3-bromo-7-iodo-2',6'-dihydrospiro[chromeno[2,3-b]pyridine-5,3'-[1,4]oxazin]-5'-amine (11A) and (S)-3-bromo-7-iodo-2',6'-dihydrospiro[chromeno[2,3-b]pyridine-5,3'-[1,4]oxazin]-5'-amine (11B) were obtained form racemic 3-bromo-7-iodo-2',6'-dihydrospiro[chromeno[2,3-b]pyridine-5,3'-[1,4]oxazin]-5'-amine using similar chiral separation conditions as described herein for intermediate 10.

Example 11

Procedure K

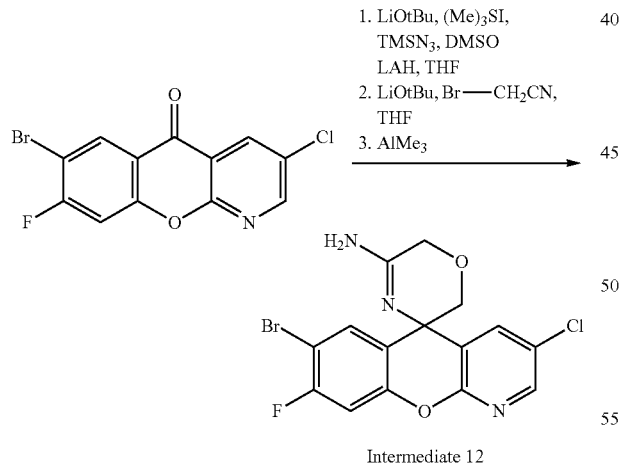

Intermediate 12

Synthesis of Intermediate 12

Step 1:

A solution of 7-bromo-3-chloro-8-fluoro-5H-chromeno[2,3-b]pyridin-5-one (10.00 g, 30.4 mmol) and trimethylsulfonium iodide (6.83 g, 33.5 mmol) in 150 mL DMSO under argon atmosphere was treated with potassium tert-butoxide (3.76 g, 33.5 mmol) at rt. After 75 minutes, trimethylsilylazide (8.08 mL, 60.9 mmol) was added, and the reaction mixture was allowed to stir overnight. The reaction mixture was then diluted with EtOAc and washed with water. The suspension was filtered, and the filtrate was dried over MgSO$_4$ and concentrated under reduced pressure. The crude residue was taken up in 100 mL THF and cooled to 0° C. LAH (1.155 g, 30.4 mmol) was added, and the reaction mixture was allowed to stir for 30 minutes. The ice bath was removed, and the reaction mixture was allowed to stir for an additional 30 minutes. The reaction mixture was then cooled back to 0° C. and quenched with sodium sulfate decahydrate (9.81 g, 30.4 mmol). After stirring for one hour, the reaction mixture was filtered through celite and concentrated under reduced pressure. Purification of the crude residue by column chromatography [0-80% (95:5 EtOAc/MeOH)/DCM] gave (5-amino-7-bromo-3-chloro-8-fluoro-5H-chromeno[2,3-b]pyridin-5-yl)methanol (2.83 g, 7.87 mmol, 25.9% yield).

Step 2:

A solution of (5-amino-7-bromo-3-chloro-8-fluoro-5H-chromeno[2,3-b]pyridin-5-yl)methanol (2.83 g, 7.87 mmol) and bromoacetonitrile (5.48 mL, 79 mmol) in 16 mL THF was heated to 40° C. and treated drop wise with lithium tert-butoxide [1N in THF (79 mL, 79 mmol)] over a time period of 4 hours. After completed addition the reaction mixture was concentrated under reduced pressure. Purification of the crude residue by column chromatography [0-40% (95:5 EtOAc/MeOH)/DCM] gave 2-((5-amino-7-bromo-3-chloro-8-fluoro-5H-chromeno[2,3-b]pyridin-5-yl)methoxy)acetonitrile (1.362 g, 3.42 mmol, 43.4% yield).

Step 3:

To a solution of 2-((5-amino-7-bromo-3-chloro-8-fluoro-5H-chromeno[2,3-b]pyridin-5-yl)methoxy)acetonitrile (1.363 g, 3.42 mmol) in 10 mL 2-MeTHF under nitrogen atmosphere was added trimethylaluminum [2N in heptane (3.42 mL, 6.84 mmol)]. After stirring for 10 minutes, the reaction mixture was heated to 80° C. overnight. The reaction mixture was then allowed to cool to RT, and quenched with MeOH. Saturated Rochelle's salt solution was added, and the reaction mixture was vigorously stirred for an additional hour. The organic layer was separated, washed with brine, dried over MgSO$_4$ and concentrated under reduced pressure. Purification of the crude residue by column chromatography [0-80% (90:10:1 DCM/MeOH/NH4OH)/DCM] gave 7-bromo-3-chloro-8-fluoro-2',6'-dihydrospiro[chromeno[2,3-b]pyridine-5,3'-[1,4]oxazin]-5'-amine (0.422 g, 1.059 mmol, 31.0% yield).

Example 12

Procedure L

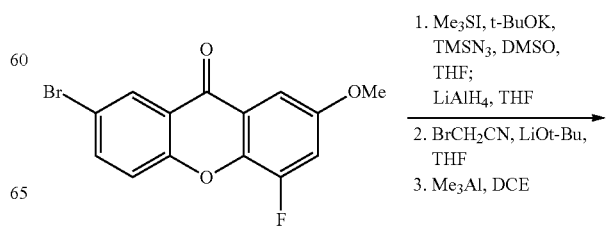

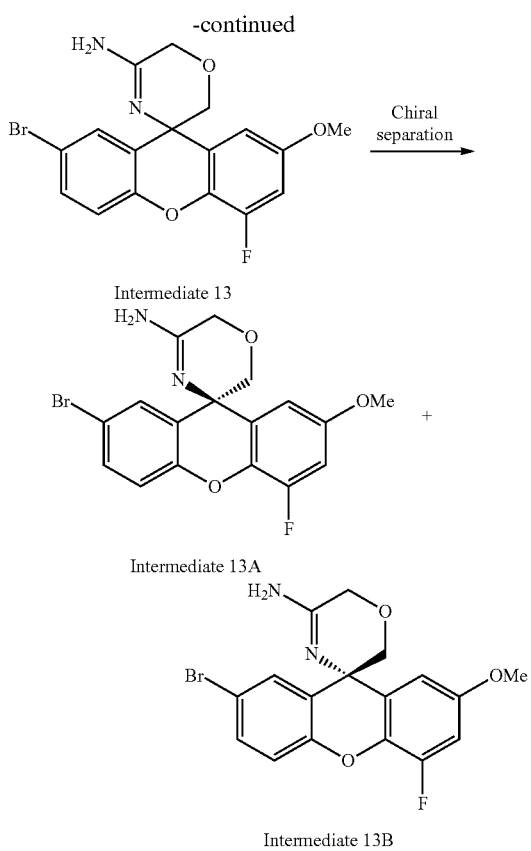

Intermediate 13

Intermediate 13A

Intermediate 13B

Synthesis of Intermediates 13, 13A and 13B
Step 1:

To a suspension of 7-bromo-4-fluoro-2-methoxy-9H-xanthen-9-one (25.00 g, 77 mmol) and trimethylsulfonium iodide (23.68 g, 116 mmol) in DMSO (130 mL)/THF (130 mL) was added drop wise potassium tert-butoxide (1M in THF) (116 mL, 116 mmol). After 15 min at RT trimethylsilyl azide (20.54 mL, 155 mmol) was added. The reaction mixture was stirred for additional 40 minutes and then quenched by addition of 100 ml of saturated aqueous sodium bicarbonate. After stirring for 10 minutes EtOAc (100 ml) and water (100 ml were added and the layers were separated. The organic layer was washed with water (3×100 ml), brine (100 ml) and dried over MgSO₄. The solvent was removed under reduced pressure to obtain a yellow residue which was dissolved in 250 ml THF. The solution was cooled to 0° C. and LAH (1 M in THF, 108 mL, 108 mmol) was added drop wise. After 5 minutes at 0° C. the reaction mixture was allowed to warm to RT. The reaction mixture was cooled again to 0° C. and sodium sulfate decahydrate (21.98 g, 155 mmol) was added portion wise. The mixture was stirred for 5 minutes and diluted with 100 ml EtOAc. The reaction mixture was filtered through a pad of Celite and the filter cake was washed with EtOAc (100 ml). The filtrate was concentrated under reduced pressure to obtain a yellow foam which was re-crystallized from DCM to afford (9-amino-7-bromo-4-fluoro-2-methoxy-9H-xanthen-9-yl)methanol as a white solid.
Step 2:

A solution of (9-amino-7-bromo-4-fluoro-2-methoxy-9H-xanthen-9-yl)methanol (9.83 g, 27.8 mmol) in THF (46.3 mL) was sequentially treated with lithium t-butoxide (1 M in THF) (30.5 mL, 30.5 mmol) and 2-bromoacetonitrile (2.90 mL, 41.6 mmol) at RT. After 2.5 hours reaction time, additional 0.5 equivalent lithium t-butoxide and 2-bromoacetonitrile (1.5 mL) were added. After 4 hours reaction time, an additional 0.25 equivalent lithium t-butoxide and bromoacetonitrile (0.75 mL) were added. After 5 hours reaction time another 0.25 equivalent of lithium t-butoxide and bromoacetonitrile (0.75 mL) were added to the mixture. Water (100 ml) was added and solvents were removed under reduced pressure. The aqueous residue was filtered, the solid was washed twice with water, dried under reduced pressure and re-suspended in ethanol. The solid was filtered off, washed with ethanol and dried under reduced pressure to afford 2-((9-amino-7-bromo-4-fluoro-2-methoxy-9H-xanthen-9-yl)methoxy)acetonitrile.
Step 3:

To a solution of 2-((9-amino-7-bromo-4-fluoro-2-methoxy-9H-xanthen-9-yl)methoxy)acetonitrile (7.72 g, 19.63 mmol) in DCE (115 mL) was added trimethylaluminum (2M in toluene) (19.63 mL, 39.3 mmol) at RT. The reaction mixture was stirred for 10 min at RT and then heated to 75° C. for 1 hour. The reaction mixture was cooled to RT and quenched with sodium sulfate decahydrate. The reaction mixture was vigorously stirred for 30 minutes, diluted with EtOAc and stirred overnight. The mixture was filtered through a pad of celite and filter cake was washed with EtOAc. The solvent was removed under reduced pressure to obtain an oily residue which crystallized to give 7'-bromo-4'-fluoro-2'-methoxy-2,6-dihydrospiro[[1,4]oxazine-3,9'-xanthen]-5-amine (7.49 g, 19.05 mmol, 97% yield) as a cream-colored solid.
Step 4:

Intermediates (R)-7'-bromo-4'-fluoro-2'-methoxy-2,6-dihydrospiro[[1,4]oxazine-3,9'-xanthen]-5-amine (13A) and (S)-7'-bromo-4'-fluoro-2'-methoxy-2,6-dihydrospiro[[1,4]oxazine-3,9'-xanthen]-5-amine (13B) were obtained from racemic product, 7'-bromo-4'-fluoro-2'-methoxy-2,6-dihydrospiro[[1,4]oxazine-3,9'-xanthen]-5-amine (Intermediate 13) using similar chiral separation conditions as described herein for intermediate 10.

Example 13

Procedure M

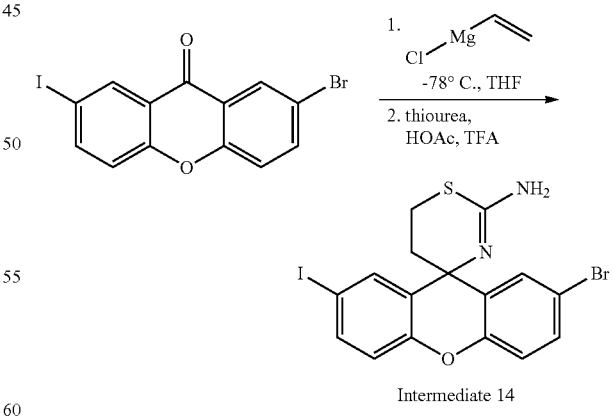

Intermediate 14

Synthesis of Intermediate 14
Step 1:

To a solution of vinylmagnesium chloride (6.86 mL, 10.97 mmol) at −78° C. under nitrogen atmosphere was added drop wise a solution of 2-bromo-7-iodo-9H-xanthen-9-one (2.00 g, 4.99 mmol) in THF (30 mL). The reaction mixture was allowed to slowly warm to −10° C., then the reaction was quenched with saturated NH₄Cl. The mixture was extracted with EtOAc followed by a solvent mixture of CHCl₃:i-PrOH (3:1). The combined organic layers were dried over Na₂SO₄ and concentrated under reduced pressure. The crude material was purified by filtration over silica gel (10% EtOAc/hexane) to give 2.14 g of 2-bromo-7-iodo-9-vinyl-9H-xanthen-9-ol as a white solid.

Step 2:

To a solution of 2-bromo-7-iodo-9-vinyl-9H-xanthen-9-ol (0.50 g, 1.16 mmol) and thiourea (0.18 g, 2.33 mmol) in acetic acid (2.00 mL) was added TFA (4.00 mL). The reaction mixture was stirred at RT overnight. The reaction mixture was concentrated under reduced pressure and extracted with EtOAc, followed by a solvent mixture of CHCl₃:i-PrOH (3:1). The combined organic layers were dried over Na₂SO₄ and concentrated in vacuo. The residue was purified by chromatography (10%-100% EtOAc/hexane) to provide 0.36 g of 2'-bromo-7'-iodo-5,6-dihydrospiro[[1,3]thiazine-4,9'-xanthen]-2-amine as a light yellow solid.

Example 14

Procedure N

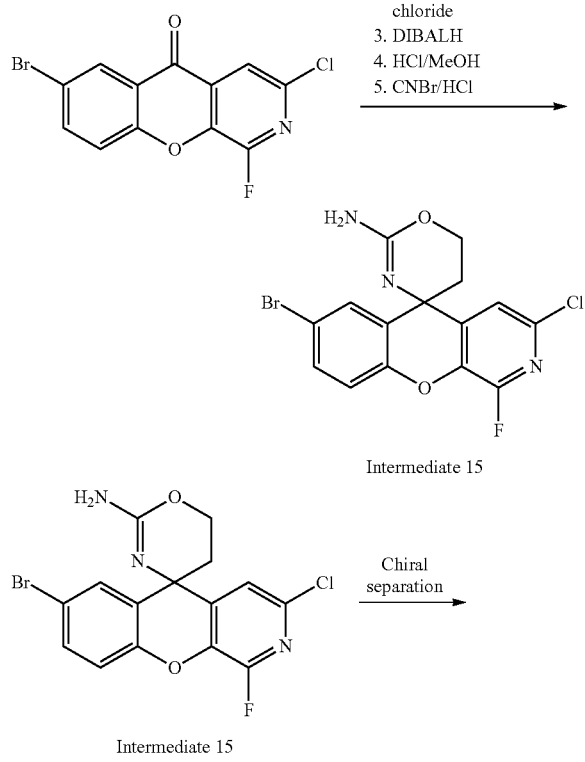

Intermediate 15

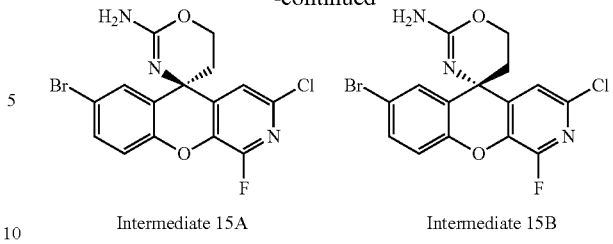

Intermediate 15A        Intermediate 15B

Synthesis of Intermediates 15, 15A and 15B

Step 1:

A suspension of 7-bromo-3-chloro-1-fluoro-5H-chromeno[2,3-c]pyridin-5-one (20 g, 60.9 mmol), (R)-2-methyl-2-propanesulfinamide (14.76 g, 122 mmol), and titanium (IV) ethoxide (25.2 mL, 122 mmol) in THF (250 mL) was heated to 70° C. for 24 h. Additional (R)-2-methyl-2-propanesulfinamide (1.0 equiv) and titanium (IV) ethoxide (1.0 equiv) were added and the reaction mixture was heated for additional 24 h. Additional (R)-2-methyl-2-propanesulfinamide (1.0 equiv) and titanium (IV) ethoxide (1.0 equiv) were added and the reaction mixture was heated for additional 8 h. The reaction mixture was quenched with brine (150 mL). The resulting suspension was filtered through celite, and the filter cake was washed with EtOAc. The filtrate was washed with brine, dried over Na₂SO₄ and concentrated under reduced pressure. The residue was purified by chromatography (100% hexanes) to afford racemic N-(7-bromo-3-chloro-1-fluoro-5H-chromeno[2,3-c]pyridin-5-ylidene)-2-methylpropane-2-sulfinamide as an orange solid (15 g, 34.7 mmol, 57.1% yield).

Step 2:

A solution of (2-tert-butoxy-2-oxoethyl)zinc(II) chloride (0.5M in Et₂O; 116 mL, 57.9 mmol) was cooled to 0° C. and a solution of (Z)—N-(7-bromo-3-chloro-1-fluoro-5H-chromeno[2,3-c]pyridin-5-ylidene)-2-methylpropane-2-sulfinamide (10 g, 23.16 mmol) in THF (100 mL) was added drop wise. The resulting mixture was stirred at for 1 hour 0° C. The reaction mixture was diluted with EtOAc and washed with aqueous saturated solution of NH₄Cl, followed by brine. The organic layer was dried over Na₂SO₄, and concentrated under reduced pressure. The obtained residue was purified by chromatography (0-20% EtOAc/hexanes) to afford tert-butyl 2-(7-bromo-3-chloro-5-(1,1-dimethylethylsulfinamido)-1-fluoro-5H-chromeno[2,3-c]pyridin-5-yl)acetate (7.5 g, 13.69 mmol, 59.1% yield) as a yellow solid.

Step 3:

A solution of tert-butyl 2-(7-bromo-3-chloro-5-(1,1-dimethylethylsulfinamido)-1-fluoro-5H-chromeno[2,3-c]pyridin-5-yl)acetate (7.5 g, 13.69 mmol) in dry THF (25 mL) was cooled to −78° C. and diisobutylaluminum hydride (54.8 mL, 54.8 mmol) was added drop wise. The mixture was warmed to 0° C. and kept at this temperature for 1 h. The reaction mixture was quenched with a aqueous, saturated solution of Rochelle's salt and vigorously stirred for 15 h. The organic layer was separated and the aqueous phase was extracted with EtOAc. The combined organic layers were washed with brine and dried over Na₂SO₄. The solution was concentrated under reduced pressure. The residue was purified by chromatography (0-30% EtOAc/hexanes) to afford N-(7-bromo-3-chloro-1-fluoro-5-(2-hydroxyethyl)-5H-chromeno[2,3-c]pyridin-5-yl)-2-methylpropane-2-sulfinamide (5.8 g, 89% yield) as a light yellow solid.

Step 4:

To a solution of N-(7-bromo-3-chloro-1-fluoro-5-(2-hydroxyethyl)-5H-chromeno[2,3-c]pyridin-5-yl)-2-methylpropane-2-sulfinamide (5.8 g, 12.14 mmol) in dry MeOH (100 mL) at −20° C. was added a mixture of MeOH (80 mL)acetylchloride (20 ml). The resulting reaction mixture was stirred at −20° C. for 30 min and then quenched with 10% aqueous solution of $Na_2CO_3$. DCM was added, the organic phase was separated and dried over $Na_2SO_4$. The solution concentrated under reduced pressure and the residue was purified by chromatography (0-50% EtOAc/hexanes) to afford 2-(5-amino-7-bromo-3-chloro-1-fluoro-5H-chromeno[2,3-c]pyridin-5-yl)ethanol (4.0 g, 10.71 mmol, 88% yield) as a light yellow solid-foam.

Step 5:

To a solution of 2-(5-amino-7-bromo-3-chloro-1-fluoro-5H-chromeno[2,3-c]pyridin-5-yl)ethanol (4.2 g, 11.24 mmol) in MeOH (40 mL) was added potassium acetate (2.207 g, 22.48 mmol) followed by the drop wise addition of cyanogen bromide (3.0 m solution in DCM; 4.50 mL, 13.49 mmol). The resulting reaction mixture was stirred at RT for 17 h. The reaction mixture was concentrated under reduced pressure, followed by the addition of 4.0 M HCl in dioxane (15 mL). The reaction mixture was stirred at RT for 2 h. The reaction mixture was concentrated under reduced pressure, The residue was dissolved in DCM, washed with aqueous, saturated $NaHCO_3$ solution and brine. The solution was dried over $Na_2SO_4$ and concentrated under reduced pressure. The residue was purified by chromatography (0-100% EtOAc/hexanes) to afford 7-bromo-3-chloro-1-fluoro-5',6'-dihydrospiro[chromeno[2,3-c]pyridine-5,4'-[1,3]oxazin]-2'-amine (Intermediate 11, 1.3 g, 3.26 mmol, 29.0% yield) as a yellow solid.

Step 6

Intermediates (R)-7-bromo-3-chloro-1-fluoro-5',6'-dihydrospiro[chromeno[2,3-c]pyridine-5,4'-[1,3]oxazin]-2'-amine (15A) and (S)-7-bromo-3-chloro-1-fluoro-5',6'-dihydrospiro[chromeno[2,3-c]pyridine-5,4'-[1,3]oxazin]-2'-amine (15B) were obtained from racemic 7-bromo-3-chloro-1-fluoro-5',6'-dihydrospiro[chromeno[2,3-c]pyridine-5,4'-[1,3]oxazin]-2'-amine using similar chiral separation conditions as described herein for intermediate 10.

Example 15

Procedure O

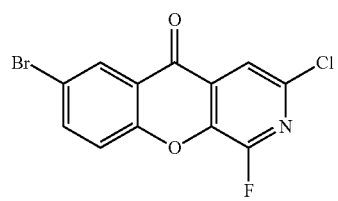

1. Ti(OEt)$_4$
   (R)-2-methyl-2-propanesulfinamide
2. (2-tert-butoxy-2-oxoethyl)zinc(II) chloride
3. DIBALH
4. 4-nitrobenzoyl isothiocyanate, rt DCC, Et$_3$N;
   MeOH, K$_2$CO$_3$, rt -continued

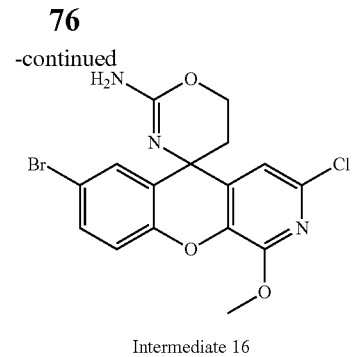

Intermediate 16

Synthesis of Intermediate 16

Step 1:

A suspension of 7-bromo-3-chloro-1-fluoro-5H-chromeno[2,3-c]pyridin-5-one (20 g, 60.9 mmol), (R)-2-methyl-2-propanesulfinamide (14.76 g, 122 mmol), and titanium (IV) ethoxide (25.2 mL, 122 mmol) in THF (250 mL) was heated to 70° C. for 24 h. Additional (R)-2-methyl-2-propanesulfinamide (1.0 equiv) and titanium (IV) ethoxide (1.0 equiv) were added and the reaction mixture was heated for additional 24 h. Additional (R)-2-methyl-2-propanesulfinamide (1.0 equiv) and titanium (IV) ethoxide (1.0 equiv) were added and the reaction mixture was heated for additional 8 h. The reaction mixture was quenched with brine (150 mL). The resulting suspension was filtered through celite, and the filter cake was washed with EtOAc. The filtrate was washed with brine, dried over $Na_2SO_4$ and concentrated under reduced pressure. The residue was purified by chromatography (100% hexanes) to afford racemic N-(7-bromo-3-chloro-1-fluoro-5H-chromeno[2,3-c]pyridin-5-ylidene)-2-methylpropane-2-sulfinamide as an orange solid (15 g, 34.7 mmol, 57.1% yield).

Step 2:

A solution of (2-tert-butoxy-2-oxoethyl)zinc(II) chloride (0.5M in Et$_2$O; 116 mL, 57.9 mmol) was cooled to 0° C. and a solution of (Z)—N-(7-bromo-3-chloro-1-fluoro-5H-chromeno[2,3-c]pyridin-5-ylidene)-2-methylpropane-2-sulfinamide (10 g, 23.16 mmol) in THF (100 mL) was added drop wise. The resulting mixture was stirred at for 1 hour 0° C. The reaction mixture was diluted with EtOAc and washed with aqueous saturated solution of NH$_4$Cl, followed by brine. The organic layer was dried over $Na_2SO_4$, and concentrated under reduced pressure. The obtained residue was purified by chromatography (0-20% EtOAc/hexanes) to afford tert-butyl 2-(7-bromo-3-chloro-5-(1,1-dimethylethylsulfinamido)-1-fluoro-5H-chromeno[2,3-c]pyridin-5-yl)acetate (7.5 g, 13.69 mmol, 59.1% yield) as a yellow solid.

Step 3:

A solution of tert-butyl 2-(7-bromo-3-chloro-5-(1,1-dimethylethylsulfinamido)-1-fluoro-5H-chromeno[2,3-c]pyridin-5-yl)acetate (7.5 g, 13.69 mmol) in dry THF (25 mL) was cooled to −78° C. and diisobutylaluminum hydride (54.8 mL, 54.8 mmol) was added drop wise. The mixture was warmed to 0° C. and kept at this temperature for 1 h. The reaction mixture was quenched with a aqueous, saturated solution of Rochelle's salt and vigorously stirred for 15 h. The organic layer was separated and the aqueous phase was extracted with EtOAc. The combined organic layers were washed with brine and dried over $Na_2SO_4$. The solution was concentrated under reduced pressure. The residue was purified by chromatography (0-30% EtOAc/hexanes) to afford N-(7-bromo-3-chloro-1-fluoro-5-(2-hydroxyethyl)-5H-chromeno[2,3-c]pyridin-5-yl)-2-methylpropane-2-sulfinamide (5.8 g, 89% yield) as a light yellow solid.

Step 4:

To a solution of 2-(5-amino-7-bromo-3-chloro-1-fluoro-5H-chromeno[2,3-c]pyridin-5-yl)ethanol (0.50 g, 1.338 mmol) in THF (10 mL) was added 4-nitrobenzoyl isothiocyanate (0.306 g, 1.472 mmol) and the reaction mixture was stirred at RT for 25 min. TEA (0.019 mL, 0.134 mmol) and 1,3-dicyclohexylcarbodiimide (0.304 g, 1.472 mmol) were added and the reaction mixture was heated at 70° C. for 1.5 h. The reaction mixture was allowed to warm to RT and concentrated under reduced pressure. The residue was dissolved in MeOH (15 mL) and potassium carbonate (0.555 g, 4.01 mmol) was added. The resulting mixture was stirred at rt overnight. The reaction mixture was concentrated under reduced pressure, washed with water and extracted with DCM. The combined organic layers were dried over Na$_2$SO$_4$ and the solvent was removed under reduced pressure. The residue was purified by chromatography (0-40% EtOAc/hexanes) to afford 7-bromo-3-chloro-1-methoxy-5',6'-dihydrospiro[chromeno[2,3-c]pyridine-5,4'-[1,3]oxazin]-2'-amine (0.45 g, 1.096 mmol, 82% yield) as a yellow solid.

Example 16

Procedure P

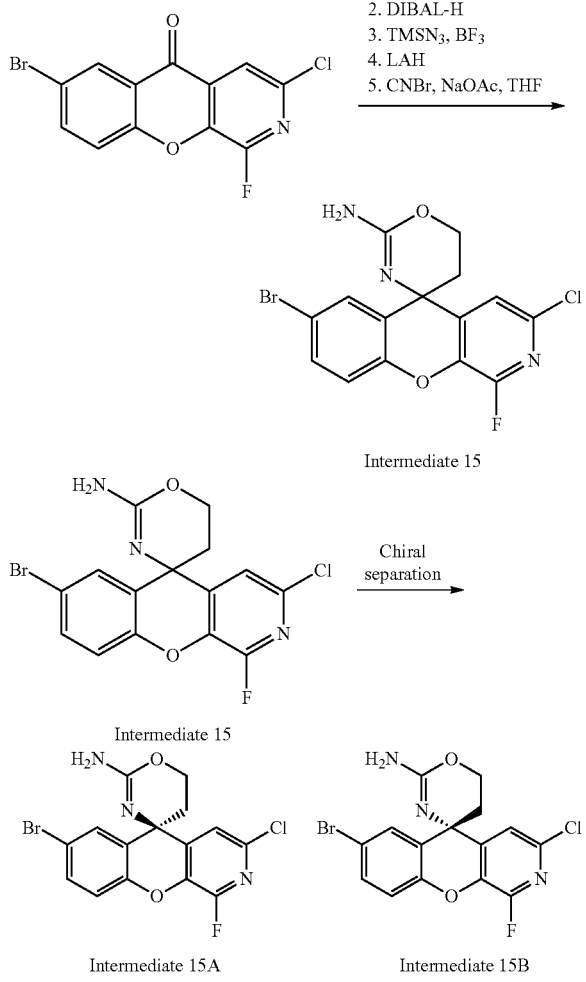

Alternative Methods for Synthesis of Intermediates 15, 15A and 15B

Step 1:

To a solution of (2-tert-butoxy-2-oxoethyl)zinc(II) chloride (0.5M in Et$_2$O; 670 ml, 335 mmol) at 0° C. was added drop wise a solution of 7-bromo-3-chloro-1-fluoro-5H-chromeno[2,3-c]pyridin-5-one (55 g, 167 mmol) in THF (30 mL). The resulting reaction mixture was stirred at 0° C. for 1 h. The reaction mixture was quenched with aqueous, saturated NH$_4$Cl solution and extracted with EtOAc. The organic extracts were dried over Na$_2$SO$_4$ and concentrated under reduced pressure to afford tert-butyl 2-(7-bromo-3-chloro-1-fluoro-5-hydroxy-5H-chromeno[2,3-c]pyridin-5-yl)acetate (66.0 g, 148 mmol, 89% yield) as a yellow solid.

Step 2:

A solution of tert-butyl 2-(7-bromo-3-chloro-1-fluoro-5-hydroxy-5H-chromeno[2,3-c]pyridin-5-yl)acetate (66 g, 148 mmol) in THF (200 mL) was cooled to −78° C. followed by the drop wise addition of diisobutylaluminum hydride (1.0 M solution in THF; 180 ml, 180 mmol). The resulting reaction mixture was cooled to 0° C. and stirred for 2 h. The reaction mixture was quenched with aqueous, saturated NH$_4$Cl solution and extracted with EtOAc. The combined organics were dried over Na$_2$SO$_4$ and concentrated under reduced pressure. The obtained residue was purified by chromatography (0-50% EtOAc/hexanes) to afford 7-bromo-3-chloro-1-fluoro-5-(2-hydroxyethyl)-5H-chromeno[2,3-c]pyridin-5-ol (48 g, 128 mmol, 86% yield) as a light yellow solid.

Step 3:

To a solution of 7-bromo-3-chloro-1-fluoro-5-(2-hydroxyethyl)-5H-chromeno[2,3-c]pyridin-5-ol (48 g, 128 mmol) in THF (58 mL) were added azidotrimethylsilane (34.0 ml, 256 mmol) and boron trifluoride diethyl etherate (31.6 ml, 256 mmol). The reaction mixture was heated to 60° C. for 15 h. Additional azidotrimethylsilane (34.0 ml, 256 mmol) and boron trifluoride diethyl etherate (31.6 ml, 256 mmol) were added and heating was continued for 3 h. The reaction mixture was quenched with aqueous, saturated NaHCO$_3$ solution and extracted with EtOAc. The organic phase was separated, dried over Na$_2$SO$_4$ and concentrated under reduced pressure. The residue was purified by chromatography (0-30% EtOAc/hexanes) to afford 2-(5-azido-7-bromo-3-chloro-1-fluoro-5H-chromeno[2,3-c]pyridin-5-yl)ethanol (41 g, 103 mmol, 80% yield) as a pale yellow solid-foam.

Step 4:

To a solution of LAH (1.0 M solution in tetrahydrafuran; 90 ml, 90 mmol) in THF (50 mL) at rt was added drop wise a solution of 2-(5-azido-7-bromo-3-chloro-1-fluoro-5H-chromeno[2,3-c]pyridin-5-yl)ethanol (24 g, 60.1 mmol) in THF (150 mL). The resulting mixture was stirred at RT for 1 h. The reaction mixture was quenched with sodiumsulfate decahydrate and stirred for 30 min. The mixture was filtered, the filtrate was concentrated under reduced pressure and the residue was purified by chromatography (0-50% EtOAc/hexanes) to afford 2-(5-amino-7-bromo-3-chloro-1-fluoro-5H-chromeno[2,3-c]pyridin-5-yl)ethanol (16.5 g, 44.2 mmol) as a colorless oil.

Step 5:

To a solution of 2-(5-amino-7-bromo-3-chloro-1-fluoro-5H-chromeno[2,3-c]pyridin-5-yl)ethanol (13 g, 34.8 mmol) in EtOH (50 mL) was added sodium acetate (5.71 g, 69.6 mmol) followed by the dropwise addition of cyanogen bromide (3.0M solution in DCM; 13.92 ml, 41.8 mmol). The resulting mixture was stirred at RT for 5 days. The reaction mixture was concentrated under reduced pressure, washed with water and extracted with DCM. The combined organic layers were dried over Na$_2$SO$_4$, concentrated under reduced pressure and azeotropically dried with toluene. The obtained residue was dissolved in DCM and TFA (40 mL) was added to the solution. The resulting mixture was stirred at RT for 30 min. The mixture was carefully quenched with aqueous, saturated NaHCO₃ solution and extracted with DCM. The combined organics were dried over Na₂SO₄ and concentrated under reduced pressure. The obtained residue was purified by chromatography (0-3% MeOH/DCM) to afford 7-bromo-3-chloro-1-fluoro-5',6'-dihydrospiro[chromeno[2,3-c]pyridine-5,4'-[1,3]oxazin]-2'-amine (6.2 g, 15.55 mmol, 44.7% yield) as a light yellow solid.

Step 6:

Intermediates (R)-7-bromo-3-chloro-1-fluoro-5',6'-dihydrospiro[chromeno[2,3-c]pyridine-5,4'-[1,3]oxazin]-2'-amine (15A) and (S)-7-bromo-3-chloro-1-fluoro-5',6'-dihydrospiro[chromeno[2,3-c]pyridine-5,4'-[1,3]oxazin]-2'-amine (15B) were obtained from racemic 7-bromo-3-chloro-1-fluoro-5',6'-dihydrospiro[chromeno[2,3-c]pyridine-5,4'-[1,3]oxazin]-2'-amine using similar chiral separation conditions as described herein for intermediate 10.

Example 17

Procedure Q

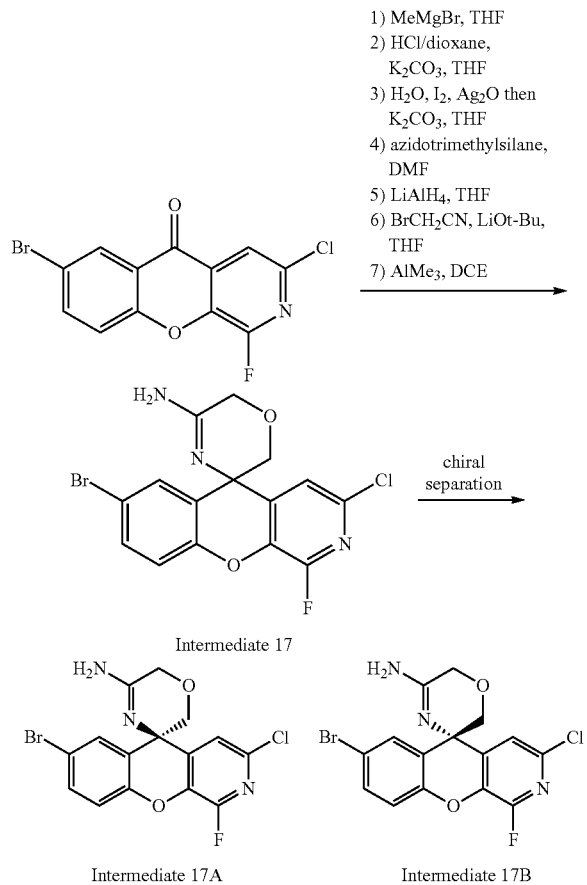

Synthesis of Intermediates 17, 17A and 17B

Step 1:

A suspension of 7-bromo-3-chloro-1-fluoro-5H-chromeno[2,3-c]pyridin-5-one (35 g, 107 mmol) in dry THF (210 mL) under nitrogen atmosphere was cooled to 0° C. and a solution of methylmagnesium bromide (3.0M solution in diethyl ether; 107 mL, 320 mmol) in dry THF (70 mL) was added over 10 minutes via an addition funnel. After complete addition a saturated aqueous solution of NH₄Cl (125 mL) was added slowly to the stirring reaction mixture, keeping the internal temperature below 30° C. Water was added and the mixture was extracted twice with EtOAc. The combined organic layers were dried over sodium sulfate before concentrating under reduced pressure to afford 7-bromo-3-chloro-1-fluoro-5-methyl-5H-chromeno[2,3-c]pyridin-5-ol (34.33 g, 100 mmol).

Step 2:

To a solution of 7-bromo-3-chloro-1-fluoro-5-methyl-5H-chromeno[2,3-c]pyridin-5-ol (50 g, 145 mmol) in THF (300 mL) was added HCl in dioxane (4M, 19.95 mL, 80 mmol). The reaction was heated to 50° C. for 16 hours. The reaction was cooled to RT and K₂CO₃ (30.1 g, 218 mmol) was added. The reaction mixture was stirred for 30 minutes before filtering. The filtrate was concentrated under reduced pressure and the resulting crude material was washed with DCM. The solid was collected by filtration to afford 7-bromo-3-chloro-1-fluoro-5-methylene-5H-chromeno[2,3-c]pyridine (33.0 g, 101 mmol, 69.6% yield).

Step 3:

To a solution of 7-bromo-3-chloro-1-fluoro-5-methylene-5H-chromeno[2,3-c]pyridine (33 g, 101 mmol) in THF (450 mL) were added successively water (69.2 mL), iodine (51.3 g, 202 mmol) and silver(II) oxide (46.8 g, 202 mmol) at RT. The reaction mixture was stirred at RT for 10 minutes before adding K₂CO₃ (41.9 g, 303 mmol). After 30 minutes, the reaction mixture was diluted with EtOAc and filtered through a pad of celite. The filter cake was washed with additional EtOAc. The combined filtrate was concentrated under reduced pressure upon which a white solid precipitated. The solid was filtered off. The filtrate was further concentrated under reduced pressure to obtain a residue which was triturated with ether to afford a white precipitate. The solid was filtered off, combined with the first solid and dried under reduced pressure to afford 7-bromo-3-chloro-1-fluorospiro[chromeno[2,3-c]pyridine-5,2'-oxirane] (23.56 g, 68.8 mmol).

Step 4:

To a solution of 7-bromo-3-chloro-1-fluorospiro[chromeno[2,3-c]pyridine-5,2'-oxirane] (23.5 g, 68.6 mmol) in DMF (600 mL) was added azidotrimethylsilane (54.6 mL, 412 mmol). The reaction mixture was stirred at RT for 6 hours. Additional azidotrimethylsilane (54.6 mL, 412 mmol) was added and the reaction was stirred at RT for 18 hours. The reaction mixture was diluted with EtOAc and water. The organic layer was separated, washed sequentially with a saturated aqueous LiCl solution and brine before drying over sodium sulfate. The solution was concentrated under reduced pressure to afford (5-azido-7-bromo-3-chloro-1-fluoro-5H-chromeno[2,3-c]pyridin-5-yl)methanol (26.12 g, 67.7 mmol, 99% yield).

Step 5:

A solution of (5-azido-7-bromo-3-chloro-1-fluoro-5H-chromeno[2,3-c]pyridin-5-yl)methanol (25.1 g, 65.1 mmol) in THF (500 mL) was cooled to −10° C. and a solution of LAH (1.0 M in THF; 65.1 mL, 65.1 mmol) was added drop wise via an addition funnel over a time period of 1.5 hours. Upon complete addition, the reaction mixture was stirred additional 20 min at −10° C. The reaction mixture was quenched with the drop wise addition of saturated aqueous potassium sodium tartarate solution (60 mL). The reaction was diluted with water and EtOAc. The organic layer was separated, washed with brine and dried over sodium sulfate.

The solvent was removed under reduced pressure to afford (5-amino-7-bromo-3-chloro-1-fluoro-5H-chromeno[2,3-c]pyridin-5-yl)methanol (21.74 g, 60.5 mmol, 93% yield).

Step 6:

A 3-neck RBF was charged with (5-amino-7-bromo-3-chloro-1-fluoro-5H-chromeno[2,3-c]pyridin-5-yl)methanol (20.7 g, 57.6 mmol) and THF (10 mL). The flask was equipped with two addition funnels which were charged with lithium tert-butoxide solution (1.0M in THF; 98 mL, 98 mmol) and a solution of bromoacetonitrile (6.82 mL, 98 mmol) in THF (10 mL), respectively. The two solutions were added simultaneously to the stirring solution at ambient temperature over a time period of 3 hours. Upon complete addition, the addition funnels were recharged with lithium tert-butoxide solution, 1.0 M in THF (98 mL, 98 mmol) and a solution of bromoacetonitrile (6.82 mL, 98 mmol) in THF (10 mL), respectively. The two solutions were added simultaneously to the stirring solution at ambient temperature over a time period of 3 hours. The reaction was quenched with saturated aqueous ammonium chloride solution and stirred for 16 hours. The reaction was diluted with water and EtOAc. The organic layer was separated and the aqueous layer was extracted twice with EtOAc. The combined organic layers were washed with brine and dried over sodium sulfate. The solution was concentrated under reduced pressure, and the resulting black solid was triturated with ether and filtered to afford a brown precipitate. The filtrate was further concentrated and purified by chromatography (50-100% EtOAc/hexanes). The solids obtained through trituration and purification by chromatography were combined to afford 2-((5-amino-7-bromo-3-chloro-1-fluoro-5H-chromeno[2,3-c]pyridin-5-yl)methoxy)acetonitrile (17.9 g, 44.9 mmol).

Step 7:

A solution of trimethylaluminum solution (2.0 M in toluene; 7.32 ml, 14.64 mmol) was added drop wise to a suspension of 2-((5-amino-7-bromo-3-chloro-1-fluoro-5H-chromeno[2,3-c]pyridin-5-yl)methoxy)acetonitrile (3.89 g, 9.76 mmol) in DCE (14.00 ml) at RT under an atmosphere of nitrogen. Upon complete addition, the reaction mixture was heated to 70° C. for 10 minutes. The reaction mixture was cooled to RT quenched with a saturated aqueous potassium sodium tartarate solution. The reaction mixture was vigorously stirred for one hour before diluting with EtOAc and water. The organic layer was separated, and the aqueous layer was washed twice with additional EtOAc. The combined organic layers were washed with brine, dried over sodium sulfate and concentrated under reduced pressure. DCM and EtOAc were added to the residue and the resulting solution was filtered. The filtrate was concentrated under reduced pressure and purified by chromatography (20-70% EtOAc/hexanes) to afford 7-bromo-3-chloro-1-fluoro-2',6'-dihydrospiro[chromeno[2,3-c]pyridine-5,3'-[1,4]oxazin]-5'-amine (Intermediate 7, 1.539 g, 3.86 mmol, 37%).

Step 8:

Intermediates (R)-7-bromo-3-chloro-1-fluoro-2',6'-dihydrospiro[chromeno[2,3-c]pyridine-5,3'-[1,4]oxazin]-5'-amine (17B) and (S)-7-bromo-3-chloro-1-fluoro-2',6'-dihydrospiro[chromeno[2,3-c]pyridine-5,3'-[1,4]oxazin]-5'-amine (17A) were obtained from racemic 7-bromo-3-chloro-1-fluoro-2',6'-dihydrospiro[chromeno[2,3-c]pyridine-5,3'-[1,4]oxazin]-5'-amine using similar chiral separation conditions as described herein for intermediate 10.

Example 18

Procedure R

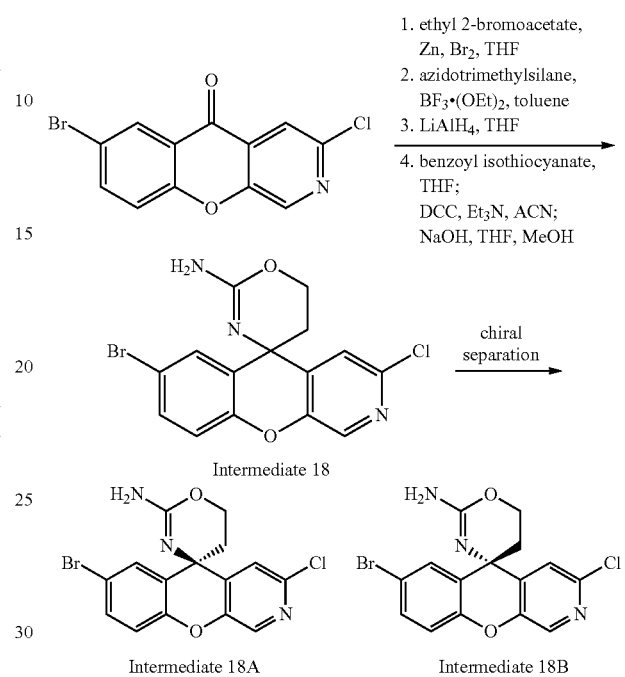

Synthesis of Intermediates 18, 18A and 18B

Step 1:

A 3-neck RBF equipped with an addition funnel and reflux condenser was charged with zinc dust (37.9 g, 580 mmol) and diethyl ether (300 ml). Bromine (1.544 ml, 29.0 mmol) was added drop wise to the stirring suspension at RT. After 5 minutes, ethyl 2-bromoacetate (32.3 ml, 290 mmol) was added drop wise via addition funnel over the time period of 1 hour. The reaction mixture was heated to reflux for one hour. 7-Bromo-3-chloro-5H-chromeno[2,3-c]pyridin-5-one (30 g, 97 mmol) was added in one portion followed by THF (200 ml). After stirring at 40° C. for 10 minutes, the reaction mixture was cooled to RT and quenched with saturated aqueous ammonium chloride solution (250 mL). The reaction mixture was stirred for 1 hour before diluting with EtOAc and filtering through a pad of celite. The organic layer was separated, washed with brine and dried over MgSO$_4$. The solution was concentrated under reduced pressure to afford ethyl 2-(7-bromo-3-chloro-5-hydroxy-5H-chromeno[2,3-c]pyridin-5-yl)acetate (40.3 g) which was used in the next step without further purification.

Step 2:

To a solution of ethyl 2-(7-bromo-3-chloro-5-hydroxy-5H-chromeno[2,3-c]pyridin-5-yl)acetate (38.5 g, 97 mmol) in toluene (400 ml) was added azidotrimethylsilane (38.4 ml, 290 mmol) followed by (diethyloxonio)trifluoroborate (24.48 ml, 193 mmol) under an atmosphere of nitrogen. The reaction mixture was stirred at RT for 16 hours. The reaction mixture was quenched with MeOH (200 mL) and diluted with EtOAc. The organic phase was separated, washed with saturated aqueous sodium bicarbonate solution and brine. The organic layer was dried over magnesium sulfate and concentrated under reduced pressure to afford ethyl 2-(5-azido-7-bromo-3-chloro-5H-chromeno[2,3-c]pyridin-5-yl)acetate (40.82 g) which was used in the next step without further purification.

Step 3:

A solution of ethyl 2-(5-azido-7-bromo-3-chloro-5H-chromeno[2,3-c]pyridin-5-yl)acetate (40.82 g, 96 mmol) in THF (400 ml) was cooled to 0° C. under nitrogen atmosphere. A solution of LAH (1.0M solution in THF; 116 ml, 116 mmol) was added drop wise at 0° C. over a time period of 90 minutes. Upon complete addition, the reaction mixture was warmed to RT and stirred for additional 10 minutes. The reaction mixture was quenched with sodium sulfate decahydrate (50 g) and stirred for 20 minutes at RT. Celite was added to the reaction mixture and the suspension was filtered. The filtrate was concentrated under reduced pressure and the crude residue was purified by chromatography [1-2% (2M ammonia in MeOH)/DCM] to afford 2-(5-amino-7-bromo-3-chloro-5H-chromeno[2,3-c]pyridin-5-yl)ethanol (17.3 g, 48.6 mmol, 50.5% yield).

Step 4:

To a solution of 2-(5-amino-7-bromo-3-chloro-5H-chromeno[2,3-c]pyridin-5-yl)ethanol (0.782 g, 2.199 mmol) in THF (15.27 ml) was added benzoyl isothiocyanate (0.325 ml, 2.419 mmol) at RT. The reaction mixture was stirred for 30 minutes after which the reaction was concentrated to dryness under reduced pressure. The residue was dissolved in ACN (15.27 ml) and triethylamine (0.031 ml, 0.220 mmol) and dicyclohexylcarbodiimide (0.476 g, 2.309 mmol) were added consecutively. The reaction mixture was heated to 80° C. for 2 hours. The reaction mixture was cooled to RT and concentrated to dryness under reduced pressure. The resulting residue was suspended in MeOH (15.27 ml) and THF (3.05 ml). A solution of NaOH (1.0M in water; 10.67 ml, 11.0 mmol) was added and the reaction mixture was heated to 70° C. for 3 hours. The reaction mixture was cooled to RT and concentrated under reduced pressure. The resulting residue was dissolved in EtOAc and washed with water and brine. The organic layer was dried over magnesium sulfate and concentrated under reduced pressure. The residue was purified chromatography [1-5% (2M ammonia in MeOH)/DCM] to afford 7-bromo-3-chloro-5',6'-dihydrospiro[chromeno[2,3-c]pyridine-5,4'-[1,3]oxazin]-2'-amine (Intermediate 10, 0.492 g, 1.293 mmol, 58.8% yield).

Step 5:

Intermediates (R)-7-bromo-3-chloro-5',6'-dihydrospiro[chromeno[2,3-c]pyridine-5,4'-[1,3]oxazin]-2'-amine (18A) and (S)-7-bromo-3-chloro-5',6'-dihydrospiro[chromeno[2,3-c]pyridine-5,4'-[1,3]oxazin]-2'-amine (18B) were obtained from racemic 7-bromo-3-chloro-5',6'-dihydrospiro[chromeno[2,3-c]pyridine-5,4'-[1,3]oxazin]-2'-amine using similar chiral separation conditions as described herein for intermediate 10.

Example 19

Procedure S

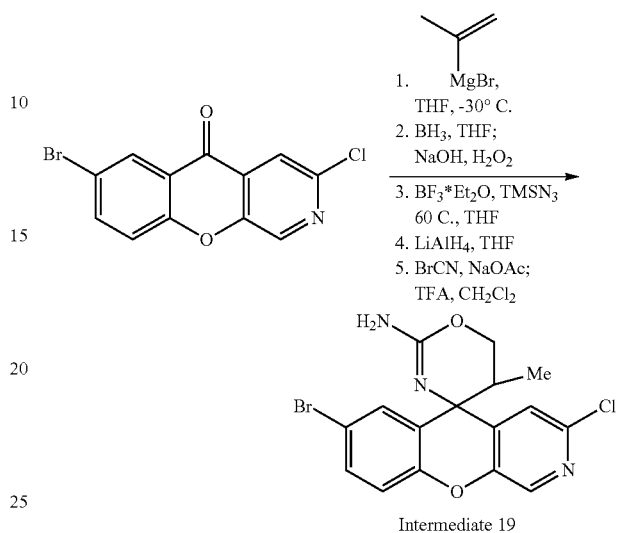

Intermediate 19

Synthesis of Intermediate 19

Step 1:

A solution of 7-bromo-3-chloro-5H-chromeno[2,3-c]pyridin-5-one (3000 mg, 9.66 mmol) in THF (70 mL) was cooled to −30° C. under nitrogen atmosphere. Isopropenylmagnesium bromide, (0.5 m solution in THF; 48.3 mL, 24.15 mmol) was added dropwise. The reaction mixture was stirred for 30 min at −30° C. Aqueous saturated ammoniumchloride solution was added, followed by EtOAc. The organic phase was separated and dried over MgSO₄. The solvent was removed under reduced pressure to yield the product as a light-yellow solid (3.2 g). The product was taken onto the next reaction step without further purification.

Step 2:

To a solution of 7-bromo-3-chloro-5-(prop-1-en-2-yl)-5H-chromeno[2,3-c]pyridin-5-ol (3.2 g, 9.08 mmol) in THF (80 mL) was added a solution of borane-THF complex (1.0M in THF; 72.6 mL, 72.6 mmol) at RT under nitrogen atmosphere. The reaction mixture was allowed to stir at RT overnight. Water (10 mL) was added, followed by 2 M NaOH (15 mL). Then hydrogen peroxide (35 wt. % solution in H₂O; 22.25 mL, 726 mmol) was added slowly. Et₂O was added, followed by water. The organic phase was separated, washed with brine and dried over MgSO₄. The solvent was removed under reduced pressure and the residue was purified by flash chromatography (5-30% EtOAc/hexanes). The desired product 7-bromo-3-chloro-5-(1-hydroxypropan-2-yl)-5H-chromeno[2,3-c]pyridin-5-ol (2.53 g, 6.83 mmol, 75% yield) was isolated as a white solid (1:1 mixture of diastereoisomers).

Step 3:

Azidotrimethylsilane (1.432 mL, 10.79 mmol) and borontrifluoride etherate (1.368 mL, 10.79 mmol) were added sequentially to a solution of 7-bromo-3-chloro-5-(1-hydroxypropan-2-yl)-5H-chromeno[2,3-c]pyridin-5-ol (2000 mg, 5.40 mmol) in THF (50 mL). The reaction mixture was heated to 66° C. After 12 h reaction time, additional azidotrimethylsilane (1.432 mL, 10.79 mmol) and borontriflouride etherate (1.368 mL, 10.79 mmol) were added and the reaction mixture was continued to be heated to 65° C. After 24 h reaction time, additional azidotrimethylsilane (1.432 mL, 10.79 mmol) and borontriflouride etherate (1.368 mL, 10.79 mmol) were added and the reaction mixture was continued to be heated to 65° C. After 32 h reaction time, the reaction mixture was cooled to rt and aqueous saturated bicarbonate solution was added carefully, followed by EtOAc. The organic phase was separated and dried over $MgSO_4$. The solvent was removed under reduced pressure and the residue was purified by flash chromatography (10-55% EtOAc/hexanes). 2-(5-azido-7-bromo-3-chloro-5H-chromeno[2,3-c]pyridin-5-yl)propan-1-ol (1.32 g, 85% purity) was isolated of a white solid and taken onto the next step without further purification.

Step 4:

A solution of 2-(5-azido-7-bromo-3-chloro-5H-chromeno[2,3-c]pyridin-5-yl)propan-1-ol (1300 mg, 3.29 mmol, 85% purity) in THF (10 mL) was cooled to 0° C. under nitrogen atmosphere. LAH (1.0M solution in THF; 3.61 mL, 3.61 mmol) was added dropwise. A mixture of celite and $Na_2SO_4*10H_2O$ was added. The reaction mixture was filtered, the solvent was removed under reduced pressure and the residue was purified by flash chromatography (10-50% EtOAc/hexanes) to afford the desired product 2-(5-amino-7-bromo-3-chloro-5H-chromeno[2,3-c]pyridin-5-yl)propan-1-ol (0.85 g, 2.300 mmol, 70.0% yield) as a white solid.

Step 5:

To a suspension of 2-(5-amino-7-bromo-3-chloro-5H-chromeno[2,3-c]pyridin-5-yl)propan-1-ol (0.85 g, 2.300 mmol) in EtOH (10 mL) was added anhydrous sodium acetate (0.377 g, 4.60 mmol) followed by the drop wise addition of cyanogen bromide (3.0M in $CH_2Cl_2$; 0.920 mL, 2.76 mmol). The suspension was stirred at RT for 48 h. Additional cyanogen bromide (0.8 mL, 0.6 eq) and NaOAc (180 mg, 1.0 eq) were added. The reaction mixture was allowed to stir for 3 days at RT. The reaction mixture was concentrated under reduced pressure, washed with water and extracted with DCM. The combined organic layers were dried over $MgSO_4$ and azeotropically dried with toluene. A white solid was obtained which was suspended in DCM (15 mL). Upon dropwise addition of TFA (2 mL) the reaction mixture turned clear and yellow. The resulting mixture was stirred at RT for 20 min. The solvent was removed under reduced pressure and aqueous saturated $NaHCO_3$ solution and $CH_2Cl_2$ were added. The suspension was filtered and 7-bromo-3-chloro-5'-methyl-5',6'-dihydrospiro[chromeno[2,3-c]pyridine-5,4'-[1,3]oxazin]-2'-amine was obtained as a white solid (305 mg). The filtrate was transferred into a separatory funnel. The organic phase was separated and dried over $MgSO_4$. The solvent was removed under reduced pressure and the residue was purified by flash chromatography to obtain additional 7-bromo-3-chloro-5'-methyl-5',6'-dihydrospiro[chromeno[2,3-c]pyridine-5,4'-[1,3]oxazin]-2'-amine (300 mg).

Example 20

Procedure T

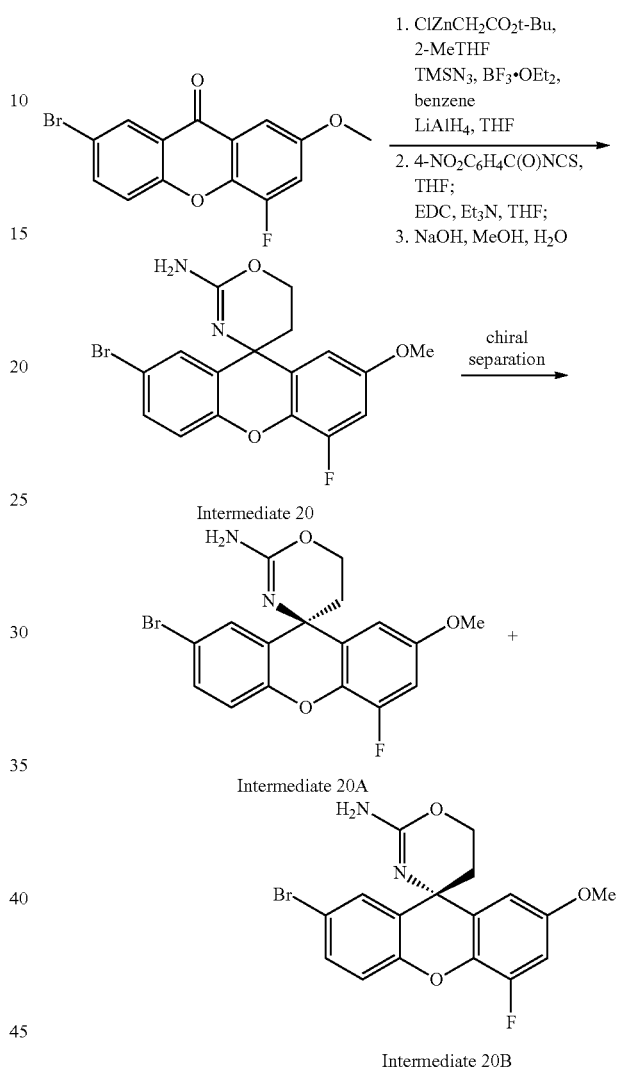

Intermediate 20

Intermediate 20A

Intermediate 20B

Synthesis of Intermediates 20, 20A and 20B

Step 1:

To a suspension of 7-bromo-4-fluoro-2-methoxy-9H-xanthen-9-one (20 g, 61.9 mmol) in 2-methyl-THF (300 mL) a solution of (2-tert-butoxy-2-oxoethyl)zinc(II) chloride (0.5 M in $Et_2O$; 186 mL, 93 mmol) was added at RT. The mixture was stirred for 10 min at RT, and then heated to 45° C. for 1 hour. The reaction mixture was cooled to RT and quenched with aqueous, saturated $NH_4Cl$ (150 mL) and water (100 mL). The organic layer was separated, washed with brine and filtered through the pad of Celite. The solvent was removed under reduced pressure to yield as a yellowish solid which was dissolved in of benzene (200 mL). Azidotrimethylsilane (12.30 mL, 93 mmol) was added and the reaction mixture was cooled to 5° C. Borontrifluoride etherate (7.84 mL, 61.9 mmol) was added drop wise. The reaction mixture was quenched by the addition of MeOH (5 mL) and aqueous, saturated $NaHCO_3$ solution (100 ml). The organic layer was separated, washed with brine, filtered through Celite and concentrated under reduced pressure to afford a yellow residue, which was dissolved in THF (300 mL). The solution was cooled to 0° C. and LAH (1M in THF; 93 mL, 93 mmol) was added drop wise at this temperature. The reaction mixture was allowed to warm to RT and quenched by the addition of sodium sulfate decahydrate (20 g). The reaction mixture was stirred for 2 hrs at RT, then filtered through celite. The filter cake was washed twice with EtOAc. The filtrate was concentrated under reduced pressure and the residue was purified by chromatography [5-50% DCM/MeOH/NH$_4$OH (90:10:1)] in DCM to afford 2-(9-amino-7-bromo-4-fluoro-2-methoxy-9H-xanthen-9-yl)ethanol (10.99 g, 29.8 mmol).

Step 2:

To a solution of 2-(9-amino-7-bromo-4-fluoro-2-methoxy-9H-xanthen-9-yl)ethanol (7.17 g, 19.47 mmol) in THF (100 mL) was added 4-nitrobenzoyl isothiocyanate (4.26 g, 20.45 mmol). The reaction mixture was stirred for 30 min at RT. EDC (5.60 g, 29.2 mmol) and TEA (0.543 ml, 3.89 mmol) were added sequentially and the reaction mixture was heated to 70° C. for 1 hr. The reaction mixture was cooled to RT and water (50 ml) was added. The reaction mixture was stirred for 1 hr, upon which a precipitate formed, which was filtered off and washed with water and MeOH. The solid was dried to afford N-(7'-bromo-4'-fluoro-2'-methoxy-5,6-dihydrospiro[[1,3]oxazine-4,9'-xanthene]-2-yl)-4-nitrobenzamide (6.0 g, 11.06 mmol, 56.8% yield).

Step 3:

A suspension of N-(7'-bromo-4'-fluoro-2'-methoxy-5,6-dihydrospiro[[1,3]oxazine-4,9'-xanthene]-2-yl)-4-nitrobenzamide (6.0 g, 11.06 mmol) in methanol (60 mL) was heated to 65° C. NaOH (2 M solution) (48.7 ml, 97 mmol) was added and the resulting mixture was heated to 65° C. for 4 hrs. The reaction mixture was concentrated under reduced pressure, the precipitate was filtered off, washed twice with water and dried to afford 7'-bromo-4'-fluoro-2'-methoxy-5,6-dihydrospiro[[1,3]oxazine-4,9'-xanthen]-2-amine (3.90 g, 9.92 mmol, 50.9% yield) as white solid.

Step 4:

Intermediates (R)-7'-bromo-4'-fluoro-2'-methoxy-5,6-dihydrospiro[[1,3]oxazine-4,9'-xanthen]-2-amine (20A) and (S)-7'-bromo-4'-fluoro-2'-methoxy-5,6-dihydrospiro[[1,3]oxazine-4,9'-xanthen]-2-amine (20B) were obtained from racemic 7'-bromo-4'-fluoro-2'-methoxy-5,6-dihydrospiro[[1,3]oxazine-4,9'-xanthen]-2-amine using similar chiral separation conditions as described herein for intermediate 10.

Example 21

Procedure U

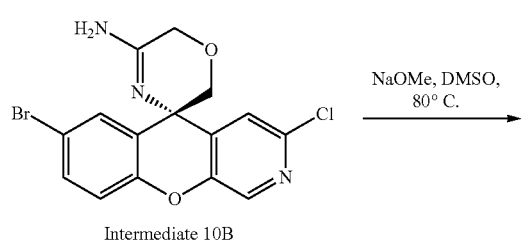

Intermediate 10B

NaOMe, DMSO, 80° C.

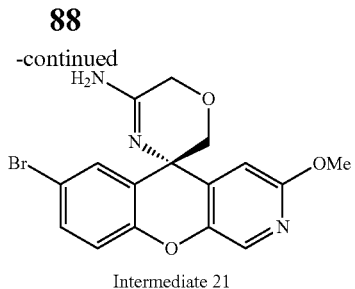

Intermediate 21

Synthesis of Intermediate 21

A vial was charged with (S)-7-bromo-3-chloro-2',6'-dihydrospiro[chromeno[2,3-c]pyridine-5,3'-[1,4]oxazin]-5'-amine (Intermediate 1B, 1.0 g, 2.63 mmol) and DMSO (13.14 mL). Sodium methoxide (0.710 g, 13.14 mmol) was added and the reaction mixture was heated to 80° C. for 2.5 hours. The reaction mixture was cooled to RT and quenched with aqueous, saturated ammonium chloride solution. Water and EtOAc were added, and the organic layer was separated and the aqueous layer was extracted with EtOAc. The combined organic layers were washed with brine, dried over sodium sulfate and concentrated under reduced pressure. The residue was purified via column chromatography (0-100% EtOAc/hexanes) to afford (S)-7-bromo-3-methoxy-2',6'-dihydrospiro[chromeno[2,3-c]pyridine-5,3'-[1,4]oxazin]-5'-amine (Example 21A; 0.611 g, 1.624 mmol, 61.8% yield) as a yellow solid.

Example 22

Procedure V

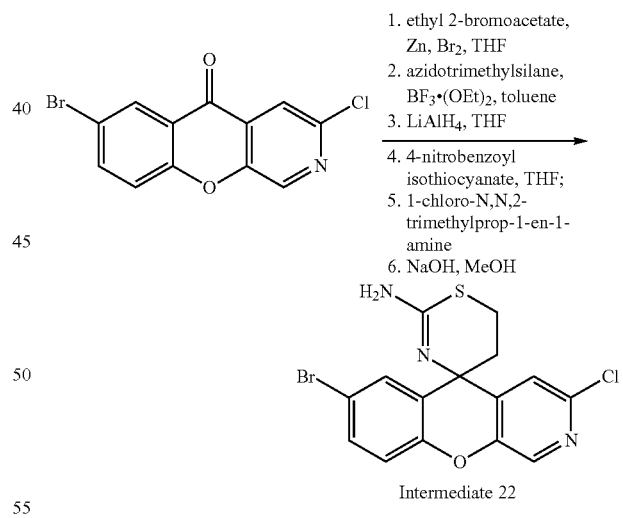

Intermediate 22

1. ethyl 2-bromoacetate, Zn, Br$_2$, THF
2. azidotrimethylsilane, BF$_3$•(OEt)$_2$, toluene
3. LiAlH$_4$, THF
4. 4-nitrobenzoyl isothiocyanate, THF;
5. 1-chloro-N,N,2-trimethylprop-1-en-1-amine
6. NaOH, MeOH Synthesis of Intermediate 22

Step 1:

Bromine (0.072 ml, 1.4 mmol) was added to a suspension of zinc dust (1.41 g, 21.57 mmol) in diethyl ether (25 ml) at RT. After 5 minutes, ethyl 2-bromoacetate (1.202 ml, 10.8 mmol) was added drop wise over a time period of 10 minutes and the reaction mixture was heated to reflux for 2 hours. 7-Bromo-3-chloro-5H-chromeno[2,3-c]pyridin-5-one (2 g, 6.44 mmol) was added in one portion, followed by THF (25.00 ml) and the reaction mixture was heated to reflux for 30 minutes. The reaction mixture was quenched with aqueous saturated NH₄Cl solution (20 mL) and water (20 mL) and stirred 30 min at RT. The solution was filtered and the organic phase was separated. The solvent was removed under educed pressure to afford ethyl 2-(7-bromo-3-chloro-5-hydroxy-5H-chromeno[2,3-c]pyridin-5-yl)acetate (2.5 g, 6.27 mmol, 97% yield).

Step 2:
To a solution of ethyl 2-(7-bromo-3-chloro-5-hydroxy-5H-chromeno[2,3-c]pyridin-5-yl)acetate (20 g, 50.2 mmol) in toluene (300 ml) was added azidotrimethylsilane (19.93 ml, 151 mmol), followed by (diethyloxonio)trifluoroborate (12.72 ml, 100 mmol). The mixture was stirred overnight at RT. The reaction mixture was quenched with MeOH (200 mL) and diluted with EtOAc. The organic phase was separated, washed with saturated aqueous sodium bicarbonate solution and brine. The organic layer was dried over magnesium sulfate and concentrated under reduced pressure to afford ethyl 2-(5-azido-7-bromo-3-chloro-5H-chromeno[2,3-c]pyridin-5-yl)acetate (21 g, 49.6 mmol, 99% yield).

Step 3:
A solution of ethyl 2-(5-azido-7-bromo-3-chloro-5H-chromeno[2,3-c]pyridin-5-yl)acetate (47 g, 111 mmol) in THF (600 ml) was cooled to 0° C. under nitrogen atmosphere. A solution of LAH (1.0M in THF; 133 ml, 133 mmol) was added drop wise at 0° C. Upon complete addition, the reaction mixture was warmed to RT and stirred for additional 10 minutes. The reaction mixture was quenched with sodium sulfate decahydrate (50 g) and stirred for 1 hour at room temperature. The suspension was filtered over celite. The filtrate was concentrated under reduced pressure and the crude residue was purified by recrystallization from cold DCM with heptane to afford 2-(5-amino-7-bromo-3-chloro-5H-chromeno[2,3-c]pyridin-5-yl)ethanol (16 g, 45.0 mmol, 40.6% yield).

Step 4:
A reaction mixture of 2-(5-amino-7-bromo-3-chloro-5H-chromeno[2,3-c]pyridin-5-yl)ethanol (2.8 g, 7.87 mmol) and 4-nitrobenzoyl isothiocyanate (1.639 g, 7.87 mmol) in THF (100 mL) was stirred at RT for 1 hour. The reaction mixture was then concentrated under reduced pressure to afford N-(7-bromo-3-chloro-5-(2-hydroxyethyl)-5H-chromeno[2,3-c]pyridin-5-ylcarbamothioyl)-4-nitrobenzamide (5 g, 8.87 mmol).

Step 5:
1-Chloro-N,N,2-trimethylprop-1-en-1-amine (2.84 ml, 21.28 mmol) was added to a solution of N-((7-bromo-3-chloro-5-(2-hydroxyethyl)-5H-chromeno[2,3-c]pyridin-5-yl)carbamothioyl)-4-nitrobenzamide (12 g, 21.28 mmol) in DCM (200 ml). The reaction mixture was stirred at RT for 8 hours and then concentrated under reduced pressure to 50% of its original volume. A precipitate formed upon cooling which was filtered off, washed with DCM and then dried under reduced pressure to afford N-(7-bromo-3-chloro-5',6'-dihydrospiro[chromeno[2,3-c]pyridine-5,4'-[1,3]thiazin]-2'-yl)-4-nitrobenzamide hydrochloride (10.5 g, 18.03 mmol, 85% yield) as an off white solid.

Step 6:
A 2 N NaOH solution (24.47 ml, 48.9 mmol) was added to a solution of N-(7-bromo-3-chloro-5',6'-dihydrospiro[chromeno[2,3-c]pyridine-5,4'-[1,3]thiazin]-2'-yl)-4-nitrobenzamide hydrochloride (9.5 g, 16.32 mmol) in MeOH (250 ml). The reaction mixture was heated to 65° C. for 3 hours. The reaction mixture was diluted with water (300 mL), stirred for 10 min, and then filtered. The solid was washed with water and dried under reduced pressure to afford 7-bromo-3-chloro-5',6'-dihydrospiro[chromeno[2,3-c]pyridine-5,4'-[1,3]thiazin]-2'-amine (3.9 g, 9.83 mmol, 60.3% yield).

Example 23

Procedure W

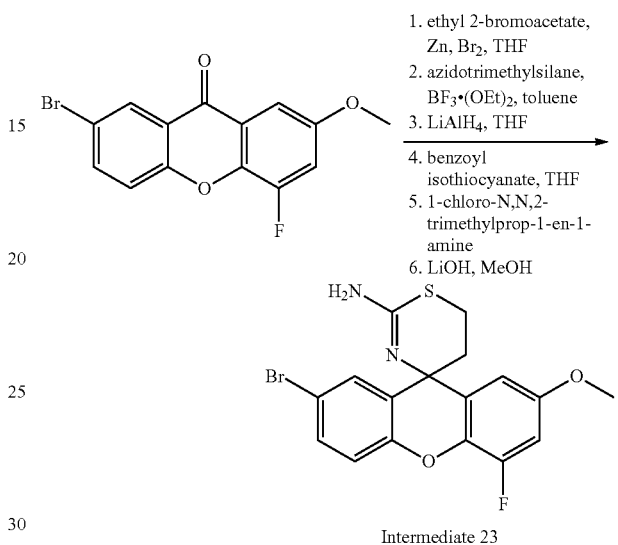

Intermediate 23

Synthesis of Intermediate 23
Step 1:
Bromine (0.797 ml, 15.47 mmol) was added to a suspension of zinc dust (8.09 g, 124 mmol in diethyl ether (150 ml) at RT. After 5 minutes, ethyl 2-bromoacetate (6.86 ml, 61.9 mmol) was added drop wise over a time period of 20 minutes and the reaction mixture was heated to reflux for 2 hours. 7-bromo-4-fluoro-2-methoxy-9H-xanthen-9-one (10 g, 30.9 mmol) was added in one portion, followed by THF (100 ml) and the reaction mixture was heated to reflux for 3 hours. The reaction mixture was quenched with aqueous saturated NH₄Cl solution (100 mL) and EtOAc (100 mL) and stirred 2 hours at RT. The solution was filtered and the organic phase was separated. The solvent was removed under educed pressure to afford ethyl 2-(7-bromo-4-fluoro-9-hydroxy-2-methoxy-9H-xanthen-9-yl)acetate (12.7 g, 30.9 mmol, 100% yield).

Step 2:
To a solution of ethyl 2-(7-bromo-4-fluoro-9-hydroxy-2-methoxy-9H-xanthen-9-yl)acetate (1.0 g, 2.432 mmol) in toluene (25 ml) was added azidotrimethylsilane (0.560 g, 4.86 mmol). The solution was cooled to 0° C. and (diethyloxonio)trifluoroborate (0.308 ml, 2.432 mmol) was added drop wise. The mixture was stirred overnight at RT. The solution was quenched with MeOH (10 ml) and diluted with EtOAc. The organic phase was separated, washed with saturated aqueous sodium bicarbonate solution and brine, and then concentrated to afford crude ethyl 2-(9-azido-7-bromo-4-fluoro-2-methoxy-9H-xanthen-9-yl)acetate (1 g, 2.292 mmol, 94% yield).

Step 3:
A solution of ethyl 2-(5-azido-7-bromo-3-chloro-5H-chromeno[2,3-c]pyridin-5-yl)acetate (13.5 g, 30.9 mmol) in THF (200 ml) was cooled to 0° C. under nitrogen atmosphere. A solution of LAH (1.0M in THF; 37.1 ml, 37.1 mmol) was added drop wise at 0° C. After 10 min, the reaction mixture was quenched with sodium sulfate decahydrate (20 g) and stirred for 5 min at RT. The suspension was filtered. The filtrate was concentrated under reduced pressure and the crude residue was purified by column chromatography [10-100% 90101 (DCM/MeOH/ammonia) in DCM] to afford 2-(9-amino-7-bromo-4-fluoro-2-methoxy-9H-xanthen-9-yl)ethanol (8.8 g, 23.90 mmol).

Step 4:

A reaction mixture of 2-(9-amino-7-bromo-4-fluoro-2-methoxy-9H-xanthen-9-yl)ethanol (8.8 g, 23.90 mmol) and benzoyl isothiocyanate (3.22 ml, 23.90 mmol) in THF (200 ml) was stirred at RT for 1 hour. The reaction mixture was then concentrated under reduced pressure to afford N-((7-bromo-4-fluoro-9-(2-hydroxyethyl)-2-methoxy-9H-xanthen-9-yl)carbamothioyl)benzamide (12.7 g, 23.90 mmol).

Step 5:

1-Chloro-N,N,2-trimethylprop-1-en-1-amine (2.012 ml, 15.05 mmol) was added to a solution of N-((7-bromo-4-fluoro-9-(2-hydroxyethyl)-2-methoxy-9H-xanthen-9-yl)carbamothioyl)-benzamide (8 g, 15.05 mmol) in DCM (3 ml). The reaction mixture was stirred at RT for 8 hours. The reaction mixture was quenched with aqueous, saturated sodium carbonate solution and stirred for 10 minutes. The organic layer was separated and concentrated under reduced pressure to afford crude N-(7'-bromo-4'-fluoro-2'-methoxy-5,6-dihydrospiro[[1,3]thiazine-4,9'-xanthen]-2-yl)-benzamide (7.7 g, 15.00 mmol, 100% yield).

Step 6:

A 2 N solution of lithium hydroxide (22.50 ml, 45.0 mmol) was added to a solution of N-(7'-bromo-4'-fluoro-2'-methoxy-5,6-dihydrospiro[[1,3]thiazine-4,9'-xanthen]-2-yl)benzamide (7.7 g, 15.00 mmol) in MeOH (250 ml). The reaction mixture was heated to 65° C. for 3 hours. The reaction mixture was diluted with water and extracted with EtOAc. The combined organic extracts were concentrated under reduced pressure. The residue was purified via column chromatography [0-70% 90/10/1 (DCM/MeOH/ammonia) in DCM] to afford 7'-bromo-4'-fluoro-2'-methoxy-5,6-dihydrospiro[[1,3]thiazine-4,9'-xanthen]-2-amine as a racemic mixture (2 g, 2.443 mmol, 32% yield).

Example 24

Procedure X

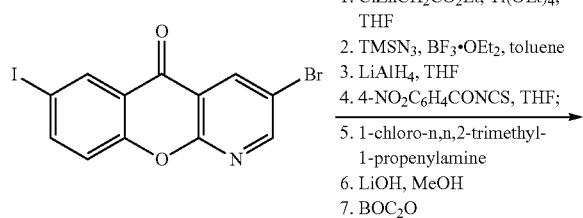

1. ClZnCH$_2$CO$_2$Et, Ti(OEt)$_4$, THF
2. TMSN$_3$, BF$_3$·OEt$_2$, toluene
3. LiAlH$_4$, THF
4. 4-NO$_2$C$_6$H$_4$CONCS, THF;
5. 1-chloro-n,n,2-trimethyl-1-propenylamine
6. LiOH, MeOH
7. BOC$_2$O

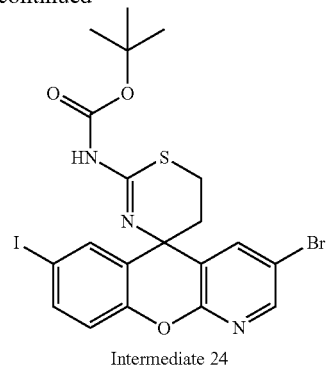

Intermediate 24

Synthesis of Intermediate 24

Step 1:

To a suspension of tetraethoxytitanium (3.40 g, 14.93 mmol) in THF (16.58 ml) was added 3-bromo-7-iodo-5H-chromeno[2,3-b]pyridin-5-one (2.00 g, 4.98 mmol). The suspension was cooled to 0° C. and (2-ethoxy-2-oxoethyl)zinc (II) bromide (149 ml, 14.93 mmol) was added drop wise. The reaction mixture was allowed to warm to RT and stirred 1 h. The reaction mixture was quenched with aqueous, half-saturated NaHCO$_3$ solution (20 mL) and stirred for 30 min. The solution was filtered through a pad of celite and the filter cake was rinsed with EtOAc. The organic layer was separated and concentrated under reduced pressure to afford ethyl 2-(3-bromo-5-hydroxy-7-iodo-5H-chromeno[2,3-b]pyridin-5-yl)acetate as a yellowish solid.

Step 2:

Azidotrimethylsilane (1.102 ml, 8.32 mmol) was added to a suspension of ethyl 2-(3-bromo-5-hydroxy-7-iodo-5H-chromeno[2,3-b]pyridin-5-yl)acetate (2.33 g, 4.75 mmol) in toluene (31.7 ml). The reaction mixture was cooled to 0° C. and (diethyloxonio) trifluoroborate (0.753 ml, 5.94 mmol) was added slowly. The reaction mixture was allowed to warm to RT. After 30 min, the reaction mixture was quenched with MeOH (5 mL) followed by aqueous, saturated NaHCO$_3$ solution (10 mL). The reaction mixture was extracted twice with EtOAc. The combined organic phases were washed with brine and dried over sodium sulfate. The solvent was removed under reduced pressure to afford ethyl 2-(5-azido-3-bromo-7-iodo-5H-chromeno[2,3-b]pyridin-5-yl)acetate as a yellow solid.

Step 3:

LAH (1M in THF; 6.12 ml, 6.12 mmol) was added slowly to a −78 C cooled solution of ethyl 2-(5-azido-3-bromo-7-iodo-5H-chromeno[2,3-b]pyridin-5-yl)acetate (2.10 g, 4.08 mmol) in THF (40.8 ml). The reaction mixture was stirred at 78° C. for 15 min, and the reaction mixture was allowed to warm to RT and stirred for additional 30 min. The reaction mixture was cooled to 0° C., quenched with sodium sulfate decahydrate (2.90 g, 20.38 mmol) and allowed to stir 20 min. The solution was filtered through a pad of celite, the filter cake was eluted with 10% MeOH/DCM and the filtrate was concentrated. The residue was purified via flash chromatography (0-25% EtOAc/CH$_2$Cl$_2$) to afford 2-(5-amino-3-bromo-7-iodo-5H-chromeno[2,3-b]pyridin-5-yl)ethanol as a yellow solid.

Step 4:

A solution of 2-(5-amino-3-bromo-7-iodo-5H-chromeno[2,3-b]pyridin-5-yl)ethanol (0.930 g, 2.080 mmol) in THF (20.80 ml) was added cooled to 0° C. and solid 4-nitrobenzoyl isothiocyanate (0.442 g, 2.122 mmol) was added. The reaction mixture was stirred at 0° C. for 20 min. The reaction mixture was concentrated under reduced pressure to yield N-((3-bromo-5-(2-hydroxyethyl)-7-iodo-5H-chromeno[2,3-b]pyridin-5-yl)carbamothioyl)-4-nitrobenzamide as a yellow solid.

Step 5:

1-Chloro-n,n,2-trimethyl-1-propenylamine (0.556 ml, 4.16 mmol) was added to a solution of N-((3-bromo-5-(2-hydroxyethyl)-7-iodo-5H-chromeno[2,3-b]pyridin-5-yl)carbamothioyl)-4-nitrobenzamide (1.363 g, 2.080 mmol) in $CH_2Cl_2$ (7 ml) at 0° C. The reaction mixture was allowed to warm to RT and stir for 2 h. The reaction mixture was quenched with aqueous, saturated $NaHCO_3$ solution (5 mL), and was further diluted with 10% MeOH/DCM and 5 mL water and N-(3-bromo-7-iodo-5',6'-dihydrospiro[chromeno[2,3-b]pyridine-5,4'-[1,3]thiazin]-2'-yl)-4-nitrobenzamide collected as a pink solid.

Step 6:

A suspension of N-(3-bromo-7-iodo-5',6'-dihydrospiro[chromeno[2,3-b]pyridine-5,4'-[1,3]thiazin]-2'-yl)-4-nitrobenzamide (0.906 g, 1.422 mmol) and lithium hydroxide hydrate (0.179 g, 4.27 mmol) in MeOH (28.4 ml) was heated to reflux for 3 hours. The solvent was removed under reduced pressure to afford 3-bromo-7-iodo-5',6'-dihydrospiro[chromeno[2,3-b]pyridine-5,4'-[1,3]thiazin]-2'-amine as a pink solid.

Step 7:

Aqueous, saturated $NaHCO_3$ solution (7.6 ml, 7.11 mmol) and boc anhydride (3.3 ml, 14.22 mmol) were added to a stirred suspension of 3-bromo-7-iodo-5',6'-dihydrospiro[chromeno[2,3-b]pyridine-5,4'-[1,3]thiazin]-2'-amine (694 mg, 1.422 mmol) in dioxane (7 ml). The reaction mixture was stirred for 16 h at RT. The reaction mixture was partitioned between EtOAc (50 mL) and water (20 ml). The aqueous layer was separated and extracted with EtOAc (1×10 mL). The combined organic extracts were washed with brine, dried over $Na_2SO_4$ and concentrated under reduced pressure. The residue was purified via flash chromatography (0-25% EtOAc/$CH_2Cl_2$) to afford tert-butyl(3-bromo-7-iodo-5',6'-dihydrospiro[chromeno[2,3-b]pyridine-5,4'-[1,3]thiazin]-2'-yl)carbamate a yellow solid.

Example 25

Procedure Y

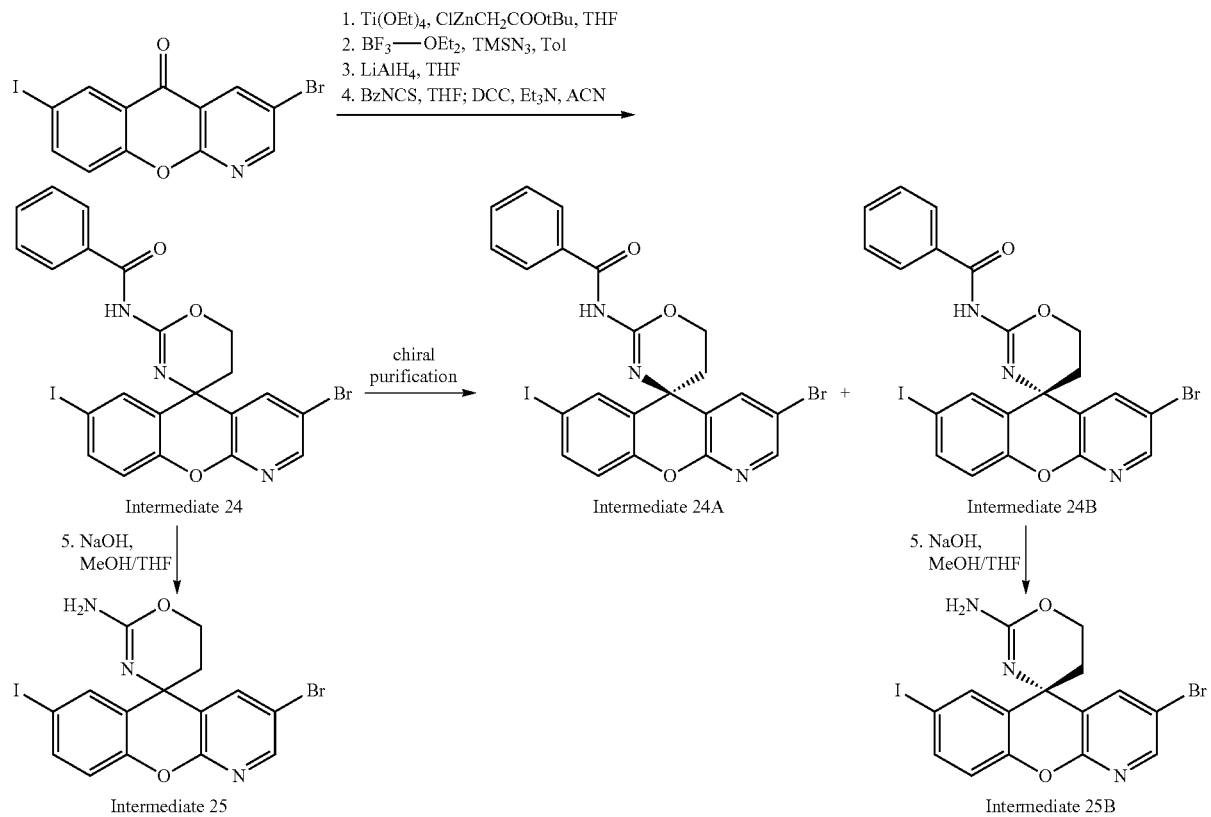

Step 1:

3-Bromo-7-iodo-5H-chromeno[2,3-b]pyridin-5-one (6.0 g, 14.93 mmol) was taken up in THF (150 mL). Neat tetraethoxytitanium (9.29 mL, 44.8 mmol) was added. An ether solution of (2-tert-butoxy-2-oxoethyl)zinc(II) chloride (0.5 M, 62.7 mL, 31.3 mmol) was added via cannula. The reaction was stirred at 0° C. for 30 min, then warmed to RT and stirred 30 min. The excess organozinc reagent was quenched at 0° C. with 250 mL of half-saturated brine. The mixture was filtered through Celite, rinsing the solid with EtOAc (700 mL). The resulting filtrate's organic layer was separated and extracted further with saturated brine (50 mL), then was dried over sodium sulfate and concentrated. The crude tert-butyl 2-(3-bromo-5-hydroxy-7-iodo-5H-chromeno[2,3-b]pyridin-5-yl)acetate (7.8 g) was used in the next step without further purification.

Step 2:

In a 1-L flask, the tert-butyl 2-(3-bromo-5-hydroxy-7-iodo-5H-chromeno[2,3-b]pyridin-5-yl)acetate (7.8 g, 15.05 mmol) was suspended in toluene (100 mL). Neat azidotrimethylsilane (2.99 mL, 22.58 mmol) was added. The mixture was cooled to 0° C., and BF$_3$-etherate (2.098 mL, 16.56 mmol) was added. The mixture was allowed to warm naturally in the ice bath. After two hours, the mixture was quenched with MeOH (3 mL), then with half-saturated aqueous NaHCO$_3$ (100 mL). The residue was extracted with 10% MeOH-EtOAc (3×200 mL). The organics were combined, washed with saturated brine (50 mL), dried over sodium sulfate and concentrated. The crude tert-butyl 2-(5-azido-3-bromo-7-iodo-5H-chromeno[2,3-b]pyridin-5-yl)acetate was used in the next step without further purification (7.27 g).
Step 3:
In a 1-L flask, the tert-butyl 2-(5-azido-3-bromo-7-iodo-5H-chromeno[2,3-b]pyridin-5-yl)acetate (7.27 g, 13.38 mmol) was suspended in THF (100 mL) and the suspension was cooled to 0° C. A THF solution of LAH (1 M, 20.08 mL, 20.08 mmol) was added. After 30 min, the reaction mixture was quenched with careful addition of water (0.75 mL), 4 M aqueous NaOH (2.2 mL), and water (0.75 mL). The mixture was filtered through Celite, rinsing with THF (60 mL), then with EtOAc (150 mL). The combined filtrate was concentrated. The residue was purified through silica gel (400 mL) which had been deactivated with Et$_3$N (40 mL), using 100:100:1 EtOAc-hexane-Et$_3$N, to afford 2-(5-amino-3-bromo-7-iodo-5H-chromeno[2,3-b]pyridin-5-yl)ethanol (2.24 g).
Step 4:
In a 250-mL flask, the 2-(5-amino-3-bromo-7-iodo-5H-chromeno[2,3-b]pyridin-5-yl)ethanol (2.24 g, 5.01 mmol) was dissolved in THF (30 mL). Benzoyl isothiocyanate (0.607 mL, 4.51 mmol) was added. After 1 h, the mixture was concentrated. The residue was taken up in ACN (30 mL), and catalytic TEA (0.069 mL, 0.501 mmol) was added, followed by DCC (1.137 g, 5.51 mmol). A water-cooled condenser was affixed, and the solution was stirred in an 80° C. oil bath for 2 h. The reaction was then concentrated. The residue was used directly in the next step without further purification or purified by column chromatography (silica gel, 10-50% EtOAc/hexanes) to obtain N-(3-bromo-7-iodo-5',6'-dihydrospiro[chromeno[2,3-b]pyridine-5,4'-[1,3]oxazin]-2'-yl) benzamide as a yellow solid. MS (m/z) 575.8/577.7 (M+H)$^+$.
Step 5:
In a 150-mL resealable vessel, the crude N-(3-bromo-7-iodo-5',6'-dihydrospiro[chromeno[2,3-b]pyridine-5,4'-[1,3]oxazine]-2'-yl)benzamide from the above procedure was dissolved in 1:1 THF-MeOH (12 mL). Aqueous NaOH (12.04 mL, 30.1 mmol) was added. The vessel was sealed and heated in a 90° C. oil bath. After 2 h, the reaction was concentrated to remove most of the THF and MeOH. The aqueous residue was diluted with water (35 mL), and the aqueous layer was extracted with 5% MeOH-dcm (3×100 mL). The organics were combined, washed with dilute brine (35 mL), dried over sodium sulfate and concentrated. The residue was purified through silica gel (300 mL) using 3% MeOH-DCM, to afford intermediate 25 (3-bromo-7-iodo-5',6'-dihydrospiro [chromeno[2,3-b]pyridine-5,4'-[1,3]oxazin]-2'-amine) (1.99 g). MS (m/z) 472/474 (M+H)$^+$.

Additionally, racemic N-(3-bromo-7-iodo-5',6'-dihydrospiro[chromeno[2,3-b]pyridine-5,4'-[1,3]oxazin]-2'-yl) benzamide (obtained in step 4, see synthesis of intermediate 24) was chromatographed using supercritical CO$_2$ (additives 30% MeOH with 0.2% DEA) on a Chiracel OD-H column (250×21 mm, 5 μm) eluting at a flow rate 100 ml/min (100 bar pressure, 40° C. column temperature). The first peak (retention time=2.53 min) provided (R)—N-(3-bromo-7-iodo-5',6'-dihydrospiro[chromeno[2,3-b]pyridine-5,4'-[1,3]oxazin]-2'-yl)benzamide (intermediate 24A; >99% ee), and the second peak (retention time=3.00 min) provided (S)—N-(3-bromo-7-iodo-5',6'-dihydrospiro[chromeno[2,3-b]pyridine-5,4'-[1,3]oxazin]-2'-yl)benzamide (intermediate 24B; >99% ee). MS (m/z) 575.8/577.7 (M+H)$^+$ for both peaks.

Enantiomerically pure (S)—N-(3-bromo-7-iodo-5',6'-dihydrospiro[chromeno[2,3-b]pyridine-5,4'-[1,3]oxazin]-2'-yl)benzamide (intermediate 24B) was subjected to the same reaction conditions described in step 5, yielding enantiomerically pure (S)-3-bromo-7-iodo-5',6'-dihydrospiro[chromeno [2,3-b]pyridine-5,4'-[1,3]oxazin]-2'-amine (intermediate 25B). MS (m/z) 472/474 (M+H)$^+$.

Example 26

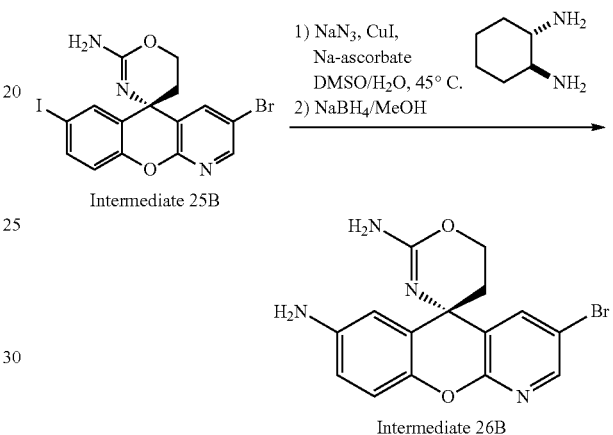

Synthesis of Intermediate 26B
Step 1:
A microwave vial was charged with (S)-3-bromo-7-iodo-5',6'-dihydrospiro[chromeno[2,3-b]pyridine-5,4'-[1,3]oxazin]-2'-amine (500 mg, 1.059 mmol, Intermediate 25), copper(I) iodide (20.17 mg, 0.106 mmol), (+)-sodium 1-ascorbate (10.49 mg, 0.053 mmol) and sodium azide (0.074 ml, 2.118 mmol). The vial was evacuated and backfilled with nitrogen. EtOH (2 ml), rac-trans-1,2-diaminocyclohexane (0.019 ml, 0.159 mmol) and water (0.9 ml) were added. The reaction mixture was heated overnight to 56° C. An additional portion of each reagent were added and the reaction was heated for additional 6 hours. The reaction mixture was partitioned between water and EtOAc. The organic phase was separated and dried over MgSO$_4$. The solvent was removed under reduced pressure and the residue was purified by flash chromatography (silical gel, 20-100% EtOAc/hexanes) to afford (S)-7-azido-3-bromo-5',6'-dihydrospiro[chromeno[2,3-b]pyridine-5,4'-[1,3]oxazin]-2'-amine as a yellow solid.
Step 2:
(S)-7-azido-3-bromo-5',6'-dihydrospiro[chromeno[2,3-b]pyridine-5,4'-[1,3]oxazin]-2'-amine (200 mg, 0.517 mmol) was dissolved in MeOH (2 mL) and sodium borohydrate (195 mg, 5.17 mmol) was added at rt. After 1 h, additional MeOH (2 mL) and 10 equiv of NaBH$_4$ were added at rt. The reaction mixture was allowed to stir overnight. Additional MeOH (2 mL) and 10 equiv of NaBH$_4$ were added and the reaction was allowed to stir for 1 h. Water was added, followed by EtOAc. The organic phase was separated, dried over MgSO$_4$. The solvent was removed under reduced pressure to give (S)-3-bromo-5',6'-dihydrospiro[chromeno[2,3-b]pyridine-5,4'-[1,3]oxazine]-2',7-diamine as a light-yellow solid. The compound was used in the next step without further purification. MS m/z=362.8 [M+H]$^+$. Calculated for $C_{15}H_{13}BrN_4O_2$: 361.19.

Example 27

Procedure ZZ

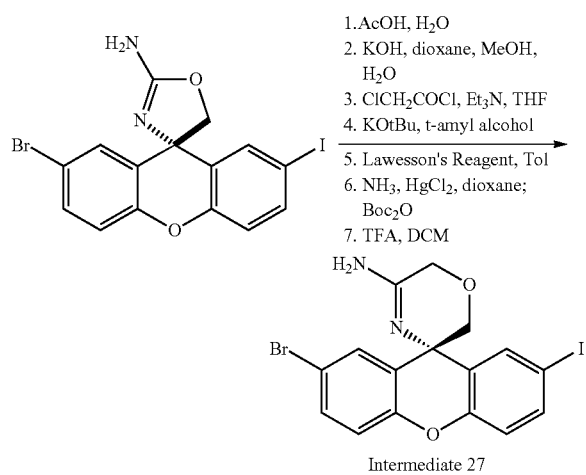

Intermediate 27

Synthesis of Intermediate 27

Step 1:

In a 350-mL resealable vessel the (S)-2'-bromo-7'-iodo-5H-spiro[oxazole-4,9'-xanthen]-2-amine (11.5 g, 25.2 mmol) was taken up in AcOH (125 mL) and water (31 mL). The vessel was sealed and heated in a 140° C. oil bath for 14 h. The reaction was concentrated to remove most of the AcOH. The reaction residue was neutralized with 1M aqueous $Na_2CO_3$ (250 mL). The residue was filtered through Celite, rinsing with 5% MeOH-DCM (800 mL). The filtrate's organic layer was separated, dried over sodium sulfate and concentrated. The crude (S)-2'-bromo-7'-iodospiro[oxazolidine-4,9'-xanthen]-2-one was used in the next step without further purification.

Step 2:

In a 350-mL resealable vessel, the (S)-2'-bromo-7'-iodospiro[oxazolidine-4,9'-xanthen]-2-one (11 g, 24.02 mmol) was dissolved in 1:1 MeOH-dioxane (160 mL). Aqueous KOH (5 M, 48.0 mL, 240 mmol) was added. The vessel was sealed and placed in a 105° C. oil bath. After 24 h, the reaction was concentrated to remove the MeOH and most of the dioxane. The residue was diluted with water (200 mL) and the aqueous phase was extracted with 5% MeOH-DCM (4×200 mL). The organics were combined, washed with dilute brine (35 mL), dried over sodium sulfate and concentrated. The residue was purified by chromatography (1.5% MeOH/DCM) to afford (S)-(9-amino-2-bromo-7-iodo-9H-xanthen-9-yl)methanol (3.84 g, 8.89 mmol).

Step 3:

The (S)-(9-amino-2-bromo-7-iodo-9H-xanthen-9-yl) methanol (3.84 g, 8.89 mmol) was dissolved in THF (200 mL). The solution was cooled to 0° C., and TEA (1.425 mL, 10.22 mmol) and 2-chloroacetyl chloride (0.707 mL, 9.07 mmol) were added. The reaction was allowed to warm naturally to RT. After 14 h, the reaction was concentrated. The residue was taken up in aqueous 1 M $Na_2CO_3$ (50 mL) and the aqueous phase was extracted with 7.5% MeOH-DCM (3×133 mL). The organics were combined, washed with aqueous 1 M $Na_2CO_3$ (30 mL), dried over sodium sulfate and concentrated. The residue was dissolved in THF (100 mL) and aqueous 1 M $Na_2CO_3$ (15 mL) was added. The reaction was concentrated. The residue was taken up in 5% MeOH-dcm (400 mL) and the organic phase was washed with dilute brine (40 mL), dried over sodium sulfate and concentrated to afford crude (S)—N-(2-bromo-9-(hydroxymethyl)-7-iodo-9H-xanthen-9-yl)-2-chloroacetamide, which was used in the next step without further purification.

Step 4:

In a 500-mL flask (S)—N-(2-bromo-9-(hydroxymethyl)-7-iodo-9H-xanthen-9-yl)-2-chloroacetamide (4.52 g, 8.89 mmol) was dissolved in t-amyl alcohol (125 mL). Potassium t-butoxide (2.244 g, 20.00 mmol) was added. After 14 h, the reaction was concentrated. The residue was taken up in dilute aqueous $NH_4Cl$ (50 mL) and the aqueous phase was extracted with 5% MeOH-DCM (3×133 mL). The organics were combined, washed with dilute brine (25 mL), dried over sodium sulfate and concentrated. The material was purified through silica gel (500 mL) using 30% EtOAc-hexane to afford (S)-2'-bromo-7'-iodospiro[morpholine-3,9'-xanthen]-5-one (1.92 g, 4.07 mmol).

Step 5:

In a 250-mL flask, the (S)-2'-bromo-7'-iodospiro[morpholine-3,9'-xanthen]-5-one (1.483 g, 3.14 mmol) was suspended in toluene (30 mL). Lawesson's reagent (0.794 g, 1.963 mmol) was added. An air-cooled condenser was affixed, and the reaction vessel was placed in a 90° C. oil bath After 7 h, the reaction was concentrated. Without working it up, the residue was purified by chromatography (15% EtOAc/hexanes) to afford (S)-2'-bromo-7'-iodospiro[morpholine-3,9'-xanthene]-5-thione (1.25 g, 2.56 mmol).

Step 6:

In a 350-mL resealable vessel, the (S)-2'-bromo-7'-iodospiro[morpholine-3,9'-xanthene]-5-thione (1.25 g, 2.56 mmol) was dissolved in a dioxane solution of ammonia (0.5 M, 61.5 mL, 30.7 mmol). After the solid had dissolved, mercury(II) chloride (1.043 g, 3.84 mmol) was added. The vessel was sealed and placed in a 55° C. oil bath overnight. The reaction was filtered through Celite, rinsing with DCM (50 mL). The mixture was concentrated to remove the DCM, and $Boc_2O$ (0.84 g, 3.84 mmol) and $Et_3N$ (0.535 mL, 3.84 mmol) were added. After 1.5 h, the mixture was concentrated, and the residue was purified by chromatography (15% EtOAc/hexanes) to afford impure (S)-tert-butyl 2'-bromo-7'-iodo-2,6-dihydrospiro[[1,4]oxazine-3,9'-xanthene]-5-ylcarbamate.

Step 7:

In a 150-mL resealable vessel, the (S)-tert-butyl 2'-bromo-7'-iodo-2,6-dihydrospiro[[1,4]oxazine-3,9'-xanthene]-5-ylcarbamate (1.475 g, 2.58 mmol) was dissolved in dcm (10 mL), and 2,2,2-trifluoroacetic acid (1.989 mL, 25.8 mmol) was added. The vessel was sealed and placed in a 50° C. oil bath. After 2 h, the reaction was concentrated and the mixture was neutralized with 0.5 M aqueous $Na_2CO_3$ (15 mL) and the aqueous phase was extracted with 5% MeOH-dcm (3×33 mL). The organics were combined, washed with dilute brine (10 mL), dried over sodium sulfate and concentrated. The residue was purified by chromatography (5.5% MeOH/DCM) to afford (S)-2'-bromo-7'-iodo-2,6-dihydrospiro[[1,4]oxazine-3,9'-xanthen]-5-amine (151 mg, 0.321 mmol). MS (m/z) 471/473 (M+H)$^+$.

Example 28

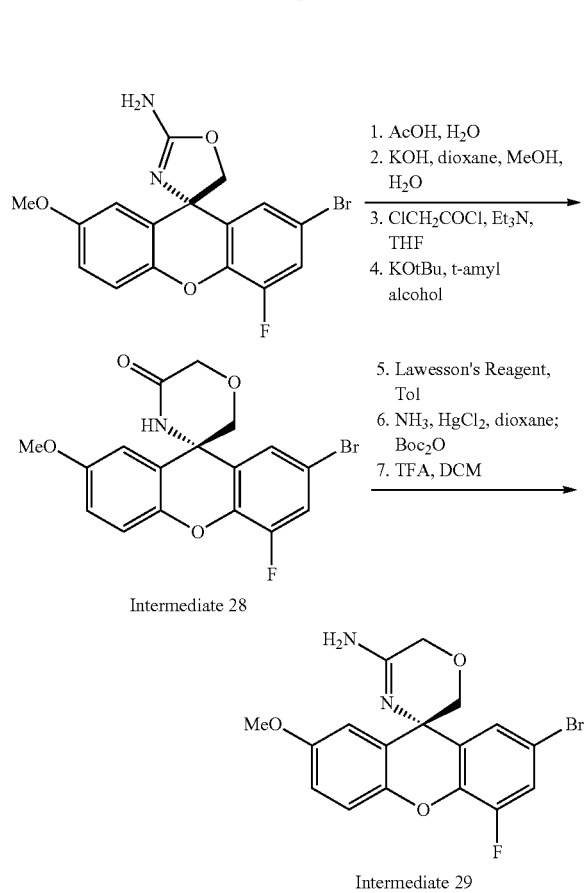

1. AcOH, H₂O
2. KOH, dioxane, MeOH, H₂O
3. ClCH₂COCl, Et₃N, THF
4. KOtBu, t-amyl alcohol Intermediate 28

5. Lawesson's Reagent, Tol
6. NH₃, HgCl₂, dioxane; Boc₂O
7. TFA, DCM

Intermediate 29

Synthesis of Intermediates 28 and 29

Step 1:

The same reagents and reaction conditions in Steps 1-4 of Procedure ZZ were used to convert (S)-2'-bromo-4'-fluoro-7'-methoxy-5H-spiro[oxazole-4,9'-xanthen]-2-amine to (S)-2'-bromo-4'-fluoro-7'-methoxyspiro[morpholine-3,9'-xanthen]-5-one. MS (m/z) 394/396 (M+H)⁺.

Step 2:

The same reagents and reaction conditions in Steps 5-7 of Procedure ZZ were used to convert (S)-2'-bromo-4'-fluoro-7'-methoxyspiro[morpholine-3,9'-xanthen]-5-one to (S)-2'-bromo-4'-fluoro-7'-methoxy-2,6-dihydrospiro[[1,4]oxazine-3,9'-xanthen]-5-amine. MS (m/z) 393/395 (M+H)⁺.

Example 29

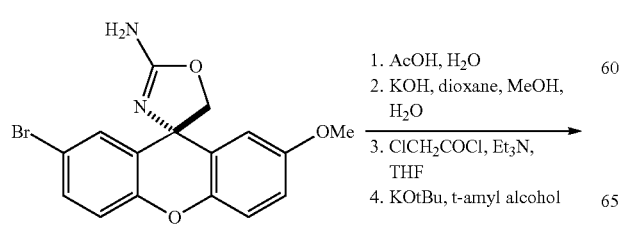

1. AcOH, H₂O
2. KOH, dioxane, MeOH, H₂O
3. ClCH₂COCl, Et₃N, THF
4. KOtBu, t-amyl alcohol

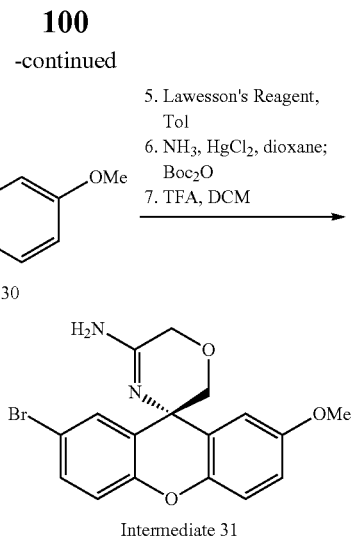

Intermediate 30

5. Lawesson's Reagent, Tol
6. NH₃, HgCl₂, dioxane; Boc₂O
7. TFA, DCM

Intermediate 31

Synthesis of Intermediates 30 and 31

Step 1:

The same reagents and conditions in Steps 1-4 in Procedure ZZ were used to convert (S)-2'-bromo-7'-methoxy-5H-spiro[oxazole-4,9'-xanthen]-2-amine to (S)-2'-bromo-7'-methoxyspiro[morpholine-3,9'-xanthen]-5-one.

Step 2:

The same reagents and conditions in Steps 5-7 of Procedure ZZ were used to convert (S)-2'-bromo-7'-methoxyspiro[morpholine-3,9'-xanthen]-5-one to (S)-2'-bromo-7'-methoxy-2,6-dihydrospiro[[1,4]oxazine-3,9'-xanthen]-5-amine. MS (m/z) 375/377 (M+H)⁺.

Example 30

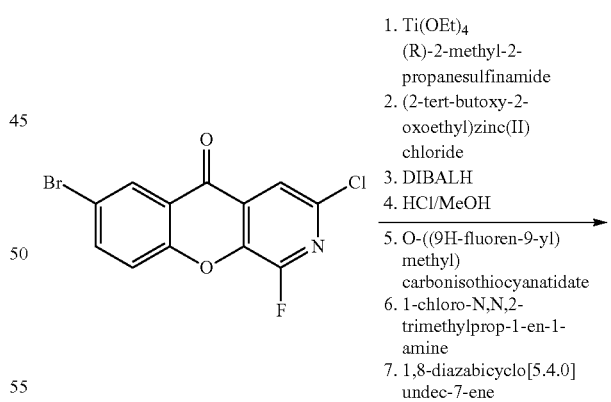

1. Ti(OEt)₄ (R)-2-methyl-2-propanesulfinamide
2. (2-tert-butoxy-2-oxoethyl)zinc(II) chloride
3. DIBALH
4. HCl/MeOH
5. O-((9H-fluoren-9-yl)methyl) carbonisothiocyanatidate
6. 1-chloro-N,N,2-trimethylprop-1-en-1-amine
7. 1,8-diazabicyclo[5.4.0]undec-7-ene

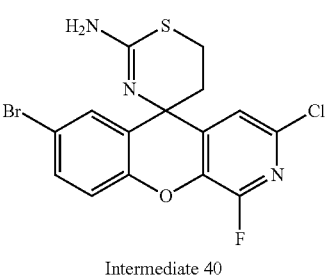

Intermediate 40

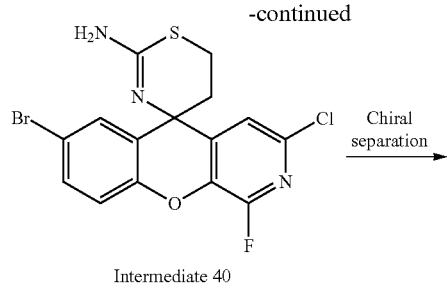

Intermediate 40

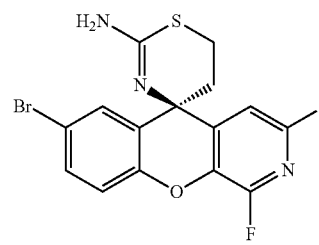

Intermediate 40A

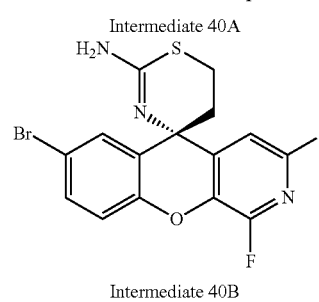

Intermediate 40B

Synthesis of Intermediates 40A and 40B
Step 1:
A suspension of 7-bromo-3-chloro-1-fluoro-5H-chromeno[2,3-c]pyridin-5-one (20 g, 60.9 mmol), (R)-2-methyl-2-propanesulfinamide (14.76 g, 122 mmol), and titanium (IV) ethoxide (25.2 mL, 122 mmol) in THF (250 mL) was heated to 70° C. for 24 h. Additional (R)-2-methyl-2-propanesulfinamide (1.0 equiv) and titanium (IV) ethoxide (1.0 equiv) were added and the reaction mixture was heated for additional 24 h. Additional (R)-2-methyl-2-propanesulfinamide (1.0 equiv) and titanium (IV) ethoxide (1.0 equiv) were added and the reaction mixture was heated for additional 8 h. The reaction mixture was quenched with brine (150 mL). The resulting suspension was filtered through celite, and the filter cake was washed with EtOAc. The filtrate was washed with brine, dried over Na$_2$SO$_4$ and concentrated under reduced pressure. The residue was purified by chromatography (100% hexanes) to afford racemic N-(7-bromo-3-chloro-1-fluoro-5H-chromeno[2,3-c]pyridin-5-ylidene)-2-methylpropane-2-sulfinamide as an orange solid (15 g, 34.7 mmol, 57.1% yield).
Step 2:
A solution of (2-tert-butoxy-2-oxoethyl)zinc(II) chloride (0.5M in Et$_2$O; 116 mL, 57.9 mmol) was cooled to 0° C. and a solution of (Z)—N-(7-bromo-3-chloro-1-fluoro-5H-chromeno[2,3-c]pyridin-5-ylidene)-2-methylpropane-2-sulfinamide (10 g, 23.16 mmol) in THF (100 mL) was added drop wise. The resulting mixture was stirred at for 1 hour 0° C. The reaction mixture was diluted with EtOAc and washed with aqueous saturated solution of NH$_4$Cl, followed by brine. The organic layer was dried over Na$_2$SO$_4$, and concentrated under reduced pressure. The obtained residue was purified by chromatography (0-20% EtOAc/hexanes) to afford tert-butyl 2-(7-bromo-3-chloro-5-(1,1-dimethylethylsulfinamido)-1-fluoro-5H-chromeno[2,3-c]pyridin-5-yl)acetate (7.5 g, 13.69 mmol, 59% yield) as a yellow solid.
Step 3:
A solution of tert-butyl 2-(7-bromo-3-chloro-5-(1,1-dimethylethylsulfinamido)-1-fluoro-5H-chromeno[2,3-c]pyridin-5-yl)acetate (7.5 g, 13.69 mmol) in dry THF (25 mL) was cooled to −78° C. and diisobutylaluminum hydride (54.8 mL, 54.8 mmol) was added drop wise. The mixture was warmed to 0° C. and kept at this temperature for 1 h. The reaction mixture was quenched with a aqueous, saturated solution of Rochelle's salt and vigorously stirred for 15 h. The organic layer was separated and the aqueous phase was extracted with EtOAc. The combined organic layers were washed with brine and dried over Na$_2$SO$_4$. The solution was concentrated under reduced pressure. The residue was purified by chromatography (0-30% EtOAc/hexanes) to afford N-(7-bromo-3-chloro-1-fluoro-5-(2-hydroxyethyl)-5H-chromeno[2,3-c]pyridin-5-yl)-2-methylpropane-2-sulfinamide (5.8 g, 89% yield) as a light yellow solid.
Step 4:
To a solution of N-(7-bromo-3-chloro-1-fluoro-5-(2-hydroxyethyl)-5H-chromeno[2,3-c]pyridin-5-yl)-2-methylpropane-2-sulfinamide (5.8 g, 12.14 mmol) in dry MeOH (100 mL) at −20° C. was added a mixture of MeOH (80 mL)acetylchloride (20 ml). The resulting reaction mixture was stirred at −20° C. for 30 min and then quenched with 10% aqueous solution of Na$_2$CO$_3$. DCM was added, the organic phase was separated and dried over Na$_2$SO$_4$. The solution concentrated under reduced pressure and the residue was purified by chromatography (0-50% EtOAc/hexanes) to afford 2-(5-amino-7-bromo-3-chloro-1-fluoro-5H-chromeno[2,3-c]pyridin-5-yl)ethanol (4.0 g, 10.71 mmol, 88% yield) as a light yellow solid-foam.
Step 5:
2-(5-amino-7-bromo-3-chloro-1-fluoro-5H-chromeno[2,3-c]pyridin-5-yl)ethanol (10 g, 26.8 mmol) and O-((9H-fluoren-9-yl)methyl)carbonisothiocyanatidate (7.53 g, 26.8 mmol) were combined in DCM 200 mL and stirred at RT for 1 hr. The crude solution of 9H-fluoren-9-yl)methyl(7-bromo-3-chloro-1-fluoro-5',6'-dihydrospiro[chromeno[2,3-c]pyridine-5,4'-[1,3]thiazin]-2'-yl)carbamate was advanced without further purification.
Step 6:
To the solution from Step 5 was added 1-chloro-N,N,2-trimethylprop-1-en-1-amine (3.54 ml, 26.8 mmol). The reaction mixture was stirred at room temperature for 30 min. The crude solution of 9H-fluoren-9-yl)methyl(7-bromo-3-chloro-1-fluoro-5',6'-dihydrospiro[chromeno[2,3-c]pyridine-5,4'-[1,3]thiazin]-2'-yl)carbamate was advanced without further purification.
Step 7:
To the solution from Step 6 was added 1,8-diazabicyclo[5.4.0]undec-7-ene (20 ml, 133 mmol) to make it a 10% solution. The reaction mixture was stirred for 1 h. The solution was diluted with ethyl acetate and washed three times with water. The organic layer was separated, dried on sodium sulfate, filtered and concentrated. The crude material was purified by column chromatography with 1-5% 2M NH$_3$ in MeOH/DCM. The fractions containing desired product was combined and further purified by column chromatography with 0-10% Et$_2$ODCM to give 7-bromo-3-chloro-1-fluoro-5',6'-dihydrospiro[chromeno[2,3-c]pyridine-5,4'-[1,3]thiazin]-2'-amine as a white solid.
Step 8:
7-Bromo-3-chloro-1-fluoro-5',6'-dihydrospiro[chromeno[2,3-c]pyridine-5,4'-[1,3]thiazin]-2'-amine was chromatographed using supercritical CO$_2$ (additives 30% MeOH with 40 mM NH₃) on a Chiralpak AD-H column (21×250 mm, 5 µm) eluting at a flow rate 70 ml/min (100 bar pressure, 40° C. column temperature). The first peak (retention time=3.5 min) provided (R)-7-bromo-3-chloro-1-fluoro-5',6'-dihydrospiro [chromeno[2,3-c]pyridine-5,4'-[1,3]thiazin]-2'-amine (intermediate 40A; >99% ee), and the second peak (retention time=4.5 min) provided (S)-7-bromo-3-chloro-1-fluoro-5', 6'-dihydrospiro[chromeno[2,3-c]pyridine-5,4'-[1,3]thiazin]-2'-amine (intermediate 40B; >99% ee).

Example 31

Method A

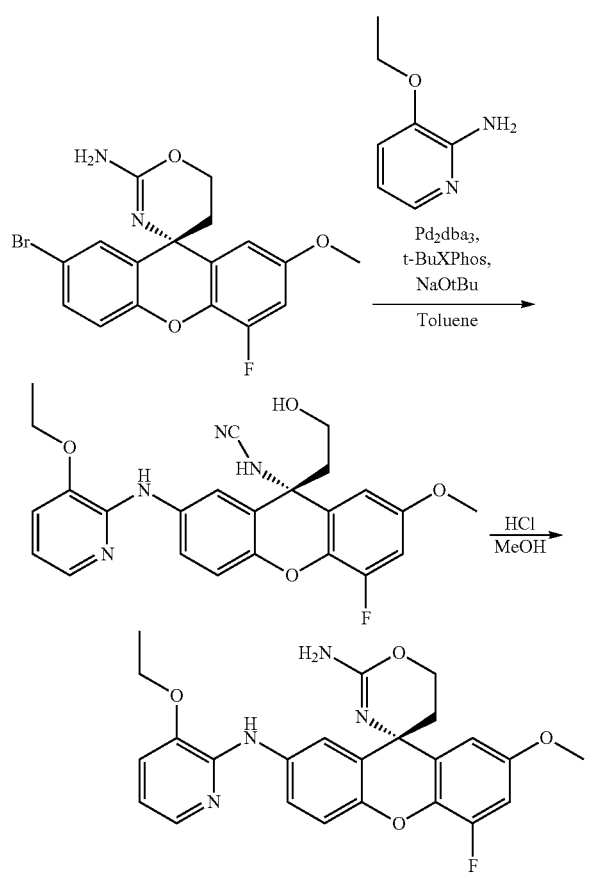

Synthesis of (S)—N7'-(3-ethoxypyridin-2-yl)-4'-fluoro-2'-methoxy-5,6-dihydrospiro[[1,3]oxazine-4, 9'-xanthene]-2,7'-diamine Step 1:
A 20 mL resealable tube was charged with 3-ethoxypyridin-2-amine (176 mg, 1.272 mmol), (S)-7'-bromo-4'-fluoro-2'-methoxy-5,6-dihydrospiro[[1,3]oxazine-4,9'-xanthen]-2-amine (250 mg, 0.636 mmol), Pd₂dba₃ (29.1 mg, 0.032 mmol), t-BuXPhos (47.2 mg, 0.111 mmol) and sodium t-butoxide (244 mg, 2.54 mmol). Toluene (6 ml) was added, the mixture was stirred for 2 min at room temperature, then heated at 100° C. for 1.5 hr. The solution was diluted with ethyl acetate and water. The organic layer was separated and concentrated. The product was purified via silica gel column chromatography (RediSep 40 g column) using 20-80% ethyl acetate in heptane to afford (S)—N-(7-((3-ethoxypyridin-2-yl)amino)-4-fluoro-9-(2-hydroxyethyl)-2-methoxy-9H-xanthen-9-yl)cyanamide (160 mg, 0.355 mmol, 55.9% yield). MS m/z=451.0 [M+H].

Step 2:
(S)—N-(7-((3-ethoxypyridin-2-yl)amino)-4-fluoro-9-(2-hydroxyethyl)-2-methoxy-9H-xanthen-9-yl)cyanamide (160 mg, 0.355 mmol) was dissolved in methanol (10 ml) and three drops of concentrated HCl was added. The solution was stirred at room temperature for 30 minutes. The solution was quenched with water and saturated sodium bicarbonate, then extracted with ethyl acetate. The organics were then separated and concentrated. The product was purified via silica gel column chromatography (RediSep 40 g column) using 50-100% ethyl acetate in heptane to afford (S)—N7'-(3-ethoxypyridin-2-yl)-4'-fluoro-2'-methoxy-5,6-dihydrospiro [[1,3]oxazine-4,9'-xanthene]-2,7'-diamine (40 mg, 0.089 mmol, 25.00% yield). MS m/z=451.0 [M+H].

Example 32

Method B

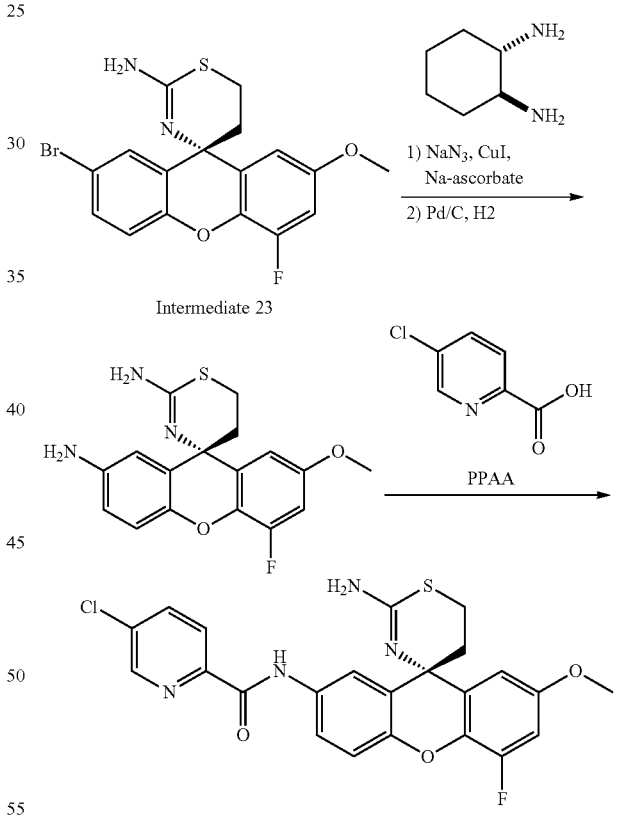

Synthesis of (S)—N-(2-amino-4'-fluoro-2'-methoxy-5,6-dihydrospiro[[1,3]thiazine-4,9'-xanthen]-7'-yl)-5-chloropicolinamide Step 1:
To a disposable vial was charged with (S)-7'-bromo-4'-fluoro-2'-methoxy-5,6-dihydrospiro[[1,3]thiazine-4,9'-xanthen]-2-amine (300 mg, 0.733 mmol), copper(I) iodide (27.9 mg, 0.147 mmol), sodium azide (143 mg, 2.199 mmol) and (+)-sodium 1-ascorbate (14.52 mg, 0.073 mmol). EtOH (1.2 mL) and water (0.5 mL) were added followed by addition of trans-N,N'-dimethyl-1,2-cyclohexanediamine (34.7 µl, 0.220 mmol). The vial was capped and subjected to three cycles of evacuation-backfilling with $N_2$. Finally it was heated in oil bath at 90° C. for 3 hrs. The reaction mixture was allowed to cool to RT. Excess of water was added and a tan precipitate formed. It was collected through Buchner funnel to yield (S)-7'-azido-4'-fluoro-2'-methoxy-5,6-dihydrospiro[[1,3]thiazine-4,9'-xanthen]-2-amine (170 mg, 0.458 mmol, 62.4% yield) as tan solid.

Step 2:

To a disposable vial was charged with (S)-7'-azido-4'-fluoro-2'-methoxy-5,6-dihydrospiro[[1,3]thiazine-4,9'-xanthen]-2-amine (170 mg, 0.458 mmol), Ethanol (1.7 ml) and EtOAc (0.8 ml). The heterogeneous mixture stirred for 5 min and palladium on carbon (48.7 mg, 0.046 mmol) was added to the vial. The mixture was hydrogenated (balloon) at room temperature overnight. The mixture was filtered through celite and concentrated. The dark residue was diluted with DCM and concentrated again. After drying in vacuo, (S)-4'-fluoro-2'-methoxy-5,6-dihydrospiro[[1,3]thiazine-4,9'-xanthene]-2,7'-diamine (120 mg, 0.347 mmol, 76% yield) was obtained as tan foam. It was used for next step without further purification.

Step 3:

To a solution of (S)-4'-fluoro-2'-methoxy-5,6-dihydrospiro[[1,3]thiazine-4,9'-xanthene]-2,7'-diamine (55 mg, 0.159 mmol), 5-chloro-2-pyridinecarboxylic acid (37.6 mg, 0.239 mmol), and TEA (0.067 mL, 0.478 mmol) in DCM (1.5 mL) was added propylphosphonic anhydride solution, 50 wt. % in ethyl acetate (0.152 mL, 0.239 mmol). The mixture was stirred at rt. 0.5 hr later, the reaction mixture was concentrated. The red residue was diluted with water and extracted with DCM. The organic extract was washed with brine and dried over MgSO4. The solution was filtered and concentrated in vacuo to give the crude material as a red solid. The crude material was purified by chromatography eluting with a gradient of DCM for 5 mins and 25% to 35% to 50% DCM/MeOH/NH4OH in (40% of EtOAc in Heptane), to provide (S)—N-(2-amino-4'-fluoro-2'-methoxy-5,6-dihydrospiro[[1,3]thiazine-4,9'-xanthen]-7'-yl)-5-chloropicolinamide (11 mg, 0.023 mmol, 14.24% yield) as off-white solid.

Example 33

Method C

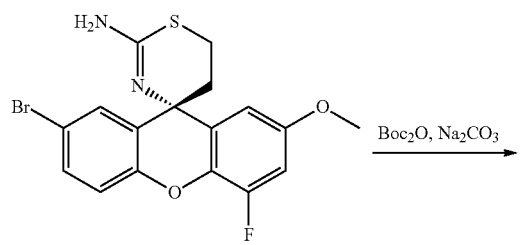

Synthesis of (S)—N7'-(3-ethoxypyridin-2-yl)-4'-fluoro-2'-methoxy-5,6-dihydrospiro[[1,3]thiazine-4,9'-xanthene]-2,7'-diamine

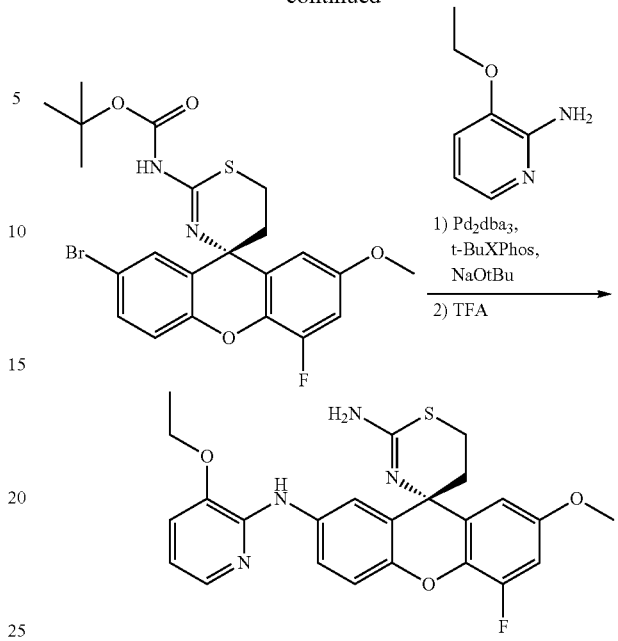

Step 1:

(S)-7'-bromo-4'-fluoro-2'-methoxy-5,6-dihydrospiro[[1,3]thiazine-4,9'-xanthen]-2-amine (400 mg, 0.977 mmol) was dissolved in dioxane (48870. Saturated aqueous sodium bicarbonate solution (5 mL) was added, followed by addition of Boc-anhydride (681 µl, 2.93 mmol). The reaction mixture was stirred at room temperature for 2 hrs. Then it was diluted with ethyl acetate and washed with water. The aqueous layer was extracted with ethyl acetate, and the combined organic layers were dried with $MgSO_4$, filtered, and concentrated. The material was purified through column chromatography eluting with a gradient of 45% to 60% to 75% EtOAc in Hexane to afford (S)-tert-butyl(7'-bromo-4'-fluoro-2'-methoxy-5,6-dihydrospiro[[1,3]thiazine-4,9'-xanthen]-2-yl)carbamate (490 mg, 0.962 mmol, 98% yield) as a yellow solid.

Step 2:

A 2-5 ml resealable tube was charged with 3-ethoxypyridin-2-amine (26.0 mg, 0.188 mmol), (S)-tert-butyl(7'-bromo-4'-fluoro-2'-methoxy-5,6-dihydrospiro[[1,3]thiazine-4,9'-xanthen]-2-yl)carbamate (80 mg, 0.157 mmol), $Pd_2$ $dba_3$ (15.82 mg, 0.017 mmol), t-BuXPhos (14.67 mg, 0.035 mmol) and sodium t-butoxide (33.2 mg, 0.346 mmol). Toluene (6280 was added, and the mixture was stirred for 2 min at RT, then was heated to 80° C. for 20 min. The reaction mixture was diluted with water and extracted with EtOAc. The organic extract was washed with saturated NaCl and dried over $MgSO_4$. The solution was filtered and concentrated in vacuo to give the crude material as a orange oil. The crude material was purified by chromatography eluting with a gradient of 0% to 15% to 30% DCM/MeOH/NH4OH in DCM, to provide Boc-protected product as yellow solid. The Boc protected product was dissolved in 1 mL of DCM and 1 mL of TFA was added. The reaction mixture was stirred at rt for 40 mins. Then the solvent was reduced and crude product was purified by chromatography eluting with a gradient of 20% to 35% to 50% DCM/MeOH/NH$_4$OH in (40% EtOAc in Heptane), to provide (S)—N7'-(3-ethoxypyridin-2-yl)-4'-fluoro-2'-methoxy-5,6-dihydrospiro[[1,3]thiazine-4,9'-xanthene]-2,7'-diamine (16 mg, 0.034 mmol, 21.84% yield) as light-yellow solid.

Example 34

Method D

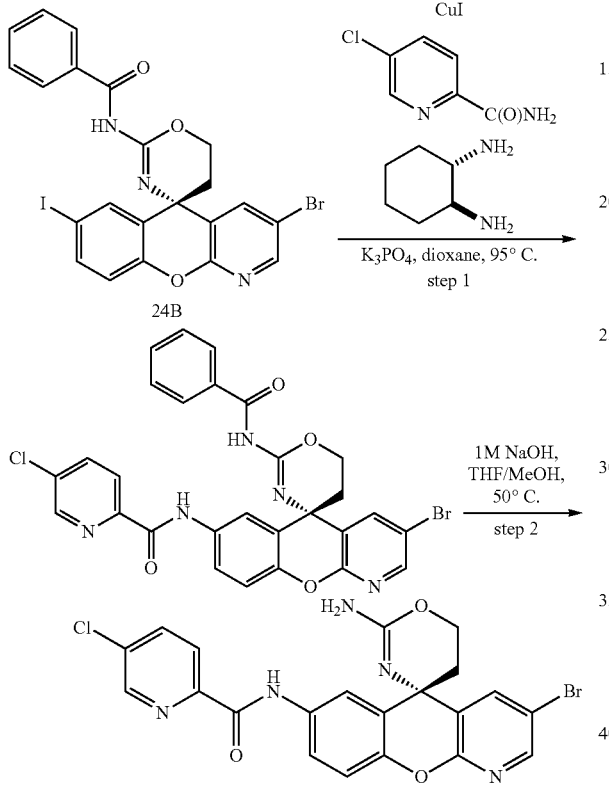

Synthesis of (S)—N-(2'-amino-3-bromo-5',6'-dihydrospiro[chromeno[2,3-b]pyridine-5,4'-[1,3]oxazin]-7-yl)-5-chloropicolinamide Step 1:

A microwave vial was charged with (S)—N-(3-bromo-7-iodo-5',6'-dihydrospiro[chromeno[2,3-b]pyridine-5,4'-[1,3]oxazin]-2'-yl)benzamide (Intermediate 24B, 60 mg, 0.104 mmol), copper(I) iodide (2.97 mg, 0.016 mmol), 5-chloropicolinamide (24.46 mg, 0.156 mmol) and anhydrous potassium phosphate, (36.3 mg, 0.208 mmol). The vial was evacuated and backfilled with nitrogen. The procedure was repeated twice. Dioxane (0.25 mL) was added followed by rac-trans-1,2-diaminocyclohexane (3.75 µl, 0.031 mmol). The reaction mixture was heated to 95° C. overnight. Aqueous, saturated ammonium chloride solution was added to the reaction mixture, followed by EtOAc. The organic phase was separated and dried over MgSO$_4$. The solvent was removed under reduced pressure. The residue was taken onto the next step without further purification Step 2:

The residue form step 1 was dissolved in THF (1 mL)/MeOH (1 mL) and sodium hydroxide (1N, 0.312 mL, 0.312 mmol) was added. The reaction mixture was heated to 70° C. for 1 h. The solvents were evaporated under reduced pressure and the residue was purified by preparative reversed-phase HPLC using a Phenomenex Gemini column, 10 micron, C18, 110 Å, 100×50 mm, 0.1% TFA in CH$_3$CNH$_2$O, gradient 10% to 100% over 20 min. The combined fractions were concentrated. The residue was dissolved in MeOH and loaded onto a Varian Bond Elut SCX column. The product was eluted with a 2M solution of NH$_3$ in MeOH. 16 mg of (S)—N-(2'-amino-3-bromo-5',6'-dihydrospiro[chromeno[2,3-b]pyridine-5,4'-[1,3]oxazin]-7-yl)-5-chloropicolinamide were obtained were obtained as a light-yellow solid. MS m/z=501.8 [M+H][11]. Calculated for C$_{21}$H$_{15}$BrClN$_5$O$_3$: 500.73. $^1$H NMR (300 MHz, DMSO-d$_6$) ppm 1.61-1.91 (m, 2H) 3.88-4.20 (m, 2H) 5.82-6.02 (m, 2H) 7.27 (d, J=9.35 Hz, 1H) 7.82-7.96 (m, 3H) 8.11-8.24 (m, 2H) 8.35 (d, J=2.63 Hz, 1H) 8.78 (d, J=1.46 Hz, 1H) 10.85 (s, 1H).

Example 34

Method E

Alternative Synthesis

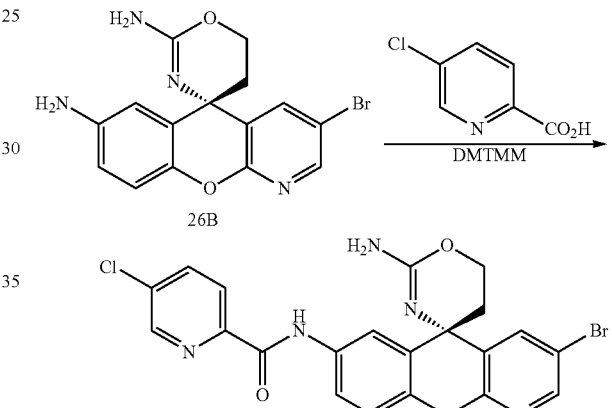

Synthesis of (S)—N-(2'-amino-3-bromo-5',6'-dihydrospiro[chromeno[2,3-b]pyridine-5,4'-[1,3]oxazin]-7-yl)-5-chloropicolinamide 4-(4,6-dimethoxy-1,3,5-triazin-2-yl)-4-methylmorpholinium chloride (228 mg, 0.775 mmol) was added to a solution of 5-chloro-2-pyridinecarboxylic acid (122 mg, 0.775 mmol) in MeOH (0.6 mL), followed by a solution of (S)-3-bromo-5',6'-dihydrospiro[chromeno[2,3-b]pyridine-5,4'-[1,3]oxazine]-2',7-diamine (140 mg, 0.388 mmol) in THF (1.6 mL) MeOH (0.5 mL). The reaction mixture was allowed to stir for 20 min at rt. Diluted, aqueous bicarbonate solution was added, followed by additional water and EtOAc. The organic phase was separated and dried over MgSO$_4$. The solvent was removed under reduced pressure and the residue was purified by flash chromatography (silica gel, 20-100% EtOAc/hexanes). 40 mg of (S)—N-(2'-amino-3-bromo-5',6'-dihydrospiro[chromeno[2,3-b]pyridine-5,4'-[1,3]oxazin]-7-yl)-5-chloropicolinamide were obtained as an off-white solid. MS m/z=501.7 [M+H][11]. Calculated for C$_{21}$H$_{15}$BrClN$_5$O$_3$: 500.73. $^1$H NMR (300 MHz, CHLOROFORM-d) ppm 1.82-1.93 (m, 1H) 1.93-2.02 (m, 1H) 4.07-4.19 (m, 1H) 4.19-4.32 (m, 1H) 7.31 (d, J=8.62 Hz, 1H) 7.71 (d, J=2.48 Hz, 1H) 7.73-7.79 (m, 1H) 7.89 (dd, J=8.33, 2.34 Hz, 1H) 7.93 (d, J=2.48 Hz, 1H) 8.26 (d, J=8.33 Hz, 1H) 8.31 (d, J=2.48 Hz, 1H) 8.58 (d, J=1.90 Hz, 1H) 9.86 (s, 1H).

Example 35

Method F

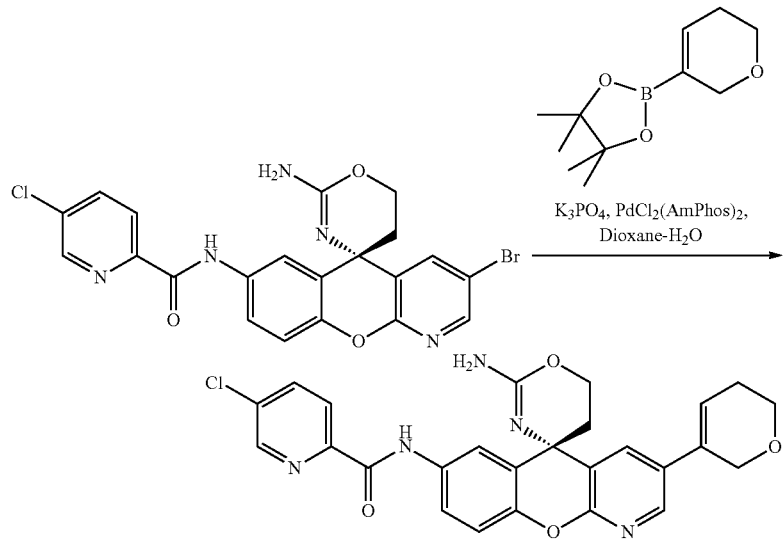

Synthesis of (S)—N-(2'-amino-3-(5,6-dihydro-2H-pyran-3-yl)-5',6'-dihydrospiro[chromeno[2,3-b]pyridine-5,4'-[1,3]oxazin]-7-yl)-5-chloropicolinamide A microwave vial was charged with 2-(5,6-dihydro-2H-pyran-3-yl)-4,4,5,5-tetramethyl-1,3,2-dioxaborolane (32.2 mg, 0.153 mmol), (S)—N-(2'-amino-3-bromo-5',6'-dihydrospiro[chromeno[2,3-b]pyridine-5,4'-[1,3]oxazin]-7-yl)-5-chloropicolinamide (64 mg, 0.128 mmol, Example 1), bis[di-tert-butyl(4 dimethylaminophenyl)phosphine]dichloropalladium(II) (4.53 mg, 6.39 μmol) and potassium phosphate (81 mg, 0.383 mmol). The vial was evacuated and backfilled with nitrogen (procedure was repeated twice). Dioxane (2 mL) and water (0.7 mL) were added and the reaction mixture was purged for 1 min with nitrogen. The vial was placed in a preheated oilbath and heated to 85° C. After 12 hours an additional portion of all reagents were added and the reaction mixture was heated for 4.5 hs to 100° C. The reaction mixture was cooled to room temperature and partitioned between EtOAc and water. The organic phase was separated and dried over MgSO$_4$. The solvent was removed under reduced pressure. The residue was purified by preparative reversed-phase HPLC using a Phenomenex Gemini column, 10 micron, C18, 110 Å, 100×50 mm, 0.1% TFA in CH$_3$CNH$_2$O, gradient 10% to 100% over 20 min. The combined fractions were concentrated. The residue was dissolved in MeOH and loaded onto a Varian Bond Elut SCX column. The product was eluted with a 2M solution of NH$_3$ in MeOH. 14 mg of (S)—N-(2'-amino-3-(5,6-dihydro-2H-pyran-3-yl)-5',6'-dihydrospiro[chromeno[2,3-b]pyridine-5,4'-[1,3]oxazin]-7-yl)-5-chloropicolinamide were obtained as a tan solid. MS m/z=503.7 [M]$^+$. Calculated for C$_{26}$H$_{22}$ClN$_5$O$_4$: 503.94.

Example 36

Method G

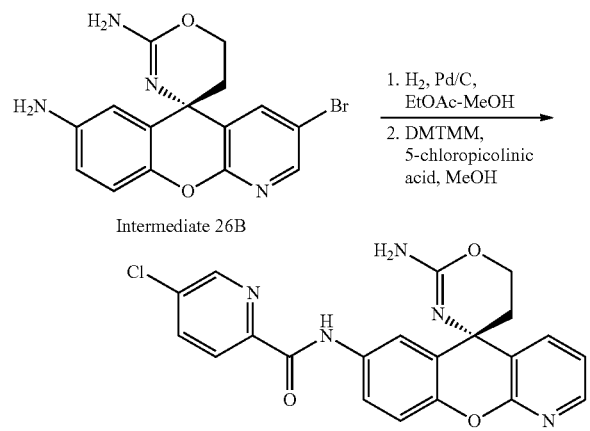

Intermediate 26B

Synthesis of (S)—N-(2'-amino-5',6'-dihydrospiro[chromeno[2,3-b]pyridine-5,4'-[1,3]oxazin]-7-yl)-5-chloropicolinamide Step 1:
A 15-mL flask was charged with (S)-3-bromo-5',6'-dihydrospiro[chromeno[2,3-b]pyridine-5,4'-[1,3]oxazine]-2',7-diamine (0.015 g, 0.042 mmol) and 10% palladium on carbon (0.075 g, 0.706 mmol). The material was suspended in MeOH (1.5 mL) and EtOAc (0.5 mL). The reaction was stirred for 2 h at rt under an atmosphere of hydrogen. The mixture was filtered through Celite, rinsing with 10% MeOH-dcm, and the filtrate was concentrated to afford crude (S)-5',6'-dihydrospiro[chromeno[2,3-b]pyridine-5,4'-[1,3]oxazine]-2',7-diamine (8 mg, 0.028 mmol).

Step 2:

The (S)-5',6'-dihydrospiro[chromeno[2,3-b]pyridine-5,4'-[1,3]oxazine]-2',7-diamine (0.008 g, 0.028 mmol) was dissolved in MeOH (1 mL). The 5-chloropicolinic acid (4.91 mg, 0.031 mmol) and 4-(4,6-dimethoxy-1,3,5-triazin-2-yl)-4-methylmorpholin-4-ium chloride (8.63 mg, 0.031 mmol) were added. After 2 h, additional MeOH (0.5 mL) was added, followed by additional 5-chloropicolinic acid (2.5 mg, 0.015 mmol) and additional 4-(4,6-dimethoxy-1,3,5-triazin-2-yl)-4-methylmorpholin-4-ium chloride (4.3 mg, 0.015 mmol). After 14 h, the reaction was taken up in EtOAc (75 mL). The organic phase was washed with half-saturated NaHCO$_3$ (2×10 mL), then with saturated brine (10 mL), dried over MgSO$_4$ and concentrated. The residue was purified by preparative TLC, using 12.5% MeOH-dcm to afford (S)—N-(2'-amino-5',6'-dihydrospiro[chromeno[2,3-b]pyridine-5,4'-[1,3]oxazin]-7-yl)-5-chloropicolinamide (3.5 mg, 0.0083 mmol). MS (m/z) 422 (M+H)$^+$. $^1$H NMR (400 MHz, CDCl$_3$) δ: 9.88 (s, 1H), 8.57 (s, 1H), 8.27 (m, 2H), 7.89 (d, 1H, J=8.4 Hz), 7.82 (d, 1H, J=7.4 Hz), 7.76 (m, 2H), 7.32 (d, 1H, J=8.4 Hz), 7.20 (m, 1H), 4.23 (m, 1H), 4.11 (m, 1H), 1.98 (m, 1H), 1.93 (m, 1H).

Example 37

Method H

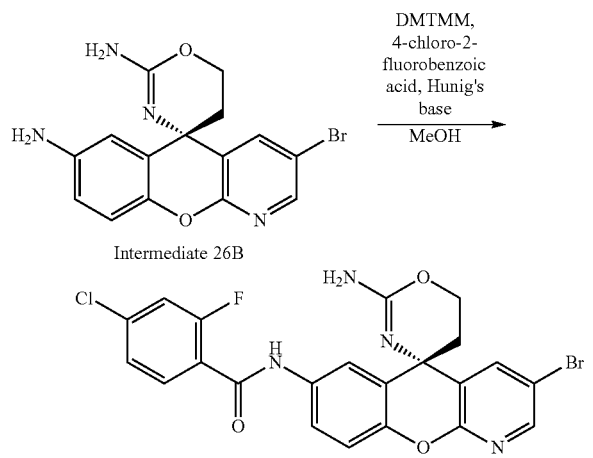

Synthesis of (S)—N-(2'-amino-3-bromo-5',6'-dihydrospiro[chromeno[2,3-b]pyridine-5,4'-[1,3]oxazin]-7-yl)-4-chloro-2-fluorobenzamide The (S)-3-bromo-5',6'-dihydrospiro[chromeno[2,3-b]pyridine-5,4'-[1,3]oxazine]-2',7-diamine (0.035 g, 0.097 mmol) was dissolved in MeOH (2 mL) and 4-chloro-2-fluorobenzoic acid (0.019 g, 0.107 mmol) and 4-(4,6-dimethoxy-1,3,5-triazin-2-yl)-4-methylmorpholin-4-ium chloride hydrate (0.031 g, 0.107 mmol) were added, followed by N-ethyl-N-isopropylpropan-2-amine (0.019 mL, 0.107 mmol). After 35 min, additional 4-chloro-2-fluorobenzoic acid (0.0095 g, 0.053 mmol) and additional 4-(4,6-dimethoxy-1,3,5-triazin-2-yl)-4-methylmorpholin-4-ium chloride hydrate (0.015 g, 0.053 mmol) were added. After 2 h, the reaction was taken up in EtOAc (75 mL), and the organic layer was washed with half-saturated NaHCO3 (2×10 mL), then with saturated brine (10 mL), dried over MgSO$_4$ and concentrated. The material was purified by preparative tlc (85% EtOAc-hexane) to afford (S)—N-(2'-amino-3-bromo-5',6'-dihydrospiro[chromeno[2,3-b]pyridine-5,4'-[1,3]oxazin]-7-yl)-4-chloro-2-fluorobenzamide (9.7 mg, 0.019 mmol). MS (m/z) 517/519 (M+H)$^+$. $^1$H NMR (400 MHz, CDCl$_3$): 8.40 (d, 1H, J=14.7 Hz), 8.31 (d, 1H, J=2.4 Hz), 8.12 (t, 1H, J=8.5 Hz), 7.91 (d, 1H, J=2.4 Hz), 7.62 (m, 2H), 7.31 (m, 1H), 7.27 (m, 1H), 7.23 (m, 1H), 4.21 (m, 1H), 4.11 (m, 1H), 1.94 (m, 1H), 1.85 (m, 1H).

Example 38

Method I

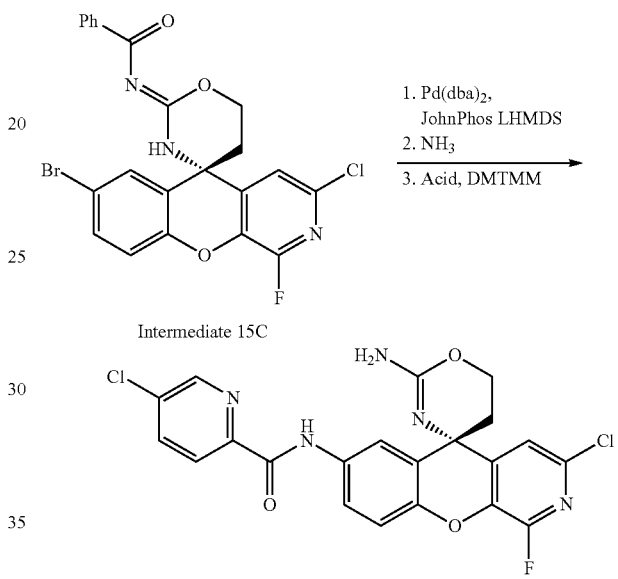

Synthesis of (S)—N-(2'-amino-3-chloro-1-fluoro-5',6'-dihydrospiro[chromeno[2,3-c]pyridine-5,4'-[1,3]oxazin]-7-yl)-5-chloropicolinamide Step 1:

A microwave vial was charged with (S,Z)—N-(7-bromo-3-chloro-1-fluorospiro[chromeno[2,3-c]pyridine-5,4'-[1,3]oxazinan]-2'-ylidene)benzamide (2.0 g, 3.98 mmol), Pd(dba)$_2$ (0.073 g, 0.080 mmol) and (2-biphenyl)dicyclohexylphosphine (0.067 g, 0.191 mmol), sealed and purged with N$_2$ followed by the addition of THF (2 mL) and lithium bis(trimethylsilyl)amide, 1.0 m solution in tetrahydrofuran (8.75 ml, 8.75 mmol). The resulting mixture was heated at 65° C. for 17 h, quenched with saturated NH$_4$Cl. The mixture was diluted with EtOAc, washed with water, brine, and dried over Na$_2$SO$_4$. The solution was concentrated and chromatographed on silica gel using 0-100% EtOAc/hexanes to afford a yellow oil as (S,Z)—N-(7-amino-3-chloro-1-fluorospiro[chromeno[2,3-c]pyridine-5,4'-[1,3]oxazinan]-2'-ylidene)benzamide.

Step 2:

(S,Z)—N-(7-amino-3-chloro-1-fluorospiro[chromeno[2,3-c]pyridine-5,4'-[1,3]oxazinan]-2'-ylidene)benzamide was dissolved in THF (5 mL) followed by the addition of ammonia, 2.0 m solution in methanol (49.7 ml, 99 mmol) and heated in a sealed tube at 50° C. for 17 h. The mixture was concentrated and chromatographed on silica gel using 0-5% MeOH/DCM to afford a yellow oil as (S)-3-chloro-1-fluoro-5',6'- dihydrospiro[chromeno[2,3-c]pyridine-5,4'-[1,3]oxazine]-2',7-diamine (0.23 g, 0.687 mmol, 17% yield).

Step 3:

A mixture of (S)-3-chloro-1-fluoro-5',6'-dihydrospiro[chromeno[2,3-c]pyridine-5,4'-[1,3]oxazine]-2',7-diamine (0.048 g, 0.143 mmol) and 5-chloro-2-pyridinecarboxylic acid (0.025 g, 0.158 mmol) was purged with N₂ followed by the addition of THF (2 mL) and MeOH (0.5 mL). 4-(4,6-dimethoxy-1,3,5-triazin-2-yl)-4-methylmorpholinium chloride (0.046 g, 0.158 mmol) was added in one portion and the resulting reaction mixture was stirred at rt for 3 h. The reaction mixture was quenched with saturated NaHCO₃, diluted with water and extracted with EtOAc. The combined organics were dried over Na₂SO₄, filtered, concentrated and chromatographed on silica gel using 0-4% MeOH/DCM and repurified by HPLC to afford (S)—N-(2'-amino-3-chloro-1-fluoro-5',6'-dihydrospiro[chromeno[2,3-c]pyridine-5,4'-[1,3]oxazin]-7-yl)-5-chloropicolinamide as a white solid (0.0258 g, 0.054 mmol, 37.9% yield). MS m/z=474.0 [M+H]⁺.

Example 39

Method J

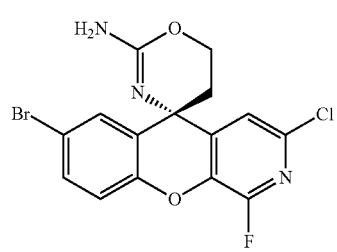
Intermediate 15B

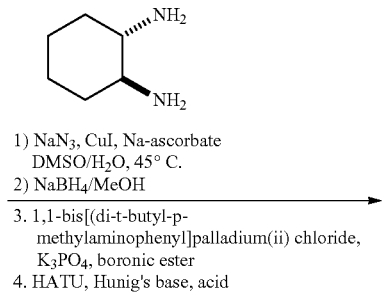

1) NaN₃, CuI, Na-ascorbate DMSO/H₂O, 45° C.
2) NaBH₄/MeOH
3. 1,1-bis[(di-t-butyl-p-methylaminophenyl]palladium(ii) chloride, K₃PO₄, boronic ester
4. HATU, Hunig's base, acid

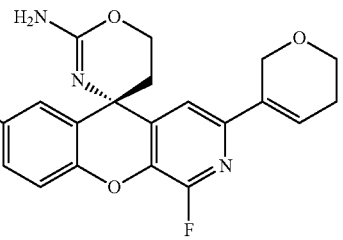

Synthesis of (S)—N-(2'-amino-3-(5,6-dihydro-2H-pyran-3-yl)-1-fluoro-5',6'-dihydrospiro[chromeno[2,3-c]pyridine-5,4'-[1,3]oxazin]-7-yl)-5-chloropicolinamide Step 1:

A microwave vial was charged with (S)-7-bromo-3-chloro-1-fluoro-5',6'-dihydrospiro[chromeno[2,3-c]pyridine-5,4'-[1,3]oxazin]-2'-amine (2.08 g, 5.22 mmol), (+)-sodium l-ascorbate (0.103 g, 0.522 mmol), sodium azide (0.550 ml, 15.65 mmol) and copper(i) iodide (0.035 ml, 1.044 mmol). The vial was sealed, purged with N₂ and followed by the addition of trans-n,n'-dimethyl-1,2-cyclohexanediamine (0.247 ml, 1.565 mmol), EtOH (12 mL) and water (4.6 mL). The resulting mixture was heated at 85° C. for 1.5 h. The mixture was poured into water and extracted with EtOAc. The combined organics were washed with brine, dried over Na₂SO₄, filtered, concentrated and chromatographed on silica gel using 0-50% MeOH/DCM to afford a light yellow solid as (S)-7-azido-3-chloro-1-fluoro-5',6'-dihydrospiro[chromeno[2,3-c]pyridine-5,4'-[1,3]oxazin]-2'-amine (0.86 g, 45.7% yield).

Step 2:

To a solution of (S)-7-azido-3-chloro-1-fluoro-5',6'-dihydrospiro[chromeno[2,3-c]pyridine-5,4'-[1,3]oxazin]-2'-amine (0.86 g, 2.384 mmol) in MeOH (15 mL) in a water bath was added sodium borohydride (0.420 ml, 11.92 mmol) in one portion. The resulting mixture was kept in the water bath and stirred for 10 min. The reaction went to completion and was carefully quenched with water, diluted with DCM and washed with 9:1 NH₄OH/sat NH₄Cl (10 mL). The combined organics were dried over Na₂SO₄, filtered, concentrated and chromatographed on silica gel using 0-5% MeOH/DCM to afford a pale yellow solid as (S)-3-chloro-1-fluoro-5',6'-dihydrospiro[chromeno[2,3-c]pyridine-5,4'-[1,3]oxazine]-2',7-diamine (0.354 g, 1.058 mmol, 44.4% yield).

Step 3:

A mixture of (S)-3-chloro-1-fluoro-5',6'-dihydrospiro[chromeno[2,3-c]pyridine-5,4'-[1,3]oxazine]-2',7-diamine (0.354 g, 1.058 mmol), 2-(5,6-dihydro-2H-pyran-3-yl)-4,4,5,5-tetramethyl-1,3,2-dioxaborolane (0.667 g, 3.17 mmol), 1,1-bis[(di-t-butyl-p-methylaminophenyl]palladium(ii) chloride (0.037 g, 0.053 mmol) and potassium phosphate tribasic (0.673 g, 3.17 mmol) in dioxane/water (42 mL) was heated in microwave at 130° C. for 40 min. The mixture was poured into water and extracted with EtOAc. The combined organics were dried over Na₂SO₄, filtered, concentrated and chromatographed on silica gel using 0-5% 2M NH₃ MeOH/DCM to afford (S)-3-(5,6-dihydro-2H-pyran-3-yl)-1-fluoro-5',6'-dihydrospiro[chromeno[2,3-c]pyridine-5,4'-[1,3]oxazine]-2',7-diamine (0.29 g, 0.758 mmol, 72% yield).

Step 4:

To a solution of (S)-3-(5,6-dihydro-2H-pyran-3-yl)-1-fluoro-5',6'-dihydrospiro[chromeno[2,3-c]pyridine-5,4'-[1,3]oxazine]-2',7-diamine (0.095 g, 0.248 mmol) in DMF (1 mL) were added 5-chloro-2-pyridinecarboxylic acid (0.043 g, 0.273 mmol), O-(-7-azabenzotriazol-1-yl)-n,'n,'n,'n'-tetramethyluronium pf6 (0.099 g, 0.261 mmol) and Hunig's base (0.086 ml, 0.497 mmol) and the resulting mixture was stirred at rt for 15 h. The mixture was quenched with 5 drops of 2 N HCl and stirred for 1 min followed by the addition of water and extracted with EtOAc. The combined organics were dried over Na$_2$SO$_4$, filtered, concentrated and chromatographed on silica gel using 0-3% MeOH/DCM. The product was repurified by HPLC to afford (S)—N-(2'-amino-3-(5,6-dihydro-2H-pyran-3-yl)-1-fluoro-5',6'-dihydrospiro[chromeno[2,3-c]pyridine-5,4'-[1,3]oxazin]-7-yl)-5-chloropicolinamide as a white solid (0.0334 g, 0.064 mmol, 25.8% yield). MS m/z=522.0 [M+H]$^+$.

Example 40

Method K

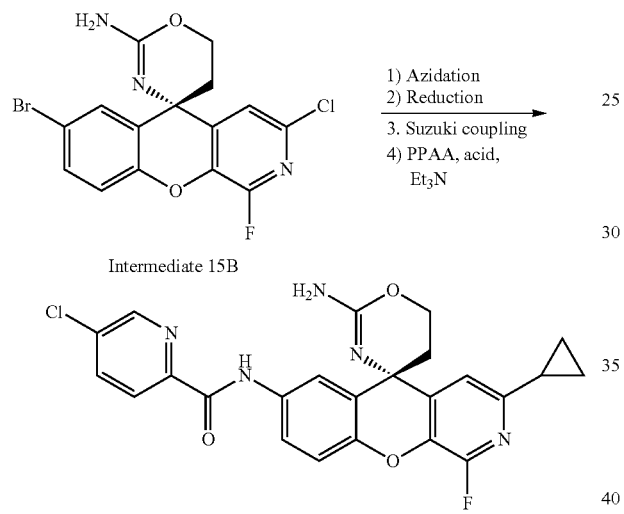

Synthesis of (S)—N-(2'-amino-3-cyclopropyl-1-fluoro-5',6'-dihydrospiro[chromeno[2,3-c]pyridine-5,4'-[1,3]oxazin]-7-yl)-5-chloropicolinamide Steps 1, 2, and 3 are the same as described in Example 39 (Method J) except using the corresponding boronic acid.
Step 4:
To a solution of (S)-3-cyclopropyl-1-fluoro-5',6'-dihydrospiro[chromeno[2,3-c]pyridine-5,4'-[1,3]oxazine]-2',7-diamine (0.0864 g, 0.254 mmol) and 5-chloro-2-pyridinecarboxylic acid (0.044 g, 0.279 mmol) in EtOAc (2 mL) was added triethylamine (0.106 ml, 0.762 mmol). The mixture was stirred for one minute and propylphosphonic anhydride solution, 50 wt. % in ethyl acetate (0.302 ml, 0.508 mmol) was added. Stirring continued for 1 h. The reaction was quenched with saturated NaHCO$_3$ and extracted with EtOAc. The combined organics were dried over Na$_2$SO$_4$, filtered, concentrated and chromatographed on silica gel using 0-5% MeOH/DCM and repurified by HPLC to afford (S)—N-(2'-amino-3-cyclopropyl-1-fluoro-5',6'-dihydrospiro[chromeno[2,3-c]pyridine-5,4'-[1,3]oxazin]-7-yl)-5-chloropicolinamide as a white solid (0.015 g, 0.031 mmol, 12.31% yield). MS m/z=480.0 [M+H]$^+$.

Example 41

Method L

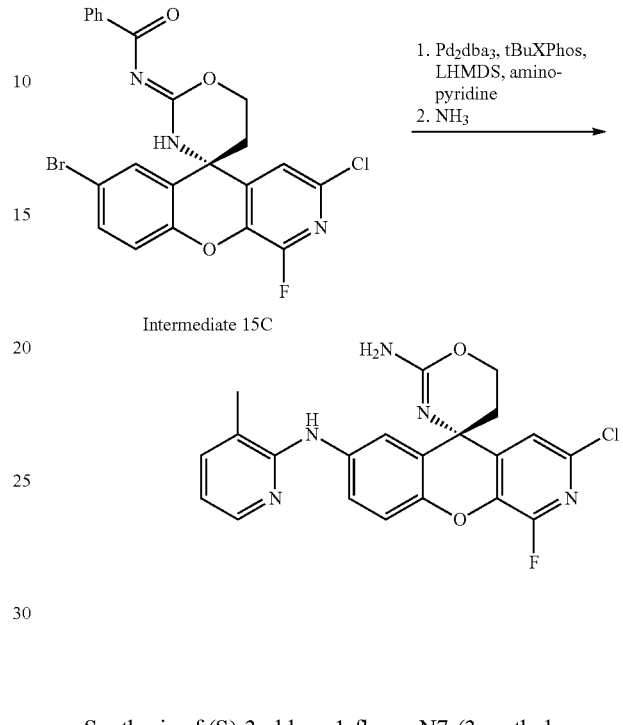

Synthesis of (S)-3-chloro-1-fluoro-N7-(3-methylpyridin-2-yl)-5',6'-dihydrospiro[chromeno[2,3-c]pyridine-5,4'-[1,3]oxazine]-2',7-diamine Step 1:
A mixture of (S,Z)—N-(7-bromo-3-chloro-1-fluorospiro[chromeno[2,3-c]pyridine-5,4'-[1,3]oxazinan]-2'-ylidene)benzamide (0.25 g, 0.497 mmol), 2-amino-3-picoline (0.055 ml, 0.547 mmol), pd2(dba)$_3$ (0.023 g, 0.025 mmol) and 2-di-t-butylphosphino-2,4,6-tri-1-propyl-1,1-biphenyl (0.037 g, 0.087 mmol) was purged with N$_2$ followed by the addition of toluene (2 mL) and lithium bis(trimethylsilyl)amide (1.243 ml, 1.243 mmol). The resulting mixture was heated at 100° C. and after 30 min the reaction was cooled, diluted with EtOAc and washed with saturated NH$_4$Cl. The organic phase was dried over Na$_2$SO$_4$, filtered, concentrated and chromatographed on silica gel using 0-100% EtOAc/hexanes. The product was repurified by HPLC to afford (S,Z)—N-(3-chloro-1-fluoro-7-((3-methylpyridin-2-yl)amino)spiro[chromeno[2,3-c]pyridine-5,4'-[1,3]oxazinan]-2'-ylidene)benzamide (0.069 g, 0.130 mmol, 26% yield).
Step 2:
To a solution of (S,Z)—N-(3-chloro-1-fluoro-7-((3-methylpyridin-2-yl)amino)spiro[chromeno[2,3-c]pyridine-5,4'-[1,3]oxazinan]-2'-ylidene)benzamide (0.069 g, 0.130 mmol) in THF (2 mL) was added ammonia, 2.0M solution in methanol (10 ml, 20.00 mmol) and heated in a sealed tube at 50° C. for 15 h. The reaction was concentrated and purified by HPLC to afford (S)-3-chloro-1-fluoro-N7-(3-methylpyridin-2-yl)-5',6'-dihydrospiro[chromeno[2,3-c]pyridine-5,4'-[1,3]oxazine]-2',7-diamine as a white solid. MS m/z=426.1 [M+H]$^+$.

Example 42

Method M

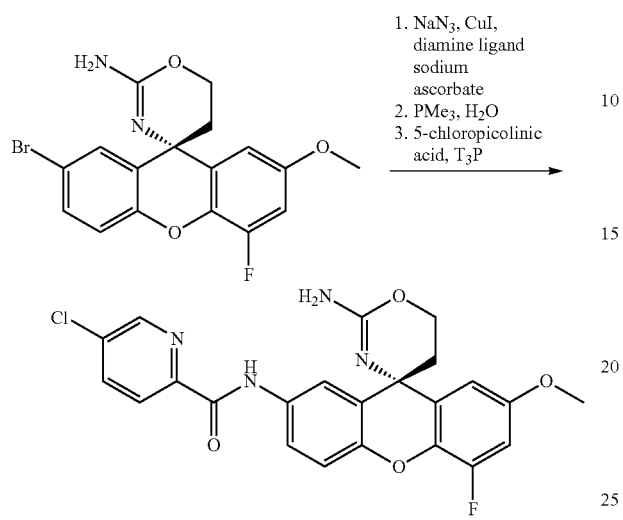

Synthesis of (S)—N-(2-amino-4'-fluoro-2'-methoxy-5,6-dihydrospiro[[1,3]oxazine-4,9'-xanthen]-7'-yl)-5-chloropicolinamide Step 1:
To a solution of (S)-7'-bromo-4'-fluoro-2'-methoxy-5,6-dihydrospiro[[1,3]oxazine-4,9'-xanthen]-2-amine (422 mg, 1.073 mmol) in ethanol (3.5 ml) was added sodium azide (209 mg, 3.22 mmol), copper(I) iodide (41 mg, 0.215 mmol), (+)-sodium L-ascorbate (21 mg, 0.107 mmol), trans-N,N'-dimethyl-1,2-cyclohexanediamine (0.05 ml, 0.322 mmol) and water (1.5 ml) and the mixture was stirred at 90° C. for 4 hrs. The mixture was cooled to RT, additional water (2 ml) was added and stirring continued for additional 30 min. Precipitated material was filtered off, washed with water twice, and dried under a stream of nitrogen overnight to afford (S)-7'-azido-4'-fluoro-2'-methoxy-5,6-dihydrospiro[[1,3]oxazine-4,9'-xanthen]-2-amine (290 mg, 0.816 mmol, 76% yield) which was used without further purification.

Step 2:
To a solution of (S)-7'-azido-4'-fluoro-2'-methoxy-5,6-dihydrospiro[[1,3]oxazine-4,9'-xanthen]-2-amine (290 mg, 0.816 mmol) in THF (3 ml) and water (1 ml) was added trimethylphosphine (1M in THF) (0.98 ml, 0.98 mmol) and the mixture was stirred at RT for 2 hrs. THF was removed under reduced pressure, water (5 ml) was added and the mixture was extracted with EtOAc. Organic extracts were washed with brine, dried with MgSO$_4$ and concentrated. Recrystallization of the residue from DCM afforded (S)-4'-fluoro-2'-methoxy-5,6-dihydrospiro[[1,3]oxazine-4,9'-xanthene]-2,7'-diamine (102 mg, 0.310 mmol, 38% yield).

Step 3:
To a suspension of (S)-4'-fluoro-2'-methoxy-5,6-dihydrospiro[[1,3]oxazine-4,9'-xanthene]-2,7'-diamine (102 mg, 0.310 mmol) and 5-chloropicolinic acid (54 mg, 0.341 mmol) in ethyl acetate (2 mL) was added triethylamine (0.13 mL, 0.929 mmol) and the mixture was stirred for 2 min, followed by addition of 1-propanephosphonic acid cyclic anhydride (T3P) (50 wt. % solution in ethyl acetate) (0.37 mL, 0.619 mmol). After 2 hr at RT, the mixture was quenched with sat NaHCO$_3$ and diluted with 3 ml EtOAc. The organic layer was separated, concentrated in vacuo, and the residue purified by FC on 12 g RediSep Gold column using 10-80% DCM/MeOH/NH$_4$OH (90:10:1) in DCM to afford (S)—N-(2-amino-4'-fluoro-2'-methoxy-5,6-dihydrospiro[[1,3]oxazine-4,9'-xanthen]-7'-yl)-5-chloropicolinamide (68 mg, 0.145 mmol, 47% yield).

Example 43

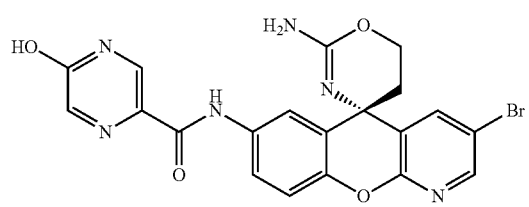 [SMILES: NC1=N[C@@]2(CCO1)c1cc(NC(=O)c3cnc(O)cn3)ccc1Oc1ncc(Br)cc12]

Synthesis of (S)—N-(2'-amino-3-bromo-5',6'-dihydrospiro[chromeno[2,3-b]pyridine-5,4'-[1,3]oxazin]-7-yl)-5-oxo-4,5-dihydropyrazine-2-carboxamide The title compound was synthesized by procedures (method D) and steps analogous to those described in example 34, but using 5-methoxypyrazine-2-carboxamide (synthesized according to method Y). MS m/z=482.9 and 484.9 [M+H][1]. Calculated for C$_{20}$H$_{15}$BrN$_6$O$_4$: 483.27. $^1$H NMR (300 MHz, DMSO-d$_6$) δ ppm 1.70-1.93 (m, 2H) 3.97-4.24 (m, 2H) 6.16 (s, 1H) 7.24 (d, J=8.48 Hz, 1H) 7.76-7.87 (m, 2H) 7.91-7.99 (m, 1H) 8.00-8.05 (m, 1H) 8.09-8.20 (m, 1H) 8.36 (d, J=2.48 Hz, 1H) 10.37 (s, 1H).

Example 44

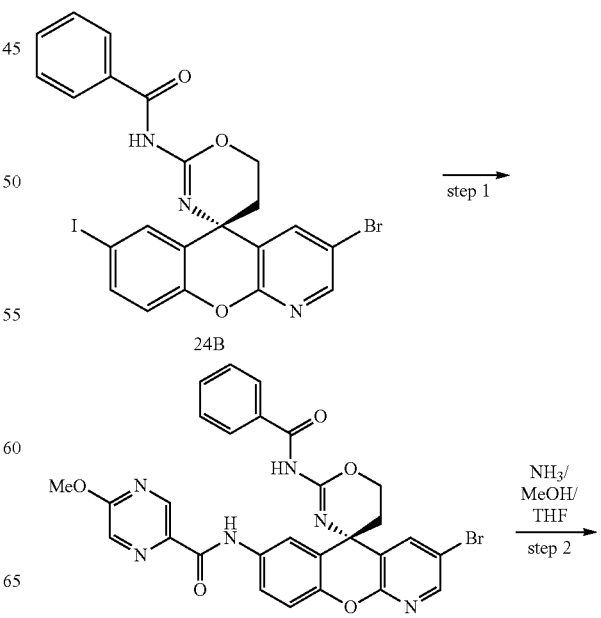

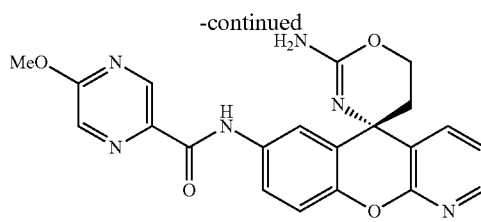

Synthesis of (S)—N-(2'-amino-3-bromo-5',6'-dihydrospiro[chromeno[2,3-b]pyridine-5,4'-[1,3]oxazin]-7-yl)-5-methoxypyrazine-2-carboxamide The title compound was synthesized analogous to step 1 (Method D) described in example 34, but using (S)—N-(3-bromo-7-iodo-5',6'-dihydrospiro[chromeno[2,3-b]pyridine-5,4'-[1,3]oxazin]-2'-yl)benzamide (88 mg, 0.153 mmol, Intermediate 24B) and 5-methoxypyrazine-2-carboxamide (28.1 mg, 0.183 mmol). The residue from step 1 was dissolved in THF (1 mL) and treated with ammonia (2.0 M solution in methanol; 1.145 mL, 2.291 mmol) at 50° C. After 12 hours another portion of ammonia, (2.0 M solution in methanol; 1.145 mL, 2.291 mmol) was added and the reaction mixture was allowed to stir for additional 5 hours The solvent was removed under reduced pressure and the residue was purified by preparative reversed-phase HPLC using a Phenomenex Gemini column, 10 micron, C18, 110 Å, 100×50 mm, 0.1% TFA in CH₃CNH₂O, gradient 10% to 100% over 20 min. The combined fractions were concentrated. The residue was dissolved in MeOH and loaded onto a Varian Bond Elut SCX column. The product was eluted with a 2M solution of NH₃ in MeOH. 10 mg of (S)—N-(2'-amino-3-bromo-5',6'-dihydrospiro[chromeno[2,3-b]pyridine-5,4'-[1,3]oxazin]-7-yl)-5-methoxypyrazine-2-10 carboxamide were obtained as an off-white solid. MS m/z=497.1 [M]⁺. Calculated for $C_{21}H_{17}BrN_6O_4$: 497.30. ¹H NMR (300 MHz, CHLOROFORM-d) δ ppm 1.82-1.92 (m, 1H) 1.94-2.04 (m, 1H) 4.08 (s, 3H) 4.11-4.18 (m, 1H) 4.20-4.30 (m, 1H) 7.31 (d, J=9.21 Hz, 1H) 7.69-7.77 (m, 2H) 7.94 (d, J=2.34 Hz, 1H) 8.18 (d, J=1.32 Hz, 1H) 8.32 (d, J=2.48 Hz, 1H) 9.04 (d, J=1.32 Hz, 1H) 9.55 (s, 1H).

Example 45 eg 7

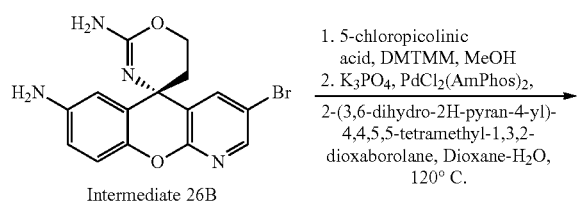

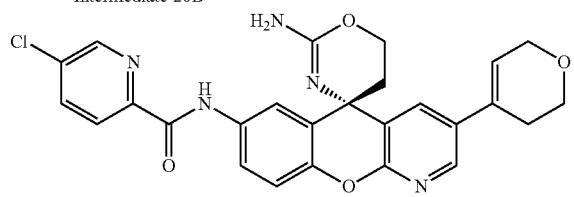

Synthesis of (S)—N-(2'-amino-3-(3,6-dihydro-2H-pyran-4-yl)-5',6'-dihydrospiro[chromeno[2,3-b]pyridine-5,4'-[1,3]oxazin]-7-yl)-5-chloropicolinamide Subjection of intermediate 26B to Method E in Example 34 followed by a modification of Method F in Example 35 (whereby 2-(3,6-dihydro-2H-pyran-4-yl)-4,4,5,5-tetramethyl-1,3,2-dioxaborolane was used instead), resulted in the conversion of intermediate 26B to (S)—N-(2'-amino-3-(3,6-dihydro-2H-pyran-4-yl)-5',6'-dihydrospiro[chromeno[2,3-b]pyridine-5,4'-[1,3]oxazin]-7-yl)-5-chloropicolinamide. MS (m/z) 504 (M+H)⁺. ¹H NMR (400 MHz, CDCl₃) δ: 9.86 (s, 1H), 8.58 (s, 1H), 8.27 (m, 2H), 7.89 (d, 1H, J=7.1 Hz), 7.75 (m, 3H), 7.32 (m, 1H), 6.16 (s, 1H), 4.34 (m, 2H), 4.20 (m, 1H), 4.11 (m, 1H), 3.96 (m, 2H), 2.56 (m, 2H), 1.96 (m, 1H), 1.87 (m, 1H).

Example 46

Method Y

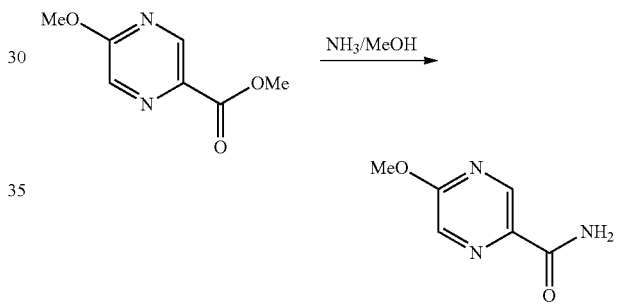

Synthesis of 5-methoxypyrazine-2-carboxamide

To a 100-mL round-bottomed flask was added methyl 5-methoxypyrazine-2-carboxylate (0.811 g, 4.82 mmol, synthesized according to *Journal of Heterocyclic Chemistry*, 19(2), 407-8; 1982) and ammonia (2 M in MeOH; 25 mL, 50.0 mmol). The reaction mixture was heated to 50° C. overnight. The reaction mixture was allowed to cool to ambient temperature, filtered and dried to afford 5-methoxypyrazine-2-carboxamide as a white crystalline solid. MS m/z=154.0 [M+H]⁺. Calculated for $C_6H_7N_3O_2$: 153.14.

The compounds provided in Tables I and II herein are additional representative examples of compounds of Formulas I, II, III and IV, including sub-formulas thereof, provided by the present invention. The methods and intermediates used to prepare each compound are also included in the Table, along with the mass found and biological data (average uM IC₅₀'s for the BACE enzyme, BACE cellular and Cathepsin D assays) where available. The names of the compounds were generated using the naming convention of the ChemDraw Ultra software, version 11 or higher. Where the example is a racemic mixture, the name for that example includes both enantiomers. Individual enantiomers of examples are as indicated in the name and/or structure provided.

TABLE I

| Ex. No. | Compound Name | Method Used | Observed Mass | Intermediate Used | BACE 1 FRET assay (uM) | HEK cell assay (uM) | Cathepsin D (uM) |
|---|---|---|---|---|---|---|---|
| 34 | N-((5S)-2'-amino-3-bromo-5',6'-dihydrospiro[chromeno[2,3-b]pyridine-5,4'-[1,3]oxazin]-7-yl)-5-chloro-2-pyridinecarboxamide | D or E | 502 | 24B or 26B | 0.0136 | 0.007 | 245.1 |
| 43 | N-((5S)-2'-amino-3-bromo-5',6'-dihydrospiro[chromeno[2,3-b]pyridine-5,4'-[1,3]oxazin]-7-yl)-5-hydroxy-2-pyrazinecarboxamide | D | 482.9 484.9 | 24B | 0.113 | 1.66 | >4.94 |
| 44 | N-((5S)-2'-amino-3-bromo-5',6'-dihydrospiro[chromeno[2,3-b]pyridine-5,4'-[1,3]oxazin]-7-yl)-5-methoxy-2-pyrazinecarboxamide | D | 497 | 24B | 0.0476 | 0.011 | >1.65 |
| 38 | N-((5S)-2'-amino-3-chloro-1-fluoro-5',6'-dihydrospiro[chromeno[2,3-c]pyridine-5,4'-[1,3]oxazin]-7-yl)-5-chloro-2-pyridinecarboxamide | I | 474 | 15C | 0.0068 | 0.031 | >400 |
| 46 | N-((5S)-2'-amino-3-chloro-1-fluoro-5',6'-dihydrospiro[chromeno[2,3-c]pyridine-5,4'-[1,3]oxazin]-7-yl)-5-cyano-2-pyridinecarboxamide | I | 465 | 15C | 0.007 | 0.023 | >400 |
| 47 | N-((5S)-2'-amino-3-chloro-1-fluoro-5',6'-dihydrospiro[chromeno[2,3-c]pyridine-5,4'-[1,3]oxazin]-7-yl)-5-methoxy-2-pyrazinecarboxamide | I | 471 | 15C | 0.0267 | 0.028 | 334.9 |
| 48 | N-((5S)-2'-amino-3-chloro-1-fluoro-5',6'-dihydrospiro[chromeno[2,3-c]pyridine-5,4'-[1,3]oxazin]-7-yl)-5-(2-butyn-1-yloxy)-2-pyrazinecarboxamide | I | 509 | 15C | 0.0004 | 0.0003 | 151.5 |
| 49 | N-((5S)-2'-amino-3-chloro-1-fluoro-5',6'-dihydrospiro[chromeno[2,3-c]pyridine-5,4'-[1,3]oxazin]-7-yl)-5-chloro-2-pyrazinecarboxamide | I | 475 | 15C | 0.0161 | 0.184 | 323 |
| 32 | N-((4S)-2-arnino-5'-fluoro-7'-rnethoxy-5,6-dihydrospiro[1,3-thiazine-4,9'-xanthen]-2'-yl)-5-chloro-2-pyridinecarboxamide | B | 485 | 23 | 0.0193 | 0.0318 | 350.2 |
| 50 | N-((4S)-2-amino-5'-fluoro-7'-methoxy-5,6-dihydrospiro[1,3-thiazine-4,9'-xanthen]-2'-yl)-5-methoxy-2-pyrazinecarboxamide | B | 482 | 23 | 0.0405 | 0.0465 | >400 |
| 45 | N-((5S)-2'-amino-3-(3,6-dihydro-2H-pyran-4-yl)-5',6'-dihydrospiro[chromeno[2,3-b]pyridine-5,4'-[1,3]oxazin]-7-yl)-5-chloro-2-pyridinecarboxamide | E & F | 504 | 26B | 0.0027 | 0.0006 | 341.5 |
| 42 | N-((4S)-2-amino-5'-fluoro-7'-methoxy-5,6-dihydrospiro[1,3-oxazine-4,9'-xanthen]-2'-yl)-5-chloro-2-pyridinecarboxamide | M | 469 | 20B | 0.0374 | 0.0205 | >400 |
| 36 | N-((5S)-2'-amino-5',6'-dihydrospiro[chromeno[2,3-b]pyridine-5,4'-[1,3]oxazin]-7-yl)-5-chloro-2-pyridinecarboxamide | G | 422 | 26B | 0.0451 | 0.0148 | >400 |
| 37 | N-((5S)-2'-amino-3-bromo-5',6'-dihydrospiro[chromeno[2,3-b]pyridine-5,4'-[1,3]oxazin]-7-yl)-4-chloro-2-fluorobenzamide | H | 517/ 519 | 25B | 0.12 | 0.125 | >400 |
| 39 | N-((5S)-2'-amino-3-(5,6-dihydro-2H-pyran-3-yl)-1-fluoro-5',6'-dihydrospiro[chromeno[2,3-c]pyridine-5,4'-[1,3]oxazin]-7-yl)-5-chloro-2-pyridinecarboxamide | J | 522 | 15B | 0.002 | 0.0005 | >400 |
| 51 | N-((5S)-2'-amino-3-(5,6-dihydro-2H-pyran-3-yl)-1-fluoro-5',6'-dihydrospiro[chromeno[2,3-c]pyridine-5,4'-[1,3]oxazin]-7-yl)-5-methoxy-2-pyrazinecarboxamide | J | 519 | 15B | 0.0027 | 0.0042 | >400 |
| 52 | N-((5S)-2'-amino-3-(5,6-dihydro-2H-pyran-3-yl)-1-fluoro-5',6'-dihydrospiro[chromeno[2,3-c]pyridine-5,4'-[1,3]oxazin]-7-yl)-5-cyano-2-pyridinecarboxamide | J | 513 | 15B | 0.002 | 0.0005 | 132 |
| 53 | N-((5S)-2'-amino-3-cyclopropyl-1-methoxy-5',6'-dihydrospiro[chromeno[2,3-c]pyridine-5,4'-[1,3]oxazin]-7-yl)-5-chloro-2-pyridinecarboxamide | K | 492 | 15B | 0.0129 | 0.0227 | >400 |
| 40 | N-((5S)-2'-amino-3-cyclopropyl-1-fluoro-5',6'-dihydrospiro[chromeno[2,3-c]pyridine-5,4'-[1,3]oxazin]-7-yl)-5-chloro-2-pyridinecarboxamide | K | 480 | 15B | 0.0024 | 0.0034 | 360 |
| 54 | N-((5S)-2'-amino-3-cyclopropyl-1-fluoro-5',6'-dihydrospiro[chromeno[2,3-c]pyridine-5,4'-[1,3]oxazin]-7-yl)-5-methoxy-2-pyrazinecarboxamide | K | 477 | 15B | 0.005 | 0.0096 | 269.4 |
| 35 | N-((5S)-2'-amino-3-(5,6-dihydro-2H-pyran-3-yl)-5',6'-dihydrospiro[chromeno[2,3-b]pyridine-5,4'-[1,3]oxazin]-7-yl)-5-chloro-2-pyridinecarboxamide | F | 504 | 26B | 0.0051 | 0.0033 | >1.65 |
| 55 | N-((5R)-2'-amino-3-chloro-1-fluoro-5',6'-dihydrospiro[chromeno[2,3-c]pyridine-5,4'-[1,3]thiazin]-7-yl)-5-methoxy-2-pyrazinecarboxamide | D | 487 | 40A | 0.9135 | 3.09 | 69.9 |
| 56 | N-((5S)-2'-amino-3-chloro-1-fluoro-5',6'-dihydrospiro[chromeno[2,3-c]pyridine-5,4'-[1,3]thiazin]-7-yl)-5-methoxy-2-pyrazinecarboxamide | D | 487 | 40B | 0.0062 | 0.167 | >400 |
| 41 | (5S)-3-chloro-1-fluoro-N~7~-(3-methyl-2-pyridinyl)-5',6'-dihydrospiro[chromeno[2,3-c]pyridine-5,4'-[1,3]oxazine]-2',7-diamine | L | 426.1 | 15C | 0.254 | 0.279 | 386.3 |
| 33 | (4S)-N~2~'-(3-ethoxy-2-pyridinyl)-5'-fluoro-7'-methoxy-5,6-dihydrospiro[1,3-thiazine-4,9'-xanthene]-2,2'-diamine | C | 466.8 | 23 | 0.0486 | 0.0659 | 262.5 |
| 57 | (4S)-N~2~'-(3-(benzyloxy)-2-pyridinyl)-5'-fluoro-7'-methoxy-5,6-dihydrospiro[1,3-oxazine-4,9'-xanthene]-2,2'-diamine | A | 512.9 | 20B | 7.29 | 3.51 | 400 |
| 31 | (4S)-N~2~'-(3-ethoxy-2-pyridinyl)-5'-fluoro-7'-methoxy-5,6-dihydrospiro[1,3-oxazine-4,9'-xanthene]-2,2'-diamine | A | 451 | 20B | 0.0696 | 0.0642 | 400 |
| 58 | 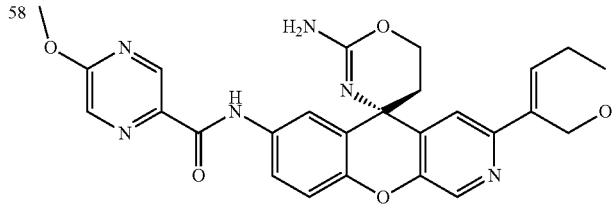 | NN | 501.4 | 18B | 0.0094 | 0.0011 | 480.0 |

TABLE I-continued

| Ex. No. | Compound Name | Method Used | Observed Mass | Intermediate Used | BACE 1 FRET assay (uM) | HEK cell assay (uM) | Cathepsin D (uM) |
|---|---|---|---|---|---|---|---|
| 59 | 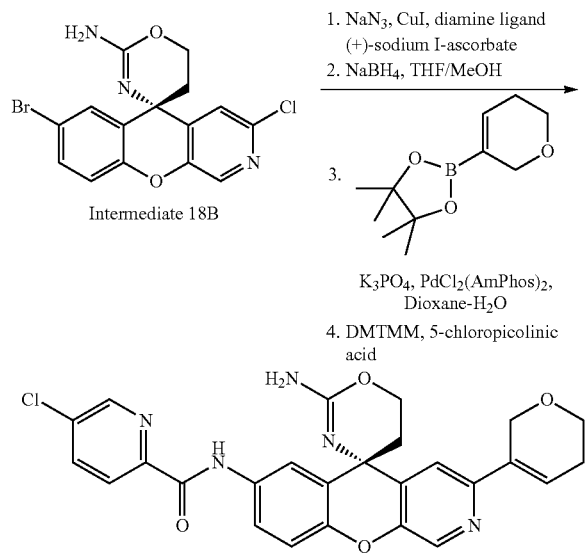 | NN | 504.2 | 18B | 0.003 | 0.0005 | 400 |

Example 59

Method NN

Synthesis of (S)—N-(2'-amino-3-(5,6-dihydro-2H-pyran-3-yl)-5',6'-dihydrospiro[chromeno[2,3-c]pyridine-5,4'-[1,3]oxazin]-7-yl)-5-chloropicolinamide Step 1:

(S)-7-Bromo-3-chloro-5',6'-dihydrospiro[chromeno[2,3-c]pyridine-5,4'-[1,3]oxazin]-2'-amine (2.356 g, 6.19 mmol), sodium azide (1.207 g, 18.57 mmol), and (+)-sodium 1-ascorbate (0.123 g, 0.619 mmol) were added to a solution of ethanol (8.5 ml) and water (3.6 ml). The solution was degassed by bubbling nitrogen gas through the solution for 10 minutes. Next, trans-n,n'-dimethyl-1,2-cyclohexanediamine (0.293 ml, 1.857 mmol) and copper(I) iodide (0.236 g, 1.238 mmol) were added and the reaction was stirred and heated in an oil bath at 85° C. for 3 hours. After cooling to RT, the reaction was poured into a 9:1 mixture of aqueous saturated ammonium chloride/ammonium hydroxide and the mixture was extracted with EtOAc. The organic extracts were combined and washed with a 9:1 mixture of aqueous saturated ammonium chloride/ammonium hydroxide, saturated aqueous sodium chloride, and dried over sodium sulfate. The solution was filtered and concentrated in vacuo to give the crude product which was used in the next step without further purification.

Step 2:

Sodium borohydride (1.170 g, 30.9 mmol) was added in portions to a solution of (S)-7-azido-3-chloro-5',6'-dihydrospiro[chromeno[2,3-c]pyridine-5,4'-[1,3]oxazin]-2'-amine (2.12 g, 6.19 mmol) in THF (40 ml) and MeOH (20 ml) with the reaction flask placed in a water bath. After 30 minutes, an additional amount of sodium tetrahydroborate (1.170 g, 30.9 mmol) was added portionwise and the reaction was allowed to stir 30 minutes. The reaction was cooled in an ice bath and was carefully quenched with saturated aqueous ammonium chloride at 0° C. After the effervescence subsided the reaction was diluted with water and EtOAc. The layers were separated and the aqueous layer was extracted with EtOAc. The combined organic extracts were washed with saturated aqueous sodium chloride and dried over sodium sulfate. The solution was filtered and concentrated in vacuo to give the crude material which was used without further purification.

Step 3:

A microwave reaction vessel was charged with potassium phosphate (tribasic) (0.670 g, 3.16 mmol), (S)-3-chloro-5',6'-dihydrospiro[chromeno[2,3-c]pyridine-5,4'-[1,3]oxazine]-2',7-diamine (0.2 g, 0.631 mmol), and 2-(5,6-dihydro-2H-pyran-3-yl)-4,4,5,5-tetramethyl-1,3,2-dioxaborolane (0.398 g, 1.894 mmol) in dioxane (4 ml) and water (2 ml). The vessel was capped and the solution was purged with nitrogen for 10 minutes. Next, bis[di-tert-butyl(4 dimethylaminophenyl)phosphine]dichloropalladium(II) (0.022 g, 0.032 mmol) was added and the vessel was sealed. The reaction mixture was stirred and heated in a Initiator microwave reactor (Personal Chemistry, Biotage AB, Inc., Upssala, Sweden) at 120° C. for 35 minutes. The reaction was poured into water and the mixture was extracted with EtOAc. The combined organic extracts were washed with saturated aqueous sodium chloride and dried over sodium sulfate. The solution was filtered and concentrated in vacuo to give the crude material. The crude material was purified by silica gel chromatography by eluting with 20:1 solution of DCM to a 2M solution of $NH_3$ in MeOH, to provide (S)-3-(5,6-dihydro-2H-pyran-3-yl)-5',6'-dihydrospiro[chromeno[2,3-c]pyridine-5,4'-[1,3]oxazine]-2',7-diamine (0.172 g, 0.472 mmol, 74.8% yield) as an off-white solid.

Step 4:

4-(4)Dimethoxy[1.3.5]triazin-2-yl)-4-methylmorpholinium chloride hydrate (0.073 g, 0.248 mmol) was added in one portion to a solution of (S)-3-(5,6-dihydro-2H-pyran-3-yl)-5',6'-dihydro spiro[chromeno[2,3-c]pyridine-5,4'-[1,3]oxazine]-2',7-diamine (0.086 g, 0.236 mmol) and 5-chloro-2-pyridinecarboxylic acid (0.039 g, 0.248 mmol) in THF (3 mL) and MeOH (1.5 mL) at RT. After 40 minutes the reaction was quenched with saturated aqueous sodium bicarbonate and diluted with water and DCM. The layers were separated and the aqueous layer was extracted with DCM. The combined organic extracts were washed with saturated aqueous sodium chloride and dried over sodium sulfate. The solution was filtered and concentrated in vacuo to give the crude material. The crude material was purified by reverse-phase preparative HPLC using a Phenomenex Gemini column, 10 micron, C18, 100 Å, 150×30 mm, 0.1% TFA in $CH_3CNH_2O$, gradient 5% to 100% over 15 min to provide (S)—N-(2'-amino-3-(5,6-dihydro-2H-pyran-3-yl)-5',6'-dihydrospiro[chromeno[2,3-c]pyridine-5,4'-[1,3]oxazin]-7-yl)-5-chloropicolinamide as the TFA salt. The purified compound was partitioned between chloroform and 10% aqueous sodium carbonate. The layers were separated and the aqueous layer was extracted with chloroform. The combined organic extracts were washed with aqueous saturated sodium chloride and dried over sodium sulfate. The solution was filtered and concentrated in vacuo to give (S)—N-(2'-amino-3-(5,6-dihydro-2H-pyran-3-yl)-5',6'-dihydrospiro[chromeno[2,3-c]pyridine-5,4'-[1,3]oxazin]-7-yl)-5-chloropicolinamide as the free base. MS m/z=504.2 [M+H]$^+$.

Example 60

Method OO

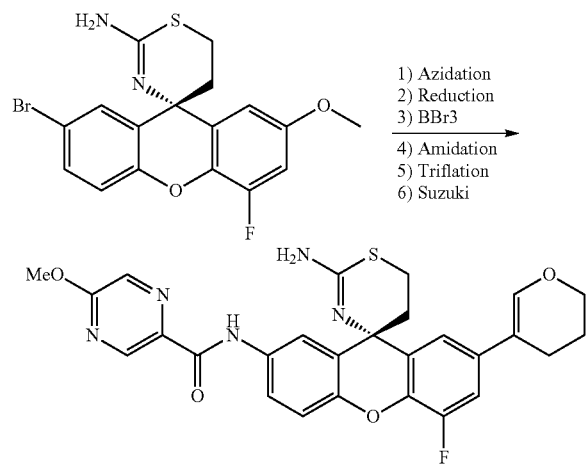

Synthesis of N-((4S)-2-amino-7'-(3,6-dihydro-2H-pyran-4-yl)-5'-fluoro-5,6-dihydrospiro[1,3-thiazine-4,9'-xanthen]-2'-yl)-5-methoxy-2-pyrazinecarboxamide Steps 1, 2, and 3 are analogous to those described in Example 16 (See Procedure P)

Step 4:

5-Methoxypyrazine-2-carboxylic acid (0.438 g, 2.84 mmol) was dissolved in DMF (15.09 ml). Pyridine, anhydrous (0.492 ml, 6.04 mmol) was added followed by HATU (1.492 g, 3.92 mmol), and the mixture was stirred for 30 minutes, then cooled to 0° C., and (S)-2,7'-diamino-4'-fluoro-5,6-dihydrospiro[[1,3]thiazine-4,9'-xanthen]-2'-ol (1.0 g, 3.02 mmol) was added. The solution was stirred at 0° C. for 45 min, then allowed to warm to RT and stirred for additional 2 hrs. At this point, LCMS (117271-22-1) indicated complete conversion to the desired product with MS+=468 (M+1). No bis-amide was detected. Water was added to quench the reaction. The resulted suspension was stirred for 25 min, then filtered. The filter cake was rinsed with water a few times, and then dried in air affording (S)—N-(2-amino-4'-fluoro-2'-hydroxy-5,6-dihydrospiro[[1,3]thiazine-4,9'-xanthen]-7'-yl)-5-methoxypyrazine-2-carboxamide (1.2 g, 2.57 mmol, 85% yield) as red solid. MS m/z=468.0 [M+H]. This intermediate was carried on without purification.

Step 5:

To a solution of (S)—N-(2-amino-4'-fluoro-2'-hydroxy-5,6-dihydrospiro[[1,3]thiazine-4,9'-xanthen]-7'-yl)-5-methoxypyrazine-2-carboxamide (1.20 g, 2.054 mmol) in DCM (100.0 mL) was added TEA (0.857 mL, 6.16 mmol) followed by 1,1,1-trifluoro-N-phenyl-N-((trifluoromethyl)sulfonyl)methanesulfonamide (1.100 g, 3.08 mmol). The mixture was stirred at ambient temperature for 2.5 hrs. LCMS indicated complete conversion to the desired product with MS+=600 (M+1). Water was added to quench the reaction. The resulted solution was extracted with DCM (2×). The combined organic layers were washed with brine, dried over Na2SO4 and filtered. The filtrate was concentrated and purified by silica gel column (0-70% EtOAc/hexane) to afford (S)-2-amino-5'-fluoro-2'-(5-methoxypyrazine-2-carboxamido)-5,6-dihydrospiro[[1,3]thiazine-4,9'-xanthen]-7'-yl trifluoromethanesulfonate (0.835 g, 1.393 mmol, 67.8% yield) as brown solid. MS m/z=600.0 [M+H].

Step 6:

To a microwave vial were charged with (S)-2-amino-5'-fluoro-2'-(5-methoxypyrazine-2-carboxamido)-5,6-dihydrospiro[[1,3]thiazine-4,9'-xanthen]-7'-yl trifluoromethanesulfonate (0.050 g, 0.083 mmol), 2-(3,6-dihydro-2H-pyran-4-yl)-4,4,5,5-tetramethyl-1,3,2-dioxaborolane (0.039 g, 0.183 mmol), and PdCl2(dppf)$_2$ (10.22 mg, 0.013 mmol). After purged with N2 for 5 min, potassium carbonate (1.5M in water) (0.167 ml, 0.250 mmol) and Dioxane (0.75 ml) were added. The reaction mixture was microwaved at 110° C. for 10 mins. LCMS indicated complete conversion to the desired product. The reaction mixture was partitioned between EtOAc and water. The organic layer was concentrated and then purified by Shimadzu HPLC to afford 50 mg of (S)—N-(2-amino-2'-(3,6-dihydro-2H-pyran-4-yl)-4'-fluoro-5,6-dihydrospiro[[1,3]thiazine-4,9'-xanthen]-7'-yl)-5-methoxypyrazine-2-carboxamide as off-white solid (TFA salt). MS m/z=534.2 [M+H].

Example 61

Method PP

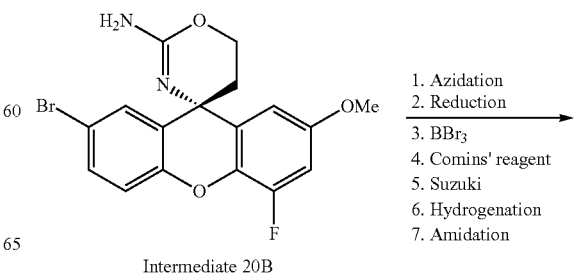

Intermediate 20B

-continued

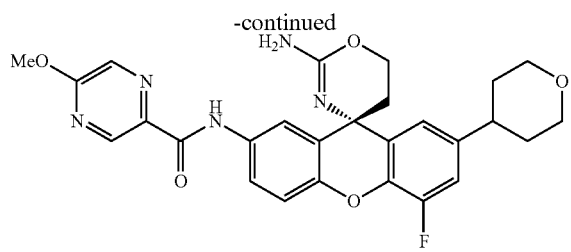

Synthesis of (S)—N-(2-amino-4'-fluoro-2'-(tetrahydro-2H-pyran-4-yl)-5,6-dihydrospiro[[1,3]oxazine-4,9'-xanthen]-7'-yl)-5-methoxypyrazine-2-carboxamide Step 1:

A resealable vessel was flushed with argon and loaded with copper(I) iodide (0.138 g, 0.726 mmol), sodium azide (0.708 g, 10.90 mmol), and sodium (R)-2-((S)-1,2-dihydroxyethyl)-4-hydroxy-5-oxo-2,5-dihydrofuran-3-olate (0.072 g, 0.363 mmol). A solution of (S)-7'-bromo-4'-fluoro-2'-methoxy-5,6-dihydrospiro[[1,3]oxazine-4,9'-xanthen]-2-amine (1.428 g, 3.63 mmol) in dmso (20 mL) was degassed and transferred via cannula into the resealable vessel. Water (4 mL) was added. The vessel was flushed with argon, and (1R,2R)—N1,N2-dimethylcyclohexane-1,2-diamine (0.163 mL, 1.090 mmol) was added. The vessel was sealed and heated in a 90° C. oil bath. After 4 h, the reaction mixture was taken up in EtOAc (600 mL) and the organic layer was extracted with quarter-saturated brine (2×70 mL), half-saturated brine (70 mL), and saturated brine (70 mL), dried over MgSO$_4$ and concentrated to afford crude (S)-7'-azido-4'-fluoro-2'-methoxy-5,6-dihydrospiro[[1,3]oxazine-4,9'-xanthen]-2-amine, which was used without purification in the next step. MS m/z=356 [M+H]$^+$.

Step 2:

The crude (S)-7'-azido-4'-fluoro-2'-methoxy-5,6-dihydrospiro[[1,3]oxazine-4,9'-xanthen]-2-amine (1.29 g, 3.63 mmol) was dissolved in THF (27 mL). A THF solution of trimethylphosphine (3.63 mL, 3.63 mmol) was added. After 5 h, the mixture was quenched with 35 mL of 1M aqueous HCl, and the mixture was stiffed overnight. The mixture was then neutralized with saturated NaHCO$_3$ (70 mL) and the aqueous layer mixture was extracted with EtOAc (500 mL). The organic layer was washed with saturated brine (35 mL), dried over MgSO$_4$ and concentrated to afford crude (S)-4'-fluoro-2'-methoxy-5,6-dihydrospiro[[1,3]oxazine-4,9'-xanthene]-2,7'-diamine, which was used without purification in the next step. MS m/z=330 [M+H]$^+$.

Step 3:

The crude (S)-4'-fluoro-2'-methoxy-5,6-dihydrospiro[[1,3]oxazine-4,9'-xanthene]-2,7'-diamine (1.196 g, 3.63 mmol) was dissolved in dcm (100 mL) and the solution was cooled to 0° C. A DCM solution of boron tribromide (14.53 mL, 14.53 mmol) was added, and the reaction was warmed to RT. After 1.5 h, the reaction was quenched with 120 mL of 10:1 saturated NH$_4$Cl and commercial NH$_4$OH. The mixture was extracted with 5% MeOH-DCM (3×250 mL). The organics were combined, washed with dilute brine (50 mL), dried over MgSO$_4$ and concentrated, affording 0.97 g of crude (S)-2,7'-diamino-4'-fluoro-5,6-dihydrospiro[[1,3]oxazine-4,9'-xanthen]-2'-ol, which was used without purification in the next step. MS m/z=316 [M+H]$^+$.

Step 4:

The (S)-2,7'-diamino-4'-fluoro-5,6-dihydrospiro[[1,3]oxazine-4,9'-xanthen]-2'-ol (0.97 g, 3.08 mmol) was suspended in DCM (30 mL). Triethylamine (0.533 mL, 3.85 mmol) was added, and the resulting solution was cooled to 0° C., and N-(5-chloropyridin-2-yl)-1,1,1-trifluoro-N-((trifluoromethyl)sulfonyl)methanesulfonamide (1.208 g, 3.08 mmol) was added. After 1 h, the reaction was quenched with 100 mL of quarter-saturated NaHCO$_3$. The mixture was extracted with 5% MeOH-DCM (3×150 mL). The organics were combined, washed with dilute brine (35 mL), dried over MgSO$_4$ and concentrated, affording crude (S)-2,2'-diamino-5'-fluoro-5,6-dihydrospiro[[1,3]oxazine-4,9'-xanthen]-7'-yl trifluoromethanesulfonate (1.37 g) contaminated with N-(5-chloropyridin-2-yl)-1,1,1-trifluoromethanesulfonamide (0.80 g). MS m/z=448 [M+H]$^+$. The mixture was used without purification in the next step.

Step 5:

In a microwave vial, 2-(3,6-dihydro-2H-pyran-4-yl)-4,4,5,5-tetramethyl-1,3,2-dioxaborolane (0.107 g, 0.509 mmol) and Pd(PPh$_3$)$_4$ (0.053 g, 0.046 mmol) were loaded. A solution of (S)-2,2'-diamino-5'-fluoro-5,6-dihydrospiro[[1,3]oxazine-4,9'-xanthen]-7'-yl trifluoromethanesulfonate (0.207 g, 0.463 mmol) in dmf (3.7 mL) was added via cannula. Aqueous 1.5 M sodium carbonate (0.925 mL, 1.388 mmol) was added. Argon was blown through the vessel, which was sealed and heated in an 85° C. oil bath. After 4 h, the reaction was concentrated. The residue was taken up in EtOAc (100 mL) and the organic layer was extracted with quarter-saturated brine (2×8 mL), half-saturated brine (8 mL), and saturated brine (8 mL), dried over MgSO$_4$ and concentrated. The material was purified through silica gel (35 mL) which had been deactivated with Et$_3$N (3.5 mL), using a gradient of 3% to 6% MeOH-dcm with 0.5% v/v Et$_3$N, affording (S)-2'-(3,6-dihydro-2H-pyran-4-yl)-4'-fluoro-5,6-dihydrospiro[[1,3]oxazine-4,9'-xanthene]-2,7'-diamine (48 mg, 0.126 mmol). MS m/z=382 [M+H]$^1$.

Step 6:

The (S)-2'-(3,6-dihydro-2H-pyran-4-yl)-4'-fluoro-5,6-dihydrospiro[[1,3]oxazine-4,9'-xanthene]-2,7'-diamine (0.231 g, 0.606 mmol) was taken up in EtOH (2 mL). Palladium (10%) on carbon (0.090 g, 0.084 mmol) was added. A 1-L balloon filled with hydrogen was emptied into the flask, venting through a needle. The vent was removed, and another 1-L balloon was attached. The reaction was stirred at RT overnight. The reaction was filtered through Celite, rinsing with 10% MeOH-DCM (60 mL). The filtrate was concentrated. The residue was purified through silica gel (35 mL) which had been deactivated with Et$_3$N (3.5 mL), eluting with 4% to 8% MeOH-DCM containing 1% v/v Et$_3$N, affording (S)-4'-fluoro-2'-(tetrahydro-2H-pyran-4-yl)-5,6-dihydrospiro[[1,3]oxazine-4,9'-xanthene]-2,7'-diamine (48 mg, 0.123 mmol). MS m/z=384 [M+H]$^+$.

Step 7:

The (S)-2'-(3,6-dihydro-2H-pyran-4-yl)-4'-fluoro-5,6-dihydrospiro[[1,3]oxazine-4,9'-xanthene]-2,7'-diamine (0.048 g, 0.126 mmol) was suspended in MeOH (2.5 mL). The 5-methoxypyrazine-2-carboxylic acid (0.019 g, 0.126 mmol) was added, followed by 4-(4,6-dimethoxy-1,3,5-triazin-2-yl)-4-methylmorpholin-4-ium chloride (0.035 g, 0.126 mmol). After 30 min another 1 mg of the acid (0.05 equiv) and 1.75 mg of the coupling agent (0.05 equiv) were added. After 2 h, the reaction was quenched with 15 mL of half-saturated NaHCO$_3$. The material was extracted with 5% MeOH-dcm (3×25 mL). The organics were combined, washed with dilute brine (8 mL), dried over MgSO$_4$ and concentrated. The material was purified through silica gel (35 mL) using 10% to 20%

EtOH in 2:1 hexane-EtOAc, affording (S)—N-(2-amino-2'-(3,6-dihydro-2H-pyran-4-yl)-4'-fluoro-5,6-dihydrospiro[[1,3]oxazine-4,9'-xanthen]-7'-yl)-5-methoxypyrazine-2-carboxamide (35 mg, 0.067 mmol). MS m/z=518 [M+H]⁻¹. ¹H NMR in CDCl₃ δ: 9.52 (s, 1H), 9.03 (s, 1H), 8.16 (s, 1H), 7.76 (dd, 1H, J=8.7, 2.4), 7.66 (d, 1H, J=2.5), 7.01 (s, 1H), 6.96 (dd, 1H, J=11.3, 1.8), 4.20-4.40 (m, 6H), 4.07 (s, 3H), 3.53 (m, 2H), 2.80 (m, 1H), 1.75-1.90 (m, 4H).

Example 62

Method QQ

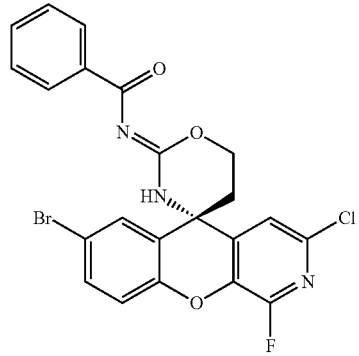

Intermediate 15C

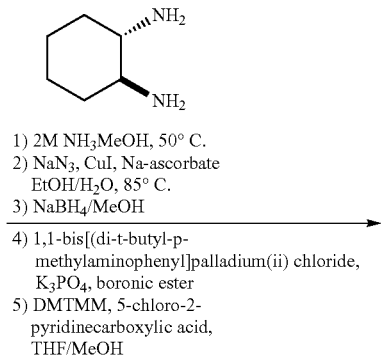

1) 2M NH₃MeOH, 50° C.
2) NaN₃, CuI, Na-ascorbate EtOH/H₂O, 85° C.
3) NaBH₄/MeOH
4) 1,1-bis[(di-t-butyl-p-methylaminophenyl]palladium(ii) chloride, K₃PO₄, boronic ester
5) DMTMM, 5-chloro-2-pyridinecarboxylic acid, THF/MeOH

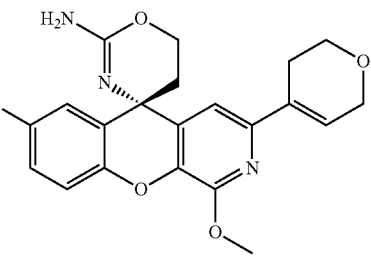

Synthesis of (S)—N-(2'-amino-3-(3,6-dihydro-2H-pyran-4-yl)-1-methoxy-5',6'-dihydrospiro[chromeno[2,3-c]pyridine-5,4'-[1,3]oxazin]-7-yl)-5-chloropicolinamide Step 1:
To a solution of (S,Z)—N-(7-bromo-3-chloro-1-fluorospiro[chromeno[2,3-c]pyridine-5,4'-[1,3]oxazinan]-2'-ylidene)benzamide (5.0 g, 9.95 mmol) in THF (10 mL) was added ammonia, 2.0 m solution in methanol (74.6 ml, 149 mmol) and the resulting mixture was heated in a sealed tube at 50° C. for 17 h. The mixture was concentrated and chromatographed on silica gel using 0-40% EtOAc/hexanes to afford a white solid as (S)-7-bromo-3-chloro-1-methoxy-5',6'-dihydrospiro[chromeno[2,3-c]pyridine-5,4'-[1,3]oxazin]-2'-amine.

Step 2:
A mixture of (S)-7-bromo-3-chloro-1-methoxy-5',6'-dihydrospiro[chromeno[2,3-c]pyridine-5,4'-[1,3]oxazin]-2'-amine, (+)-sodium 1-ascorbate (0.10 eq), sodium azide (3.0 eq) and copper(i) iodide (0.20 eq) was purged with N₂ followed by the addition of trans-n,n'-dimethyl-1,2-cyclohexanediamine (0.30 eq) and EtOH (20 mL) and water (8 mL). The resulting mixture was heated at 85° C. for 1.5 h. The mixture was poured into water and extracted with EtOAc. The combined organics were washed with brine, dried over Na₂SO₄, filtered, concentrated and chromatographed on silica gel using 0-50% MeOH/DCM to afford a light yellow solid (S)-7-azido-3-chloro-1-methoxy-5',6'-dihydrospiro[chromeno[2,3-c]pyridine-5',4'-[1,3]oxazin]-2'-amine.

Step 3:
To a solution of (S)-7-azido-3-chloro-1-methoxy-5',6'-dihydrospiro[chromeno[2,3-c]pyridine-5',4'-[1,3]oxazin]-2'-amine, in MeOH (15 mL) in a water bath was added sodium borohydrate (5 eq) in one portion. The resulting mixture was kept in the water bath and stirred for 10 min. The reaction went to completion, carefully quenched with water, diluted with DCM and washed with 9:1 NH₄OH/sat NH₄Cl (10 mL). The combined organics were dried over Na₂SO₄, filtered, concentrated and chromatographed on silica gel using 0-4% MeOH/DCM to afford a white solid as (S)-3-chloro-1-methoxy-5',6'-dihydrospiro[chromeno[2,3-c]pyridine-5',4'-[1,3]oxazin]-2',7-diamine.

Step 4:
A mixture of (S)-3-chloro-1-methoxy-5',6'-dihydrospiro[chromeno[2,3-c]pyridine-5,4'-[1,3]oxazine]-2',7-diamine (0.183 g, 0.528 mmol), 2-(3,6-dihydro-2H-pyran-4-yl)-4,4,5,5-tetramethyl-1,3,2-dioxaborolane (0.222 g, 1.055 mmol), 1,1-bis[(di-t-butyl-p-methylaminophenyl]palladium(ii) chloride (0.019 g, 0.026 mmol) and potassium phosphate tribasic (0.336 g, 1.583 mmol) in dioxane/water (21 mL) was heated in microwave at 130° C. for 40 min. The mixture was poured into water and extracted with EtOAc. The combined organics were dried over Na₂SO₄, filtered, concentrated and chromatographed on silica gel using 0-5% 2M NH₃ MeOH/DCM to afford a yellow solid as (S)-3-(3,6-dihydro-2H-pyran-4-yl)-1-methoxy-5',6'-dihydrospiro[chromeno[2,3-c]pyridine-5,4'-[1,3]oxazine]-2',7-diamine (0.166 g, 0.421 mmol, 80% yield).

Step 5:
To a solution of (S)-3-(3,6-dihydro-2H-pyran-4-yl)-1-methoxy-5',6'-dihydrospiro[chromeno[2,3-c]pyridine-5,4'-

[1,3]oxazine]-2',7-diamine (0.080 g, 0.203 mmol) in THF/MeOH (20.3 mL) were added 5-chloro-2-pyridinecarboxylic acid (0.035 g, 0.223 mmol) and 4-(4,6-dimethoxy-1,3,5-triazin-2-yl)-4-methylmorpholinium chloride (0.066 g, 0.223 mmol). The resulting reaction mixture was stirred at RT for 2 h. The mixture was quenched with sat. NaHCO$_3$ and extracted with DCM. The combined organic layers were dried over Na$_2$SO$_4$, filtered, concentrated, chromatographed on silica gel using 0-5% MeOH/DCM and repurified by HPLC to afford a white solid as (S)—N-(2'-amino-3-(3,6-dihydro-2H-pyran-4-yl)-1-methoxy-5',6'-dihydrospiro[chromeno[2,3-c]pyridine-5,4'-[1,3]oxazin]-7-yl)-5-chloropicolinamide (0.0401 g, 0.075 mmol, 37.0% yield).

TABLE II

| Ex. No. | Compound Name | Method Used | Observed Mass | Intermediate Used | BACE 1 FRET assay (uM) | HEK cell assay (uM) | Cathepsin D (uM) |
|---|---|---|---|---|---|---|---|
| 63 | (structure shown) | K | 522 | 15B | 0.0014 | 0.0001 | 400 |
| 64 | N-((5S)-2'-amino-3-(3,6-dihydro-2H-pyran-4-yl)-1-fluoro-5',6'-dihydrospiro[chromeno[2,3-c]pyridine-5,4'-[1,3]oxazin]-7-yl)-5-cyano-2-pyridinecarboxamide | K | 513 | 15B | 0.00074 | 0.000039 | 400 |
| 65 | N-((5S)-2'-amino-3-(3,6-dihydro-2H-pyran-4-yl)-1-fluoro-5',6'-dihydrospiro[chromeno[2,3-c]pyridine-5,4'-[1,3]oxazin]-7-yl)-5-methoxy-2-pyrazinecarboxamide | K | 519.2 | 15B | 0.0009 | 0.000051 | 400 |
| 66 | N-((5S)-2'-amino-3-(5,6-dihydro-2H-pyran-3-yl)-1-fluoro-5',6'-dihydrospiro[chromeno[2,3-c]pyridine-5,4'-[1,3]thiazin]-7-yl)-5-methoxy-2-pyrazinecarboxamide | D | 534.8 | 40B | 0.0018 | 0.0010 | 179.3 |
| 67 | N-((5S)-2'-amino-3-(3,6-dihydro-2H-pyran-4-yl)-1-fluoro-5',6'-dihydrospiro[chromeno[2,3-c]pyridine-5,4'-[1,3]thiazin]-7-yl)-5-methoxy-2-pyrazinecarboxamide | D | 535 | 40B | 0.0016 | 0.0014 | 159.8 |
| 68 | N-((5S)-2'-amino-3-(5,6-dihydro-2H-pyran-3-yl)-1-fluoro-5',6'-dihydrospiro[chromeno[2,3-c]pyridine-5,4'-[1,3]thiazin]-7-yl)-5-chloro-2-pyridinecarboxamide | D | 538 | 40B | 0.0008 | 0.0005 | 217 |
| 69 | N-((5S)-2'-amino-1-fluoro-3-(5-fluoro-3-pyridinyl)-5',6'-dihydrospiro[chromeno[2,3-c]pyridine-5,4'-[1,3]oxazin]-7-yl)-5-cyano-2-pyridinecarboxamide | K | 526.1 | 15B | 0.0006 | 0.000082 | 133 |
| 70 | N-((5S)-2'-amino-1-fluoro-3-(5-fluoro-3-pyridinyl)-5',6'-dihydrospiro[chromeno[2,3-c]pyridine-5,4'-[1,3]oxazin]-7-yl)-5-methoxy-2-pyrazinecarboxamide | K | 532.1 | 15B | 0.0013 | 0.0006 | 400 |
| 71 | N-((5S)-2'-amino-1-fluoro-3-(5-fluoro-3-pyridinyl)-5',6'-dihydrospiro[chromeno[2,3-c]pyridine-5,4'-[1,3]oxazin]-7-yl)-5-chloro-2-pyridinecarboxainide | K | 535.1 | 15B | 0.0006 | 0.0003 | 400 |
| 72 | N-((5S)-2'-amino-3-(3,6-dihydro-2H-pyran-4-yl)-1-fluoro-5',6-dihydrospiro[chromeno[2,3-c]pyridine-5,4'-[l,3]oxazin]-7-yl)-5-fluoro-2-pyridinecarboxamide | K | 506.1 | 15B | 0.0011 | 0.0002 | 357.9 |
| 58 | N-((5S)-2'-amino-3-(5,6-dihydro-2H-pyran-3-yl)-5',6'-dihydrospiro[chromeno[2,3-c]pyridine-5,4'-[1,3]oxazin]-7-yl)-5-methoxy-2-pyrazinecarboxamide | NN | 501.4 | 18B | 0.0094 | 0.0011 | 480.0 |
| 59 | N-((5S)-2'-amino-3-(5,6-dihydro-2H-pyran-3-yl)-5',6'-dihydrospiro[chromeno[2,3-c]pyridine-5,4'-[1,3]oxazin]-7-yl)-5-chloro-2-pyridinecarboxamide | NN | 504.2 | 18B | 0.003 | 0.0005 | 400 |
| 73 | N-((5S)-2'-amino-3-cyclopropyl-5',6'-dihydrospiro[chromeno[2,3-b]pyridine-5,4'-[1,3]oxazin]-7-yl)-5-chloro-2-pyridinecarboxamide | D | 462 | 24B | 0.0127 | 0.0032 | 432.5 |
| 74 | N-((4S)-2-amino-5'-fluoro-7'-methoxy-5,6-dihydrospiro[1,3-oxazine-4,9'-xanthen]-2'-yl)-5-cyano-2-pyridinecarboxamide | M | 460 | 20B | 0.0108 | 0.0046 | 147 |
| 75 | N-((4S)-2-amino-5'-fluoro-7'-methoxy-5,6-dihydrospiro[1,3-oxazine-4,9'-xanthen]-2'-yl)-5-methoxy-2-pyrazinecarboxamide | M | 466 | 20B | 0.0953 | 0.0270 | 400 |
| 76 | N-((4S)-2-amino-5'-fluoro-7'-methoxy-5,6-dihydrospiro[l,3-oxazine-4,9'-xanthen]-2'-yl)-4-chloro-2-fluorobenzamide | M | 486 | 20B | 0.1815 | 0.206 | 400 |
| 77 | N-((4S)-2-amino-5'-fluoro-7'-methoxy-5,6-dihydrospiro[1,3-oxazine-4,9'-xanthen]-2'-yl)-2-fluoro-4-methoxybenzamide | M | 482 | 20B | 0.315 | 0.181 | 331.1 |
| 78 | N-((5S)-2'-amino-3-(3,6-dihydro-2H-pyran-4-yl)-1-fluoro-5',6'-dihydrospiro[chromeno[2,3-c]pyridine-5,4'-[1.3]oxazin]-7-yl)-5-methoxy-2-pyridinecarboxamide | K | 518.2 | 15B | 0.0015 | 0.0002 | 184.0 |
| 79 | N-((5S)-2'-amino-3-chloro-5',6'-dihydrospiro[chromeno[2,3-c]pyridine-5,4'-[1,3]oxazin]-7-yl)-5-chloro-2-pyridinecarboxamide | NN | 456.2 | 18B | 0.0386 | 0.0099 | 400 |
| 80 | N-((5S)-2'-amino-3-cyclopropyl-5',6'-dihydrospiro[chromeno[2,3-c]pyridine-5,4'-[1,3]oxazin]-7-yl)-5-methoxy-2-pyrazinecarboxamide | NN | 459.2 | 18B | 0.0068 | 0.0015 | 962.7 |
| 81 | N-((5S)-2'-amino-3-cyclopropyl-5',6'-dihydrospiro[chromeno[2,3-c]pyridine-5,4'-[1,3]oxazin]-7-yl)-5-chloro-2-pyridinecarboxamide | NN | 462 | 18B | 0.0107 | 0.0011 | 400 |

TABLE II-continued

| Ex. No. | Compound Name | Method Used | Observed Mass | Intermediate Used | BACE 1 FRET assay (uM) | HEK cell assay (uM) | Cathepsin D (uM) |
|---|---|---|---|---|---|---|---|
| 82 | N-((5S)-2'-amino-3-(3,3-dimethyl-1-butyn-1-yl)-5',6'-dihydrospiro[chromeno[2,3-c]pyridine-5,4'-[1,3]oxazin]-7-yl)-5-chloro-2-pyridinecarboxamide | OO | 501.2 | 18B | 0.010 | 0.0019 | 400 |
| 83 | N-((5S)-2'-amino-3-(5,6-dihydro-2H-pyran-3-yl)-1-fluoro-5',6'-dihydrospiro[chromeno[2,3-c]pyridine-5,4'-[1,3]oxazin]-7-yl)-5-fluoro-2-pyridinecarboxamide | K | 506.1 | 15B | 0.0093 | 0.0004 | 255 |
| 84 | N-((5S)-2'-amino-3-(5,6-dihydro-2H-pyran-3-yl)-1-fluoro-5',6'-dihydrospiro[chromeno[2,3-c]pyridine-5,4'-[1,3]oxazin]-7-yl)-5-methoxy-2-pyridinecarboxamide | K | 518.2 | 15B | 0.0009 | 0.0001 | 312.7 |
| 85 | N-((5S)-2'-amino-3-(5,6-dihydro-2H-pyran-3-yl)-1-fluoro-5',6'-dihydrospiro[chromeno[2,3-c]pyridine-5,4'-[1,3]oxazin]-7-yl)-2-methyl-1,3-thiazole-4-carboxamide | K | 508.1 | 15B | 0.0009 | 0.00008 | 411.1 |
| 86 | N-((5S)-2'-amino-3-(3,3-dimethyl-1-butyn-1-yl)-5',6'-dihydrospiro[chromeno[2,3-c]pyridine-5,4'-[1,3]oxazin]-7-yl)-5-methoxy-2-pyrazinecarboxamide | OO | 499.2 | 18B | 0.012 | 0.0012 | 452.3 |
| 87 | N-((5S)-2'-amino-1-fluoro-3-(5-fluoro-3-pyridinyl)-5',6'-dihydrospiro[chromeno[2,3-c]pyridine-5,4'-[1,3]oxazin]-7-yl)-5-methoxy-2-pyridinecarboxamide | K | 531 | 15B | 0.0014 | 0.0005 | 256.4 |
| 88 | N-((5S)-2'-amino-1-fluoro-3-(5-fluoro-3-pyridinyl)-5',6'-dihydrospiro[chromeno[2,3-c]pyridine-5,4'-[1,3]oxazin]-7-yl)-2-methyl-1,3-thiazole-4-carboxamide | K | 521 | 15B | 0.0006 | 0.0002 | 361.6 |
| 89 | N-((5S)-2'-amino-1-fluoro-3-(5-fluoro-3-pyridinyl)-5',6'-dihydrospiro[chromeno[2,3-c]pyridine-5,4'-[1,3]oxazin]-7-yl)-5-fluoro-2-pyridinecarboxamide | K | 519 | 15B | 0.0016 | 0.0006 | 400 |
| 90 | N-((5S)-2'-amino-3-(2-fluoro-4-pyridinyl)-5',6'-dihydrospiro[chromeno[2,3-b]pyridine-5,4'-[1,3]oxazin]-7-yl)-5-chloro-2-pyridinecarboxamide | E & F | 517 | 26B | 0.0034 | 0.0007 | 400.8 |
| 91 | N-((5S)-2'-amino-1-fluoro-3-(2-fluoro-4-pyridinyl)-5',6'-dihydrospiro[chromeno[2,3-c]pyridine-5,4'-[1,3]oxazin]-7-yl)-5-chloro-2-pyridinecarboxamide | K | 535.1 | 15B | 0.0009 | 0.0004 | 400 |
| 92 | N-((5S)-2'-amino-1-fluoro-3-(2-fluoro-4-pyridinyl)-5',6'-dihydrospiro[chromeno[2,3-c]pyridine-5,4'-[1,3]oxazin]-7-yl)-5-methoxy-2-pyrazinecarboxamide | K | 532.1 | 15B | 0.0018 | 0.0009 | 400 |
| 93 | N-((5S)-2'-amino-3-(2-fluoro-4-pyridinyl)-5',6'-dihydrospiro[chromeno[2,3-c]pyridine-5,4'-[1,3]oxazin]-7-yl)-5-methoxy-2-pyrazinecarboxamide | NN | 514.1 | 18B | 0.0029 | 0.0005 | 400 |
| 94 | N-((5S)-2'-amino-3-(2-fluoro-4-pyridinyl)-5',6'-dihydrospiro[chromeno[2,3-c]pyridine-5,4'-[1,3]oxazin]-7-yl)-5-chloro-2-pyridinecarboxamide | NN | 517.1 | 18B | 0.0016 | 0.0007 | 400 |
| 95 | N-((4S)-2-amino-5'-fluoro-7'-(2-fluoro-4-pyridinyl)-5,6-dihydrospiro[1,3-oxazine-4,9'-xanthen]-2'-yl)-5-methoxy-2-pyrazinecarboxamide | PP | 531 | 20B | 0.0065 | 0.0056 | 400 |
| 62 | N-((5S)-2'-amino-3-(3,6-dihydro-2H-pyran-4-yl)-1-methoxy-5',6'-dihydrospiro[chromeno[2,3-c]pyridine-5,4'-[1,3]oxazin]-7-yl)-5-chloro-2-pyridinecarboxamide | QQ | 534 | 15B | 0.007 | 0.0036 | 400 |
| 96 | N-((5S)-2'-amino-3-(3,6-dihydro-2H-pyran-4-yl)-1-methoxy-5',6'-dihydrospiro[chromeno[2,3-c]pyridine-5,4'-[1,3]oxazin]-7-yl)-5-fluoro-2-pyridinecarboxamide | QQ | 518.2 | 15B | 0.0259 | 0.0088 | 400 |
| 97 | N-((5S)-2'-amino-1-fluoro-3-(2-fluoro-4-pyridinyl)-5',6'-dihydrospiro[chromeno[2,3-c]pyridine-5,4'-[1,3]oxazin]-7-yl)-5-fluoro-2-pyridinecarboxamide | K | 519 | 15B | 0.0012 | 0.0011 | 400 |
| 98 | N-((5S)-2'-amino-1-fluoro-3-(2-fluoro-4-pyridinyl)-5',6'-dihydrospiro[chromeno[2,3-c]pyridine-5,4'-[1,3]oxazin]-7-yl)-5-methoxy-2-pyridinecarboxamide | K | 531 | 15B | 0.0011 | 0.0011 | 400 |
| 99 | N-((5S)-2'-amino-1-fluoro-3-(2-fluoro-4-pyridinyl)-5',6'-dihydrospiro[chromeno[2,3-c]pyridine-5,4'-[1,3]oxazin]-7-yl)-2-methyl-1,3-thiazole-4-carboxamide | K | 521 | 15B | 0.0008 | 0.0004 | 400 |
| 100 | N-((5S)-2'-amino-1-fluoro-3-(2-fluoro-4-pyridinyl)-5',6'-dihydrospiro[chromeno[2,3-c]pyridine-5,4'-[1,3]oxazin]-7-yl)-5-cyano-2-pyridinecarboxamide | K | 526.1 | 15B | 0.0006 | 0.0004 | 517.7 |
| 101 | N-((5S)-2'-amino-3-(3,6-dihydro-2H-pyran-4-yl)-1-fluoro-5',6'-dihydrospiro[chromeno[2,3-c]pyridine-5,4'-[1,3]thiazin]-7-yl)-5-methoxy-2-pyridinecarboxamide | D | 534 | 40B | 0.0015 | 0.0007 | 197.6 |
| 61 | N-((4S)-2-amino-5'-fluoro-7'-(tetrahydro-2H-pyran-4-yl)-5,6-dihydrospiro[1,3-oxazine-4,9'-xanthen]-2'-yl)-5-methoxy-2-pyrazinecarboxamide | PP | 520 | 20B | 0.032 | 0.0078 | 378.5 |
| 102 | N-((4S)-2-amino-5'-fluoro-7'-(2-fluoro-4-pyridinyl)-5,6-dihydrospiro[1,3-oxazine-4,9'-xanthen]-2'-yl)-5-fluoro-2-pyridinecarboxamide | PP | 518 | 20B | 0.0088 | 0.0057 | 400 |
| 103 | N-((5S)-2'-amino-3-(3,6-dihydro-2H-pyran-4-yl)-5',6'-dihydrospiro[chromeno[2,3-c]pyridine-5,4'-[1,3]thiazin]-7-yl)-5-methoxy-2-pyridinecarboxamide | K | 517.1 | 22 | 0.0017 | 0.0011 | 400 |
| 104 | N-((5S)-2'-amino-3-(5,6-dihydro-2H-pyran-3-yl)-5',6'-dihydrospiro[chromeno[2,3-c]pyridine-5,4'-[1,3]thiazin]-7-yl)-5-methoxy-2-pyrazinecarboxamide | K | 517.1 | 22 | 0.0031 | 0.0010 | 294.5 |

TABLE II-continued

| Ex. No. | Compound Name | Method Used | Observed Mass | Intermediate Used | BACE 1 FRET assay (uM) | HEK cell assay (uM) | Cathepsin D (uM) |
|---|---|---|---|---|---|---|---|
| 105 | N-((4S)-2-amino-5'-fluoro-7'-hydroxy-5,6-dihydrospiro[1,3-thiazine-4,9'-xanthen]-2'-yl)-5-methoxy-2-pyridinecarboxamide | PP | 466.9 | 23B | 0.0294 | 0.0823 | 225 |
| 106 | N-((4S)-2-amino-7'-(5,6-dihydro-2H-pyran-3-yl)-5'-fluoro-5,6-dihydrospiro[1,3-oxazine-4,9'-xanthen]-2'-yl)-5-methoxy-2-pyrazinecarboxamide | PP | 518 | 20B | 0.0068 | 0.0016 | 106.5 |
| 107 | N-((4S)-2-amino-5'-fluoro-7'-(4-morpholinyl)-5,6-dihydrospiro[1,3-thiazine-4,9'-xanthen]-2'-yl)-5-methoxy-2-pyridinecarboxamide | PP | 535.7 | 23B | 0.0078 | 0.0087 | 326.4 |
| 108 | N-((4S)-2-amino-5'-fluoro-7'-(2-fluoro-4-pyridinyl)-5,6-dihydrospiro[1,3-oxazine-4,9'-xanthen]-2'-yl)-5-cyano-2-pyridinecarboxamide | PP | 525 | 20B | 0.001 | 0.0005 | 400 |
| 109 | N-((4S)-2-amino-5'-fluoro-7'-hydroxy-5,6-dihydrospiro[1,3-thiazine-4,9'-xanthen]-2'-yl)-5-methoxy-2-pyridinecarboxamide | PP | 468 | 23B | 0.0284 | 0.0646 | 400 |
| 110 | N-((4S)-2-amino-5'-fluoro-7'-(4-morpholinyl)-5,6-dihydrospiro[1,3-thiazine-4,9'-xanthen]-2'-yl)-5-methoxy-2-pyrazinecarboxamide | PP | 537.1 | 23B | 0.0153 | 0.0077 | 229.5 |
| 60 | N-((4S)-2-amino-7'-(3,6-dihydro-2H-pyran-4-yl)-5'-fluoro-5,6-dihydrospiro[1,3-thiazine-4,9'-xanthen]-2'-yl)-5-methoxy-2-pyrazinecarboxamide | PP | 533.8 | 23B | 0.0062 | 0.0043 | 173.6 |
| 111 | N-((5S)-2'-amino-3-(5,6-dihydro-2H-pyran-3-yl)-1-fluoro-5',6'-dihydrospiro[chromeno[2,3-c]pyridine-5,4'-[1,3]thiazin]-7-yl)-5-methoxy-2-pyridinecarboxamide | D | 534 | 40B | 0.0025 | 0.0008 | 569 |
| 112 | N-((5S)-2'-amino-1-fluoro-3-(5-fluoro-3-pyridinyl)-5',6'-dihydrospiro[chromeno[2,3-c]pyridine-5,4'-[1,3]thiazin]-7-yl)-5-methoxy-2-pyrazinecarboxamide | D | 548.1 | 40B | 0.0028 | 0.0012 | 223.5 |
| 113 | N-((5S)-2'-amino-1-fluoro-3-(5-fluoro-3-pyridinyl)-5',6'-dihydrospiro[chromeno[2,3-c]pyridine-5,4'-[1,3]thiazin]-7-yl)-5-methoxy-2-pyridinecarboxamide | D | 547.1 | 40B | 0.0011 | 0.0018 | 120.1 |
| 114 | N-((5S)-2'-amino-1-fluoro-3-(2-fluoro-4-pyridinyl)-5',6'-dihydrospiro[chromeno[2,3-c]pyridine-5,4'-[1,3]thiazin]-7-yl)-5-methoxy-2-pyrazinecarboxamide | D | 548 | 40B | 0.0031 | 0.0038 | 400 |
| 115 | N-((5S)-2'-amino-1-fluoro-3-(2-fluoro-4-pyridinyl)-5',6'-dihydrospiro[chromeno[2,3-c]pyridine-5,4'-[1,3]thiazin]-7-yl)-5-methoxy-2-pyridinecarboxamide | D | 547.1 | 40B | 0.0004 | 0.0022 | 162.1 |
| 116 | N-((5S)-2'-amino-3-(3,6-dihydro-2H-pyran-4-yl)-1-fluoro-5',6'-dihydrospiro[chromeno[2,3-c]pyridine-5,4'-[1,3]thiazin]-7-yl)-5-fluoro-2-pyridinecarboxamide | D | 522 | 40B | 0.001 | 0.0006 | 210.7 |
| 117 | N-((5S)-2'-amino-3-(3,6-dihydro-2H-pyran-4-yl)-1-fluoro-5',6'-dihydrospiro[chromeno[2,3-c]pyridine-5,4'-[1,3]thiazin]-7-yl)-5-chloro-2-pyridinecarboxamide | D | 538.1 | 40B | 0.001 | 0.0006 | 133 |
| 118 | N-((5S)-2'-amino-1-fluoro-3-(2-fluoro-4-pyridinyl)-5',6'-dihydrospiro[chromeno[2,3-c]pyridine-5,4'-[1,3]thiazin]-7-yl)-5-fluoro-2-pyridinecarboxamide | D | 535.1 | 40B | 0.0015 | 0.0042 | 400 |
| 119 | N-((5S)-2'-amino-3-(3,6-dihydro-2H-pyran-4-yl)-1-fluoro-5',6'-dihydrospiro[chromeno[2,3-c]pyridine-5,4'-[1,3]thiazin]-7-yl)-5-chloro-3-fluoro-2-pyridinecarboxamide | D | 556 | 40B | 0.0026 | 0.0006 | 311 |
| 120 | N-((5S)-2'-amino-3-(3,6-dihydro-2H-pyran-4-yl)-1-fluoro-5',6'-dihydrospiro[chromeno[2,3-c]pyridine-5,4'-[1,3]thiazin]-7-yl)-5-bromo-3-methyl-2-pyridinecarboxamide | D | 598 | 40B | 0.0014 | 0.0005 | 88.3 |
| 121 | N-((5S)-2'-amino-3-(3,6-dihydro-2H-pyran-4-yl)-1-fluoro-5',6'-dihydrospiro[chromeno[2,3-c]pyridine-5,4'-[1,3]thiazin]-7-yl)-5-methoxy-3-methyl-2-pyridinecarboxamide | D | 548 | 40B | 0.0054 | 0.0018 | 158.8 |
| 122 | N-((5S)-2'-amino-3-(3,6-dihydro-2H-pyran-4-yl)-1-fluoro-5',6'-dihydrospiro[chromeno[2,3-c]pyridine-5,4'-[1,3]thiazin]-7-yl)-5-chloro-3-methyl-2-pyridinecarboxamide | D | 552 | 40B | 0.0029 | 0.0008 | 133 |

The present invention also provides methods for making compounds of Formulas I-IV, and sub-formulas thereof. For example, and in addition to the methods described herein, the compounds of the invention may be made by the methods similar to those described in the literature references cited below.

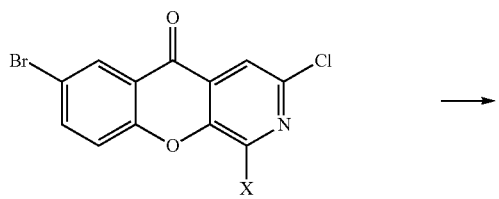

General review of sulfinylimine chemistry
Accounts of Chemical Research (2002), 35(11), 984-995

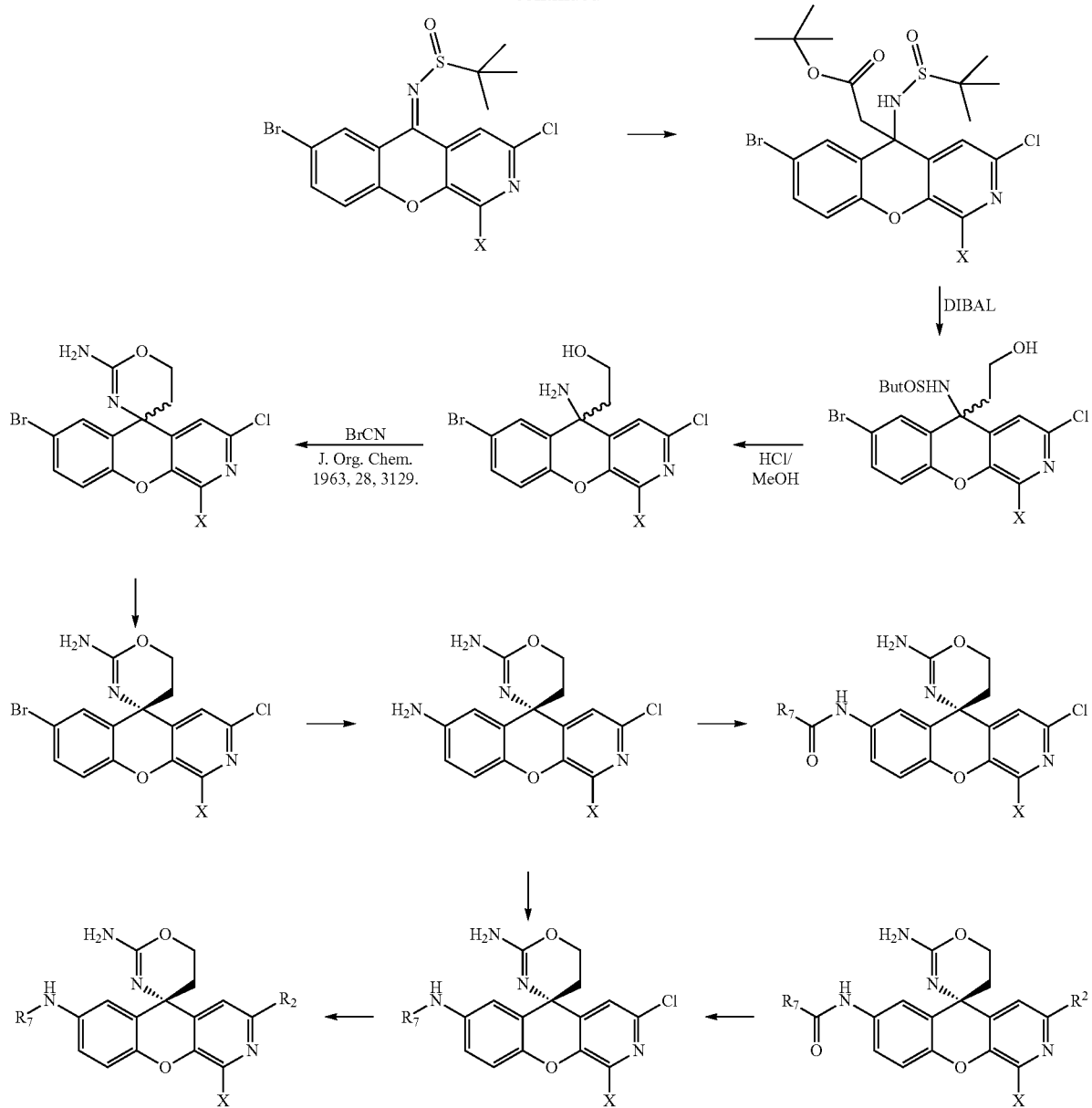

In one embodiment of the invention, there is provided a method of making a compound having a general Formula A

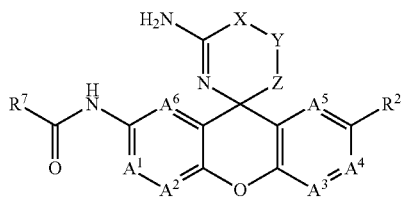

the method comprising the step of reacting a compound 20

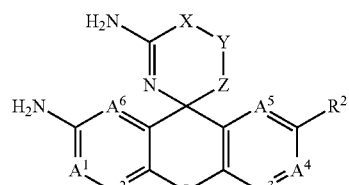

wherein $A^1, A^2, A^3, A^4, A^5, A^6, R^2, X, Y$ and Z of the Formula are as defined herein in formula I, II or III, with a compound having the structure $R^7$—COOH, wherein $R^7$ is as defined herein, to make a compound of Formula A.

In another embodiment of the invention, there is provided a method of making a compound of Formula I-A, the method comprising the step of reacting a compound 20

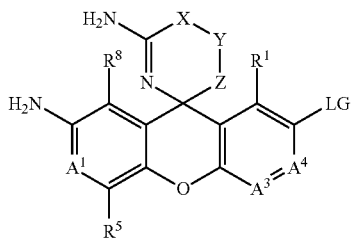

wherein $A^1$, $A^3$, $A^4$, $R^7$, X, Y and Z of Formula I-A are as defined herein and LG is Br, Cl or —O-protecting group, with a compound having the structure $R^2$—COOH, wherein $R^2$ is as defined herein, to make a compound of Formula I-A.

In another embodiment of the invention, there is provided a method of making a compound of Formula III-A-1, the method comprising the step of reacting a compound 20

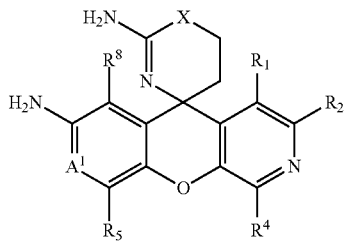

wherein $R^1$, $R^2$, $R^4$, $R^5$, $R^8$ and X of Formula III-A-1 are as defined herein, with a compound having the structure $R^2$—COOH, wherein $R^2$ is as defined herein, to make a compound of Formula III-A-1.

In another embodiment of the invention, there is provided a method of making a compound of Formula II, the method comprising the step of reacting a compound 20

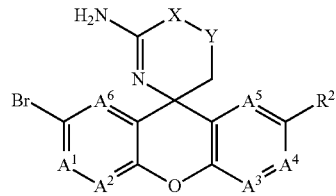

wherein $A^1$, $A^2$, $A^3$, $A^4$, $A^5$, $A^6$, $R^2$, X and Y of Formula II are as defined herein, with a compound having the structure or $R^7$—$NH_2$, wherein $R^7$ is as defined herein, to make a compound of Formula II.

In one embodiment of the invention, there is provided a method of making a compound having a general Formula III-A-a III-A-a

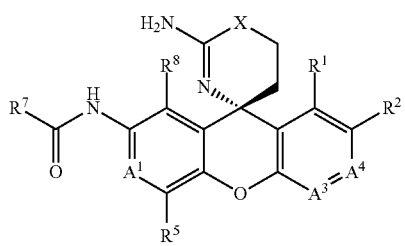

the method comprising the step of reacting a compound 21

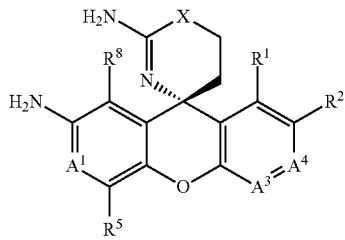

wherein $A^1$, $A^3$, $A^4$, $R^1$, $R^2$, $R^5$, $R^8$ and X of compound 21 are as defined herein with respect to embodiments of Formula III-A, with a compound having the structure $R^7$—COOH, wherein $R^7$ is as defined herein with respect to embodiments of Formula III-A, to make a compound of Formula III-A.

As can be appreciated by the skilled artisan, the above synthetic schemes and representative examples are not intended to comprise a comprehensive list of all means by which the compounds described and claimed in this application may be synthesized. Further methods will be evident to those of ordinary skill in the art. Additionally, the various synthetic steps described above may be performed in an alternate sequence or order to give the desired compounds.

For example, in these procedures, the steps may be preceded, or followed, by additional protection/deprotection steps as necessary. Particularly, if one or more functional groups, for example carboxy, hydroxy, amino, or mercapto groups, are or need to be protected in preparing the compounds of the invention, because they are not intended to take part in a specific reaction or chemical transformation, various known conventional protecting groups may be used. For example, protecting groups typically utilized in the synthesis of natural and synthetic compounds, including peptides, nucleic acids, derivatives thereof and sugars, having multiple reactive centers, chiral centers and other sites potentially susceptible to the reaction reagents and/or conditions, may be used.

Synthetic chemistry transformations and protecting group methodologies (protection and deprotection) useful in synthesizing the inhibitor compounds described herein are known in the art and include, for example, those such as described in R. Larock, Comprehensive Organic Transformations, VCH Publishers (1989); T. W. Greene and P. G. M. Wuts, Protective Groups in Organic Synthesis, $3^{rd}$ edition, John Wiley and Sons (1999); L. Fieser and M. Fieser, Fieser and Fieser's Reagents for Organic Synthesis, John Wiley and Sons (1994); A. Katritzky and A. Pozharski, Handbook of Heterocyclic Chemistry, $2^{nd}$ edition (2001); M. Bodanszky, A. Bodanszky, The Practice of Peptide Synthesis, Springer-Verlag, Berlin Heidelberg (1984); J. Seyden-Penne, Reductions by the Alumino- and Borohydrides in Organic Synthesis, $2^{nd}$ edition, Wiley-VCH, (1997); and L. Paquette, editor, Encyclopedia of Reagents for Organic Synthesis, John Wiley and Sons (1995).

Salts, including pharmaceutically acceptable salts, of a compound of the invention having a salt-forming group may be prepared in a conventional manner or manner known to persons skilled in the art. For example, acid addition salts of compounds of the invention may be obtained by treatment with an acid or with a suitable anion exchange reagent. A salt with two acid molecules (for example a dihalogenide) may also be converted into a salt with one acid molecule per compound (for example a monohalogenide); this may be done by heating to a melt, or for example by heating as a solid under a high vacuum at elevated temperature, for example from 50° C. to 170° C., one molecule of the acid being expelled per molecule of the compound.

Acid salts can usually be converted to free-base compounds, e.g. by treating the salt with suitable basic agents, for example with alkali metal carbonates, alkali metal hydrogen carbonates, or alkali metal hydroxides, typically potassium carbonate or sodium hydroxide. Exemplary and suitable salts, and their preparation, are described herein in the Definition section of the application.

All synthetic procedures described herein can be carried out under known reaction conditions, advantageously under those described herein, either in the absence or in the presence (usually) of solvents or diluents. As appreciated by those of ordinary skill in the art, the solvents should be inert with respect to, and should be able to dissolve, the starting materials and other reagents used. Solvents should be able to partially or wholly solubilize the reactants in the absence or presence of catalysts, condensing agents or neutralizing agents, for example ion exchangers, typically cation exchangers for example in the H$^+$ form. The ability of the solvent to allow and/or influence the progress or rate of the reaction is generally dependant on the type and properties of the solvent(s), the reaction conditions including temperature, pressure, atmospheric conditions such as in an inert atmosphere under argon or nitrogen, and concentration, and of the reactants themselves.

Suitable solvents for conducting reactions to synthesize compounds of the invention include, without limitation, water; esters, including lower alkyl-lower alkanoates, e.g., EtOAc; ethers including aliphatic ethers, e.g., Et$_2$O and ethylene glycol dimethylether or cyclic ethers, e.g., THF; liquid aromatic hydrocarbons, including benzene, toluene and xylene; alcohols, including MeOH, EtOH, 1-propanol, IPOH, n- and t-butanol; nitriles including CH$_3$CN; halogenated hydrocarbons, including CH$_2$Cl$_2$, CHCl$_3$ and CCl$_4$; acid amides including DMF; sulfoxides, including DMSO; bases, including heterocyclic nitrogen bases, e.g. pyridine; carboxylic acids, including lower alkanecarboxylic acids, e.g., AcOH; inorganic acids including HCl, HBr, HF, H$_2$SO$_4$ and the like; carboxylic acid anhydrides, including lower alkane acid anhydrides, e.g., acetic anhydride; cyclic, linear, or branched hydrocarbons, including cyclohexane, hexane, pentane, isopentane and the like, and mixtures of these solvents, such as purely organic solvent combinations, or water-containing solvent combinations e.g., aqueous solutions. These solvents and solvent mixtures may also be used in "working-up" the reaction as well as in processing the reaction and/or isolating the reaction product(s), such as in chromatography.

Purification methods are known in the art and include, for example, crystallization, chromatography (liquid and gas phase, and the like), extraction, distillation, trituration, reverse phase HPLC and the like. Reactions conditions such as temperature, duration, pressure, and atmosphere (inert gas, ambient) are known in the art and may be adjusted as appropriate for the reaction.

The invention further encompasses "intermediate" compounds, including structures produced from the synthetic procedures described, whether isolated or generated in-situ and not isolated, prior to obtaining the finally desired compound. Structures resulting from carrying out steps from a transient starting material, structures resulting from divergence from the described method(s) at any stage, and structures forming starting materials under the reaction conditions are all "intermediates" included in the invention. Further, structures produced by using starting materials in the form of a reactive derivative or salt, or produced by a compound obtainable by means of the process according to the invention and structures resulting from processing the compounds of the invention in situ are also within the scope of the invention.

The invention also provides new starting materials and/or intermediates, as well as processes for the preparation thereof. In select embodiments, such starting materials are used and reaction conditions so selected as to obtain the desired compound(s). Starting materials of the invention, are either known, commercially available, or can be synthesized in analogy to or according to methods that are known in the art. Many starting materials may be prepared according to known processes and, in particular, can be prepared using processes described in the examples. In synthesizing starting materials, functional groups may be protected with suitable protecting groups when necessary. Protecting groups, their introduction and removal are described above.

Compounds of the present invention can possess, in general, one or more asymmetric carbon atoms and are thus capable of existing in the form of optical isomers as well as in the form of racemic or non-racemic mixtures thereof. While shown without respect to stereochemistry in Formulas I-IV, the present invention includes such optical isomers and diastereomers, as well as the racemic and resolved, enantiomerically pure R and S stereoisomers, as well as other mixtures of R and S stereoisomers and pharmaceutically acceptable salts thereof.

The optical isomers can be obtained by resolution of the racemic mixtures according to conventional processes, e.g., by formation of diastereoisomeric salts, by treatment with an optically active acid or base. Examples of appropriate acids are tartaric, diacetyltartaric, dibenzoyltartaric, ditoluoyltartaric, and camphorsulfonic acid and then separation of the mixture of diastereoisomers by crystallization followed by liberation of the optically active bases from these salts. A different process for separation of optical isomers involves the use of a chiral chromatography column optimally chosen to maximize the separation of the enantiomers. Still another available method involves synthesis of covalent diastereoisomeric molecules by reacting compounds of the invention with an optically pure acid in an activated form or an optically pure isocyanate. The synthesized diastereoisomers can be separated by conventional means such as chromatography, distillation, crystallization or sublimation, and then hydrolyzed to deliver the enantiomerically pure compound. The optically active compounds of the invention can likewise be obtained by using optically active starting materials. These isomers may be in the form of a free acid, a free base, an ester or a salt. All such isomeric forms of such compounds are expressly included in the present invention.

The compounds of the invention may also be represented in multiple tautomeric forms. Tautomers often exist in equilibrium with each other, and interconvert under environmental and physiological conditions. The compounds of the invention may also occur in cis- or trans- or E- or Z-double bond isomeric forms. The invention expressly includes all tautomeric forms of the compounds described herein.

All crystal forms of the compounds described herein are expressly included in the present invention.

The present invention also includes isotopically-labeled compounds, which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine and chlorine, such as $^2$H (deuterium), $^3$H (tritium), $^{13}$C, $^{14}$C, $^{15}$N, $^{16}$O, $^{17}$O, $^{31}$P, $^{32}$P, $^{35}$S, $^{18}$F, and $^{36}$Cl.

Compounds of the present invention that contain the aforementioned isotopes and/or other isotopes of other atoms are within the scope of this invention. Certain isotopically-labeled compounds of the present invention, for example those into which radioactive isotopes such as $^3$H and $^{14}$C are incorporated, are useful in drug and/or substrate tissue distribution assays. Deuterated ($^2$H), Tritiated ($^3$H) and carbon-14, i.e., $^{14}$C, u isotopes are particularly preferred for their ease of preparation and detection. Further, substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances. Isotopically labeled compounds of this invention can generally be prepared by substituting a readily available isotopically labeled reagent for a non-isotopically labeled reagent.

Biological Evaluation

The compounds of the invention may be modified by appending appropriate functionalities to enhance selective biological properties. The pharmacokinetic and pharmacodynamic properties of a compound relate, directly and indirectly, to the ability of the compound to be effective for its intended use.

Although the pharmacological properties of the compounds of the invention (Formulas I-IV and sub-Formulas thereof) vary with structural change, in general, activity possessed by compounds of Formulas I-IV may be demonstrated both in vitro as well as in vivo. The following exemplified pharmacological assays have been carried out with the compounds according to the invention, to assess and characterize the compound's ability to modulate BACE activity and to regulate the cleavage of amyloid beta precursor protein, thereby reducing or inhibiting the production of amyloid beta.

In Vitro Enzymatic BACE FRET (Fluorescence Resonance Energy Transfer) Assay

The assay buffer used in this screen is 0.05 M acetate, pH 4.2, 10% DMSO final, 100 uM genapol (which is a nonionic detergent, below its Critical Micelle Concentration). The beta secretase enzyme (0.2 nM) is pre-incubated for one hour with inhibitors, typically in about 1 uL of DMSO according to a serial dilution, are added thereto. This assay is effectively started by the addition of FRET substrate (50 nM) and the combination is incubated for one hour. The FRET assay is terminated with by addition of Tris buffer, which raises the pH to neutrality, and the fluorescence is determined. The FRET substrate is a peptide with commercially available fluorophore and quencher, on opposite sides of the BACE cleavage site. Proteolytic cleavage of the FRET substrate releases quenching of fluorescence (excitation 488 nm and emission 425 nm).

Where available, the in-vitro BACE FRET enzyme data for each of the Examples is provided in Tables I and II.

In Vitro BACE Cell-Based Assay

The cell-based assay measures inhibition or reduction of Aβ40 in conditioned medium of test compound treated cells expressing amyloid precursor protein.

Cells stably expressing Amyloid Precursor Protein (APP) were plated at a density of 40K cells/well in 96 well plates (Costar). The cells were cultivated for 24 hours at 37° C. and 5% $CO_2$ in DMEM supplemented with 10% FBS. The test compounds were then added to cells in 10-point dose response concentrations with the starting concentration being either 100 µM or 10 µM. The compounds were diluted from stock solutions in DMSO and the final DMSO concentration of the test compounds on cells was 0.1%. After 24 h of incubation with the test compounds the supernatant conditioned media was collected and the Aβ 40 levels were determined using a sandwich ELISA. The $IC_{50}$ of the compound was calculated from the percent of control or percent inhibition of Aβ 40 as a function of the concentration of the test compound.

The sandwich ELISA to detect Aβ 40 was performed in 96 well microtiter plates, which were pre-treated with goat anti-rabbit IgG (Pierce). The capture and detecting antibody pair that were used to detect Aβ 40 from cell supernatants were affinity purified pAb40 (Biosource) and biotinylated 6E10 (Signet Labs Inc.), respectively. The optimal concentration for the pAb40 antibody was 3 µg/ml in Superblock/TBS (Pierce) that was supplemented with 0.05% Tween 20 (Sigma). Optimal concentration for the detection antibody 6E10-biotinylated was 0.5 µg/ml in Superblock/TBS (Pierce) that had been supplemented with 2% normal goat serum and 2% normal mouse serum.

Cellular supernatants were incubated with the capture antibody for 3 h at 4° C., followed by 3 wash steps in TBS-tween (0.05%). The detecting antibody incubation was for 2 h at 4° C., again followed by the wash steps as described previously. The final readout of the ELISA is Time-Resolved Fluorescence (counts per minute) using Delfia reagents Streptavidin-Europium and Enhancement solutions (Perkin Elmer) and the Victor 2 multilabel counter (Perkin Elmer).

Where available, the in-vitro BACE cell based data for each of the Examples is provided in Tables I and II.

In Vitro Enzymatic Cat D (Cathepsin D) FRET (Fluorescence Resonance Energy Transfer) Assay Recombinant CathepsinD was expressed in CHO cells. The assay buffer for CathepsinD is 0.05 M citrate pH 3.5, 10% DMSO final, 5 mM CHAPS. The CathepsinD enzyme (9 nM) is pre-incubated for one hour with inhibitors, typically in about 1 uL of DMSO according to a serial dilution, is added thereto. The assays are effectively started by the addition of different FRET substrates (20 nM for CathepsinD) and the combination is incubated for one hour. The FRET assay is terminated with by addition of Tris buffer, which raises the pH to neutrality, and the fluorescence is determined. The FRET substrate is a peptide with commercially available fluorophore and quencher, on opposite sides of the BACE cleavage site. The CathepsinD substrate peptide sequence is based on sequence #1 of Table 1 from Gulnik et al. FEBS Letters v413 p 379-384 1997. Proteolytic cleavage of the FRET substrate releases quenching of fluorescence (CathepsinD excitation 500 nm and emission 580 nm).

Alternatively, a Cat D assay may also be run according to the procedure described in the article, Characterization of new fluorogenic substrates for the rapid and sensitive assay of cathepsin E and cathepsin D, *J. Biochem.*, 125:1137, 1999.

Where available, the in-vitro CatD FRET assay data for each of the Examples, conducted by the first procedure, is provided in Tables I and II. As shown by the high micromolar CatD data (very poorly active or inactive against catD), the compounds of the present invention possess the unexpected property of little to no ability to inhibit the activity of CatD. It was surprisingly found that incorporation of a linker "L" between the core of the compounds and the $R^7$ group has conferred a significantly reduced, poor or no potency on the protein CatD. Thus, with this surprising selectivity profile, the compounds of the present invention are believed to minimize, reduce or completely eliminate any risk of retinal atrophy and abnormal development of the eye and of the retinal pigmented epithelium as it relates to the normal function and activity of CatD.

In Vivo Inhibition of Beta-Secretase

Several animal models, including mouse, rat, dog, and monkey, may be used to screen for inhibition of beta-secretase activity in vivo following administration of a test compound sample. Animals used in this invention can be wild type, transgenic, or gene knockout animals. For example, the Tg2576 mouse model, prepared and conducted as described in Hsiao et al., 1996, *Science* 274, 99-102, and other non-transgenic or gene knockout animals are useful to analyze in vivo inhibition of Amyloid beta peptide (Abeta) production in the presence of inhibitory test compounds. Generally, 2 to 18 month old Tg2576 mice, gene knockout mice or non-transgenic animals are administered test compounds formulated in vehicles, such as cyclodextran, phosphate buffers, hydroxypropyl methylcellulose or other suitable vehicles. One to twenty-four hours following the administration of compound, animals are sacrificed, and brains as well as cerebrospinal fluid (CSF) and plasma are removed for analysis of A-beta levels and drug or test compound concentrations (Dovey et al., 2001, *Journal of Neurochemistry*, 76, 173-181) Beginning at time 0, animals are administered by oral gavage, or other means of delivery such as intravenous injection, an inhibitory test compound of up to 100 mg/kg in a standard, conventional formulation, such as 2% hydroxypropyl methylcellulose, 1% Tween80. A separate group of animals receive 2% hydroxypropyl methylcellulose, 1% Tween80 alone, containing no test compound, and serve as a vehicle-control group. At the end of the test period, animals are sacrificed and brain tissues, plasma or cerebrospinal fluid are collected. Brains are either homogenized in 10 volumes (w/v) of 0.2% diethylamine (DEA) in 50 mM NaCl (Best et al., 2005, *Journal of Pharmacology and Experimental Therapeutics*, 313, 902-908), or in 10 volumes of 0.5% TritonX-100 in Tris-buffered saline (pH at about 7.6). Homogenates are centrifuged at 355,000 g, 4° C. for 30 minutes. CSF or brain supernatants are then analyzed for the presence of A-beta peptide by specific sandwich ELISA assays based on ECL (Electrochemiluminescence) technology. For example, rat Abeta40 is measured using biotinylated-4G8 (Signet) as a capture antibody and Fab40 (an in-house antibody specific to the C-terminal of Abeta40) as a detection antibody. For example, 4 hours after administration of 30 mg/kg oral dose of the test compound in 2% hydroxypropyl methylcellulose, 1% Tween80 (pH2.2) to 200 g male Sprague Dawley rats, amyloid beta peptide levels are measured for reduction by X % and Y % in cerebrospinal fluid and brain, respectively, when compared to the levels measured in the vehicle-treated rats.

Actual vehicles used:
 Oral: 2% HPMC, 1% Tween80, pH 2.2
 IV: 5% EtOH, 45% Propylene glycol in 5% Dextrose The compounds of the invention may be shown to reduce the formation and/or deposition of amyloid beta peptide in the cerebrospinal fluid (CSF) as well as in the brain of a mouse or rat at either 3 mpk, 10 mpk or 30 mpk (mpk=mg compound per kg weight of the animal) dosing concentrations after 4 hrs. The following examples exhibited the following percent Abeta 40 reductions at 10 mpk (unless otherwise noted) in the CSF and brain of the rat, respectively.

| Ex. No. | % reduction of rat CSF levels at 10 pmk | % reduction of rat brain levels at 10 mpk |
|---|---|---|
| 34 | 64 | 17 |
| 45 | 27 | 14 |
| 39 | 85 | 80 |
| 51 | 85 | 76 |
| 40 | 75 | 58 |
| 54 | 77 | 65 |
| 63 | 80 | 75 |
| 65 | 83 | 71 |
| 66 | 77 | 66 |
| 67 | 66 | 58 |
| 68 | 77 | 73 |
| 70 | 70 | 59 |
| 71 | 79 | 70 |
| 72 | 78 | 72 |
| 58 | 55 | 36 |
| 59 | 57 | 50 |
| 73 | 38 | 7 |
| 78 | 77 | 70 |
| 80 | 82 | 80 |
| 81 | 76 | 64 |
| 82 | 67 | 42 |
| 84 | 83 | 71 |
| 87 | 75 | 53 |
| 88 | 49 | 27 |
| 89 | 69 | 46 |
| 92 | 79 | 70 |
| 95 | 54 | 21 |
| 97 | 63 | 44 |
| 101 | 76 | 59 |
| 104 | 64 | 43 |
| 106 | 43 | 16 |
| 111 | 76 | 58 |
| 116 | 73 | 56 |
| 117 | 80 | 70 |

Indications

The compounds of the invention have been shown to modulate, and specifically inhibit the activity of beta-secretase (Memapsin 2) enzyme, thereby reducing the A-beta peptide fragments believed to be responsible for Alzheimer's Disease (AD). Bapineuzamab, a monoclonal amino-terminus specific anti-amyloid antibody is presently in Phase III clinical trials for the treatment of AD. *Alzheimer's Research & Therapy*, 1:2, 2009. Bapineuzumab targets beta amyloid protein involved in AD. It is the most advanced monoclonal antibody in clinical development to stop the disease progression and degradation of cognitive function. The drug has fast track regulatory status with the USFDA (Medpedia, 2011). Hence, it must clearly show a beneficial and lasting effect through validated biomarker of underlying AD disease mechanism. Clinical trials in AD now measure CSF $A\beta$ levels, brain amyloid load, CSF tau, brain volume by MRI and FDG PET scan. Each of the known genetic causes of AD is linked to A-beta.

Other conditions including dementia, Down's Syndrome to APP over-production, are all believed to be linked to the deposition of A-beta on the brain. With methods for identifying brain amyloid deposition, positron emission scanning (PET) and CSF measurements of Ab42, identification of AD suffering individuals needing treatment is becoming more easy. It is firmly believed that by reducing the formation of A-beta, one can begin to pre-treat AD. Vassar et al, *Journal of Neuroscience*, 29 (41):12787-12794, 2009. One published pathway for treatment of AD is inhibition of beta-secretase. Tirrell, Bloomberg News, *The Boston Globe*, Jan. 7, 2010; *Curr. Alzheimer's Res.* 2008, Apr. 5 (2):121-131; *Expert Opin. Drug Discov.* (200( ) 4(4):319-416.

Accordingly, compounds of the invention, and pharmaceutical compositions comprising said compounds, are useful for, but not limited to, the prevention or treatment of beta-secretase related diseases, including Alzheimer's disease, the leading cause of dementia. Particularly, the compounds of the invention are useful to treat various stages of AD, including without limitation mild to moderate AD and prodromal patients pre-disposed to developing AD. The compounds of the invention have the ability to modulate the activity of beta secretase enzyme, thereby regulating the production of amyloid beta (Abeta peptide) and slowing or reducing the formation and deposition of Abeta peptide in both the cerebral spinal fluid as well as in the brain, resulting in a decrease of amyloid plaque on the brain. In one embodiment of the invention, there is provided a method of treating a disorder related to a beta-secretase enzyme in a subject, the method comprising administering to the subject an effective dosage amount of a compound of Formulas I, II, III, IV, and sub-formulas thereof, such as formulas II-A and II-B. In another embodiment, there is provided a method of reducing production of amyloid beta, and of slowing plaque formation on the brain. In another embodiment, there is provided a method for the treatment, prevention or amelioration of a disease or disorder characterized by the elevated beta-amyloid deposits or beta-amyloid levels in a subject, the method comprising administering to the subject a therapeutically effective amount of a compound according to any of Formulas I-IV, and sub-Formulas thereof. In yet another embodiment, the invention provides a method of treating Alzheimer's disease, cognitive impairment including mild, moderate and/or severe, Down's Syndrome, cognitive decline, senile dementia, cerebral amyloid angiopathy or a neurodegenerative disorder.

Accordingly, the compounds of the invention would be useful in therapy as CNS agents in treating neurological disorders and related conditions.

In one embodiment, the compounds of the invention are provided for the manufacture of a medicament, or a pharmaceutical composition, for the therapeutic and/or prophylactic treatment of diseases and disorders characterized by elevated levels of β-amyloid and/or β-amyloid oligomers and/or b-amyloid plaques and further deposits, including Alzheimer's Disease. In another embodiment, the invention provides compounds, in effective dosage amounts, for the therapeutic and/or prophylactic treatment of AD. Thus, the compounds of the invention may be used to treat prodromol patients, i.e., subjects exhibiting the biomarkers and/or hallmarks of developing AD.

Besides being useful for human treatment, these compounds are useful for veterinary treatment of companion animals, exotic animals and farm animals, including mammals, rodents, and the like. For example, animals including horses, dogs, and cats may be treated with compounds provided by the invention.

Formulations and Method of Use

Treatment of diseases and disorders herein is intended to also include therapeutic administration of a compound of the invention, or a pharmaceutical salt thereof, or a pharmaceutical composition of either to a subject (i.e., an animal, preferably a mammal, most preferably a human) which may be in need of preventative treatment, such as, for example, for pain, inflammation and the like. Treatment also encompasses prophylactic administration of a compound of the invention, or a pharmaceutical salt thereof, or a pharmaceutical composition of either to a subject (i.e., an animal, preferably a mammal, most preferably a human). Generally, the subject is initially diagnosed by a licensed physician and/or authorized medical practitioner, and a regimen for prophylactic and/or therapeutic treatment via administration of the compound(s) or compositions of the invention is suggested, recommended or prescribed.

The amount of compound(s) which is/are administered and the dosage regimen for treating neurological disorders and beta-secretase mediated diseases with the compounds and/or compositions of this invention depends on a variety of factors, including the age, weight, sex and medical condition of the subject, the type of disease, the severity of the disease, the route and frequency of administration, and the particular compound employed. Thus, the dosage regimen may vary widely, but can be determined routinely using standard methods. A daily dose of about 0.01 to 500 mg/kg, advantageously between about 0.01 and about 50 mg/kg, more advantageously about 0.01 and about 30 mg/kg, and even more advantageously between about 0.1 and about 10 mg/kg body weight may be appropriate, and should be useful for all methods of use disclosed herein. The daily dose can be administered in one to four doses per day.

While it may be possible to administer a compound of the invention alone, in the methods described, the compound administered normally will be present as an active ingredient in a pharmaceutical composition. Thus, in another embodiment of the invention, there is provided a pharmaceutical composition comprising a compound of this invention in combination with a pharmaceutically acceptable excipient, which includes diluents, carriers, adjuvants and the like (collectively referred to herein as "excipient" materials) as described herein, and, if desired, other active ingredients. A pharmaceutical composition of the invention may comprise an "effective amount" of a compound of the invention or an "effective dosage amount" of a compound of the invention. An "effective dosage amount" of a compound of the invention includes an amount less than, equal to or greater than an effective amount of the compound. For example, a pharmaceutical composition in which two or more unit dosages, such as in tablets, capsules and the like, are required to administer an effective amount of the compound, or alternatively, a multi-dose pharmaceutical composition, such as powders, liquids and the like, in which an effective amount of the compound is administered by administering a portion of the composition.

The compound(s) of the present invention may be administered by any suitable route, preferably in the form of a pharmaceutical composition adapted to such a route, and in a dose effective for the treatment intended. The compounds and compositions of the present invention may, for example, be administered orally, mucosally, topically, rectally, pulmonarily such as by inhalation spray, or parentally including intravascularly, intravenously, intraperitoneally, subcutaneously, intramuscularly intrasternally and infusion techniques, in dosage unit formulations containing conventional pharmaceutically acceptable carriers, adjuvants, and vehicles.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are tablets or capsules. For example, these may contain an amount of active ingredient from about 1 to 2000 mg, advantageously from about 1 to 500 mg, and typically from about 5 to 150 mg. A suitable daily dose for a human or other mammal may vary widely depending on the condition of the patient and other factors, but, once again, can be determined using routine methods and practices.

For therapeutic purposes, the active compounds of this invention are ordinarily combined with one or more adjuvants or other "excipients" appropriate to the indicated route of administration. If orally administered on a per dose basis, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, to form the final formulation. For example, the active compound(s) and excipient(s) may be tableted or encapsulated by known and accepted methods for convenient administration. Examples of suitable formulations include, without limitation, pills, tablets, soft and hard-shell gel capsules, troches, orally-dissolvable forms and delayed or controlled-release formulations thereof. Particularly, capsule or tablet formulations may contain one or more controlled-release agents, such as hydroxypropylmethyl cellulose, as a dispersion with the active compound(s).

Formulations for parenteral administration may be in the form of aqueous or non-aqueous isotonic sterile injection solutions or suspensions. These solutions and suspensions may be prepared from sterile powders or granules using one or more of the carriers or diluents mentioned for use in the formulations for oral administration or by using other suitable dispersing or wetting agents and suspending agents. The compounds may be dissolved in water, polyethylene glycol, propylene glycol, ethanol, corn oil, cottonseed oil, peanut oil, sesame oil, benzyl alcohol, sodium chloride, tragacanth gum, and/or various buffers. Other adjuvants and modes of administration are well and widely known in the pharmaceutical art. The active ingredient may also be administered by injection as a composition with suitable carriers including saline, dextrose, or water, or with cyclodextrin (ie. Captisol), cosolvent solubilization (ie. propylene glycol) or micellar solubilization (ie. Tween 80).

The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

The active ingredient may also be administered by injection as a composition with suitable carriers including saline, dextrose, or water. The daily parenteral dosage regimen will be from about 0.1 to about 30 mg/kg of total body weight, and preferably from about 0.1 to about 10 mg/kg.

For pulmonary administration, the pharmaceutical composition may be administered in the form of an aerosol or with an inhaler including dry powder aerosol.

The pharmaceutical compositions may be subjected to conventional pharmaceutical operations such as sterilization and/or may contain conventional adjuvants, such as preservatives, stabilizers, wetting agents, emulsifiers, buffers etc. Tablets and pills can additionally be prepared with enteric coatings. Such compositions may also comprise adjuvants, such as wetting, sweetening, flavoring, and perfuming agents. Accordingly, in yet another embodiment of the present invention, there is provided a method of manufacturing a medicament, the method comprising combining an amount of a compound according to Formulas I-IV with a pharmaceutically acceptable carrier to manufacture the medicament.

In yet another embodiment, the invention provides a method of manufacturing a medicament for the treatment of Alzheimer's disease, the method comprising combining an amount of a compound according to Formulas I-IV with a pharmaceutically acceptable carrier to manufacture the medicament.

Combinations

While the compounds of the invention can be dosed or administered as the sole active pharmaceutical agent, they can also be used in combination with one or more compounds of the invention or in conjunction with other agents. When administered as a combination, the therapeutic agents can be formulated as separate compositions that are administered simultaneously or sequentially at different times, or the therapeutic agents can be given as a single composition.

The phrase "co-therapy" (or "combination-therapy"), in defining use of a compound of the present invention and another pharmaceutical agent, is intended to embrace administration of each agent in a sequential manner in a regimen that will provide beneficial effects of the drug combination, and is intended as well to embrace co-administration of these agents in a substantially simultaneous manner, such as in a single capsule having a fixed ratio of these active agents or in multiple, separate capsules for each agent.

Specifically, the compounds of the present invention may be administered in conjunction with additional therapies known to those skilled in the art in the prevention or treatment of beta-secretase, gamma-secretase and/or other reagents known in influence the formation and/or deposition of amyloid beta, otherwise responsible for the formation of plaque on the brain. Thus, the compounds may be co-administered simultaneously or sequentially along with the other therapeutic agent.

If formulated as a fixed dose, such combination products employ the compounds of this invention within the accepted dosage ranges. Compounds of Formulas I and II may also be administered sequentially with known CNS treating agents when a combination formulation is inappropriate. The invention is not limited in the sequence of administration; compounds of the invention may be administered either prior to, simultaneous with or after administration of the known and used CNS agent.

The foregoing description is merely illustrative of the invention and is not intended to limit the invention to the disclosed compounds, compositions and methods. Variations and changes, which are obvious to one skilled in the art, are intended to be within the scope and nature of the invention, as defined in the appended claims. From the foregoing description, one skilled in the art can easily ascertain the essential characteristics of this invention, and without departing from the spirit and scope thereof, can make various changes and modifications of the invention to adapt it to various usages and conditions. All patents and other publications recited herein are hereby incorporated by reference in their entireties.

What is claimed is:

1. A compound of Formula I:

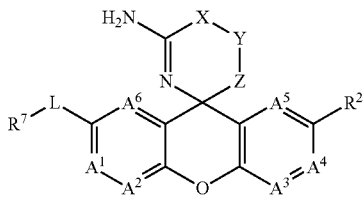

or a stereoisomer, tautomer, hydrate, solvate or pharmaceutically acceptable salt thereof, wherein
$A^1$ is $CR^6$;
$A^2$ is $CR^5$;
$A^3$ is $CR^4$;
$A^4$ is N;
$A^5$ is $CR^1$;
$A^6$ is $CR^8$;
L is —C(=O)NH—, —C(=O)N(CH$_3$)—, —NH—, —N(CH$_3$)— or —O—;
each of $R^1$, $R^4$, $R^5$ and $R^8$, independently, is H, F, Cl, Br, CF$_3$, OCF$_3$, C$_{1-6}$-alkyl, CN, OH, —OC$_{1-6}$-alkyl, —NHC$_{1-6}$-alkyl or —C(O)C$_{1-6}$-alkyl, wherein the C$_{1-6}$-alkyl and C$_{1-6}$-alkyl portion of —OC$_{1-6}$-alkyl, —NHC$_{1-6}$-alkyl and —C(O)C$_{1-6}$-alkyl are optionally substituted with 1-3 substituents of F, oxo or OH;
each of $R^2$ and $R^7$, independently, is F, Cl, Br, I, haloalkyl, haloalkoxyl, C$_{1-6}$-alkyl, C$_{2-6}$alkenyl, C$_{2-6}$alkynyl, CN, —OC$_{1-6}$alkyl, —SC$_{1-6}$alkyl, —NHC$_{1-6}$alkyl, —N(C$_{1-3}$alkyl)$_2$, —NH-phenyl, —NH-benzyl, —Si(CH$_3$)$_3$ or a ring selected from the group consisting of phenyl, pyridyl, pyrimidyl, pyrazinyl, pyridazinyl, triazinyl, thienyl, pyrazolyl, imidazolyl, oxazolyl, isoxazolyl, thiazolyl, isothiazolyl, diazolyl, triazolyl, tetrazolyl, pyranyl, dihydropyranyl, tetrahydropyranyl, furanyl, dihydrofuranyl, tetrahydrofuranyl, pyrrolyl, dihydropyrrolyl, pyrrolidinyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopropyl, cyclobutyl, cyclopentyl and cyclohexyl, wherein the C$_{1-6}$-alkyl, C$_{2-6}$alkenyl, C$_{2-6}$alkynyl, —OC$_{1-6}$alkyl, —SC$_{1-6}$alkyl, —NHC$_{1-6}$alkyl, —N(C$_{1-3}$alkyl)$_2$, —NH-phenyl, —NH-benzyl and ring are optionally substituted, independently, with 1-3 substituents of $R^9$;
$R^6$ is H, halo, haloalkyl, haloalkoxyl, C$_{1-6}$-alkyl, CN, OH, OC$_{1-6}$-alkyl, NHC$_{1-6}$-alkyl or C(O)C$_{1-6}$-alkyl;
each $R^9$, independently, is halo, haloalkyl, haloalkoxyl, CN, OH, NO$_2$, NH$_2$, acetyl, —C(O)NHCH$_3$, oxo, C$_{1-6}$alkyl, C$_{2-6}$alkenyl, C$_{2-6}$alkynyl, C$_{3-6}$cycloalkyl, C$_{1-6}$alkylamino-, C$_{1-6}$dialkylamino-, C$_{1-6}$alkoxyl, C$_{1-6}$thioalkoxyl, morpholinyl, pyrazolyl, isoxazolyl, dihydropyranyl, pyrrolidinyl, piperazinyl, oxetanyl or dioxolyl, wherein each of the C$_{1-6}$alkyl, C$_{2-6}$alkenyl, C$_{2-6}$alkynyl, C$_{3-6}$cycloalkyl, C$_{1-6}$alkylamino-, C$_{1-6}$dialkylamino-, C$_{1-6}$alkoxyl, C$_{1-6}$thioalkoxyl, morpholinyl, pyrazolyl, isoxazolyl, dihydropyranyl, pyrrolidinyl, oxetanyl or dioxolyl, is optionally substituted independently with 1-5 substituents of F, Cl, CN, NO$_2$, NH$_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutyl, isobutoxyl, tert-butoxyl, isobutyl, sec-butyl, tert-butyl, C$_{1-3}$alkylamino-, C$_{1-3}$dialkylamino, C$_{1-3}$thioalkoxyl or oxetanyl;
X is —O— or —S—;
Y is —CH$_2$; and
Z is CH$_2$.

2. The compound of claim 1 having a Formula II:

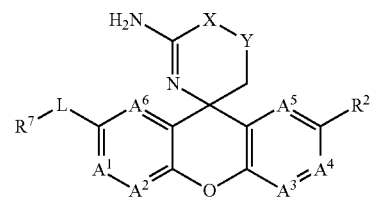

or a stereoisomer, tautomer, hydrate, solvate or pharmaceutically acceptable salt thereof, wherein
$A^1$ is $CR^6$;
$A^2$ is $CR^5$;
$A^3$ is $CR^4$;
$A^4$ is N;
$A^5$ is $CR^1$;
$A^6$ is $CR^8$;
L is —C(=O)NH—, —C(=O)N(CH$_3$)—, —NH—, —N(CH$_3$)— or —O—;
each of $R^1$, $R^4$, $R^5$ and $R^8$, independently, is H, F, Cl, Br, CF$_3$, OCF$_3$, C$_{1-6}$-alkyl, CN, OH, —OC$_{1-6}$-alkyl, —NHC$_{1-6}$-alkyl or —C(O)C$_{1-6}$-alkyl, wherein the C$_{1-6}$-alkyl and C$_{1-6}$-alkyl portion of —OC$_{1-6}$-alkyl, —NHC$_{1-6}$-alkyl and —C(O)C$_{1-6}$-alkyl are optionally substituted with 1-3 substituents of F, oxo or OH;
$R^2$ is Cl, Br, C$_{1-6}$-alkyl, C$_{2-4}$alkenyl, C$_{2-4}$alkynyl, CN, —OC$_{1-6}$alkyl, —SC$_{1-6}$alkyl, —NHC$_{1-6}$alkyl, —N(C$_{1-3}$alkyl)$_2$, —NH-phenyl, —NH-benzyl, phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, pyrrolidinyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopropyl, cyclobutyl, cyclopentyl, cyclohexyl or —Si(CH$_3$)$_3$, wherein the C$_{1-6}$-alkyl, C$_{2-4}$alkenyl, C$_{2-4}$alkynyl, —OC$_{1-6}$alkyl, —SC$_{1-6}$alkyl, —NHC$_{1-6}$alkyl, —N(C$_{1-3}$alkyl)$_2$, —NH-phenyl, —NH-benzyl, phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, pyrrolidinyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopropyl, cyclobutyl, cyclopentyl and cyclohexyl are optionally substituted, independently, with 1-3 substituents of $R^9$;
$R^6$ is H, halo, haloalkyl, haloalkoxyl, C$_{1-6}$-alkyl, CN, OH, OC$_{1-6}$-alkyl, NHC$_{1-6}$-alkyl or C(O)C$_{1-6}$-alkyl;
$R^7$ is C$_{1-6}$-alkyl, C$_{2-4}$alkenyl, C$_{2-4}$alkynyl, CN, —OC$_{1-6}$alkyl, —SC$_{1-6}$alkyl, —NHC$_{1-6}$alkyl, —N(C$_{1-3}$alkyl)$_2$, —NH-phenyl, —NH-benzyl, phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, pyrrolidinyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopentyl or cyclohexyl, wherein the $C_{1-6}$-alkyl, $C_{2-4}$alkenyl, $C_{2-4}$alkynyl, —$OC_{1-6}$alkyl, —$SC_{1-6}$alkyl, —$NHC_{1-6}$alkyl, —$N(C_{1-3}$alkyl$)_2$, —NH-phenyl, —NH-benzyl, phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, pyrrolidinyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopentyl and cyclohexyl are optionally substituted, independently, with 1-3 substituents of $R^9$;

each $R^9$, independently, is halo, haloalkyl, CN, OH, $NO_2$, $NH_2$, acetyl, —C(O)NHCH$_3$, oxo, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolidinyl, piperazinyl, oxetanyl or dioxolyl, wherein each of the $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolidinyl, oxetanyl or dioxolyl, is optionally substituted independently with 1-5 substituents of F, Cl, CN, $NO_2$, $NH_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, $C_{1-3}$alkylamino-, $C_{1-3}$dialkylamino, $C_{1-3}$thioalkoxyl or oxetanyl;

X is —O— or —S—; and
Y is —CH$_2$—.

3. The compound according to claim 2 or a stereoisomer, tautomer or pharmaceutically acceptable salt thereof, wherein
$A^1$ is CH or CF;
$A^2$ is CH or CF;
$A^3$ is CH, CF, or COCH$_3$;
$A^4$ is N;
$A^5$ is CH, CF or CBr;
$A^6$ is CH or CF;
L is —C(=O)NH—, —NH— or —O—;
X is —O— or —S—; and
Y is —CH$_2$—.

4. The compound according to claim 2 or a stereoisomer or pharmaceutically acceptable salt thereof, wherein $R^7$ is a ring selected from the group consisting of phenyl, pyridyl, pyrimidyl, pyrazinyl, pyridazinyl or thiazolyl, said ring optionally substituted, independently, with 1-3 substituents of $R^9$.

5. The compound of claim 1, or a stereoisomer or pharmaceutically acceptable salt thereof, wherein
$A^1$ is CH;
$A^2$ is CH;
$A^3$ is CH, CF or COCH$_3$;
$A^4$ is N;
$A^5$ is CH;
$A^6$ is CH;
L is —C(=O)NH—, —NH— or —O—;
$R^2$ is F, Cl, Br, I, $C_{1-6}$-alkyl, $C_{2-6}$alkenyl, $C_{2-6}$alkynyl, CN, —$OC_{1-6}$alkyl, —$SC_{1-6}$alkyl, —$NHC_{1-6}$alkyl, —$N(C_{1-3}$alkyl$)_2$, —NH-phenyl, —NH-benzyl, —Si(CH$_3$)$_3$ or a ring selected from the group consisting of phenyl, pyridyl, pyrimidyl, pyrazinyl, pyridazinyl, triazinyl, thienyl, pyrazolyl, imidazolyl, oxazolyl, isoxazolyl, thiazolyl, isothiazolyl, diazolyl, triazolyl, tetrazolyl, pyranyl, dihydropyranyl, tetrahydropyranyl, furanyl, dihydrofuranyl, tetrahydrofuranyl, pyrrolyl, dihydropyrrolyl, pyrrolidinyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopropyl, cyclobutyl, cyclopentyl and cyclohexyl, wherein the $C_{1-6}$-alkyl, $C_{2-6}$alkenyl, $C_{2-6}$alkynyl, —$OC_{1-6}$alkyl, —$SC_{1-6}$alkyl, —$NHC_{1-6}$alkyl, —$N(C_{1-3}$alkyl$)_2$, —NH-phenyl, —NH-benzyl and ring are optionally substituted, independently, with 1-3 substituents of $R^9$;

$R^7$ is a ring selected from the group consisting of phenyl, pyridyl, pyrimidyl, pyrazinyl, pyridazinyl, thiazolyl or thienyl, said ring optionally substituted, independently, with 1-3 substituents of $R^9$;

each $R^9$, independently, is F, Cl, Br, CH$_2$F, CHF$_2$, CF$_3$, CN, OH, $NO_2$, $NH_2$, acetyl, —C(O)NHCH$_3$, oxo, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolidinyl, piperazinyl, oxetanyl or dioxolyl, wherein each of the $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolidinyl, oxetanyl or dioxolyl, is optionally substituted independently with 1-5 substituents of F, Cl, CN, $NO_2$, $NH_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, $C_{1-3}$alkylamino-, $C_{1-3}$dialkylamino, $C_{1-3}$thioalkoxyl or oxetanyl;

X is —O— or —S—;
Y is —CH$_2$—; and
Z is CH$_2$.

6. The compound of claim 5, or a stereoisomer or pharmaceutically acceptable salt thereof, wherein
$A^1$ is CH;
$A^2$ is CH;
$A^3$ is CH, CF or COCH$_3$;
$A^4$ is N;
$A^5$ is CH;
$A^6$ is CH;
L is —C(=O)NH—;
$R^2$ is F, Cl, Br, I, $C_{1-6}$-alkyl, $C_{2-6}$alkenyl, $C_{2-6}$alkynyl, CN, —$OC_{1-6}$alkyl, —$SC_{1-6}$alkyl, —$NHC_{1-6}$alkyl, —$N(C_{1-3}$alkyl$)_2$, —NH-phenyl, —NH-benzyl, —Si(CH$_3$)$_3$ or a ring selected from the group consisting of phenyl, pyridyl, pyrimidyl, pyrazinyl, pyridazinyl, triazinyl, thienyl, pyrazolyl, imidazolyl, oxazolyl, isoxazolyl, thiazolyl, isothiazolyl, diazolyl, triazolyl, tetrazolyl, pyranyl, dihydropyranyl, tetrahydropyranyl, furanyl, dihydrofuranyl, tetrahydrofuranyl, pyrrolyl, dihydropyrrolyl, pyrrolidinyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopropyl, cyclobutyl, cyclopentyl and cyclohexyl, wherein the $C_{1-6}$-alkyl, $C_{2-6}$alkenyl, $C_{2-6}$alkynyl, —$OC_{1-6}$alkyl, —$SC_{1-6}$alkyl, —$NHC_{1-6}$alkyl, —$N(C_{1-3}$alkyl$)_2$, —NH-phenyl, —NH-benzyl and ring are optionally substituted, independently, with 1-3 substituents of $R^9$;

$R^7$ is a ring selected from the group consisting of phenyl, pyridyl, pyrimidyl, pyrazinyl, pyridazinyl, thiazolyl or thienyl, said ring optionally substituted, independently, with 1-3 substituents of $R^9$;

each $R^9$, independently, is F, Cl, Br, CH$_2$F, CHF$_2$, CF$_3$, CN, OH, $NO_2$, $NH_2$, acetyl, —C(O)NHCH$_3$, oxo, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolidinyl, piperazinyl, oxetanyl or dioxolyl, wherein each of the $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolidinyl, oxetanyl or dioxolyl, is optionally substituted independently with 1-5 substituents of F, Cl, CN, $NO_2$, $NH_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, $C_{1-3}$alkylamino-, $C_{1-3}$dialkylamino, $C_{1-3}$thioalkoxyl, or oxetanyl;

X is —O— or —S—;

Y is —$CH_2$—; and

Z is $CH_2$.

7. The compound of claim 1, or a stereoisomer, tautomer or pharmaceutically acceptable salt thereof, having a general formula I-A

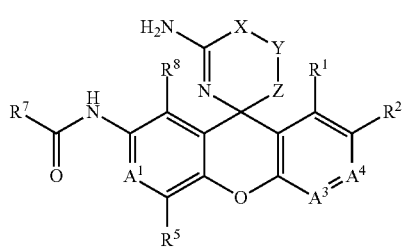

I-A wherein $A^1$ is $CR^6$;

$A^3$ is $CR^4$;

$A^4$ is N;

each of $R^1$, $R^4$, $R^5$, $R^6$ and $R^8$, independently, is H, F, Cl, $CF_3$, $OCF_3$, methyl, ethyl, CN, OH, $OCH_3$, $NHCH_3$ or $C(O)CH_3$;

one of $R^2$ and $R^7$, independently, is F, Cl, Br, I, haloalkyl, haloalkoxyl, $C_{1-6}$-alkyl, $C_{2-6}$alkenyl, $C_{2-6}$alkynyl, CN, —$OC_{1-6}$alkyl, —$SC_{1-6}$alkyl, —$NHC_{1-6}$alkyl, —$N(C_{1-3}$alkyl$)_2$, —NH-phenyl, —NH-benzyl, —Si$(CH_3)_3$ or a ring selected from the group consisting of phenyl, pyridyl, pyrimidyl, pyrazinyl, pyridazinyl, triazinyl, thienyl, pyrazolyl, imidazolyl, oxazolyl, isoxazolyl, thiazolyl, isothiazolyl, diazolyl, triazolyl, tetrazolyl, pyranyl, dihydropyranyl, tetrahydropyranyl, furanyl, dihydrofuranyl, tetrahydrofuranyl, pyrrolyl, dihydropyrrolyl, pyrrolidinyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopropyl, cyclobutyl, cyclopentyl and cyclohexyl, wherein the $C_{1-6}$-alkyl, $C_{2-6}$alkenyl, $C_{2-6}$alkynyl, —$OC_{1-6}$alkyl, —$SC_{1-6}$alkyl, —$NHC_{1-6}$alkyl, —$N(C_{1-3}$alkyl$)_2$, —NH-phenyl, —NH-benzyl and ring are optionally substituted, independently, with 1-3 substituents of $R^9$;

the other of $R^2$ and $R^7$, independently, is $C_{1-6}$-alkyl, $C_{2-4}$alkenyl, $C_{2-4}$alkynyl, CN, —$OC_{1-6}$alkyl, —$SC_{1-6}$alkyl, —$NHC_{1-6}$alkyl, —$N(C_{1-3}$alkyl$)_2$, —NH-phenyl or —NH-benzyl, phenyl, pyridyl, pyrimidyl or thienyl, wherein the $C_{1-6}$-alkyl, $C_{2-4}$alkenyl, $C_{2-4}$alkynyl, —$OC_{1-6}$alkyl, —$SC_{1-6}$alkyl, —$NHC_{1-6}$alkyl, —$N(C_{1-3}$alkyl$)_2$, —NH-phenyl, —NH-benzyl, phenyl, pyridyl, pyrmidinyl and thienyl are optionally substituted, independently, with 1-3 substituents of $R^9$;

each $R^9$, independently, is halo, haloalkyl, CN, OH, $NO_2$, $NH_2$, acetyl, —C(O)$NHCH_3$, oxo, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolidinyl, piperazinyl, oxetanyl or dioxolyl, wherein each of the $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolidinyl, oxetanyl or dioxolyl, is optionally substituted independently with 1-5 substituents of F, Cl, CN, $NO_2$, $NH_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, $C_{1-3}$alkylamino-, $C_{1-3}$dialkylamino, $C_{1-3}$thioalkoxyl or oxetanyl;

X is —O— or —S—;

Y —$CH_2$—; and

Z is $CH_2$.

8. The compound of claim 7, or a stereoisomer or pharmaceutically acceptable salt thereof, wherein $A^1$ is $CR^6$;

$A^3$ is CH, CF or $COCH_3$;

$A^4$ is N; and each of $R^1$, $R^5$, $R^6$ and $R^8$, independently, is H, F, $CF_3$, methyl or CN;

$R^2$ is F, Cl, Br, I, $C_{1-6}$alkyl, $C_{2-6}$alkenyl, $C_{2-6}$alkynyl, CN, —$OC_{1-6}$alkyl, —$SC_{1-6}$alkyl, 3-methyl-3-oxetanyl-ethynyl, 3-methyl-3-oxetanyl-methoxyl, 3,3-dimethyl-butyn-1-yl, 3-methyl-butyn-1-yl, 2,2-dimethyl-3-cyano-propoxyl, 2-fluoro-2-methyl-propoxyl, or a ring selected from the group consisting of phenyl, 2-pyridyl, 3-pyridyl, 4-pyridyl, dihydro-2H-pyran-4-yl, dihydro-2H-pyran-3-yl, tetrahydropyran-4-yl, dihydrofuranyl, tetrahydrofuranyl, pyrrolidin-1-yl, piperidin-1-yl, morpholinyl, 8-oxo-3-aza-bicyclo[3.2.1]oct-3-yl, aza-bicyclo[2.2.1]hept-5-yl and 2-oxo-7-aza-[3,5]-spironon-7-yl, wherein the $C_{1-6}$-alkyl, $C_{2-6}$alkenyl, $C_{2-6}$alkynyl —$OC_{1-6}$alkyl, —$SC_{1-6}$alkyl, 3-methyl-3-oxetanyl-ethynyl, 3-methyl-3-oxetanyl-methoxyl, 3,3-dimethyl-butyn-1-yl, 3-methyl-butyn-1-yl, 2,2-dimethyl-3-cyano-propoxyl, 2-fluoro-2-methyl-propoxyl and ring are optionally substituted, independently, with 1-3 substituents of $R^9$;

$R^7$ is a ring selected from the group consisting of phenyl, pyridyl, pyrimidyl, pyrazinyl, pyridazinyl, thiazolyl or thienyl, said ring optionally substituted, independently, with 1-3 substituents of $R^9$;

each $R^9$, independently, is halo, haloalkyl, CN, OH, $NO_2$, $NH_2$, acetyl, —C(O)$NHCH_3$, oxo, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolidinyl, piperazinyl, oxetanyl or dioxolyl, wherein each of the $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolidinyl, oxetanyl or dioxolyl, is optionally substituted independently with 1-5 substituents of F, Cl, CN, $NO_2$, $NH_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, $C_{1-3}$alkylamino-, $C_{1-3}$dialkylamino, $C_{1-3}$thioalkoxyl or oxetanyl;

X is —O— or —S—;
Y is —CH₂—; and
Z is CH₂.

9. The compound of claim 8, or a stereoisomer or pharmaceutically acceptable salt thereof, wherein
A¹ is CH;
A³ is CH, CF or COCH₃;
A⁴ is N; and
each of R¹, R⁵, R⁶ and R⁸, independently, is H, F, CF₃, methyl or CN;
R² is F, Cl, Br, I, $C_{1-6}$alkyl, $C_{2-6}$alkenyl, $C_{2-6}$alkynyl, CN, —O$C_{1-6}$alkyl, —S$C_{1-6}$alkyl, 3-methyl-3-oxetanyl-ethynyl, 3-methyl-3-oxetanyl-methoxyl, 3,3-dimethyl-butyn-1-yl, 3-methyl-butyn-1-yl, 2,2-dimethyl-3-cyano-propoxyl, 2-fluoro-2-methyl-propoxyl, or a ring selected from the group consisting of phenyl, 2-pyridyl, 3-pyridyl, 4-pyridyl, dihydro-2H-pyran-4-yl, dihydro-2H-pyran-3-yl, tetrahydropyran-4-yl, dihydrofuranyl, tetrahydrofuranyl, pyrrolidin-1-yl, piperidin-1-yl, morpholinyl, 8-oxo-3-aza-bicyclo[3.2.1]oct-3-yl, aza-bicyclo[2.2.1]hept-5-yl and 2-oxo-7-aza-[3,5]-spironon-7-yl, wherein the $C_{1-6}$-alkyl, $C_{2-6}$alkenyl, $C_{2-6}$alkynyl, —O$C_{1-6}$alkyl, —S$C_{1-6}$alkyl, 3-methyl-3-oxetanyl-ethynyl, 3-methyl-3-oxetanyl-methoxyl, 3,3-dimethyl-butyn-1-yl, 3-methyl-butyn-1-yl, 2,2-dimethyl-3-cyano-propoxyl, 2-fluoro-2-methyl-propoxyl and ring are optionally substituted, independently, with 1-3 substituents of R⁹;
R⁷ is a ring selected from the group consisting of phenyl, pyridyl, pyrimidyl, pyrazinyl, pyridazinyl, thiazolyl or thienyl, said ring optionally substituted, independently, with 1-3 substituents of R⁹;
each R⁹, independently, is halo, haloalkyl, CN, OH, NO₂, NH₂, acetyl, —C(O)NHCH₃, oxo, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolidinyl, piperazinyl, oxetanyl or dioxolyl, wherein each of the $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolidinyl, oxetanyl or dioxolyl, is optionally substituted independently with 1-5 substituents of F, Cl, CN, NO₂, NH₂, OH, oxo, methyl, methoxyl, ethyl, ethoxyl, propyl, propoxyl, isopropyl, isopropoxyl, cyclopropyl, cyclopropyl-methoxyl, butyl, butoxyl, isobutoxyl, tert-butoxyl, isobutyl, sec-butyl, tert-butyl, $C_{1-3}$alkylamino-, $C_{1-3}$dialkylamino, $C_{1-3}$thioalkoxyl or oxetanyl;
X is —O— or —S—;
Y is —CH₂—; and
Z is CH₂.

10. The compound of claim 1, or a stereoisomer or pharmaceutically acceptable salt thereof, selected from
N-((5S)-2'-amino-3-chloro-1-fluoro-5',6'-dihydrospiro[chromeno[2,3-c]pyridine-5,4'-[1,3]oxazin]-7-yl)-5-chloro-2-pyridinecarboxamide;
N-((5S)-2'-amino-3-chloro-1-fluoro-5',6'-dihydrospiro[chromeno[2,3-c]pyridine-5,4'-[1,3]oxazin]-7-yl)-5-cyano-2-pyridinecarboxamide;
N-((5S)-2'-amino-3-chloro-1-fluoro-5',6'-dihydrospiro[chromeno[2,3-c]pyridine-5,4'-[1,3]oxazin]-7-yl)-5-methoxy-2-pyrazinecarboxamide;
N-((5S)-2'-amino-3-chloro-1-fluoro-5',6'-dihydrospiro[chromeno[2,3-c]pyridine-5,4'-[1,3]oxazin]-7-yl)-5-(2-butyn-1-yloxy)-2-pyrazinecarboxamide;
N-((5S)-2'-amino-3-chloro-1-fluoro-5',6'-dihydrospiro[chromeno[2,3-c]pyridine-5,4'-[1,3]oxazin]-7-yl)-5-chloro-2-pyrazinecarboxamide;
N-((5S)-2'-amino-3-(5,6-dihydro-2H-pyran-3-yl)-1-fluoro-5',6'-dihydrospiro[chromeno[2,3-c]pyridine-5,4'-[1,3]oxazin]-7-yl)-5-chloro-2-pyridinecarboxamide;
N-((5S)-2'-amino-3-(5,6-dihydro-2H-pyran-3-yl)-1-fluoro-5',6'-dihydrospiro[chromeno[2,3-c]pyridine-5,4'-[1,3]oxazin]-7-yl)-5-methoxy-2-pyrazinecarboxamide;
N-((5S)-2'-amino-3-(5,6-dihydro-2H-pyran-3-yl)-1-fluoro-5',6'-dihydrospiro[chromeno[2,3-c]pyridine-5,4'-[1,3]oxazin]-7-yl)-5-cyano-2-pyridinecarboxamide;
N-((5S)-2'-amino-3-cyclopropyl-1-methoxy-5',6'-dihydrospiro[chromeno[2,3-c]pyridine-5,4'-[1,3]oxazin]-7-yl)-5-chloro-2-pyridinecarboxamide
N-((5S)-2'-amino-3-cyclopropyl-1-fluoro-5',6'-dihydrospiro[chromeno[2,3-c]pyridine-5,4'-[1,3]oxazin]-7-yl)-5-chloro-2-pyridinecarboxamide;
N-((5S)-2'-amino-3-cyclopropyl-1-fluoro-5',6'-dihydrospiro[chromeno[2,3-c]pyridine-5,4'-[1,3]oxazin]-7-yl)-5-methoxy-2-pyrazinecarboxamide;
N-((5R)-2'-amino-3-chloro-1-fluoro-5',6'-dihydrospiro[chromeno[2,3-c]pyridine-5,4'-[1,3]thiazin]-7-yl)-5-methoxy-2-pyrazinecarboxamide;
N-((5S)-2'-amino-3-chloro-1-fluoro-5',6'-dihydrospiro[chromeno[2,3-c]pyridine-5,4'-[1,3]thiazin]-7-yl)-5-methoxy-2-pyrazinecarboxamide
N-((5S)-2'-amino-3-(5,6-dihydro-2H-pyran-3-yl)-5',6'-dihydrospiro[chromeno[2,3-c]pyridine-5,4'-[1,3]oxazin]-7-yl)-5-methoxy-2-pyrazinecarboxamide;
N-((5S)-2'-amino-3-(5,6-dihydro-2H-pyran-3-yl)-5',6'-dihydrospiro[chromeno[2,3-c]pyridine-5,4'-[1,3]oxazin]-7-yl)-5-chloro-2-pyridinecarboxamide;
N-((5S)-2'-amino-3-(3,6-dihydro-2H-pyran-4-yl)-1-fluoro-5',6'-dihydrospiro[chromeno[2,3-c]pyridine-5,4'-[1,3]oxazin]-7-yl)-5-chloro-2-pyridinecarboxamide;
N-((5S)-2'-amino-3-(3,6-dihydro-2H-pyran-4-yl)-1-fluoro-5',6'-dihydrospiro[chromeno[2,3-c]pyridine-5,4'-[1,3]oxazin]-7-yl)-5-cyano-2-pyridinecarboxamide;
N-((5S)-2'-amino-3-(3,6-dihydro-2H-pyran-4-yl)-1-fluoro-5',6'-dihydrospiro[chromeno[2,3-c]pyridine-5,4'-[1,3]oxazin]-7-yl)-5-methoxy-2-pyrazinecarboxamide;
N-((5S)-2'-amino-3-(5,6-dihydro-2H-pyran-3-yl)-1-fluoro-5',6'-dihydrospiro[chromeno[2,3-c]pyridine-5,4'-[1,3]thiazin]-7-yl)-5-methoxy-2-pyrazinecarboxamide;
N-((5S)-2'-amino-3-(3,6-dihydro-2H-pyran-4-yl)-1-fluoro-5',6'-dihydrospiro[chromeno[2,3-c]pyridine-5,4'-[1,3]thiazin]-7-yl)-5-methoxy-2-pyrazinecarboxamide;
N-((5S)-2'-amino-3-(5,6-dihydro-2H-pyran-3-yl)-1-fluoro-5',6'-dihydrospiro[chromeno[2,3-c]pyridine-5,4'-[1,3]thiazin]-7-yl)-5-chloro-2-pyridinecarboxamide;
N-((5S)-2'-amino-1-fluoro-3-(5-fluoro-3-pyridinyl)-5',6'-dihydrospiro[chromeno[2,3-c]pyridine-5,4'-[1,3]oxazin]-7-yl)-5-cyano-2-pyrazinecarboxamide;
N-((5S)-2'-amino-1-fluoro-3-(5-fluoro-3-pyridinyl)-5',6'-dihydrospiro[chromeno[2,3-c]pyridine-5,4'-[1,3]oxazin]-7-yl)-5-methoxy-2-pyrazinecarboxamide;
N-((5S)-2'-amino-1-fluoro-3-(5-fluoro-3-pyridinyl)-5',6'-dihydrospiro[chromeno[2,3-c]pyridine-5,4'-[1,3]oxazin]-7-yl)-5-chloro-2-pyridinecarboxamide;
N-((5S)-2'-amino-3-(3,6-dihydro-2H-pyran-4-yl)-1-fluoro-5',6'-dihydrospiro[chromeno[2,3-c]pyridine-5,4'-[1,3]oxazin]-7-yl)-5-fluoro-2-pyridinecarboxamide;

N-((5S)-2'-amino-3-(3,6-dihydro-2H-pyran-4-yl)-1-fluoro-5',6'-dihydrospiro[chromeno[2,3-c]pyridine-5,4'-[1,3]oxazin]-7-yl)-5-methoxy-2-pyridinecarboxamide;

N-((5S)-2'-amino-3-chloro-5',6'-dihydrospiro[chromeno[2,3-c]pyridine-5,4'-[1,3]oxazin]-7-yl)-5-chloro-2-pyridinecarboxamide;

N-((5S)-2'-amino-3-cyclopropyl-5',6'-dihydrospiro[chromeno[2,3-c]pyridine-5,4'-[1,3]oxazin]-7-yl)-5-methoxy-2-pyrazinecarboxamide;

N-((5S)-2'-amino-3-cyclopropyl-5',6'-dihydrospiro[chromeno[2,3-c]pyridine-5,4'-[1,3]oxazin]-7-yl)-5-chloro-2-pyridinecarboxamide;

N-((5S)-2'-amino-3-(3,3-dimethyl-1-butyn-1-yl)-5',6'-dihydrospiro[chromeno[2,3-c]pyridine-5,4'-[1,3]oxazin]-7-yl)-5-chloro-2-pyridinecarboxamide;

N-((5S)-2'-amino-3-(5,6-dihydro-2H-pyran-3-yl)-1-fluoro-5',6'-dihydrospiro[chromeno[2,3-c]pyridine-5,4'-[1,3]oxazin]-7-yl)-5-fluoro-2-pyridinecarboxamide;

N-((5S)-2'-amino-3-(5,6-dihydro-2H-pyran-3-yl)-1-fluoro-5',6'-dihydrospiro[chromeno[2,3-c]pyridine-5,4'-[1,3]oxazin]-7-yl)-5-methoxy-2-pyridinecarboxamide;

N-((5S)-2'-amino-3-(5,6-dihydro-2H-pyran-3-yl)-1-fluoro-5',6'-dihydrospiro[chromeno[2,3-c]pyridine-5,4'-[1,3]oxazin]-7-yl)-2-methyl-1,3-thiazole-4-carboxamide;

N-((5S)-2'-amino-3-(3,3-dimethyl-1-butyn-1-yl)-5',6'-dihydrospiro[chromeno[2,3-c]pyridine-5,4'-[1,3]oxazin]-7-yl)-5-methoxy-2-pyrazinecarboxamide;

N-((5S)-2'-amino-1-fluoro-3-(5-fluoro-3-pyridinyl)-5',6'-dihydrospiro[chromeno[2,3-c]pyridine-5,4'-[1,3]oxazin]-7-yl)-5-methoxy-2-pyridinecarboxamide;

N-((5S)-2'-amino-1-fluoro-3-(5-fluoro-3-pyridinyl)-5',6'-dihydrospiro[chromeno[2,3-c]pyridine-5,4'-[1,3]oxazin]-7-yl)-2-methyl-1,3-thiazole-4-carboxamide;

N-((5S)-2'-amino-1-fluoro-3-(5-fluoro-3-pyridinyl)-5',6'-dihydrospiro[chromeno[2,3-c]pyridine-5,4'-[1,3]oxazin]-7-yl)-5-fluoro-2-pyridinecarboxamide;

N-((5S)-2'-amino-1-fluoro-3-(2-fluoro-4-pyridinyl)-5',6'-dihydrospiro[chromeno[2,3-c]pyridine-5,4'-[1,3]oxazin]-7-yl)-5-chloro-2-pyridinecarboxamide;

N-((5S)-2'-amino-1-fluoro-3-(2-fluoro-4-pyridinyl)-5',6'-dihydrospiro[chromeno[2,3-c]pyridine-5,4'-[1,3]oxazin]-7-yl)-5-methoxy-2-pyrazinecarboxamide;

N-((5S)-2'-amino-3-(2-fluoro-4-pyridinyl)-5',6'-dihydrospiro[chromeno[2,3-c]pyridine-5,4'-[1,3]oxazin]-7-yl)-5-methoxy-2-pyrazinecarboxamide;

N-((5S)-2'-amino-3-(2-fluoro-4-pyridinyl)-5',6'-dihydrospiro[chromeno[2,3-c]pyridine-5,4'-[1,3]oxazin]-7-yl)-5-chloro-2-pyridinecarboxamide;

N-((5S)-2'-amino-3-(3,6-dihydro-2H-pyran-4-yl)-1-methoxy-5',6'-dihydrospiro[chromeno[2,3-c]pyridine-5,4'-[1,3]oxazin]-7-yl)-5-chloro-2-pyridinecarboxamide;

N-((5S)-2'-amino-3-(3,6-dihydro-2H-pyran-4-yl)-1-methoxy-5',6'-dihydrospiro[chromeno[2,3-c]pyridine-5,4'-[1,3]oxazin]-7-yl)-5-fluoro-2-pyridinecarboxamide;

N-((5S)-2'-amino-1-fluoro-3-(2-fluoro-4-pyridinyl)-5',6'-dihydrospiro[chromeno[2,3-c]pyridine-5,4'-[1,3]oxazin]-7-yl)-5-fluoro-2-pyridinecarboxamide;

N-((5S)-2'-amino-1-fluoro-3-(2-fluoro-4-pyridinyl)-5',6'-dihydrospiro[chromeno[2,3-c]pyridine-5,4'-[1,3]oxazin]-7-yl)-5-methoxy-2-pyridinecarboxamide;

N-((5S)-2'-amino-1-fluoro-3-(2-fluoro-4-pyridinyl)-5',6'-dihydrospiro[chromeno[2,3-c]pyridine-5,4'-[1,3]oxazin]-7-yl)-2-methyl-1,3-thiazole-4-carboxamide;

N-((5S)-2'-amino-1-fluoro-3-(2-fluoro-4-pyridinyl)-5',6'-dihydrospiro[chromeno[2,3-c]pyridine-5,4'-[1,3]oxazin]-7-yl)-5-cyano-2-pyridinecarboxamide;

N-((5S)-2'-amino-3-(3,6-dihydro-2H-pyran-4-yl)-1-fluoro-5',6'-dihydrospiro[chromeno[2,3-c]pyridine-5,4'-[1,3]thiazin]-7-yl)-5-methoxy-2-pyridinecarboxamide;

N-((5S)-2'-amino-3-(3,6-dihydro-2H-pyran-4-yl)-5',6'-dihydrospiro[chromeno[2,3-c]pyridine-5,4'-[1,3]thiazin]-7-yl)-5-methoxy-2-pyrazinecarboxamide;

N-((5S)-2'-amino-3-(5,6-dihydro-2H-pyran-3-yl)-5',6'-dihydrospiro[chromeno[2,3-c]pyridine-5,4'-[1,3]thiazin]-7-yl)-5-methoxy-2-pyrazinecarboxamide;

N-((5S)-2'-amino-3-(5,6-dihydro-2H-pyran-3-yl)-1-fluoro-5',6'-dihydrospiro[chromeno[2,3-c]pyridine-5,4'-[1,3]thiazin]-7-yl)-5-methoxy-2-pyridinecarboxamide;

N-((5S)-2'-amino-1-fluoro-3-(5-fluoro-3-pyridinyl)-5',6'-dihydrospiro[chromeno[2,3-c]pyridine-5,4'-[1,3]thiazin]-7-yl)-5-methoxy-2-pyrazinecarboxamide;

N-((5S)-2'-amino-1-fluoro-3-(5-fluoro-3-pyridinyl)-5',6'-dihydrospiro[chromeno[2,3-c]pyridine-5,4'-[1,3]thiazin]-7-yl)-5-methoxy-2-pyridinecarboxamide;

N-((5S)-2'-amino-1-fluoro-3-(2-fluoro-4-pyridinyl)-5',6'-dihydrospiro[chromeno[2,3-c]pyridine-5,4'-[1,3]thiazin]-7-yl)-5-methoxy-2-pyrazinecarboxamide;

N-((5S)-2'-amino-1-fluoro-3-(2-fluoro-4-pyridinyl)-5',6'-dihydrospiro[chromeno[2,3-c]pyridine-5,4'-[1,3]thiazin]-7-yl)-5-methoxy-2-pyridinecarboxamide;

N-((5S)-2'-amino-3-(3,6-dihydro-2H-pyran-4-yl)-1-fluoro-5',6'-dihydrospiro[chromeno[2,3-c]pyridine-5,4'-[1,3]thiazin]-7-yl)-5-fluoro-2-pyridinecarboxamide;

N-((5S)-2'-amino-3-(3,6-dihydro-2H-pyran-4-yl)-1-fluoro-5',6'-dihydrospiro[chromeno[2,3-c]pyridine-5,4'-[1,3]thiazin]-7-yl)-5-chloro-2-pyridinecarboxamide;

N-((5S)-2'-amino-1-fluoro-3-(2-fluoro-4-pyridinyl)-5',6'-dihydrospiro[chromeno[2,3-c]pyridine-5,4'-[1,3]thiazin]-7-yl)-5-fluoro-2-pyridinecarboxamide;

N-((5S)-2'-amino-3-(3,6-dihydro-2H-pyran-4-yl)-1-fluoro-5',6'-dihydrospiro[chromeno[2,3-c]pyridine-5,4'-[1,3]thiazin]-7-yl)-5-chloro-3-fluoro-2-pyridinecarboxamide;

N-((5S)-2'-amino-3-(3,6-dihydro-2H-pyran-4-yl)-1-fluoro-5',6'-dihydrospiro[chromeno[2,3-c]pyridine-5,4'-[1,3]thiazin]-7-yl)-5-bromo-3-methyl-2-pyridinecarboxamide;

N-((5S)-2'-amino-3-(3,6-dihydro-2H-pyran-4-yl)-1-fluoro-5',6'-dihydrospiro[chromeno[2,3-c]pyridine-5,4'-[1,3]thiazin]-7-yl)-5-methoxy-3-methyl-2-pyridinecarboxamide; or N-((5S)-2'-amino-3-(3,6-dihydro-2H-pyran-4-yl)-1-fluoro-5',6'-dihydrospiro[chromeno[2,3-c]pyridine-5,4'-[1,3]thiazin]-7-yl)-5-chloro-3-methyl-2-pyridinecarboxamide.

11. A pharmaceutical composition comprising a compound according to claim 1 and a pharmaceutically acceptable excipient.

* * * * *